US012766295B2

(12) United States Patent
Heilman et al.

(10) Patent No.: US 12,766,295 B2
(45) **Date of Patent: *Oct. 20, 2026**

(54) METHODS AND SYSTEMS FOR DRAINING CEREBROSPINAL FLUID INTO THE VENOUS SYSTEM

(71) Applicant: CEREVASC, INC., Charlestown, MA (US)

(72) Inventors: Carl Heilman, Wayland, MA (US); Adel M. Malek, Weston, MA (US); David A. Rezac, Westborough, MA (US); Timothy W. Robinson, Sandown, NH (US); Joseph Ting, Auburndale, MA (US)

(73) Assignee: CereVasc, Inc., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/635,753

(22) Filed: Mar. 31, 2026

(65) Prior Publication Data

US 2026/0224866 A1 Aug. 6, 2026

Related U.S. Application Data

(60) Continuation of application No. 18/926,899, filed on Oct. 25, 2024, which is a continuation of application (Continued)

(51) Int. Cl.
*A61M 27/00* (2006.01)
*A61B 18/14* (2006.01)
(Continued)

(52) U.S. Cl.
CPC ....... *A61M 27/006* (2013.01); *A61B 18/1477* (2013.01); *A61B 34/20* (2016.02); (Continued)

(58) Field of Classification Search
CPC ............ A61M 27/002; A61M 25/0067; A61M 25/0108; A61M 25/0155; A61M 25/09; (Continued)

(56) References Cited

U.S. PATENT DOCUMENTS 575,997 A 1/1897 Spencer
3,492,996 A 2/1970 Fountain
(Continued)

FOREIGN PATENT DOCUMENTS

CN 189564 1/2007
CN 1895694 1/2007
(Continued)

OTHER PUBLICATIONS

Amendment Response to Office Action for U.S. Appl. No. 15/862,120 dated May 1, 2018.
(Continued)

*Primary Examiner* — Philip R Wiest
(74) *Attorney, Agent, or Firm* — Vista IP Law Group, LLP

(57) ABSTRACT

A shunt and methods for treating hydrocephalus using the shunt, the shunt having one or more CSF intake openings and an expandable anchoring mechanism in a distal portion, one or more CSF outflow openings disposed in a proximal portion, and a lumen extending between the one or more CSF intake openings and the one or more CSF outflow openings, the method including intravascularly deploying the shunt in a patient so that the distal portion is at least partially disposed within a subarachnoid space of the patient, and the proximal portion is at least partially disposed within a venous system of the patient, wherein, after deployment of the shunt, CSF flows from the subarachnoid space into the venous system via the shunt lumen.

28 Claims, 76 Drawing Sheets

Related U.S. Application Data

No. 18/668,055, filed on May 17, 2024, which is a continuation of application No. 16/998,606, filed on Aug. 20, 2020, now Pat. No. 12,011,557, which is a continuation of application No. 15/981,118, filed on May 16, 2018, now Pat. No. 10,765,846, which is a continuation of application No. 15/862,120, filed on Jan. 4, 2018, now Pat. No. 10,058,686, which is a continuation of application No. 15/668,657, filed on Aug. 3, 2017, now Pat. No. 10,279,154, which is a continuation of application No. 15/432,818, filed on Feb. 14, 2017, now Pat. No. 9,724,501, which is a continuation of application No. 15/289,790, filed on Oct. 10, 2016, now Pat. No. 9,669,195, which is a continuation of application No. 15/195,139, filed on Jun. 28, 2016, now Pat. No. 9,662,479, which is a continuation of application No. 15/065,766, filed on Mar. 9, 2016, now Pat. No. 9,387,311, which is a division of application No. 14/929,066, filed on Oct. 30, 2015, now abandoned.

(60) Provisional application No. 62/156,152, filed on May 1, 2015, provisional application No. 62/142,895, filed on Apr. 3, 2015, provisional application No. 62/073,766, filed on Oct. 31, 2014.

(51) Int. Cl.
*A61B 34/20* (2016.01)
*A61M 25/00* (2006.01)
*A61M 25/01* (2006.01)
*A61M 25/09* (2006.01)
*A61M 25/10* (2013.01)
*A61M 39/24* (2006.01)

(52) U.S. Cl.
CPC .... *A61M 25/0067* (2013.01); *A61M 25/0108* (2013.01); *A61M 25/0155* (2013.01); *A61M 25/09* (2013.01); *A61M 25/10* (2013.01); *A61M 39/24* (2013.01); *A61B 18/1492* (2013.01); *A61M 2039/242* (2013.01); *A61M 2039/2426* (2013.01); *A61M 2210/06* (2013.01)

(58) Field of Classification Search
CPC .................. A61M 25/10; A61M 39/24; A61M 2039/242; A61M 2039/2426; A61B 34/20; A61B 18/1477
See application file for complete search history.

(56) References Cited

U.S. PATENT DOCUMENTS 3,894,541 A * 7/1975 El-Shafei ............ A61M 27/006 604/10
4,413,985 A 11/1983 Wellner et al.
4,474,569 A 10/1984 Newkirk
4,475,898 A 10/1984 Brodner et al.
4,631,051 A 12/1986 Harris
4,737,153 A 4/1988 Shimamura et al.
4,932,938 A 6/1990 Goldberg et al.
4,950,232 A 8/1990 Ruzicka et al.
5,000,731 A 3/1991 Wong et al.
5,137,288 A 8/1992 Starkey et al.
5,160,325 A 11/1992 Nichols et al.
5,193,546 A 3/1993 Shaknovich
5,221,261 A 6/1993 Termin et al.
5,385,541 A 1/1995 Kirsch et al.
5,405,316 A 4/1995 Magram
5,496,329 A 3/1996 Reisinger
5,562,641 A 10/1996 Flomenblit et al.
5,634,475 A 6/1997 Wolvek
5,725,571 A 3/1998 Imbert et al.
5,725,572 A 3/1998 Lam et al.
5,746,725 A 5/1998 Shalon et al.
5,792,157 A 8/1998 Mische et al.
5,800,520 A 9/1998 Fogarty et al.
5,830,222 A 11/1998 Makower
5,851,199 A 12/1998 Peerless et al.
5,885,258 A 3/1999 Sachdeva et al.
5,976,131 A 11/1999 Guglielmi et al.
5,984,929 A 11/1999 Bashiri et al.
6,015,405 A 1/2000 Schwartz et al.
6,066,158 A 5/2000 Engelson et al.
6,068,638 A 5/2000 Makower
6,071,292 A 6/2000 Makower et al.
6,093,199 A 7/2000 Brown et al.
6,096,053 A 8/2000 Bates
6,126,628 A 10/2000 Nissels
6,126,649 A 10/2000 VanTassel et al.
6,126,672 A 10/2000 Berryman et al.
6,159,225 A 12/2000 Makower
6,186,972 B1 2/2001 Nelson et al.
6,190,353 B1 2/2001 Makower et al.
6,231,587 B1 5/2001 Makower
6,283,934 B1 9/2001 Borgeson
6,283,951 B1 9/2001 Flaherty et al.
6,283,983 B1 9/2001 Makower et al.
6,287,317 B1 9/2001 Makower et al.
6,302,875 B1 10/2001 Makower et al.
6,330,884 B1 12/2001 Kim
6,350,271 B1 2/2002 Kurz et al.
6,375,615 B1 4/2002 Flaherty et al.
6,379,319 B1 4/2002 Garibotto et al.
6,402,771 B1 6/2002 Palmer et al.
6,425,909 B1 7/2002 Dieck et al.
6,432,127 B1 8/2002 Kim et al.
6,491,707 B2 12/2002 Makower et al.
6,508,824 B1 1/2003 Flaherty et al.
6,527,790 B2 3/2003 Chien et al.
6,530,935 B2 3/2003 Wensel et al.
6,544,230 B1 4/2003 Flaherty et al.
6,561,998 B1 5/2003 Roth et al.
6,569,145 B1 5/2003 Shmulewitz et al.
6,575,997 B1 6/2003 Palmer et al.
6,579,302 B2 6/2003 Duerig et al.
6,579,311 B1 6/2003 Makower
6,589,164 B1 7/2003 Flaherty
6,602,241 B2 8/2003 Makower et al.
6,613,081 B2 9/2003 Kim et al.
6,616,675 B1 9/2003 Evard et al.
6,638,293 B1 10/2003 Makower et al.
6,655,386 B1 12/2003 Makower et al.
6,660,021 B1 12/2003 Palmer et al.
6,660,024 B1 12/2003 Flaherty et al.
6,663,650 B2 12/2003 Sepetka et al.
6,685,648 B2 2/2004 Flaherty et al.
6,685,716 B1 2/2004 Flaherty et al.
6,709,444 B1 3/2004 Makower
6,716,238 B2 4/2004 Elliott
6,719,750 B2 4/2004 Varner et al.
6,726,677 B1 4/2004 Flaherty et al.
6,730,104 B1 5/2004 Sepetka et al.
6,746,426 B1 6/2004 Flaherty et al.
6,746,464 B1 6/2004 Makower
6,863,684 B2 3/2005 Kim et al.
7,056,325 B1 6/2006 Makower et al.
7,083,588 B1 8/2006 Shmulewitz et al.
7,094,230 B2 8/2006 Flaherty et al.
7,134,438 B2 11/2006 Makower et al.
7,172,571 B2 * 2/2007 Moskowitz ......... A61M 27/006 604/9
7,179,270 B2 2/2007 Makower
7,191,015 B2 3/2007 Lamson et al.
7,300,458 B2 11/2007 Henkes et al.
7,303,571 B2 12/2007 Makower et al.
7,316,655 B2 1/2008 Garibotto et al.
7,316,692 B2 1/2008 Huffmaster
7,357,794 B2 4/2008 Makower et al.
7,407,506 B2 8/2008 Makower

(56) References Cited

U.S. PATENT DOCUMENTS

| | | | | |
|---|---|---|---|---|
| 7,606,615 | B2 | 10/2009 | Makower et al. | |
| 7,621,950 | B1 | 11/2009 | Globernnan | |
| 7,637,870 | B2 | 12/2009 | Flaherty et al. | |
| 7,648,517 | B2 | 1/2010 | Makower et al. | |
| 7,670,329 | B2 | 3/2010 | Flaherty et al. | |
| 7,729,738 | B2 | 6/2010 | Flaherty et al. | |
| 7,797,053 | B2 | 9/2010 | Atkinson et al. | |
| 7,846,172 | B2 | 12/2010 | Makower | |
| 7,955,343 | B2 | 6/2011 | Makower et al. | |
| 7,966,057 | B2 | 6/2011 | Macaulay et al. | |
| 7,989,042 | B2 | 8/2011 | Obara et al. | |
| 8,075,580 | B2 | 12/2011 | Makower | |
| 8,083,708 | B2 | 12/2011 | Flaherty et al. | |
| 8,088,140 | B2 | 1/2012 | Ferrera et al. | |
| 8,090,430 | B2 | 1/2012 | Makower et al. | |
| 8,118,827 | B2 | 2/2012 | Duerig | |
| 8,214,015 | B2 | 7/2012 | Macaulay et al. | |
| 8,292,950 | B2 | 10/2012 | Dorn et al. | |
| 8,295,947 | B2 | 10/2012 | Lamson et al. | |
| 8,317,748 | B2 | 11/2012 | Fiorella et al. | |
| 8,486,104 | B2 | 7/2013 | Samson et al. | |
| 8,540,684 | B2 | 9/2013 | Yeung et al. | |
| 8,540,759 | B2 | 9/2013 | Porter | |
| 8,585,596 | B1 | 11/2013 | Flaherty et al. | |
| 8,672,871 | B2 | 3/2014 | Heilman et al. | |
| 8,672,920 | B2 | 3/2014 | Makower et al. | |
| 8,715,314 | B1 | 5/2014 | Janardhan et al. | |
| 8,727,988 | B2 | 5/2014 | Flaherty et al. | |
| 8,740,833 | B2 | 6/2014 | Moskowitz et al. | |
| 8,753,366 | B2 | 6/2014 | Makower et al. | |
| 8,795,317 | B2 | 8/2014 | Grandfield et al. | |
| 8,852,205 | B2 | 10/2014 | Brady et al. | |
| 8,876,792 | B2 | 11/2014 | Holmin et al. | |
| 8,926,680 | B2 | 1/2015 | Ferrera et al. | |
| 8,974,513 | B2 | 3/2015 | Ford et al. | |
| 8,992,456 | B1 | 3/2015 | Powell | |
| 9,039,749 | B2 | 5/2015 | Shrivastava et al. | |
| 9,113,936 | B2 | 8/2015 | Palmer et al. | |
| 9,119,656 | B2 | 9/2015 | Bose et al. | |
| 9,204,893 | B2 | 12/2015 | Rizk et al. | |
| 9,387,311 | B1 | 7/2016 | Heilman et al. | |
| 9,387,331 | B2 | 7/2016 | Zhao et al. | |
| 9,402,982 | B2 | 8/2016 | Baert et al. | |
| 9,433,429 | B2 | 9/2016 | Vale et al. | |
| 9,545,505 | B2 | 1/2017 | Heilman et al. | |
| 9,669,195 | B2 | 6/2017 | Heilman et al. | |
| 9,682,216 | B2 | 6/2017 | Teitelbaum | |
| 9,724,501 | B2 | 8/2017 | Heilman et al. | |
| 10,004,621 | B2 | 6/2018 | Kelly | |
| 10,022,251 | B2 | 7/2018 | Teitelbaum | |
| 10,058,686 | B2 * | 8/2018 | Heilman ............ | A61B 17/3401 |
| 10,272,230 | B2 | 4/2019 | Malek et al. | |
| 10,279,154 | B2 | 5/2019 | Heilman et al. | |
| 10,307,576 | B2 * | 6/2019 | Heilman ............ | A61B 17/3401 |
| 10,307,577 | B2 | 6/2019 | Malek et al. | |
| 10,625,061 | B2 | 4/2020 | Borgesen | |
| 10,758,718 | B2 | 9/2020 | Malek | |
| 10,765,846 | B2 * | 9/2020 | Heilman ............ | A61B 17/3401 |
| 12,011,557 | B2 * | 6/2024 | Heilman ............ | A61B 17/3401 |
| 12,458,782 | B2 * | 11/2025 | Gobin ................ | A61M 27/006 |
| 2001/0041899 | A1 | 11/2001 | Foster | |
| 2002/0183786 | A1 | 12/2002 | Girton | |
| 2002/0188308 | A1 | 12/2002 | Tu et al. | |
| 2003/0040754 | A1 | 2/2003 | Mitchell | |
| 2003/0135147 | A1 | 7/2003 | Rosenberg et al. | |
| 2003/0181938 | A1 | 9/2003 | Roth et al. | |
| 2003/0187495 | A1 | 10/2003 | Cully et al. | |
| 2003/0191520 | A1 | 10/2003 | Pelton | |
| 2003/0220604 | A1 | 11/2003 | Al-Anazi | |
| 2003/0225395 | A1 | 12/2003 | Griffis et al. | |
| 2003/0229366 | A1 | 12/2003 | Reggie et al. | |
| 2004/0059280 | A1 | 3/2004 | Makower et al. | |
| 2004/0073242 | A1 | 4/2004 | Chanduszko | |
| 2004/0087887 | A1 | 5/2004 | Nilsson | |
| 2004/0147871 | A1 | 7/2004 | Burnett | |
| 2004/0153110 | A1 | 8/2004 | Kurz et al. | |
| 2004/0176743 | A1 | 9/2004 | Morris et al. | |
| 2004/0186368 | A1 | 9/2004 | Ramzipoor et al. | |
| 2004/0236309 | A1 | 11/2004 | Yang | |
| 2004/0236409 | A1 | 11/2004 | Pelton et al. | |
| 2004/0254517 | A1 | 12/2004 | Quiroz-Mercado et al. | |
| 2004/0260249 | A1 | 12/2004 | Kulessa | |
| 2004/0260384 | A1 | 12/2004 | Allen | |
| 2005/0033334 | A1 | 2/2005 | Santra et al. | |
| 2005/0119602 | A1 | 6/2005 | Murphy et al. | |
| 2005/0119668 | A1 | 6/2005 | Teague | |
| 2005/0137646 | A1 | 6/2005 | Wallace et al. | |
| 2005/0234509 | A1 | 10/2005 | Widomski et al. | |
| 2005/0245906 | A1 | 11/2005 | Makower et al. | |
| 2005/0251151 | A1 | 11/2005 | Teague | |
| 2005/0256510 | A1 | 11/2005 | Moskowitz et al. | |
| 2006/0015089 | A1 | 1/2006 | Meglin et al. | |
| 2006/0015152 | A1 | 1/2006 | Wallace | |
| 2006/0079915 | A1 | 4/2006 | Chin et al. | |
| 2006/0089704 | A1 | 4/2006 | Douglas | |
| 2006/0173440 | A1 | 8/2006 | Lamson et al. | |
| 2006/0217755 | A1 | 9/2006 | Eversull et al. | |
| 2006/0224101 | A1 | 10/2006 | Glenn | |
| 2006/0224102 | A1 | 10/2006 | Glenn | |
| 2006/0241687 | A1 | 10/2006 | Glaser et al. | |
| 2006/0259063 | A1 | 11/2006 | Bates et al. | |
| 2007/0005125 | A1 | 1/2007 | Berenstein et al. | |
| 2007/0073337 | A1 | 3/2007 | Abbott et al. | |
| 2007/0112291 | A1 | 5/2007 | Borgesen | |
| 2007/0129746 | A1 | 6/2007 | Mische | |
| 2007/0156230 | A1 | 7/2007 | Dugan et al. | |
| 2007/0179426 | A1 | 8/2007 | Selden | |
| 2007/0179428 | A1 | 8/2007 | Kralick, D.O. et al. | |
| 2007/0208376 | A1 | 9/2007 | Meng | |
| 2007/0225794 | A1 | 9/2007 | Thramann et al. | |
| 2007/0276316 | A1 | 11/2007 | Haffner et al. | |
| 2008/0045863 | A1 | 2/2008 | Bakos | |
| 2008/0057106 | A1 | 3/2008 | Erickson et al. | |
| 2008/0058759 | A1 | 3/2008 | Makower et al. | |
| 2008/0082036 | A1 | 4/2008 | Trescony et al. | |
| 2008/0097398 | A1 | 4/2008 | Mitelberg et al. | |
| 2008/0125805 | A1 | 5/2008 | Mische | |
| 2008/0249458 | A1 | 10/2008 | Yamasaki | |
| 2009/0005645 | A1 | 1/2009 | Frassica et al. | |
| 2009/0017098 | A1 | 1/2009 | Bartolomeo | |
| 2009/0069828 | A1 | 3/2009 | Martin et al. | |
| 2009/0076357 | A1 | 3/2009 | Purdy | |
| 2009/0125093 | A1 | 5/2009 | Hansen | |
| 2009/0171293 | A1 | 7/2009 | Yang et al. | |
| 2009/0287291 | A1 | 11/2009 | Becking et al. | |
| 2010/0010476 | A1 | 1/2010 | Galdonik et al. | |
| 2010/0016887 | A1 | 1/2010 | Inderbitzi | |
| 2010/0063531 | A1 | 3/2010 | Rudakov et al. | |
| 2010/0076366 | A1 | 3/2010 | Henderson, Sr. et al. | |
| 2010/0076404 | A1 | 3/2010 | Ring | |
| 2010/0121357 | A1 | 5/2010 | Flaherty et al. | |
| 2010/0191168 | A1 * | 7/2010 | Heilman ............ | A61M 27/006 604/9 |
| 2010/0222732 | A1 * | 9/2010 | Sevrain .............. | A61M 27/006 604/8 |
| 2011/0082385 | A1 | 4/2011 | Diaz et al. | |
| 2011/0319917 | A1 | 12/2011 | Ferrera et al. | |
| 2012/0130467 | A1 | 5/2012 | Selden et al. | |
| 2012/0130468 | A1 | 5/2012 | Khosravi et al. | |
| 2012/0172844 | A1 | 7/2012 | Mullen | |
| 2013/0035628 | A1 | 2/2013 | Garrison et al. | |
| 2013/0144328 | A1 | 6/2013 | Weber et al. | |
| 2013/0178828 | A1 | 7/2013 | Takagi et al. | |
| 2014/0005586 | A1 | 1/2014 | Feinstein | |
| 2014/0052047 | A1 | 2/2014 | Wilson | |
| 2014/0052160 | A1 | 2/2014 | Singh et al. | |
| 2014/0128905 | A1 | 5/2014 | Molaei | |
| 2014/0180098 | A1 | 6/2014 | Flaherty et al. | |
| 2014/0180222 | A1 | 6/2014 | Flaherty et al. | |
| 2014/0236207 | A1 | 8/2014 | Makower et al. | |
| 2014/0276342 | A1 | 9/2014 | Stone et al. | |
| 2014/0277079 | A1 | 9/2014 | Vale et al. | |
| 2014/0288414 | A1 | 9/2014 | Makower et al. | |
| 2014/0336559 | A1 | 11/2014 | Heilman et al. | |

(56) References Cited

U.S. PATENT DOCUMENTS

| | | | |
|---|---|---|---|
| 2015/0196741 A1 | 7/2015 | Heilman et al. |
| 2015/0201303 A1 | 7/2015 | Ji et al. |
| 2015/0209058 A1 | 7/2015 | Ferrera et al. |
| 2015/0223908 A1 | 8/2015 | Westerfeld et al. |
| 2015/0258260 A1 | 9/2015 | Tuseth |
| 2015/0305756 A1 | 10/2015 | Rosenbluth et al. |
| 2016/0136398 A1 | 5/2016 | Heilman et al. |
| 2016/0143756 A1 | 5/2016 | Rezac et al. |
| 2016/0287276 A1 | 10/2016 | Cox et al. |
| 2017/0050000 A1 | 2/2017 | Randall |
| 2018/0015267 A1 | 1/2018 | Heilman et al. |
| 2018/0126132 A1 | 5/2018 | Heilman et al. |
| 2018/0296810 A1 | 10/2018 | Chen et al. |
| 2019/0021750 A1 | 1/2019 | Heilman et al. |
| 2020/0376239 A1 | 12/2020 | Heilman |
| 2021/0220135 A1 | 7/2021 | Kovalsky et al. |

FOREIGN PATENT DOCUMENTS

| | | |
|---|---|---|
| EP | 0964636 | 12/1999 |
| EP | 1047341 | 11/2000 |
| EP | 1067869 | 1/2001 |
| EP | 1067874 | 1/2001 |
| EP | 1082070 | 3/2001 |
| EP | 1171183 | 1/2002 |
| EP | 1253859 | 11/2002 |
| EP | 1359967 | 11/2003 |
| EP | 1377335 | 1/2004 |
| EP | 1496956 | 1/2005 |
| EP | 1839602 B1 | 7/2009 |
| EP | 1854499 | 12/2009 |
| EP | 2589344 | 5/2013 |
| EP | 1981413 | 11/2014 |
| GB | 2089215 | 6/1982 |
| JP | 2006-289086 | 8/2011 |
| WO | WO1998016161 | 4/1998 |
| WO | WO2002/022028 | 3/2002 |
| WO | WO2006/080113 | 8/2006 |
| WO | WO2007115314 | 10/2007 |
| WO | WO2009014723 | 1/2009 |
| WO | WO2009036039 | 3/2009 |
| WO | WO2009/088783 | 7/2009 |
| WO | WO2009126935 | 10/2009 |
| WO | WO2011011787 | 1/2011 |
| WO | WO2012009518 | 1/2012 |
| WO | WO2012158152 | 11/2012 |
| WO | WO2013034602 | 3/2013 |
| WO | WO2014165754 | 10/2014 |
| WO | WO2015108917 | 7/2015 |
| WO | WO2016070147 | 5/2016 |
| WO | WO201707554 | 5/2017 |
| WO | WO2017117427 | 7/2017 |
| WO | WO2018005621 | 1/2018 |
| WO | WO2018071600 | 4/2018 |
| WO | WO2018160966 | 9/2018 |

OTHER PUBLICATIONS

Supplemental Amendment for U.S. Appl. No. 15/862,120 dated May 7, 2018.
PCT Invitation to Pay Additional Fees for International Appln. No. PCT/US2018/020667, dated May 29, 2018 (17 pages).
International Search Report and Written Opinion for International Appln. No. PCT/US2018/020667, dated Aug. 1, 2018 (21 pages)].
Examination Report mailed Jan. 25, 2019 for EP Appln. No. 15791220.5.
Non-Final Office Action mailed Nov. 6, 2018 for U.S. Appl. No. 15/668,657.
Response to Non Final Office Action filed Nov. 14, 2018 for U.S. Appl. No. 15/668,657.
Notice of Allowance mailed Dec. 14, 2018 for U.S. Appl. No. 15/668,657.
Notice of Allowance mailed Dec. 14, 2018 for U.S. Appl. No. 15/745,961.
Non-final office action mailed Mar. 21, 2019 for U.S. Appl. No. 16/212,511.
Amendment Response to Office Action for U.S. Appl. No. 16/212,547 dated Mar. 4, 2019.
Notice of Allowance mailed Apr. 17, 2019 for U.S. Appl. No. 16/212,511.
Notice of Rejection for JP International Patent Appln. No. 2017-542811 dated Nov. 13, 2018.
Office Action dated Mar. 5, 2019 for Japanese Patent Appln. No. 2017-542811, with English translation provided by Foreign Associate.
Notice of Allowance mailed Apr. 9, 2019 for U.S. Appl. No. 16/212,547.
PCT Invitation to Pay Additional Fees for International Appln. No. PCT/US2019/021471, dated Jun. 28, 2019 (10 pages).
PCT International Search Report and Written Opinion mailed Aug. 20, 19 for PCT Appln. No. PCT/US2019/021471, 17 pages.
Office action and search report mailed Jul. 29, 2019 for Chinese Application No. 2015800588073, in Chinese with English translation provided by foreign associate.
Response to Examination Report filed Jun. 4, 2019 for EP Appln. No. 15791220.5.
Response to Foreign Office Action filed Jun. 24, 2019 for JP Patent Appln. No. 2017- 542811.
PCT Invitation to Pay Additional Fees mailed Jan. 5, 2018 for PCT/US2017/056227, Applicant Cerevasc, LLC, 17 pages.
Response to Office action filed Oct. 29, 2019 for Chinese Application No. 2015800588073.
EPO communication Rule 71(3) allowance mailed Nov. 7, 2019 for European patent application No. 15791220.5.
PCT International Search Report and Written Opinion for International Application No. PCT/2015/011317, Applicant Tufts Medical Center, Inc., Forms PCT/ISA/210, 220, and 237, dated Mar. 26, 2015 (15 pages).
Non-Final Office Action for U.S. Appl. No. 14/179,622, dated May 13, 2015 (13 pages).
PCT Notification of Transmittal of the International Search Report and Written Opinion, mailed Feb. 17, 2016, for PCT/US2015/058505, Applicant CereVasc, LLC., international filing date Oct. 30, 2015 (16 pages).
Non-Final Office Action for U.S. Appl. No. 14/596,335, dated Jul. 7, 2016 (16 pages).
PCT International Search Report and Written Opinion for International Appln. No. PCTIUS2016/069280, applicant Cerevasc, LLC, dated Mar. 27, 2017 (80 pages).
Non-Final Office Action for U.S. Appl. No. 15/294,000, dated Feb. 16, 2017 (26 pages).
Final Office Action for U.S. Appl. No. 14/596,335, dated Oct. 26, 2016 (19 pages).
Interview Summary for U.S. Appl. No. 14/596,335, dated Oct. 11, 2016 (3 pages).
PCT Notification of Transmittal of the International Search Report and Written Opinion of the I.S.A. for PCT/US2016/0595952, mailed Jan. 20, 2017, 14 pages.
PCT International Search Report and Written Opinion for International Appln. No. PCT/US2017/056227, Applicant Cerevasc, LLC, Forms PCT/ISA/210, 220, and 237, dated Mar. 29, 2018 (24 pages).
Non-Final Office Action for U.S. Appl. No. 15/862,120, dated Apr. 19, 2018.
Extended European Search Report fot EP Patent Appln. No. 20189096.9 dated Sep. 11, 2020.
Foreign Office Action for Japanese Patent Application No. 2019-116178 dated Sep. 28, 2020 (translated).
Non-Final Office Action for the U.S. Appl. No. 16/976,057 dated Nov. 16, 2020.
Foreign OA for JP Patent Appln. No. 2019-116178 dated Jun. 30, 2021 (with attached machine translation).
Final Office Action for U.S. Appl. No. 16/337,346 dated Oct. 3, 2022.
Extended European Search Report for EP Patent Appln. No. 23197404.9 dated Jan. 16, 2024.

(56) References Cited

OTHER PUBLICATIONS

Non-Final Office Action for U.S. Appl. No. 18/759,779 dated Sep. 25, 2025.
Extended European Search Report for EP Patent Appln. No. 26161684.1 dated Jun. 11, 2026.

* cited by examiner

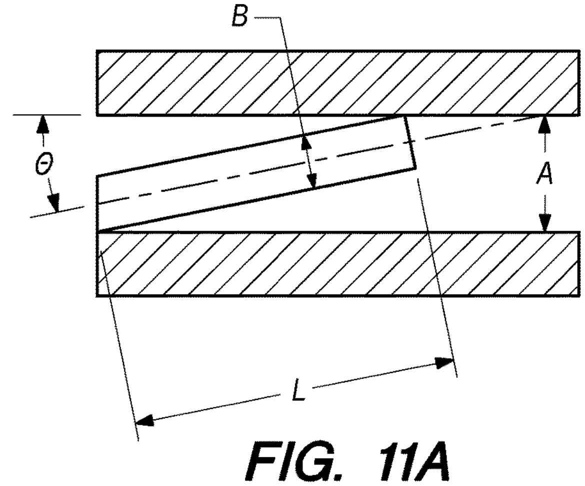
FIG. 11A
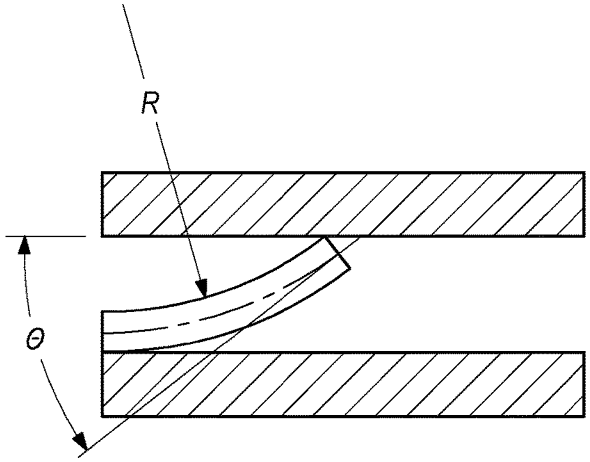
FIG. 11B
Variable Limits
| | Min | Max |
|---|---|---|
| A | 2 | 4mm |
| B | 0.93 | 1.8mm |
| L | 7 | 15mm |
| R | 3 | 20mm |
Largest Straight-Stick Angle
| | |
|---|---|
| A | 4mm |
| B | 0.93mm |
| L | 7mm |
| Θ | 26.5 deg |
Smallest Straight-Stick Angle
| | |
|---|---|
| A | 2mm |
| B | 1.8mm |
| L | 15mm |
| Θ | 0.5 deg |
Largest Bend Angle
| | |
|---|---|
| A | 4mm |
| B | 0.93mm |
| R | 3mm |
| Θ | 91.33702 deg |
Smallest Bend Angle
| | |
|---|---|
| A | 2mm |
| B | 1.8mm |
| R | 20mm |
| Θ | 8.109614 deg |
FIG. 11C

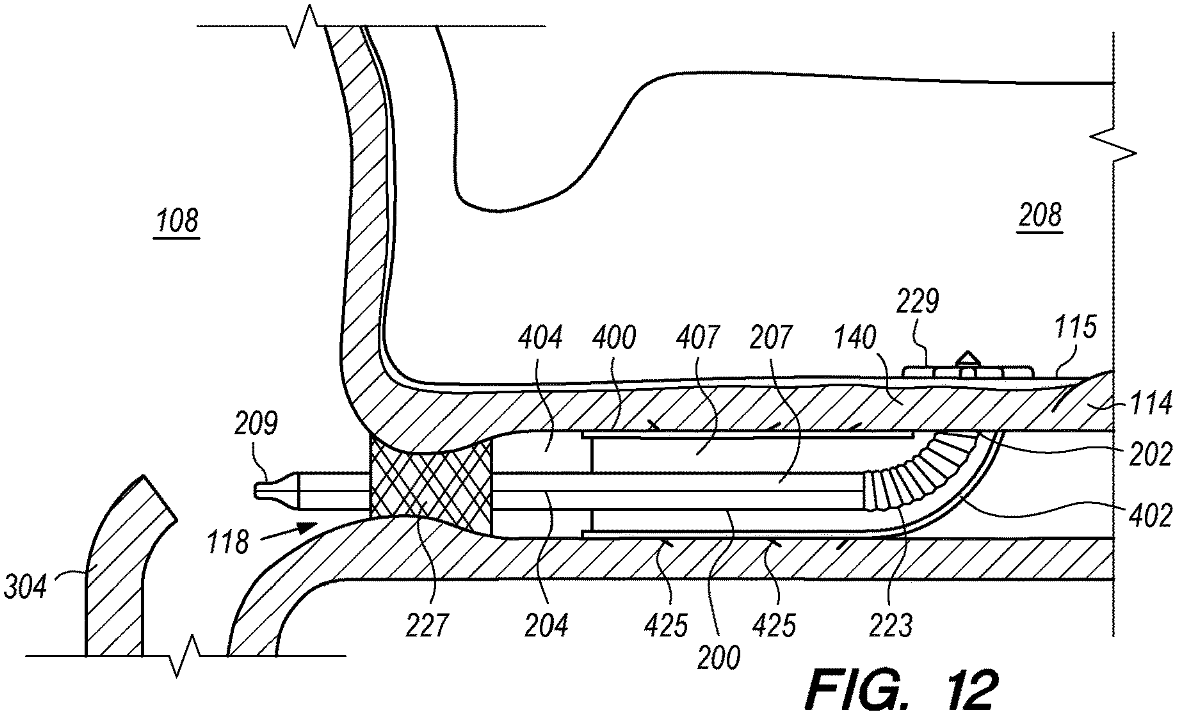
FIG. 12
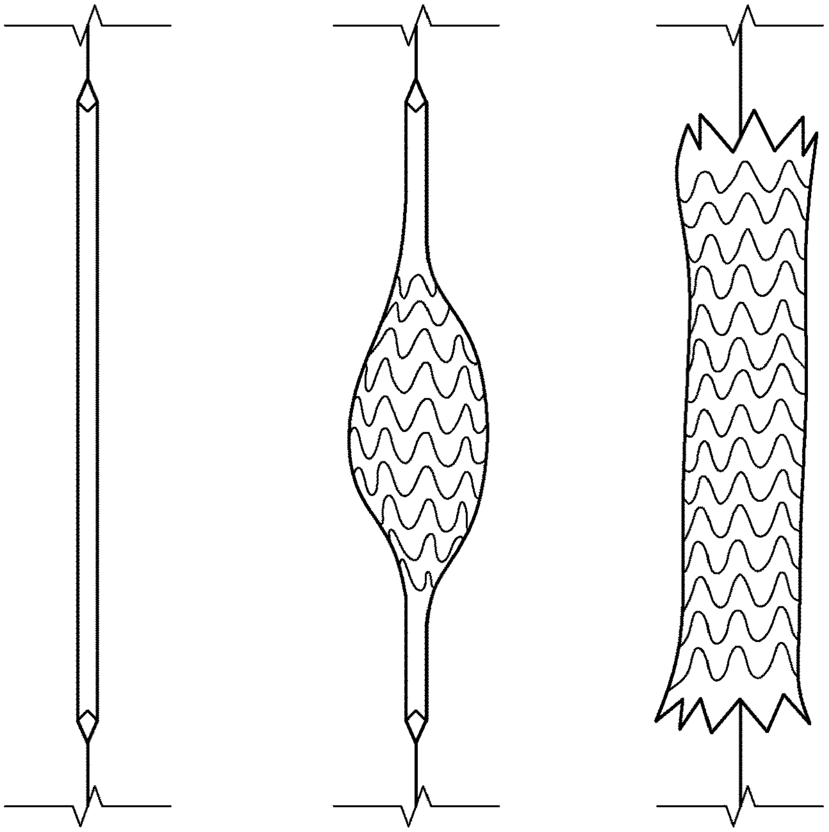
FIG. 13A
(Prior Art)
FIG. 13B
(Prior Art)
FIG. 13C
(Prior Art)

| SHAPE | MATERIAL | ANGLE | SIZE | PEAK PENETRATION FORCE | RETRACTION FORCE |
|---|---|---|---|---|---|
| Blunt | SS | 15°-45° | 27G | 1.8N-6.6N | 0.1N |
| Blunt | NT | 15°-45° | 27G | 1.5N-4.7N | 0.1N |
| Blunt | SS | 15°-45° | 33G | 1.7N-2.6N | 0.1N |
| Blunt | NT | 15°-45° | 33G | 1.2N-2.1N | 0.1N |
| Quincke | SS | 10°-90° | 27G | 0.2N-0.8N | 0.1N-0.5N |
| Quincke | SS | 10°-90° | 33G | 0.2N-1.8N | 0.1N |
| Pencil | SS | 10°-90° | 27G | 0.2N-2.0N | 0.1N-0.5N |
| Pencil | SS | 10°-90° | 26G | 0.7N-1.3N | 0.1N-0.2N |
| Pencil | SS | 10°-90° | 24G | 0.3N | 0.2N |
| Bevel | SS | 10°-45° | 27G | 1.4N-1.7N | 0.1N |
| Bevel | NT | 10°-45° | 27G | 0.5N-3.0N | 0.1N-0.2N |
| Bevel | SS | 10°-45° | 33G | 0.7N-1.4N | 0.1N |
| Bevel | NT | 10°-45° | 33G | 0.8N-1.6N | 0.1N-0.4N |

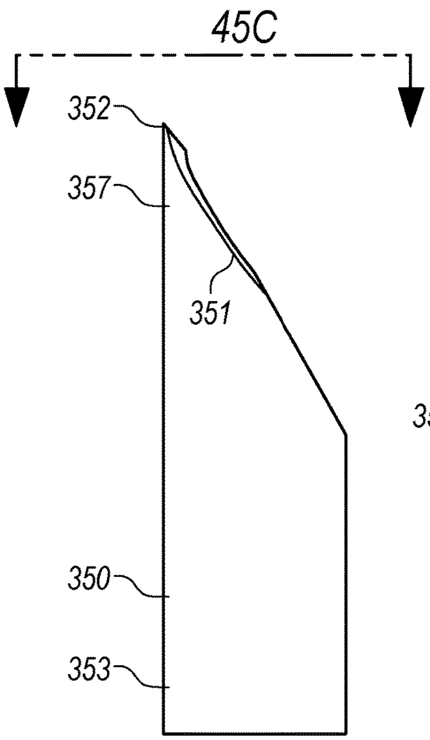
FIG. 45A
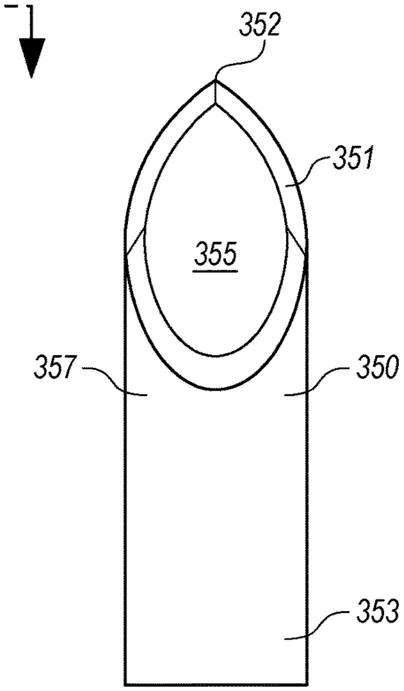
FIG. 45B
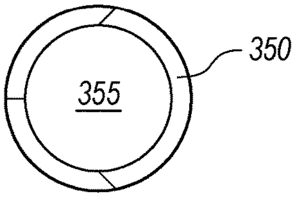
FIG. 45C
| NEEDLE TIP TABULATED DIMENSIONS | | | | |
|---|---|---|---|---|
| DASH NO. | ID | OD | LENGTH | POINT |
| -01 | 0.024 | 0.03 | 0.150±0.005 | BEVEL |
| -02 | 0.024 | 0.03 | MIN | QUINCKE |
| -03 | 0.0235 | 0.028 | 0.150±0.005 | BEVEL |
| -04 | 0.0235 | 0.028 | MIN | QUINCKE |
| -05 | 0.0205 | 0.026 | 0.150±0.005 | BEVEL |
| -06 | 0.0205 | 0.026 | MIN | QUINCKE |
FIG. 45D

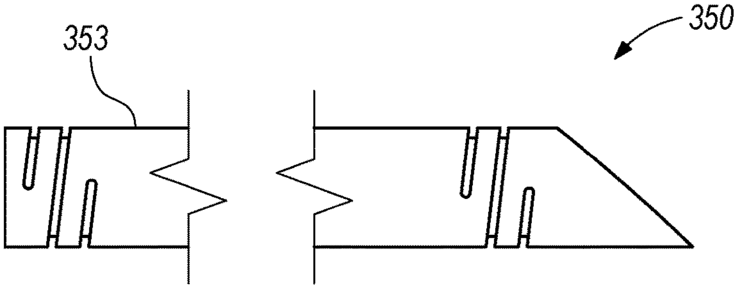
FIG. 46E
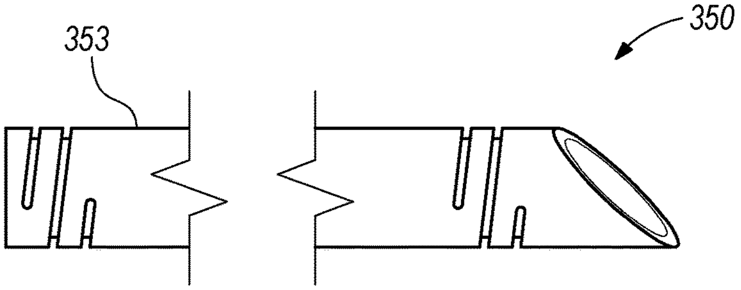
FIG. 46F
| INTEGRATED COIL AND NEEDLE TABULATED DIMENSIONS | | | |
|---|---|---|---|
| DASH NO. | GAUGE | OD | ID |
| -01 | 21.5 | .03 | .024 |
| -02 | 22XX | .028 | .0235 |
| -03 | 22.5 | .026 | .0205 |
FIG. 46G

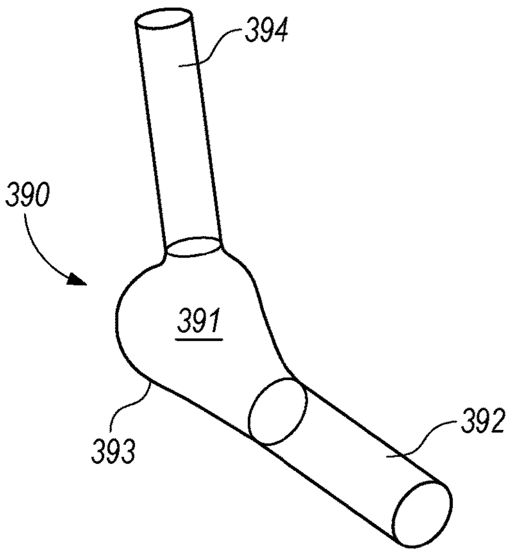
FIG. 47A
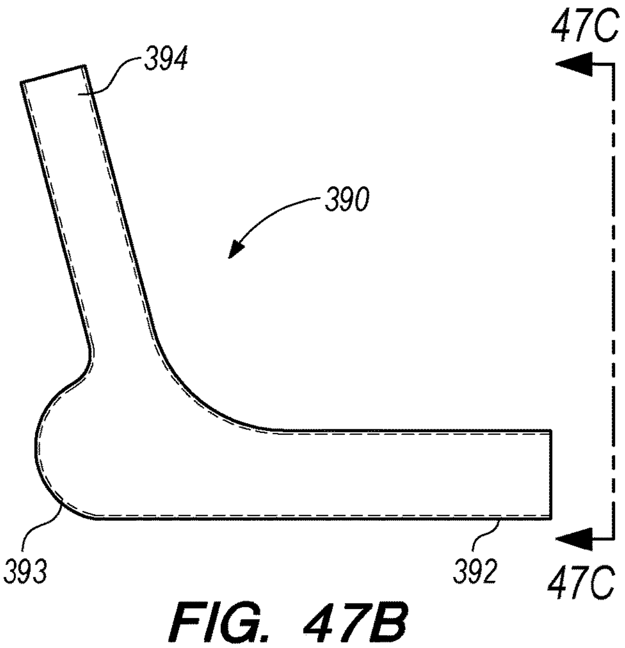
FIG. 47B
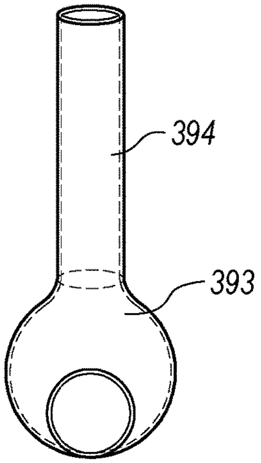
FIG. 47C
| TABULATED PROPERTIES | |
|---|---|
| DASH NO. | MATERIAL |
| -01 | URETHANE - HIGH DUROMETER |
| -02 | URETHANE - MEDIUM DUROMETER |
| -03 | URETHANE - LOW DUROMETER |
FIG. 47D

METHODS AND SYSTEMS FOR DRAINING CEREBROSPINAL FLUID INTO THE VENOUS SYSTEM

RELATED APPLICATION DATA

The present application is a continuation of U.S. patent application Ser. No. 18/926,899, filed Oct. 25, 2024, which is a continuation of U.S. patent application Ser. No. 18/668,055, filed May 17, 2024, which is a continuation of U.S. Pat. No. 12,011,557, filed Aug. 20, 2020, which is a continuation of U.S. Pat. No. 10,765,846, filed May 16, 2018, which is a continuation of U.S. Pat. No. 10,058,686, filed Jan. 4, 2018, which is a continuation of U.S. Pat. No. 10,279,154, filed Aug. 3, 2017, which is a continuation of U.S. Pat. No. 9,724,501, filed Feb. 14, 2017, which is a continuation of U.S. Pat. No. 9,669,195, filed Oct. 10, 2016, which is a continuation of U.S. Pat. No. 9,662,479, filed Jun. 28, 2016, which is a continuation of U.S. Pat. No. 9,387,311, filed Mar. 9, 2016, which is a divisional of U.S. patent application Ser. No. 14/929,066, filed Oct. 30, 2015, now abandoned, which claims the benefit under 35 U.S.C. § 119 to U.S. Provisional Application Ser. No. 62/073,766, filed Oct. 31, 2014, 62/142,895, filed Apr. 3, 2015, and 62/156,152, filed May 1, 2015. The foregoing applications are hereby incorporated by reference into the present application in their entirety.

FIELD OF THE INVENTION

The present disclosure pertains generally to systems and methods for accessing cerebral cisterns and draining cerebrospinal fluid (CSF), (e.g., to relieve elevated intracranial pressure), using an endovascular approach. More particularly, the present disclosure pertains to systems and methods for treatment of hydrocephalus, pseudotumor cerebri, and/or intracranial hypertension.

BACKGROUND

Hydrocephalus is one of the most common and important neurosurgical conditions affecting both, children and adults. Hydrocephalus, meaning “water on the brain,” refers to the abnormal CSF accumulation in the brain. The excessive intracranial pressure resulting from hydrocephalus can lead to a number of significant symptoms ranging from headache to neurological dysfunction, coma, and death.

Cerebrospinal fluid is a clear, physiologic fluid that bathes the entire nervous system, including the brain and spinal cord. Cells of the choroid plexus present inside the brain ventricles produce CSF. In normal patients, cells within arachnoid granulations reabsorb CSF produced in the choroid plexus. Arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm H2O. This reabsorption pathway has been dubbed the “third circulation,” because of its importance to the homeostasis of the central nervous system.

Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus.

A positive pressure gradient between the intracranial pressure of the subarachnoid space and the blood pressure of the venous system may contribute to the natural absorption of CSF through arachnoid granulations. For example, in non-hydrocephalic individuals ICPs can range from about 6 cm H2O to about 20 cm H2O. ICP greater than 20 cm H2O is considered pathological of hydrocephalus, although ICP in some forms of the disease can be lower than 20 cm H2O. Venous blood pressure in the intracranial sinuses and jugular bulb and vein can range from about 4 cm H2O to about 11 cm H2O in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

Normal pressure hydrocephalus (NPH) is one form of communicating hydrocephalus. NPH patients typically exhibit one or more symptoms of gait disturbance, dementia, and urinary incontinence, which can lead to misdiagnosis of the disease. Unlike other forms of communicating hydrocephalus, NPH patients may exhibit little or no increase in ICP. It is believed that the CSF-filled ventricles in the brain enlarge in NPH patients to accommodate the increased volume of CSF in the subarachnoid space. For example, while non-hydrocephalic patients typically have ICPs ranging from about 6 cm H2O to about 20 cm H2O, ICPs in NPH patients can range from about 6 cm H2O to about 27 cm H2O. It has been suggested that NPH is typically associated with normal intracranial pressures during the day and intermittently increased intracranial pressure at night.

Other conditions characterized by elevated intracranial pressure include pseudotumor cerebri (benign intracranial hypertension). The elevated ICP of pseudotumor cerebri causes symptoms similar to, but that are not, a brain tumor. Such symptoms can include headache, tinnitus, dizziness, blurred vision or vision loss, and nausea. While most common in obese women 20 to 40 years old, pseudotumor cerebri can affect patients in all age groups.

Prior art techniques for treating communicating hydrocephalus (and in some cases, pseudotumor cerebri) rely on ventriculoperitoneal shunts (“VPS” or “VP shunt” placement), a medical device design introduced more than 60 years ago. VPS placement involves an invasive surgical procedure performed under general anesthesia, typically resulting in hospitalization ranging from two to four days. The surgical procedure typically involves placement of a silicone catheter in the frontal horn of the lateral ventricle of the brain through a burr hole in the skull. The distal portion of the catheter leading from the lateral ventricle is then connected to a pressure or flow-regulated valve, which is placed under the scalp. A separate incision is then made through the abdomen, into the peritoneal cavity, into which the distal portion of a tubing catheter is placed. The catheter/valve assembly is then connected to the tubing catheter, which is tunneled subcutaneously from the neck to the abdomen.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage. Among these complications, infection is one of the most serious, since infection rates in adults are reported between 1.6% and 16.7%. These VPS failures require "shunt revision" surgeries to repair/replace a portion or the entirety of the VP shunt system, with each of these revision surgeries carrying the same risk of general anesthesia, post-operative infection, and associated cost of hospitalization as the initial VPS placement; provided, however, that shunt infections often cost significantly more, e.g., about three to five times more, than the cost of the initial VP shunt placement. Often these infections require additional hospital stays where the proximal portion of the VPS is externalized and long-term antibiotic therapy is instituted. The rate of failure is a constant consideration by clinicians as they assess patients who may be candidates for VPS placement. Age, existing co-morbidities and other patient-specific factors are weighed against the likelihood of VP shunt failure that is virtually assured during the first 4-5 years following initial VP shunt placement.

Despite significant advances in biomedical technology, instrumentation, and medical devices, there has been little change in the design of basic VPS hardware since its introduction in 1952.

SUMMARY

Embodiments of the disclosed inventions include a method for treating hydrocephalus using a shunt, the shunt having one or more cerebrospinal fluid (CSF) intake openings in a distal portion of the shunt, a valve disposed in a proximal portion of the shunt, and a lumen extending between the one or more CSF intake openings and the valve. The method comprises deploying the shunt in a body of a patient so that the distal portion of the shunt is at least partially disposed within a cerebellopontine (CP) angle cistern of the patient, a body of the shunt is at least partially disposed within an inferior petrosal sinus (IPS) of the patient, and the proximal portion of the shunt is at least partially disposed within or proximate to a jugular vein (JV) of the patient, wherein, after deployment of the shunt, CSF flows from the CP angle cistern to the JV via the shunt lumen at a flow rate in a range of 5 ml per hour to 15 ml per hour.

In various embodiments of the method, deployment of the shunt comprises: introducing the shunt percutaneously through a venous access location in the patient, delivering of the shunt so that the proximal portion of the deployed shunt is disposed adjacent to a jugular bulb, advancing the distal portion of the shunt from the IPS into the CP angle cistern using a tissue penetrating member, and/or imaging the shunt while deploying the shunt in the patient.

In other embodiments, the method includes that the distal portion of the shunt is expanded or self-expands from a collapsed delivery configuration to an expanded deployed configuration as, or after, it is advanced into the CP angle cistern. The tissue penetrating member is coupled to a distal end of the shunt, and advancing the distal portion of the shunt from the IPS into the CP angle cistern comprises advancing the tissue penetrating member and distal portion of the shunt through a dura mater tissue wall of the IPS, and through an arachnoid tissue layer, respectively, into the CP angle cistern. Further, during advancement of the distal portion of the shunt in this method, the distal portion of the shunt is at least partially disposed in a delivery lumen of a delivery catheter, the tissue penetrating member comprises a tissue penetrating tip of the delivery catheter, and advancing the distal portion of the shunt from the IPS into the CP angle cistern comprises advancing the delivery catheter so that the tissue penetrating tip penetrates through a dura mater tissue wall of the IPS, and through an arachnoid tissue layer, respectively, into the CP angle cistern.

In some embodiments of the method, the delivery catheter includes a distal portion that assumes a curved configuration that guides the tissue penetrating tip into contact with the dura mater tissue at an angle in a range of 30 degrees to 90 degrees thereto. The distal portion of the delivery catheter comprises an expandable element or wall portion that is expanded to cause the distal portion of the delivery catheter to assume the curved configuration. The expandable element or wall portion comprises a balloon that is inflated to cause expansion thereof. The balloon is inflated to a first expanded state causing the tissue penetrating tip to engage the dura, and thereafter inflated to a second expanded state causing the tissue penetrating tip to penetrate through the dura and arachnoid tissue layers, respectively, into the CP angle cistern. The delivery catheter comprises one or more radiopaque markers located and dimensioned to indicate a position and orientation of the distal portion of the delivery catheter when in the curved configuration. In deploying the shunt, the method further comprises withdrawing the distal portion of the delivery catheter from the CP angle cistern, while maintaining the distal portion of the shunt at least partially disposed in the CP angle cistern.

In some embodiments, where the method of deployment of the shunt includes advancing the distal portion of the shunt from the IPS into the CP angle cistern using a tissue penetrating member, the tissue penetrating member comprising an elongate pusher member having a tissue penetrating distal tip, the elongate pusher member extends though the valve, lumen, and distal opening of the shunt, respectively, wherein the elongate pusher member is moveable relative to the shunt so that the tissue penetrating distal tip may be advanced out of, and withdrawn into, a distal opening of the shunt in communication with the lumen. Further, the method of advancing the distal portion of the shunt from the IPS into the CP angle cistern may include advancing the elongate pusher member so that the tissue penetrating distal tip penetrates through a dura mater tissue wall of the IPS, and through an arachnoid tissue layer, respectively, into the CP angle cistern, with the distal portion of the shunt being carried on the tissue penetrating member. In these embodiments, deploying the shunt further comprises, after advancing the distal portion of the shunt into the CP angle cistern, withdrawing the tissue penetrating member through the distal opening, lumen and valve of the shunt, respectively, wherein CSF flows through the respective distal opening, lumen and valve of the shunt after withdrawal of the tissue penetrating member.

In various embodiments of the method, the shunt comprises a first engaging member protruding and/or extending radially inward from an inner wall of the shunt, the elongate pusher member comprises a second engaging member protruding and/or extending radially outward towards the inner shunt wall, where the second engaging member engages the first engaging member to thereby advance the distal portion of the shunt from the IPS into the CP angle cistern on the tissue penetrating member. In these embodiments, prior to advancing the tissue penetrating member into the CP angle cistern, the method of deployment of the shunt further includes adjusting a rotational orientation of the delivery catheter about an axis of the delivery catheter so that the tissue penetrating distal tip of the tissue penetrating member is thereafter advanced out of the distal opening of the delivery catheter into contact with the dura mater tissue at an angle in a range of 30 degrees to 90 degrees thereto.

In some embodiments of the method, deployment of the shunt further includes advancing a delivery catheter into the IPS with the shunt and tissue penetrating member at least partially disposed in a delivery lumen of the delivery catheter, the delivery catheter having a distal opening in communication with the delivery lumen through which the respective tissue penetrating member and shunt may be advanced into the CP angle cistern.

In various embodiments of the method, deployment of the shunt includes: introducing the shunt into the patient's body while the shunt is at least partially disposed in a delivery catheter, and where the delivery catheter is advanced over a guidewire extending through a lumen of the delivery catheter, which may be a same or different lumen in which the shunt is at least partially disposed, until a distal portion of the delivery catheter is positioned in the IPS. The proximal portion of the deployed shunt is at least partially disposed within, or proximate to, an intersection of a superior vena cava and right atrium of the patient.

In other embodiments of the method, the distal portion of the deployed shunt comprises a distal anchoring mechanism that positions the distal portion of the shunt so as to maintain the one or more CSF intake openings separated, apart and/or directed away from an arachnoid layer of the CP angle cistern; and/or the proximal portion of the deployed shunt comprises a proximal anchoring mechanism that positions the proximal portion of the shunt to thereby maintain a CSF outflow port and/or valve opening disposed in the proximal portion of the shunt separated, apart and/or directed away from a wall of the JV.

Embodiments of the disclosed inventions include a method for relieving a patient's elevated intracranial pressure by implanting a shunt in the patient, the shunt comprising one or more cerebrospinal fluid (CSF) intake openings in a distal portion of the shunt, a valve disposed in a proximal portion of the shunt, and a lumen extending between the one or more CSF intake openings and the valve. The method comprises: introducing a deployment system including a tissue penetrating element and the shunt from a venous access location in the patient; navigating the deployment system, including the penetrating element and shunt, from the venous access location to a target penetration site within an inferior petrosal sinus (IPS) of the patient, via a jugular vein (JV) of the patient; assessing a trajectory of the tissue penetrating element at the target penetration site from the IPS into a cerebellopontine (CP) angle cistern of the patient; advancing the tissue penetrating element through dura and arachnoid tissue layers at the target penetration site, and into the CP angle cistern; advancing the distal portion of the shunt into the CP angle cistern through an opening in the respective dura and arachnoid tissue layers created by the tissue penetrating element; deploying a distal anchoring mechanism of the shunt in the CP angle cistern; withdrawing the delivery system from the target penetration site towards the JV, wherein the shunt is expelled from the delivery system and thereby deployed in the IPS as the delivery system is withdrawn toward the JV; deploying a proximal anchoring mechanism of the shunt about a junction of the JV and IPS, such that the proximal portion of the shunt is oriented away from a medial wall of the JV; and removing the delivery system from the patient, wherein the deployed shunt provides a one-way flow path for CSF to flow from the CP angle cistern to the JV via the shunt lumen in order to maintain a normal differential pressure between the patient's subarachnoid space and venous system.

In various embodiments, the method further comprises: confirming that the tissue penetrating element has accessed the CP angle cistern by withdrawing CSF from the CP angle cistern through the delivery system, prior to withdrawing the delivery system from the patient'; and/or imaging the shunt while deploying the shunt in the patient.

In some embodiments of the method, the proximal portion of the deployed shunt is disposed adjacent to a jugular bulb; and/or the distal portion of the shunt is expanded or self-expands from a collapsed delivery configuration to an expanded deployed configuration as or after it is advanced into the CP angle cistern. In further embodiments of the method, the delivery system comprises a delivery catheter, and the tissue penetrating element comprises a tissue penetrating tip of the delivery catheter, wherein advancing the distal portion of the shunt into the CP angle cistern comprises advancing the delivery catheter into the CP angle cistern with the shunt positioned in a lumen of the delivery catheter.

In various embodiments of the method, the delivery catheter comprises a distal portion that assumes a curved configuration that guides the tissue penetrating tip into contact with the dura mater tissue at an angle in a range of 30 degrees to 90 degrees thereto; the distal portion of the delivery catheter comprises an expandable element or wall portion that is expanded to cause the distal portion of the delivery catheter to assume the curved configuration; the expandable element or wall portion comprises a balloon that is inflated to cause expansion thereof; the balloon is inflated to a first expanded state causing the tissue penetrating tip to engage the dura, and thereafter inflated to a second expanded state causing the tissue penetrating tip to penetrate through the dura and arachnoid tissue layers, respectively, into the CP angle cistern. In the embodiments of the method, the delivery catheter comprises one or more radiopaque markers located and dimensioned to indicate a position and orientation of the distal portion of the delivery catheter when in the curved configuration.

In some embodiments of the method, the tissue penetrating element comprises an elongate pusher member having a tissue penetrating tip, the elongate pusher member extending though the valve, lumen, and distal opening of the shunt, respectively, wherein the elongate pusher member is moveable relative to the shunt so that the tissue penetrating distal tip may be advanced out of, and withdrawn into, a distal opening of the shunt in communication with the shunt lumen, wherein the distal portion of the shunt is advanced into the CP angle cistern on the elongate pusher member. In these embodiments, the delivery system comprises a delivery catheter having a lumen in which the respective shunt and elongate pusher member are at least partially disposed when the tissue penetrating tip of the elongate pusher member is advanced through the respective dura and arachnoid tissue layers, the method further comprising withdrawing the elongate pusher member through the distal opening, lumen and valve of the shunt, respectively, after the distal portion of the shunt is advanced into the CP angle cistern, wherein CSF flows through the respective distal opening, lumen and valve of the shunt after withdrawal of the elongate pusher member.

In some embodiments, the method further comprises adjusting a rotational orientation of the delivery catheter about an axis of the delivery catheter so that the tissue penetrating tip of the elongate pusher member is thereafter advanced out of a distal opening of the delivery catheter into contact with the dura mater tissue at an angle in a range of 30 degrees to 90 degrees thereto, prior to advancing the tissue penetrating tip of the elongate pusher member into the CP angle cistern.

In various embodiments of the method, the proximal portion of the deployed shunt is at least partially disposed within, or proximate to, an intersection of a superior vena cava and right atrium of the patient, and/or the deployed distal anchoring mechanism positions the distal portion of the shunt so as to maintain the one or more CSF intake openings separated, apart and/or directed away from an arachnoid layer of the CP angle cistern.

Embodiments of the disclosed inventions include a method for treating normal pressure hydrocephalus (NPH) using a shunt, the shunt comprising one or more cerebrospinal fluid (CSF) intake openings in a distal portion of the shunt, a valve disposed in a proximal portion of the shunt, and a lumen extending between the one or more CSF intake openings and the valve, the lumen having an inner diameter in a range of 0.008" to 0.014". The method comprises: deploying the shunt in a body of an NPH patient so that the distal portion of the shunt is at least partially disposed within a cerebellopontine (CP) angle cistern of the patient, a body of the shunt is at least partially disposed within an inferior petrosal sinus (IPS) of the patient, and the proximal portion of the shunt is at least partially disposed within, or proximate to, a jugular vein (JV) of the patient, wherein the shunt valve opens at a pressure differential between the CP angle cistern and JV in a range of 3 mm Hg to 5 mm Hg, so that, after deployment of the shunt, CSF flows from the CP angle cistern to the JV via the shunt lumen.

Other and further aspects and features of embodiments will become apparent from the ensuing detailed description in view of the accompanying figures.

BRIEF DESCRIPTION OF THE DRAWINGS

FIGS. 11A-C are cross-sectional views of distal portions of an endovascular and/or catheters, including experimental data, according to embodiments of the disclosed inventions;

FIG. 12 is a cross-sectional view of a deployed endovascular shunt and a conduit according to embodiments of the disclosed inventions;

FIGS. 13A-13C are side views of prior art self-expanding stent-grafts;

FIGS. 45A-D are side and cross-sectional views of a piercing element constructed according to one embodiment of the disclosed inventions;

FIGS. 46A-G are side and cross-sectional views of a piercing element constructed according to another embodiment of the disclosed inventions;

FIGS. 47A-50B are perspective, side and cross-sectional views of an expandable balloon constructed according to various embodiments of the disclosed inventions;

DETAILED DESCRIPTION OF THE ILLUSTRATED EMBODIMENTS

Figure 1:
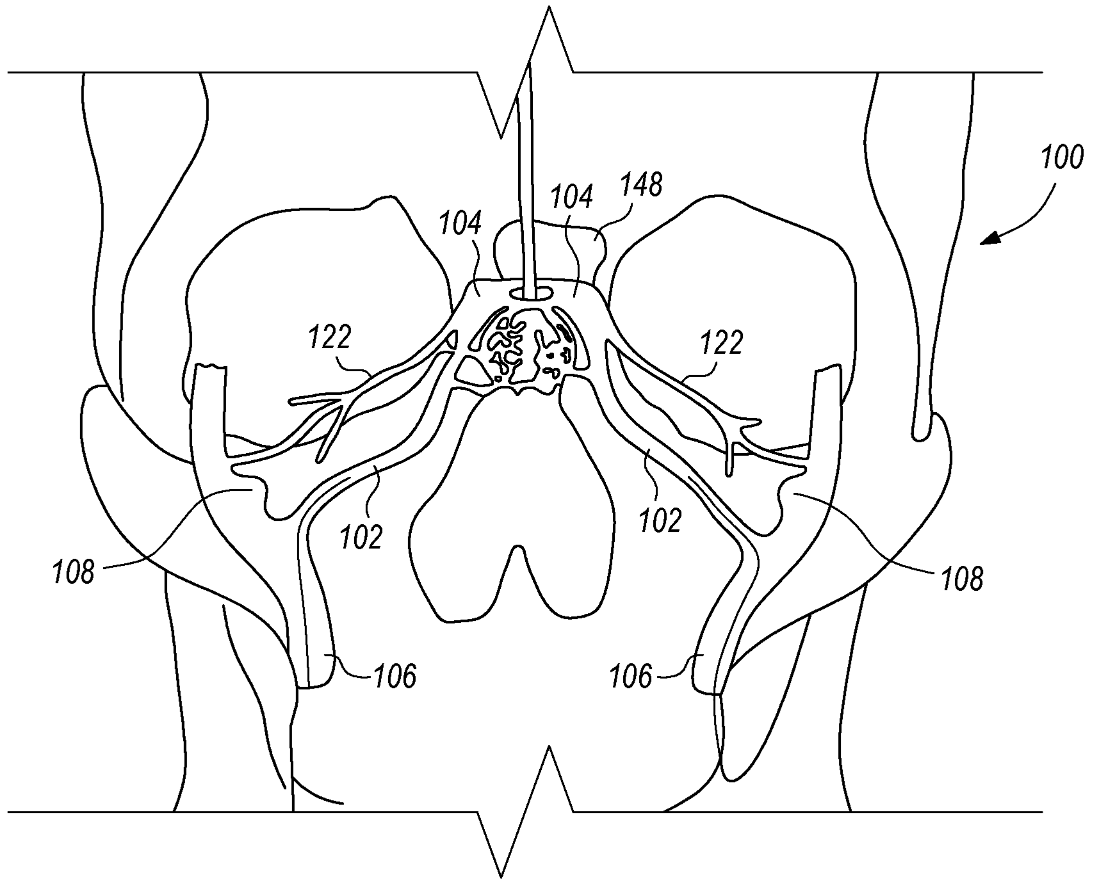
FIG. 1 is a schematic diagram of a head of a human patient.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Reference herein to the term "endovascular," such as endovascular shunt or endovascular approach, generally refer to minimally-invasive devices, systems, and procedures configured for introduction into a patient's vasculature through a small access device (e.g., needle or introducer sheath) without a large incision or open surgical procedure, and using the vasculature to guide various catheters, shunts, and other system elements described herein percutaneously to a target procedural location disposed within or about the patient's vasculature (e.g., intracranial venous sinuses). It should be appreciated that the terms implanting and/or deploying, and the terms implanted and/or deployed, are used interchangeably herein. Additionally, the terms member or element are interchangeably herein.

FIG. 1 is a schematic diagram showing the head 100 of a human patient. Within each side of the patient's head, an inferior petrosal sinus (IPS) 102 connects a cavernous sinus (CS) 104 to a jugular vein 106 and/or a jugular bulb 108. For clarity, the acronym "IPS" is used herein to refer generally to the inferior petrosal sinus and more particularly to the interior space (or lumen) of the inferior petrosal sinus. The IPS 102 facilitates drainage of venous blood into the jugular veins 106. In some patients, the junction of the IPS 102 and the jugular vein 106 occurs within the jugular bulb 108. However, in other patients, this junction can occur at other locations in the jugular vein 106. Moreover, while the IPS 102 in FIG. 1 is a single sinus passageway, in some patients the IPS can be a plexus of separate channels that connect the CS to jugular vein 106 (not shown) and/or jugular bulb 108.

Figure 2:
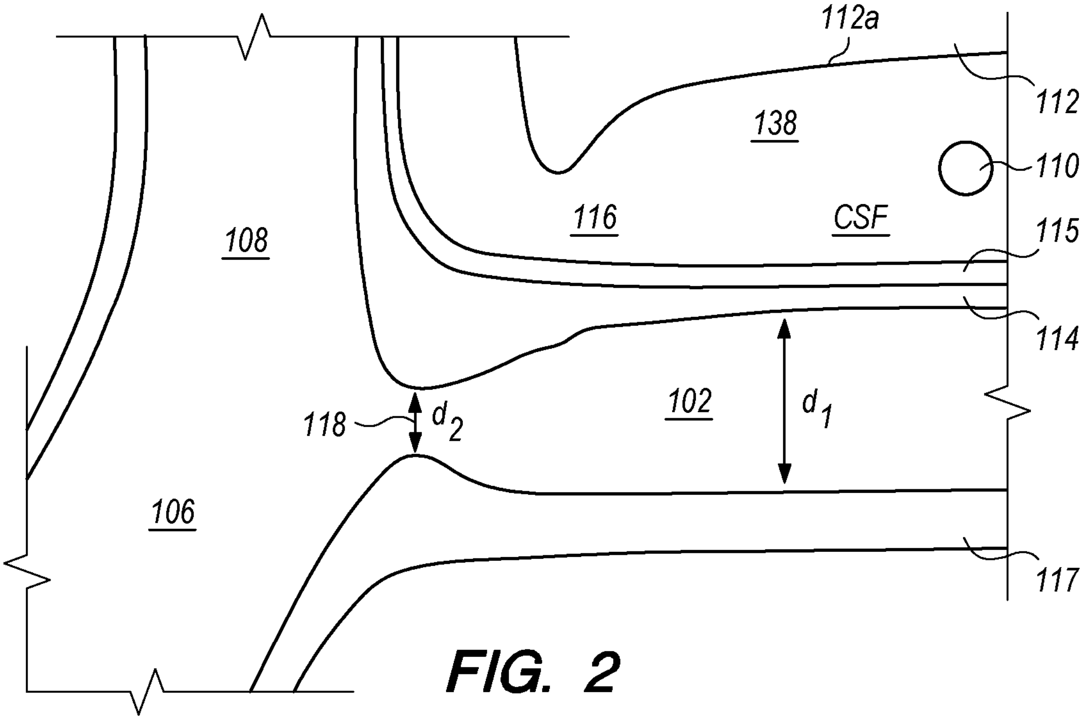
FIG. 2 is a cross-sectional view of a portion of the head of a human patient.
Figure 42A:
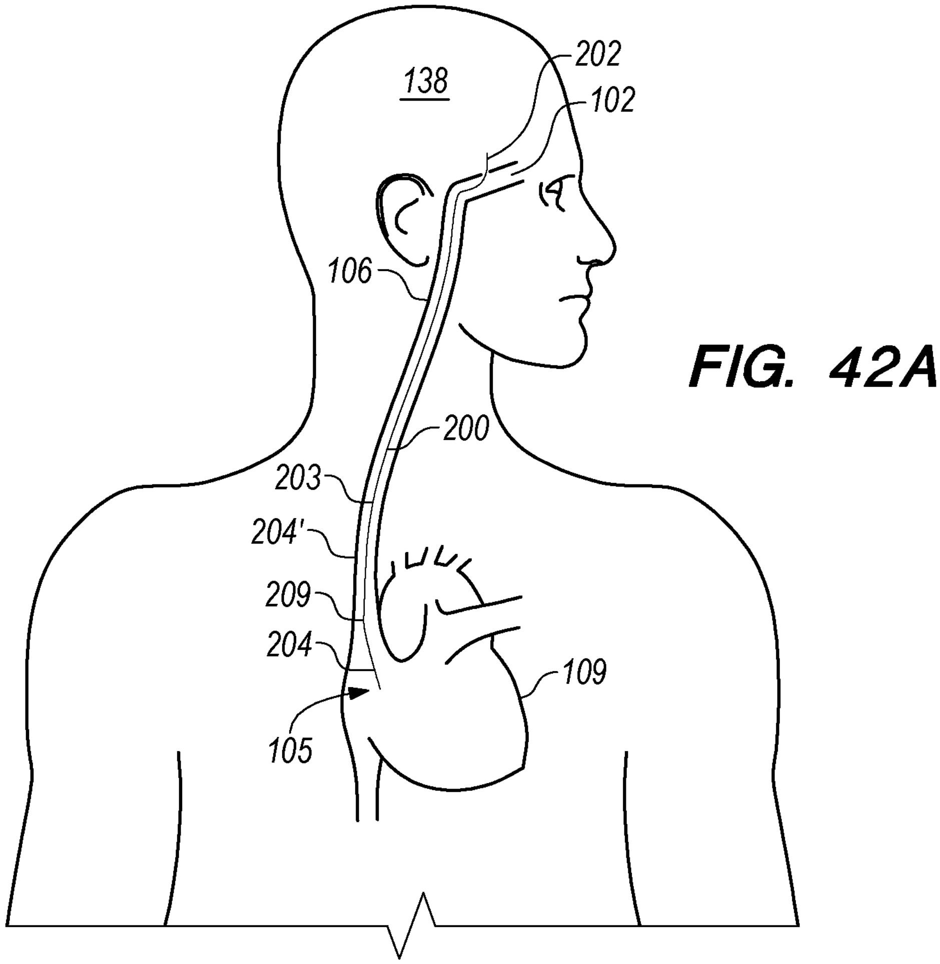
FIGS. 42A-B are cross-sectional views of a deployed endovascular shunt according to embodiments of the disclosed inventions.
Figure 42B:
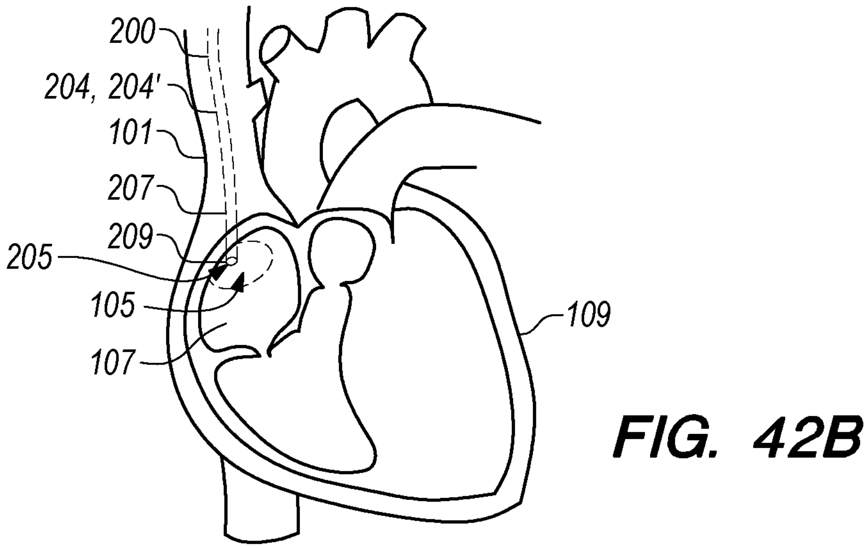
Figure 43A:
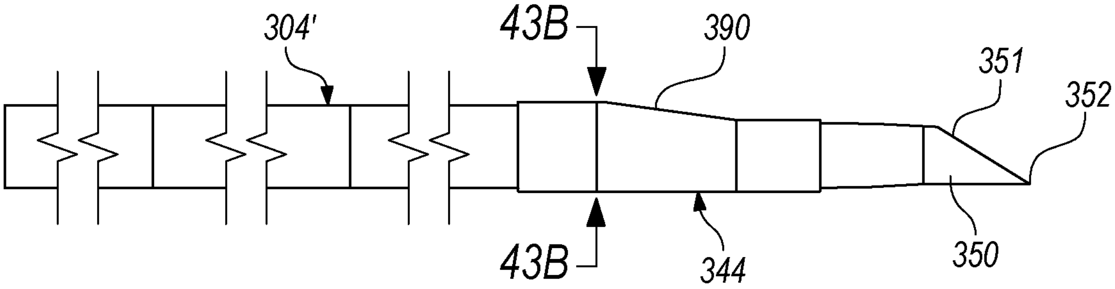
FIGS. 43A-D are perspective, side and cross-sectional views of a delivery catheter, according to one embodiment of the disclosed inventions.
Figure 43B:
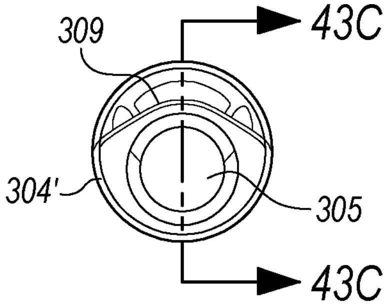
Figure 43C:
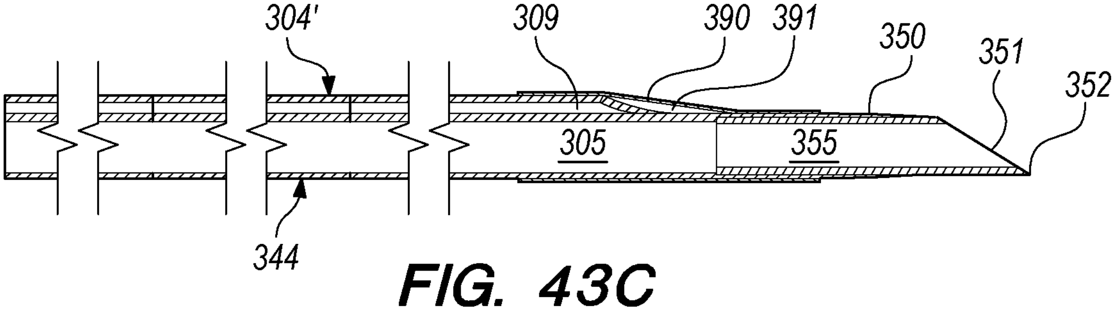
Figure 43D:
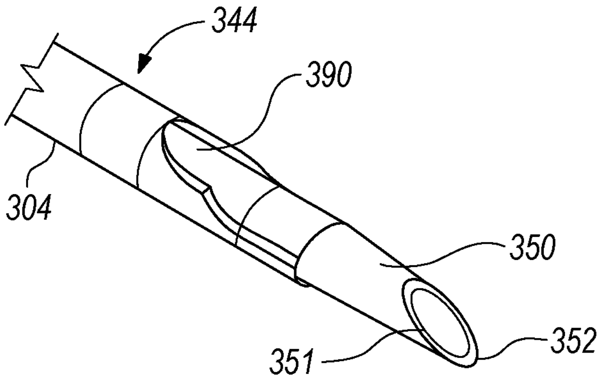

Embodiments of the disclosed inventions are described with respect to a target penetration site in the IPS 102 to access the CSF-filled cerebellopontine (CP) angle cistern 138, which provide a conduit for CSF to flow from the subarachnoid space 116 into the jugular bulb 108, jugular vein 106, and/or the superior vena cava-right atrium junction 105 (FIGS. 1, 2, and 42B). The delivery assemblies and shunts described herein can access the target penetration site in the IPS 102 through a venous access location in the patient. The delivery assemblies and shunts described herein can penetrate the dura mater IPS wall 114 and the arachnoid layer 115 to access the CP angle cistern 138 from within a superior petrosal sinus (SPS) 122 (FIGS. 1 and 2) for delivery and implantation of the shunt at the target site. The dura mater IPS wall 114 is also referred to herein as the dura IPS wall 114, or simply as the IPS wall 114. The SPS is a small diameter venous sinus that connects from the sigmoid sinus (distally located to jugular bulb 108) to the cavernous sinus 104 (FIG. 1). Further, the delivery assemblies and shunts described herein can be advanced through the IPS 102 and into the cavernous sinus 104, so that an anastomosis (not shown) can be created in the upper portion or roof of the cavernous sinus 104 to access the CSF-filled suprasellar cistern 148, shown in FIG. 1, for implantation of the shunt at such target site. Whether penetration to access a target site, deployment and implantation of a shunt occurs from the lumen of the SPS or cavernous sinus to access CSF in the subarachnoid space, the embodiments of the inventions described herein provide a conduit for CSF to flow from the subarachnoid space into the jugular bulb 108, jugular vein 106, and/or the superior vena cava-right atrium junction 105.

FIG. 2 shows a cross-sectional view of a portion of head 100, including IPS 102, jugular vein 106, and jugular bulb 108. In addition, basilar artery 110, brain stem 112, pia 112*a*, and IPS wall 114 are also shown in FIG. 2. The IPS is a relatively small diameter intracranial venous sinus that facilitates drainage of cerebral venous blood into the jugular vein; the IPS is formed by a cylindrical layer of dura mater, typically about 0.9 mm to 1.1 mm thick for the portion of IPS wall 114 shown in FIG. 2, which creates a hollow lumen through which blood flows. In the cross-section view of FIG. 2, the hollow lumen of the IPS resides between upper IPS wall 114 and a lower IPS wall 117, also comprised of dura mater; the IPS itself lies in a bony groove or channel in the clivus bone (not shown) beneath IPS wall 117 in FIG. 2.

A cross-section of the IPS 102 orthogonal to the plane depicted in FIG. 2 would show that the cylindrical layer of dura mater forming IPS 102 is surrounded by bone for about 270 degrees of its circumference with the remaining portion of the IPS circumference (i.e., IPS wall 114 in FIG. 2) covered by arachnoid matter 115 and facing CP angle cistern 138. Arachnoid mater 115 (also referred to herein as the arachnoid tissue layer or the arachnoid layer) is a delicate and avascular layer, typically about 0.05 mm to 0.15 mm thick, that lies in direct contact with the dura mater comprising the exterior of IPS wall 114; arachnoid layer 115 is separated from the pia mater surrounding brain stem 112 by the CSF-filled subarachnoid space 116 (e.g., CP angle cistern 138). The lower portion of the IPS 102, opposite to the IPS wall 114 is the IPS wall 117 formed by dura mater that sits in a channel in the clivus bone (not shown).

It should be appreciated that for the embodiments of the disclosed inventions, the methods and devices are configured to create an anastomosis via an endovascular approach by piercing or penetrating from within the hollow IPS 102 to pass through the dura of IPS wall 114, and continue penetrating through the arachnoid layer 115 until reaching the CSF-filled subarachnoid space 116 (e.g., CP angle cistern 138). For ease of illustration, it should be appreciated that the arachnoid matter 115 covering the IPS wall 114 is present, although, not shown in certain figures.

The diameter $d_1$ of IPS 102 is approximately 3 mm but can range from approximately 1 mm to about 6 mm. As shown in FIG. 2, at the junction 118 between the IPS 102 and the jugular bulb 108 and/or jugular vein 106, the diameter $d_2$ of the IPS 102 can narrow. For example, $d_2$ is approximately 2 mm, but can be as small as about 0.5 mm. The length of the IPS 102 from the junction 118 with the jugular vein 106 to the cavernous sinus 104 (shown in FIG. 1) is approximately in a range between 3.5 cm to 4 cm.

As shown in FIG. 1, most patients have two IPS 102 and two jugular veins 106 (left and right). In a very small percentage of patients (e.g., less than 1%), there is no connection between one IPS and the corresponding jugular vein. It is highly unlikely, however, that any given patient will lack connections to the corresponding jugular veins on both left and right IPS.

Subarachnoid spaces are naturally occurring separations between the pia mater and the arachnoid layer where the CSF pools. Typically, the CSF is passed into a subarachnoid space over the cerebral hemispheres and then into the venous system by arachnoid granulations. The subarachnoid space 116 in FIG. 2 corresponds to a cerebellopontine (CP) angle cistern 138, which acts as a reservoir for CSF. In patients with hydrocephalus, a build-up of CSF within the CP angle cistern 138 (in addition to other cisterns) can occur, for example, if patients lack properly functioning arachnoid granulations. If the excess CSF is not removed, the resulting excess intracranial pressure can lead to symptoms such as headache, neurological dysfunction, coma, and even death.

Figure 3A:
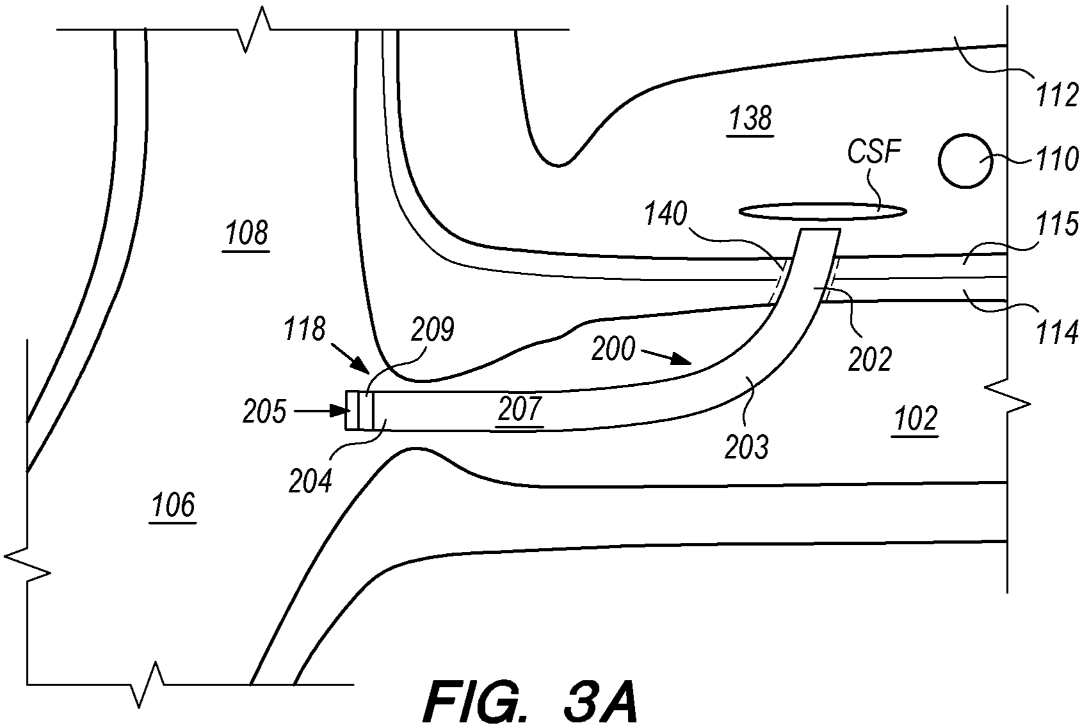
FIG. 3A is a cross-sectional view of a deployed endovascular shunt according to embodiments of the disclosed inventions.

FIG. 3A illustrates an exemplary endovascular shunt 200 implanted in the IPS 102 according to the embodiments of the disclosed inventions. The shunt 200 is delivered and implanted into a patient percutaneously via a catheter inserted into the venous system of the body through a needle hole (e.g., in the femoral or jugular vein), without requiring boring into a patient's skull, general anesthesia, or other open surgical techniques. The shunt 200 includes a tubular configuration having a proximal portion 204, an elongate body 203, a distal portion 202, and an inner lumen 207 extending therebetween. When the shunt 200 is implanted in a target site of the patient (e.g., inferior petrosal sinus), the distal portion 202 of the shunt has accessed and is at least partially disposed in the CSF-filled CP angle cistern 138, so that the body 203 of the shunt 200 is disposed in the IPS 102, and the proximal portion 204 is at least partially disposed in the jugular bulb 108 and/or the jugular vein 106. The implanted shunt 200 provides a fluid communication between the CP angle cistern 138 into the jugular bulb 108 and/or jugular vein 106 so that CSF is drained through the lumen 207 of the shunt 200 from the subarachnoid space 116 to the venous system (e.g., jugular vein 106). When the shunt 200 is deployed at the target site, CSF enters the distal intake opening 251 (FIG. 6), flows through the lumen 207, and exits out the proximal opening 205 (FIG. 6) of the shunt 200.

Shunt 200 capitalizes on a favorable pressure gradient between the subarachnoid space 116 and venous system (e.g., jugular vein 106) to drive CSF through the lumen 207. In patients without hydrocephalus, the normal differential pressure between the intracranial pressure of the subarachnoid space 116 (e.g., CP angle cistern) and blood pressure of the venous system (e.g., IPS or jugular vein) is about 5 to 12 cm H2O; this differential pressure between the subarachnoid space and venous system can be significantly higher in hydrocephalic patients. Once deployed and implanted, the shunt 200 facilitates one-way flow of CSF from the CP angle cistern 138 into the jugular bulb 108 and/or jugular vein 106 where CSF is carried away by venous circulation, similar to the way that normally functioning arachnoid granulations drain CSF into the venous system. Shunt 200 prevents backflow of venous blood through inner lumen 207 into subarachnoid space 116 via one or more one-way valves or other flow regulating mechanisms described herein. The shunt 200 allows for a more physiologic drainage of CSF by directing CSF into the cerebral venous system, a process that occurs naturally in people without hydrocephalus. In this manner, the pressure created by the excess CSF in the subarachnoid space 116 is relieved, and patient symptoms due to hydrocephalus can thereby be ameliorated or even eliminated. The shunt 200 may also include a flow regulating mechanism 209 configured to regulate fluid flow through the shunt lumen 207.

The IPS 102 anatomy supports long-term stability of the shunt 200 relative to other locations potentially suitable for endovascular shunt deployment for treating hydrocephalus. Particularly, the relatively long length and narrow diameter of the IPS 102 (compared to other venous sinuses) provides a natural housing for the shunt 200. The foundation provided by the grooved portion of the clivus bone that surrounds about two-thirds of the IPS circumference further supports long-term stability of the shunt 200, and presents a stable platform that delivery systems disclosed herein can leverage during shunt implant procedures. Proximity to a well-established, CSF-filled cistern such as the CP angle cistern 138 further supports IPS 102 as a preferred implant location compared to other endovascular shunting techniques. Moreover, occlusion of the IPS 102 from shunt 200 placement represents little to no risk for the patient, as the IPS 102 plays a relatively unimportant role in the overall intracranial venous blood circulation scheme unlike larger diameter dural venous sinuses such as the sagittal sinus, sigmoid sinus, straight sinus, and transverse sinus.

The proximal portion 204 of the deployed shunt 200 that extends from the junction 118 into the jugular bulb 108 and/or the jugular vein 106 may be in a range between 1 mm to 5 mm (e.g., 2-3 mm), or any other suitable length configured to extend into the jugular bulb 108 and/or the jugular vein 106 from the junction 118. The proximal portion 204 of the deployed shunt 200 is disposed adjacent to the jugular bulb 108. The circulation of venous blood flow around the proximal portion 204 of the shunt 200, disposed in the jugular bulb 108 and/or the jugular vein 106, constantly and gently agitates the proximal portion 204, minimizing, deterring or avoiding growth of endothelial cells and clogging of the lumen 207 opening 205 at the proximal portion 204 of the shunt 200. Venous blood flow rates in jugular vein 106 can be significantly higher than the blood flow rates in larger diameter dural venous sinuses (i.e., sagittal, sigmoid, straight, transverse), which favor long-term shunt patency of the disclosed embodiments.

Alternatively, the proximal portion 204 of the shunt 200 further extends from the jugular vein 106 and/or jugular bulb 108 into the superior vena cava-right atrium junction 105, in one or more embodiments of the disclosed inventions, as shown in FIGS. 42A-B. In such embodiments, the implanted shunt 200 is configured to extend from the CP angle cistern 138 through IPS 102 and jugular vein 106 into the right atrium 107 of the heart 109 (FIG. 42A); particularly, the proximal portion 204 having the proximal opening 205 in communication with the lumen 207 of the shunt 200, and/or the valve 209, is disposed at the junction 105 between the superior vena cava 101 and the right atrium 107 of the heart 109, preventing or avoiding extending into the right atrium 107 (FIG. 42B). Alternatively or additionally, the shunt 200 can include a tubular extension 204' (e.g., silicone or other biocompatible material catheter or the like) coupled to the proximal portion 204 of the shunt 200 disposed in the jugular vein 106 and/or jugular bulb 108, so that the proximal portion 204 further extends into the superior vena cava-right atrium junction 105. In this embodiment, the proximal portion 204 of the deployed shunt 200 is at least partially disposed within, or proximate to, an intersection of a superior vena cava and right atrium of the patient. In such embodiments, the extended proximal portion 204, 204' of the shunt 200 relies on turbulent blood flow proximate to the superior vena cava-right atrium junction 105 to maintain patency and avoid clogging (e.g., by endothelial cell ingrowth) of the extended proximal portion 204, 204' of the shunt 200. In this embodiment, the valve 209 can be disposed in the extended proximal portion 204, 204' within the superior vena cava-right atrium junction 105.

The implanted shunt 200 may not occlude the IPS 102, for example, when the diameter of the shunt 200 is smaller than the diameter of the IPS 102, so that venous blood flow continues through the IPS 102 into the jugular vein 106. Alternatively, the implanted shunt 200 may occlude the IPS 102 preventing venous blood flow from the cavernous sinus into the jugular vein 106. However, it has been observed that an occluded IPS, whether resulting from a surgical procedure or thrombosis, typically has no impact on a patient's venous circulatory function.

Figure 3B:
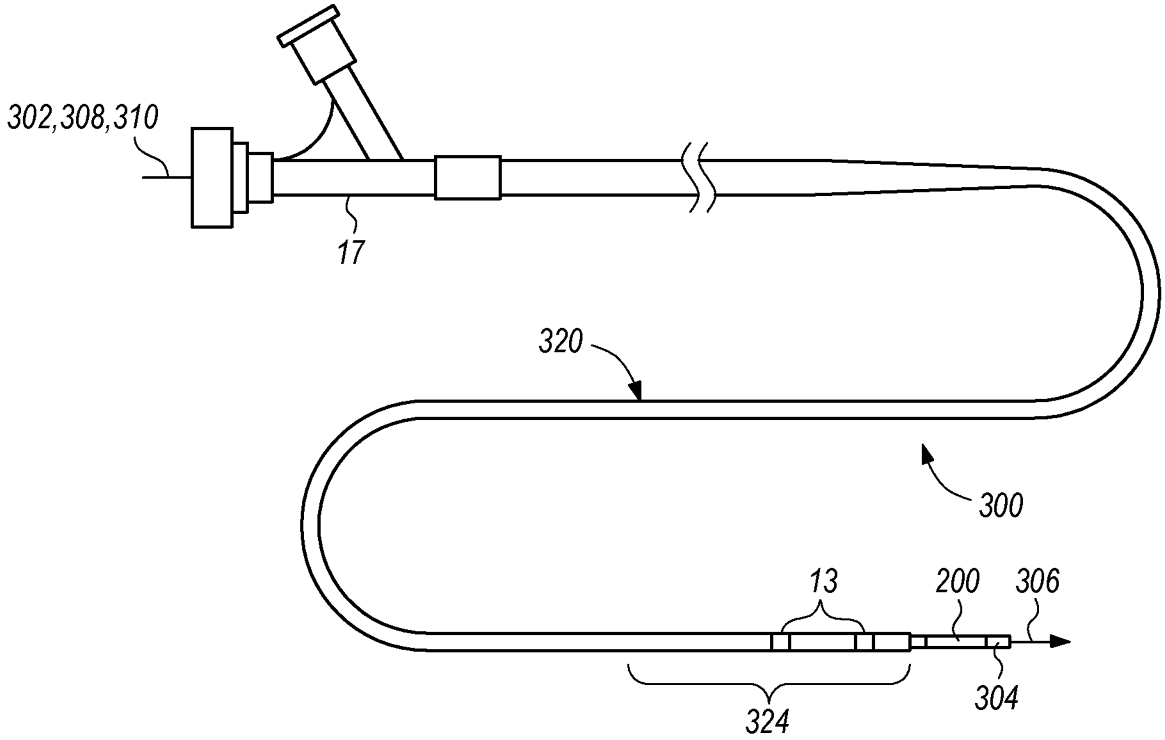
FIG. 3B is a side view of a delivery assembly according to embodiments of the disclosed inventions.

FIG. 3B is a side view of a delivery assembly 300 for delivering the shunt 200 into a target site of a patient, constructed in accordance with embodiments of the disclosed inventions. The delivery assembly 300 includes the shunt 200 detachably coupled to the delivery assembly 300. The delivery assembly 300 and shunt 200 may be composed of suitable biocompatible materials. The delivery assembly 300 is dimensioned to reach remote locations of the vasculature and is configured to deliver the shunt 200 percutaneously to the target location (e.g., inferior petrosal sinus). The delivery assembly 300 includes a tubular member interface having an outer tubular member 320 (i.e., guide catheter) and an inner tubular member 304 (i.e., delivery catheter/microcatheter) coaxially disposed within the outer tubular member 320 and movable relative to the outer tubular member 320. The delivery assembly 300 may include a guidewire 302 coaxially disposed within the guide catheter 320 and/or the delivery catheter 304. The guidewire 302 can be, for example, 0.035 inches (0.889 mm) in diameter. Additionally to the guidewire 302, the delivery assembly 300 may include a delivery guidewire 308 disposed within the delivery catheter 304. The delivery guidewire 308 has a smaller diameter (e.g., approximately 0.010 inches-0.254 mm—to 0.018 inches-0.4572 mm-) compared to guidewire 302.

The guide catheter 320, delivery catheter 304, and guidewires 302/308 may be formed of suitable biocompatible materials, and may include markings for purposes of imaging (e.g., markers composed of radio-opaque materials). Further, the delivery catheter 304 may include one or more anchoring mechanisms disposed along the body of the catheter allowing temporary anchoring of the catheter 304 within IPS 102 during the deployment of the shunt 200. The anchoring mechanisms configuration and actuation may be similar as the anchoring mechanisms of the shunt 200 described in further detail below. For example, the anchoring mechanism of the delivery catheter 304 may be actuated (e.g., engagement and disengagement within the IPS 102) using a guidewire.

Various known and often necessary accessories to the delivery assembly 300, e.g., one or more radiopaque marker bands 13 at the distal portion 324 of the guide catheter 320 to allow viewing of the position of the distal portion under fluoroscopy and a Luer assembly 17 for guidewires and/or fluids access, are shown in FIG. 3B.

The delivery assembly 300 may include a tissue penetrating element 306 coaxially disposed within the delivery catheter 304 and/or guide catheter 320 and/or shunt 200. The tissue penetrating element 306 is configured to pierce the IPS wall 114 and arachnoid layer 115 to access the CP angle cistern 138 for implantation of the shunt 200. Alternatively, the shunt 200 includes a tissue penetrating member 250 on the distal portion 202 of the shunt 200' (e.g., FIGS. 5C-I and FIGS. 14F-H), so the tissue penetrating element 306 is not required in the delivery assembly 300, since the tissue penetrating member 250 incorporated in the shunt 200' is configured to pierce the IPS wall 114 and arachnoid layer 115. (For ease in illustration, the various embodiments of the shunt disclosed and illustrated herein are given the reference number 200 or 200', although the embodiments may differ from each other in certain aspects and features.)

FIGS. 4A-4D illustrate an exemplary method of delivering the shunt 200 into the target site (e.g., inferior petrosal sinus) to drain CSF from a cistern in the subarachnoid space 116 (e.g., CP angle cistern 138) in accordance with embodiments of the disclosed inventions. After gaining access to the vasculature of a patient (e.g., via the femoral vein or the jugular vein 106), the guide catheter 320 and/or the guidewire 302 of the delivery assembly 300 may be advanced through the vasculature into the IPS 102 or a location proximate to the IPS 102 and IPS wall 114. When the guidewire 302 is used for navigation of the delivery assembly 300 into the target site, the guidewire 302 is further advanced to establish a pathway along which the delivery assembly 300 may be advanced. After the guidewire 302 has been positioned in a desired location, the guide catheter 320 may be advanced over the guidewire 302, so that a distal portion 324 of guide catheter 320 is within the jugular bulb 108, near the junction 118 between the IPS 102 and jugular vein 106. Alternatively, the guide catheter 320 may be advanced to the location near the junction 118, and the guidewire 302 is further advanced into the IPS 102. In a further alternative method, the guide catheter 320 is advanced to the desired location near the junction 118 without the use of the guidewire 302.

Figure 4A:
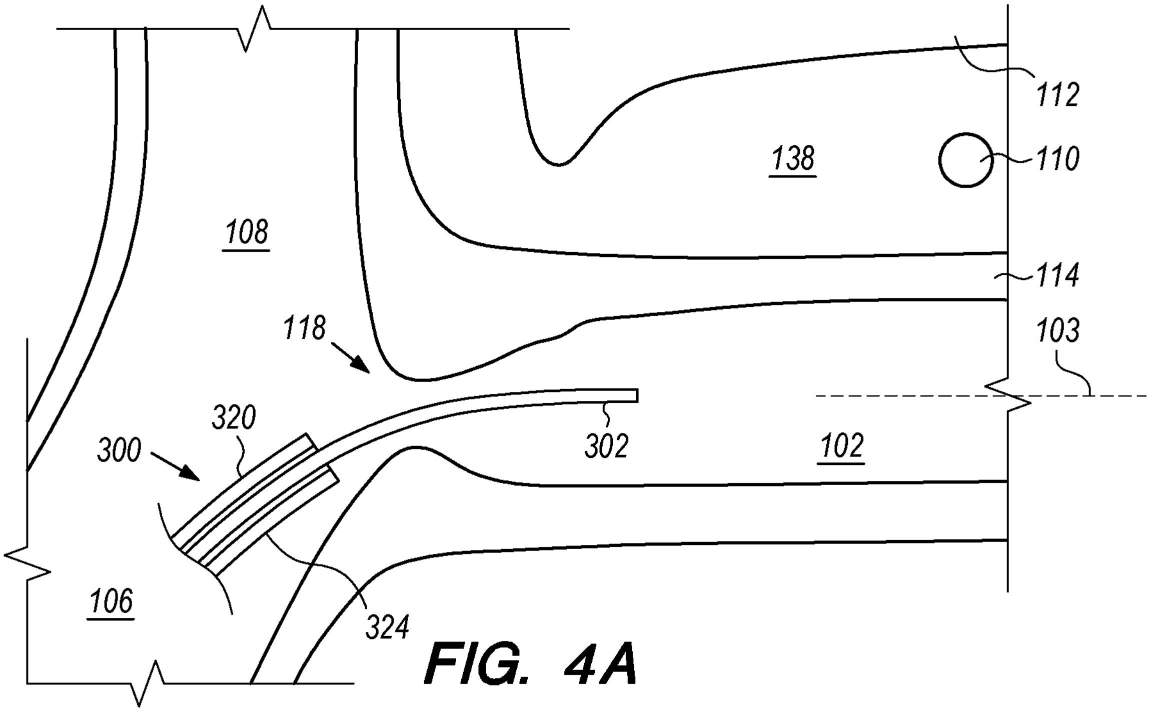
FIGS. 4A-D are cross-sectional views of deployment of endovascular shunt according to embodiments of the disclosed inventions.
Figure 4B:
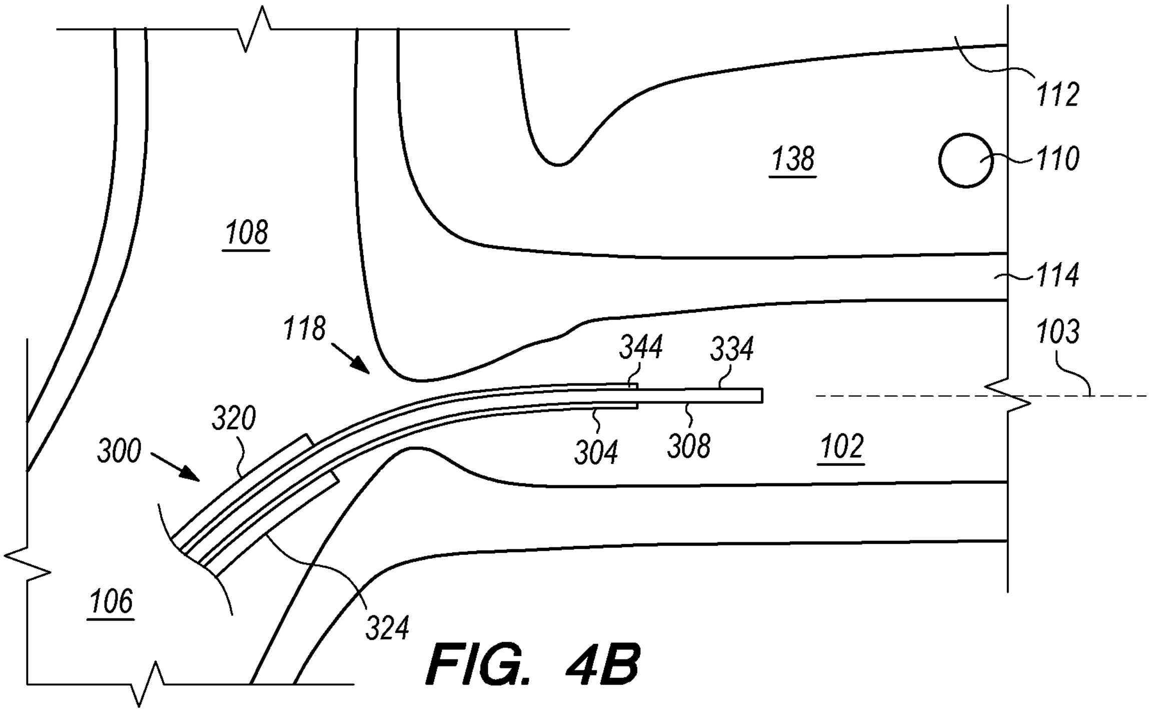

With the guide catheter 320 positioned at or about the junction 118 between jugular vein 106 and IPS 102, as shown in FIG. 4B, the delivery catheter 304 and the delivery guidewire 308, disposed within the delivery catheter 304, are advanced within the guide catheter 320. The delivery catheter 304 and delivery guidewire 308 are further advanced to the distal portion 324 of guide catheter 320, which is located in the jugular vein 106. The delivery guidewire 308 is then passed through the junction 118 between jugular vein 106 and IPS 102 and into the opening of IPS 102 in the medial wall of the jugular dome. The delivery guidewire 308 is then further advanced within IPS 102 to the posterior aspect of the cavernous sinus. The distal portion 334 of delivery guidewire 308 may be more flexible than other portions of the delivery guidewire 308 to facilitate navigation into the IPS 102 from jugular vein 106 and into the cavernous sinus.

Next, the delivery catheter 304 is advanced over the delivery guidewire 308 and into IPS 102. Advancement of delivery catheter 304 continues until a distal portion 344 of delivery catheter 304 is positioned adjacent or proximate to a desired point on IPS wall 114 where the shunt 200 is to be inserted to form an anastomosis between the CP angle cistern 138 and the lumen of IPS 102. Alternatively, the delivery guidewire 308 and the delivery catheter 304 may be advanced incrementally and sequentially into the opening of the IPS 102 at junction 118 and through one or more portions of the IPS 102.

Once the delivery guidewire 308 and delivery catheter 304 are located at a desired location within the IPS 102 for shunt deployment, the delivery guidewire 308 can be advanced to the posterior aspect of the cavernous sinus. The delivery guidewire 308 can serve as a support for the delivery catheter 304 within the IPS 102 and for shunt 200 deployment.

A variety of different imaging methods can be used to ensure accurate positioning of the shunt 200, guide catheter 320, guidewire 302, delivery catheter 304, and/or delivery guidewire 308, described above. Examples of suitable imaging methods include biplane fluoroscopy, digital subtraction angiography with road mapping technology, venous angiography with road mapping technology, 3D-rotational angiography or venography (3DRA or 3DRV), and cone-beam computed tomographic angiography or venography (CBCTA or CBCTV). Both 3DRA/V and CBCTA/V enable volumetric reconstruction showing the relationship between the bony anatomy, the venous anatomy and the radiopaque catheters and guidewires used for shunt deployment. The methods of deploying the shunt 200 comprise imaging the shunt 200 while deploying the shunt 200 in the patient.

Figure 4C:
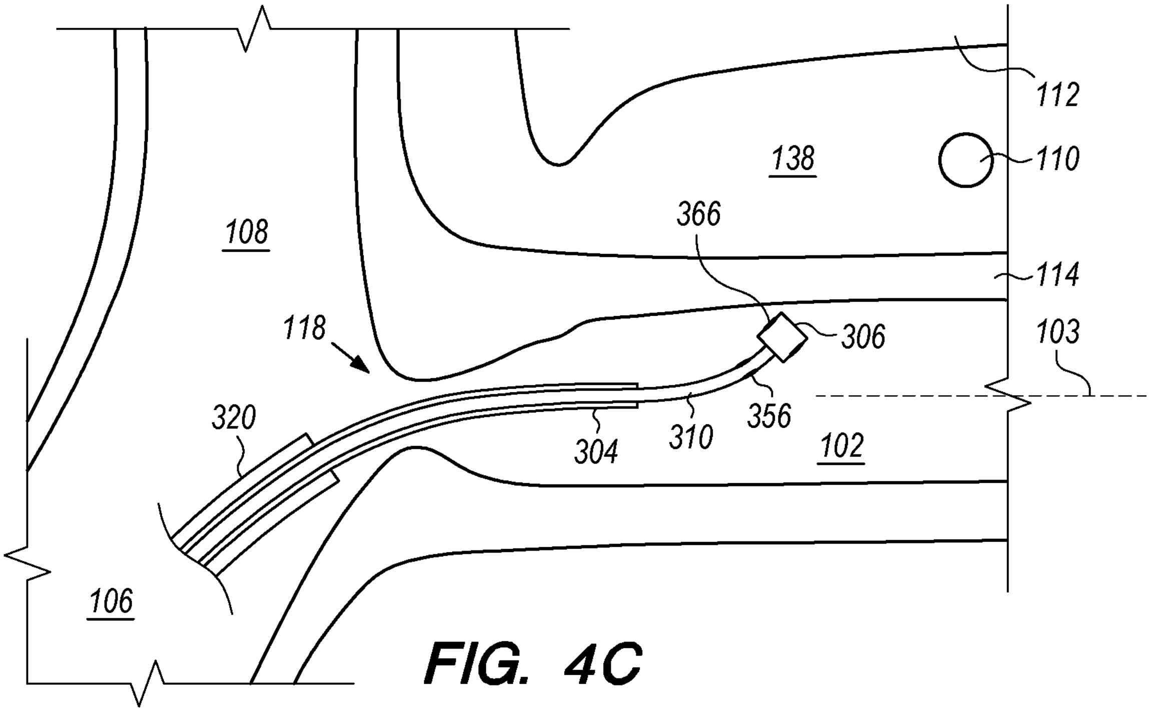
Figure 4D:
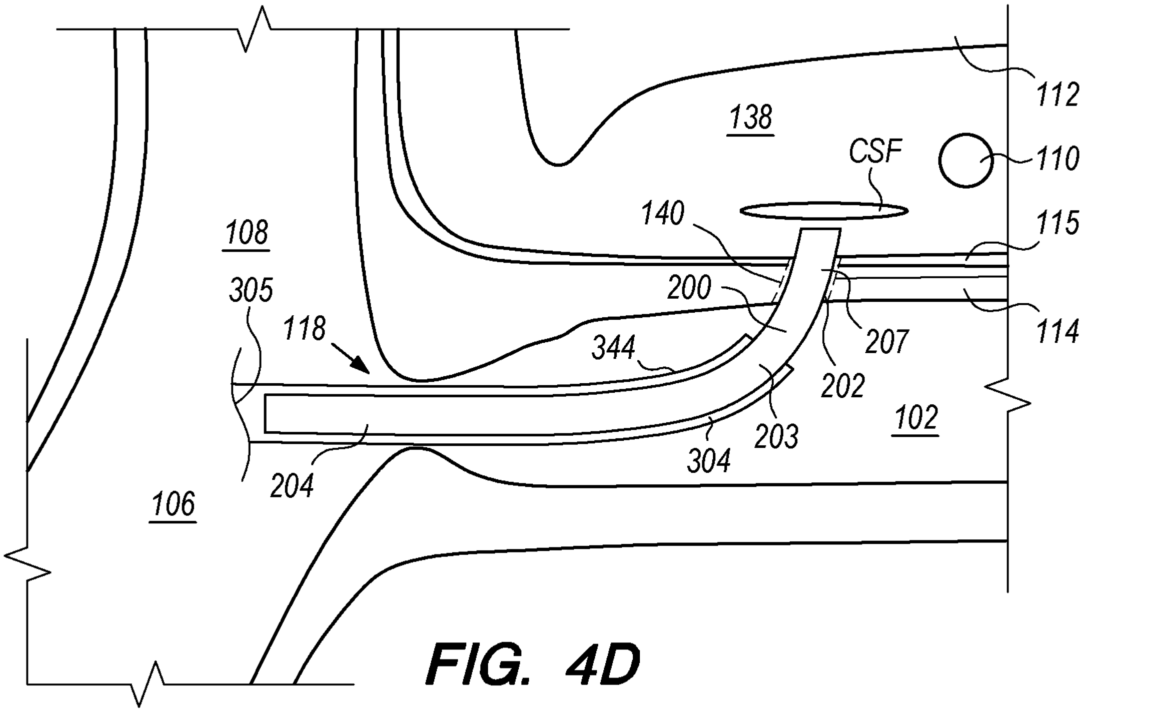

In some embodiments, positioning the delivery catheter 304 within the IPS 102 also includes rotating the delivery catheter 304 about its central axis to properly orient the delivery catheter 304 prior to deploying the shunt 200 or introducing the shunt 200 into the distal portion 344 of the delivery catheter 304. As shown in FIG. 4D (described in greater detail below), in certain embodiments, the delivery catheter 304 is curved (e.g., pre-curved, biasedly curved, flexible, drivable distal portion via control wires, or the like, or combinations thereof) near the distal portion 344 of the catheter so that when the delivery guidewire 308 and/or the shunt 200 are advanced through the delivery catheter 304, they approach and reach the IPS wall 114 at an angle relative to a central axis 103 of IPS 102 (FIGS. 4B-C). The delivery catheter 304 can be rotated, for example, by applying a rotational force directly to the body of the delivery catheter 304, or to the delivery guidewire 308 if the guide wire is connected to the delivery catheter 304. Positioning the curved distal portion 344 of the delivery catheter 304 in the desired orientation adjacent to the IPS wall 114 can facilitate puncturing of the IPS wall 114 and arachnoid layer 115 to access the CP angle cistern 138. When deploying the shunt 200, the methods of deployment comprises introducing the shunt 200 into the patient's body while the shunt 200 is at least partially disposed in the delivery catheter 304, and wherein the delivery catheter 304 is advanced over guidewire extending through a lumen of the delivery catheter 304, which may be a same or different lumen in which the shunt 200 is at least partially disposed, until a distal portion of the delivery catheter 304 is positioned in the IPS 102 (FIG. 4B).

Referring to FIG. 4C, prior to introducing the shunt 200, a tissue penetrating element 306 located at a distal portion 354 of an elongate pusher member 310 (e.g., piercing micro-wire) having a penetrating member 306, can be used to pierce the IPS wall 114 and arachnoid layer 115, creating anastomosis 140 (e.g., a connection channel, hole, space into which the shunt 200 is later delivered and implanted). The elongate pusher member 310 may be advanced through either the guide catheter 320 or delivery catheter 304. By applying a suitable mechanical force to the elongate pusher member 310, the penetrating member 306 can be advanced through the IPS wall dura mater 114 and the arachnoid layer 115 that separate the lumen of IPS 102 from subarachnoid space 116 (FIG. 2), creating the anastomosis 140 for the shunt 200 deployment. For example, the penetrating element 306 may include a needle tip with a rounded or bullet-like configuration. The penetrating element 306 rounded or bullet-like tip separates the dura fibers without damaging them while the elongate pusher member 310 having sufficient stiffness passes through the dura mater of IPS wall 114 and the arachnoid layer 115 into the CP angle cistern 138.

Alternatively, the penetrating element 306 includes a sharpened tip or trocar, which cuts through the IPS wall dura mater 114 and the arachnoid layer 115 to create the anastomosis 140 for the shunt 200 deployment. In certain embodiments, the penetrating element 306 includes a controllable radiofrequency ablation device for creating the anastomosis 140 through the dura mater of IPS wall 114 and the arachnoid layer 115 to access the CSF-filled space of the CP angle cistern 138.

Further, an interface between the penetrating element 306 and the shunt 200 is provided to collaboratively create the anastomosis 140, which will be described in greater detail in FIG. 33A-C.

The location of the penetrating element 306 relative to the IPS wall 114 can be monitored using any of the imaging techniques described above, and/or can be detected based on a tactile feedback communicated by the elongate pusher member 310 to a clinician. For example, a clinician can detect a brief "click" or "snap" (e.g., tactile feedback) as the penetrating element 306 passes and creates anastomosis 140 through IPS the wall 114. The elongate pusher member 310 and/or penetrating element 306 can include one or more radio-opaque markers 356, 366 to assist in vivo imaging and guidance while the clinician creates the anastomosis 140 for shunt deployment. For example, suitable markers can be included (e.g., embedded) or applied (e.g., coatings) to the outer surface of the penetrating element 306 and/or elongate pusher member 310 in a pattern that is readily/visually recognized by the clinician. An example of a radio-opaque material that can be used to apply suitable markings is barium sulfate.

Once the IPS wall 114 and arachnoid layer 115 are pierced creating the anastomosis 140, the elongate pusher member 310 and the penetrating element 306 are withdrawn. Next, as shown in FIG. 4D, the shunt 200 is advanced through the delivery catheter 304 (i.e., inner lumen 305 of the delivery catheter 304) into the anastomosis channel 140 formed by piercing the IPS wall 114 and arachnoid layer 115. Alternatively, when the shunt 200' that includes a piercing element is used in the delivery assembly 300, the shunt 200' pierces the IPS wall 114 and arachnoid layer 115 creating the anastomosis; so that the distal portion 202 of the shunt 200' is disposed into the anastomosis channel 140 without requiring withdrawal of the piercing element, elongate pusher member 310 or penetrating element 306. The alternative method using the shunt 200' having a piercing element will be described in greater detail in FIGS. 5A-I and FIGS. 14F-H. As further alternatives, the shunt 200 can accompany a penetrating element through the dura of IPS wall 114 and arachnoid 115 (e.g., as described in FIG. 20A-F) or shunt 200 can be delivered through a lumen of the penetrating element (e.g., as described in connection with FIGS. 43, 44, 47), without an exchange or removal of delivery system components between the penetration and shunt deployment steps of the implant procedure.

Referring back to FIG. 4D, the shunt 200 can be delivered through the delivery catheter 304 by advancing over the delivery guidewire 308. The distal portion 202 of the deployed shunt 200 comprises a distal anchoring mechanism 229, as shown, for example in FIG. 22A, that positions the distal portion 202 of the shunt so as to maintain the one or more CSF intake openings 201 separated, apart and/or directed away from an arachnoid layer 115 of the CP angle cistern 138. The proximal portion 204 of the deployed shunt 200 comprises a proximal anchoring mechanism 227, as shown, for example in FIG. 22A, that positions the proximal portion 204 of the shunt to thereby maintain a CSF outflow port and/or valve 209 opening disposed in the proximal portion of the shunt 200 separated, apart and/or directed away from a wall of the jugular vein 106. To facilitate placement of shunt 200 using a guidewire, the body of shunt 200 can include an interior lumen 217, separate from the lumen 215 used to communicate CSF (FIG. 8), which is dimensioned to receive or slide over the delivery guidewire 308, or a groove or rail (e.g., on an internal surface or on the external surface of the shunt body) that mates in complementary fashion with a corresponding structural feature of the delivery guidewire 308. In addition to forward advancement of shunt 200 relative to the delivery catheter 304, a connection interface 213 and 313 (FIG. 7) between the delivery guidewire 308 and the shunt 200 permits rotation (e.g., by rotating guidewire 308) of the shunt 200 about a central axis of the shunt body 203 to ensure that the distal portion 202 of shunt 200 is properly oriented to track toward a deployment site in the CP angle cistern 138.

The delivery catheter 304 disposed within the IPS 102 and, when present, the curved end distal portion 344 of the delivery catheter 304, allows for the distal portion 202 of the shunt 200 to be delivered into the anastomosis channel 140 and to extend into the CP angle cistern 138, while allowing the body portion 203 of shunt 200 to be disposed within the IPS 102, and the proximal portion 204 of the shunt 200 to extend through the junction 118 and into the jugular bulb 108 and/or jugular vein 106. After the shunt 200 is properly positioned, the delivery catheter 304, and any remaining elements of the delivery assembly 300 (e.g., delivery guidewire 308, guidewire 302, and guide catheter 320) are withdrawn, leaving the implanted shunt 200 in situ, as shown in FIG. 3A. The implanted shunt 200 provides a fluid communication between the CP angle cistern 138 and into the jugular vein 106, so that CSF is drained through the lumen 207 (or 215 when the shunt 200 includes multiple lumens) of the shunt 200. The CSF within the CP angle cistern 138 enters the lumen 207 opening at the distal portion 202 of the shunt 200, flows through the lumen 207 at the body 203, and emerges from the lumen 207 opening at the proximal portion 204 of the shunt 200, so that CSF is then carried away by venous circulation within jugular bulb 108 and/or jugular vein 106.

As discussed above in connection with the guide catheter 320 and the delivery catheter 304, a variety of different imaging techniques can be used to ensure proper or desirable deployment of the shunt 200 within the CP angle cistern 138 and IPS 102. A clinician deploying the shunt 200 can also rely on tactile feedback, communicated through the delivery guidewire 308 or the delivery catheter 304, to ensure proper positioning of the shunt 200. Typically, once properly deployed, the distal portion 202 of the shunt 200 extends above arachnoid layer 115 into the CP angle cistern 138 at a distance between 1 mm to 5 mm (e.g., 2-3 mm), or any other suitable length configured to extend into the CP angle cistern 138 while leaving suitable clearance between the distal tip of the shunt 200 and the brain stem 112.

In some embodiments, the shunt 200 and/or penetrating member of the delivery system includes measurement features to confirm appropriate placement within the CP angle cistern 138 (e.g., an electrical resistance detector configured to differentiate between dura mater and CSF, a fluid composition detector configured to differentiate between blood and CSF, and/or a light source and sensor configured to differentiate between dura mater, blood, and CSF based on reflected light). Further, in some embodiments a stop member is proximally disposed to the penetrating element 306 (surgical tool or any other piercing element) preventing the penetrating element 306 and/or the shunt 200/200' from being deployed beyond a suitable distal length into the CP angle cistern 138, allowing suitable clearance between the distal tip of the shunt 200/200' and the brain stem 112, while avoiding abutting or the damaging brain stem 112. In some embodiments, a cover 260 slidably disposed over the tissue penetrating member 250 of the shunt 200' is provided to cover the tissue penetrating member 250 after deployment of the shunt 200', which will be described in greater detail in FIG. 61 A-D.

Before or after deployment of the shunt 200, confirmation that the anastomosis 140 has been created between the CP angle cistern 138 and IPS 102 may be performed. For example, CSF can be withdrawn through the delivery catheter 320 using a syringe connected to the Luer assembly 17 of the delivery assembly 300 (FIG. 3B), confirming that the wall 114 and arachnoid 115 have been penetrated, the CP angle cistern 138 has been accessed, and/or the anastomosis 140 has been created. In some embodiments, the delivery catheter 320 includes measurement features to confirm that the anastomosis 140 has been created with the CP angle cistern 138 (e.g., an electrical resistance detector configured to differentiate between dura mater and CSF, a fluid composition detector configured to differentiate between blood and CSF, and/or a light source and sensor configured to differentiate between dura mater, blood, and CSF based on reflected light).

FIGS. 4A-D disclose one exemplary method for deploying the shunt 200 to treat hydrocephalus. According to the disclosed inventions, the steps, sequence of steps, shunt, and delivery assembly 300 elements to perform the steps, can be modified in a variety of ways. For example, in an alternative method, the shunt 200 is deployed without using the delivery catheter 304. That is, the shunt 200 is detachably coupled to the delivery guidewire 308 and advanced through the guide catheter 320 until it is properly positioned within the CP angle cistern 138 and IPS 102. Then, the delivery guidewire 308 can be detached from the shunt 200, and the guidewire 308 and guide catheter 320 are withdrawn, allowing the shunt 200 to remain in situ and facilitate flow of CSF from the CP angle cistern 138 into jugular bulb 108 and/or jugular vein 106.

In a further alternative method, the delivery catheter 304 can be used to pierce IPS wall 114 creating all or a portion of the anastomosis 140. For example, the distal portion 344 of delivery catheter 304 can be cut at an angle with respect to a central axis of the catheter body, forming a sharp, tapered, cannula-like end, which will be described in greater detail below. By applying a suitable force to the delivery catheter 304, the distal portion 344 can be pushed through and pierce the IPS wall 114 to create all or a portion of the anastomosis 140. This method can be used together with, or instead of, the use of the penetrating element 306 connected to the elongate pusher member 310 to complete the connection between the lumen of IPS 102 and CP angle cistern 138.

It should be appreciated that more than one shunt 200 can be implanted at the target site. For example, when the implanted shunt 200 does not completely occupy the IPS 102, a clinician may have sufficient space within the IPS 102 to deploy a second shunt. The second shunt may be implanted in the IPS 102 adjacently or proximate to the previously implanted shunt 200.

Figure 5A:
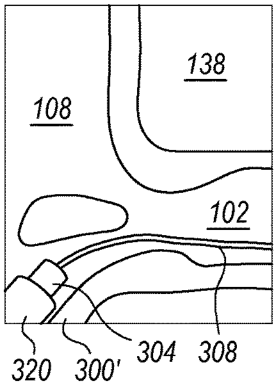
FIGS. 5A-J are side and cross-sectional views of deployment of an endovascular shunt according to another embodiment of the disclosed inventions.
Figure 5B:
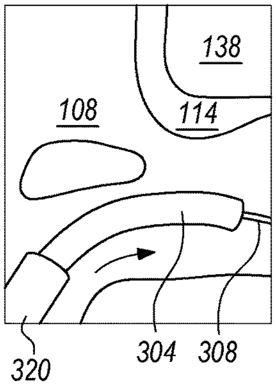
Figure 5C:
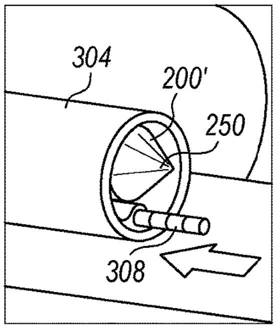
Figure 5D:
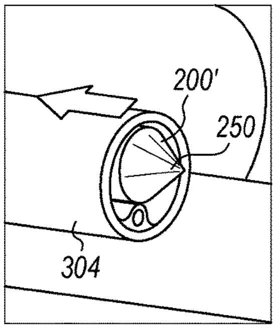
Figure 5E:
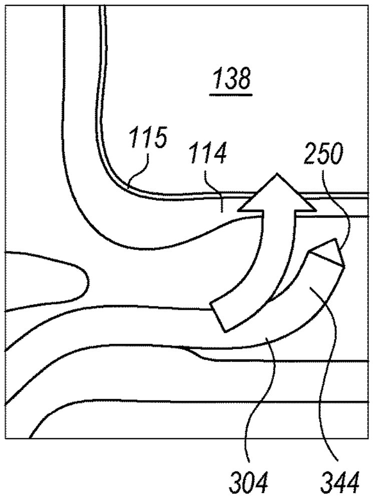
Figure 5F:
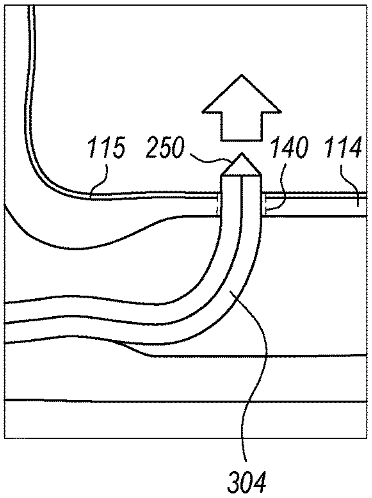
Figure 5G:
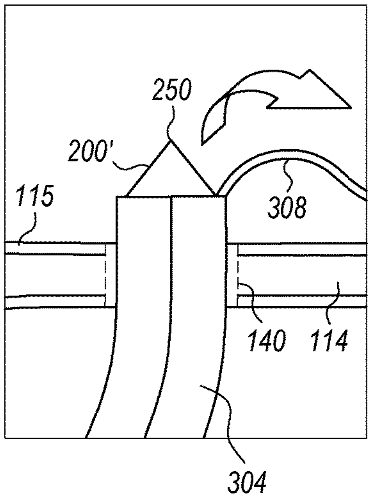
Figure 5H:
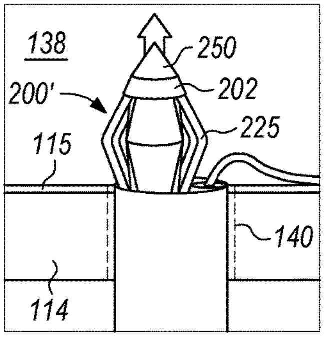
Figure 5I:
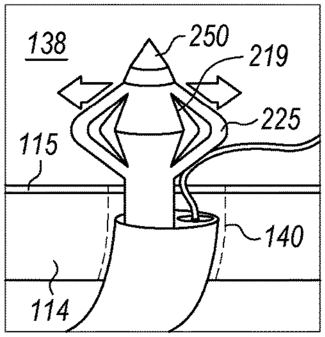
Figure 5J:
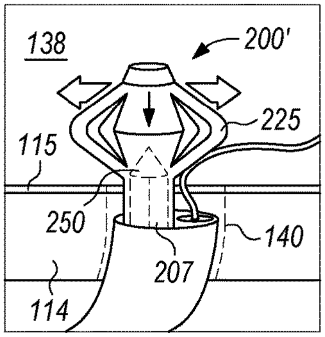

FIGS. 5A-J illustrate an alternative method of delivering and implanting the shunt 200 into the target site to drain CSF from a cerebral cistern, in accordance with embodiments of the disclosed inventions. For ease in illustration, the features, functions, and configurations of the delivery assembly 300' are the same as in the assembly 300 of FIGS. 4A-D are given the same reference numerals. The delivery assembly 300' of FIGS. 5A-J includes the guide catheter 320, the delivery catheter 304, the delivery guidewire 308 of the assembly 300. The delivery assembly 300' further includes a detachably coupled shunt 200' having a tissue penetrating member 250 disposed on the distal portion 202 of the shunt 200'. Alternatively, the tissue penetrating member 250 may be a cut of the distal portion 202 of the shunt 200' to form an angled, sharp, cannula-like end or include a tip needle or the like. Further, the tissue penetrating member 250 may be detachably coupled to the shunt 200' so that the tissue penetrating member 250 is detached and removed from the shunt 200', once the anastomosis is created and/or the shunt 200' implanted in the target site (e.g., as shown in FIGS. 5H-J).

Once the delivery catheter 304 carrying the shunt 200' has been advanced and positioned, using any of the methods described above, adjacent or proximate to a desired point on the IPS wall 114 where the shunt 200' is to be implanted (FIG. 5B), the guidewire 308 may be withdrawn and the shunt 200' is advanced (FIG. 5C). The clinician may verify the orientation of the shunt 200', confirming the orientation of the tissue penetrating member 250 with any of the methods described above (e.g., fluoroscopic) (FIG. 5D). The method includes positioning the distal portion 344 (e.g., pre-curved, biasedly curved, flexible, drivable distal portion via control wires, or the like, or combinations thereof) of the delivery catheter 304 in the proper orientation relative to the IPS wall 114 (e.g., so that the open distal end of delivery catheter 304 faces and/or abuts IPS wall 114) to facilitate puncturing of the IPS wall 114 and arachnoid layer 115, and access to the CP angle cistern 138 (FIG. 5E). The positioning of the distal portion 344 of the delivery catheter 304 may include adjusting the rotational orientation of the delivery catheter 304; so that the tissue penetrating member 250 carried on the distal portion 202' of the shunt 200' pierces the IPS wall 114 and arachnoid layer 115 creating the anastomosis 140 at a target penetration site. In some embodiments, the delivery catheter 304 contains a second opening spaced proximally from the distal end 344 of the delivery catheter 304, on an axial location of the catheter body 304 (e.g., at the location of reference line 304 in FIG. 5E). The second opening is configured to allow the delivery guidewire 308 to emerge from the delivery catheter 304 and extend through the IPS 102 (e.g., to the posterior aspect of the cavernous sinus) beyond the shunt 200 deployment site. This configuration of the delivery catheter 304 and the delivery guidewire 308 allows the clinician to orient the delivery catheter 304 about the proposed shunt 200' deployment location in the IPS 102 and supports the delivery and piercing assembly during penetration of the IPS wall 114 to create anastomosis 140.

By applying suitable mechanical force to the shunt 200', tissue penetrating member 250 and/or the delivery catheter 304, the tissue penetrating member 250 can be advanced through the dura mater of IPS wall 114 and arachnoid layer 115 that separates the lumen of IPS 102 from the subarachnoid space 116 (FIG. 2), creating the anastomosis 140 (FIG. 5F). Alternatively, the delivery guidewire 308 may be advanced into the CP angle cistern 138 (FIG. 5G). The distal portion 202' of the shunt 200' is further advanced into the CP angle cistern 138 (FIG. 5H); once the shunt 200' is in the desired location, the distal portion 202' is secured against the arachnoid layer 115 and within the CP angle cistern 138 (FIG. 5I). In some embodiments, deploying the shunt 200' comprises advancing the distal portion 202' of the shunt 200' from the IPS 102 into the CP angle cistern 138 using the tissue penetrating member 250. The tissue penetrating member 250 is coupled to a distal end 202' of the shunt 200, so that advancing the distal portion 202' of the shunt 200' from the IPS 102 into the CP angle cistern 138 comprises advancing the tissue penetrating member 250 and distal portion 202' of the shunt 200' through the dura mater tissue wall of the IPS 114, and through the arachnoid tissue layer 115, respectively, into the CP angle cistern 138. Verification of the desired position of the distal portion 202' end of the shunt 200' may be performed with any of the methods described above.

The distal portion 202' of the shunt 200' may include an anchoring mechanism 225 that extends from, or is adjacent to, the distal portion 202'. The anchoring mechanism 225 has a delivery configuration and a deployed configuration. In the delivery configuration, the anchoring mechanism 225 is configured to advance through the delivery assembly 300 (e.g., delivery catheter 304) and pass through the anastomosis channel 140. In the deployed configuration, the anchoring mechanism 225 is configured to secure the distal portion 202' of the shunt 200 over the arachnoid layer 115 and/or within the CP angle cistern 138 to allow fluid communication of CSF from the CP angle cistern 138 into the jugular bulb 108 and/or jugular vein 106. The method depicted in FIG. 5I includes actuating the anchoring mechanism 225 into the deployed configuration to secure the shunt 200' against the arachnoid layer 115 and within the CP angle cistern 138. Alternatively, the anchoring mechanism 225 is biased to its deployed, expanded configuration (e.g., by heat setting Nitinol to a malecot form) and constrained to a delivery configuration to pass through delivery catheter 304 to the deployment site. As the anchoring mechanism 225 is advanced through the delivery catheter 304 and the anastomosis 140 into the CP angle cistern 138 where CSF pools, anchoring mechanism 225 resumes its biased, deployed configuration to anchor the shunt 200' in the subarachnoid space 116. The method may include imaging the shunt 200' during positioning, securing and implanting of the shunt 200'.

The distal portion 202' of the shunt 200' and/or the distal portion 202 of the shunt 200, may include one or more openings 219 (e.g., hole, perforation, mesh, porous material, or the like, or a combination thereof) that allow for fluid communication into the lumen 207 of the shunt 200', so that CSF in the CP angle cistern 138 flows through the implanted shunt 200' into the jugular bulb 138 and/or jugular vein 106. Opening(s) 219 is placed closest the distal end of shunt 200 such that, once deployed, opening 219 is sufficiently spaced away from the arachnoid layer (e.g., 2 mm to 3 mm) to prevent arachnoid from creeping into or otherwise occluding CSF flow into shunt lumen 207.

Alternatively, when the tissue penetrating member 250 is detachably coupled to the shunt 200', the tissue penetrating member 250 is disengaged and removed from the implanted shunt 200' (e.g., via a guidewire, elongate pusher member 310, or the like), as shown in FIG. 5J, once the anastomosis has been created. In this embodiment, the lumen 207 of the shunt 200', particularly, the lumen 207 opening at the distal portion 202 of the shunt 200' remains in fluid communication with the CP angle cistern 138 for drainage of CSF. In this embodiment, CSF enters the shunt lumen 207 through the distal tip of shunt 200' and openings 219.

It should be appreciated that the method disclosed in FIGS. 5A-J may include any steps and features disclosed herein, including steps and features disclosed in connection with different embodiments, in any combination as appropriate.

Figure 6:
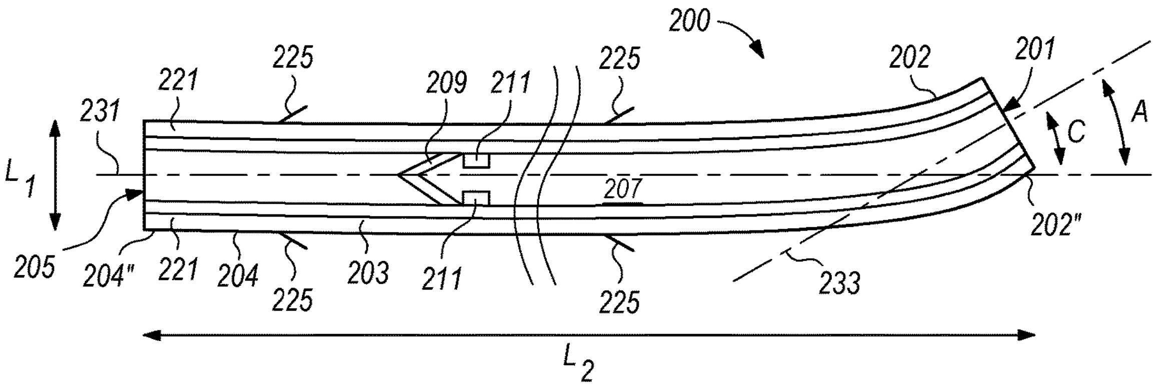
FIG. 6 is a cross-sectional view of an endovascular shunt according to embodiments of the disclosed inventions.
Figure 6A:
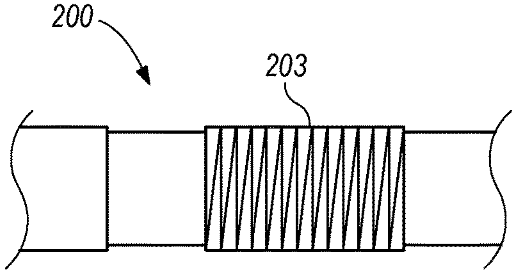
FIGS. 6A-T are side and cross-sectional views of features of the endovascular shunt of FIG. 6 according to embodiments of the disclosed inventions.

FIG. 6 shows a cross-sectional view of the shunt 200 constructed in accordance with embodiments of the disclosed inventions. As described above, the shunt 200 includes proximal portion 204, distal portion 202, and elongate body 203 extending between the proximal portion 204 and the distal portion 202. The lumen 207 extends within body 203 from a proximal end 204" of the proximal portion 204 to distal end 202" of the distal portion 202, allowing CSF to pass through the body of shunt 200. The shunt 200 includes a proximal opening 205 in the proximal end 204" and/or proximal portion 204, in fluid communication with the lumen 207. The shunt 200 further includes a distal CSF intake opening 201 in the distal end 202" and/or distal portion 202 in fluid communication with the lumen 207. The proximal opening 205 and the distal CSF intake opening 201 may include one or more openings. The shunt 200 has a length $L_2$, measured along an elongate central axis 231 of the shunt 200, selected so that shunt 200 extends from the CP angle cistern 138 to the jugular bulb 108 and/or the jugular vein 106. In one embodiment, $L_2$ is in a range between 15 mm to 30 mm. In further embodiments, the elongate body 203 may have variable $L_2$ within said range of 15 mm to 30 mm, in which the elongate body 203 includes expandable members, such as bellows (FIG. 6A in a compressed configuration and FIG. 6B in an expanded configuration), folds (FIG. 6C in a folded configuration and FIG. 6D in an unfolded/expanded configuration), slidably disposed concentric tubular elements (FIG. 6E shorter $L_2$ compared to larger $L_2$ of FIG. 6F), spring-like, coil-like (FIG. 6G more tightly wound coil-shorter $L_2$—than of FIG. 6H), configurations, or the like, or combinations thereof.

In some embodiments, the distal portion 202 of the shunt 202 is expanded or self-expands from a collapsed delivery configuration to an expanded deployed configuration as, or after, it is advanced into the CP angle cistern 138.

The shunt lumen 207 has an inner diameter $L_1$ measured in a direction orthogonal to axis 231 depicted in FIG. 6. The diameter $L_1$ can range between 0.1 mm (0.004 inches) to 5 mm (0.2 inches) in different embodiments, and preferably falls within the range of about 0.2 mm (0.008 inches) to about 0.36 mm (0.014 inches). Further, $L_1$ and/or $L_2$ may have any suitable dimension for implantation of the shunt 200 in the target site (e.g., IPS, CP angle cistern, or the like).

In some embodiments of the inventions, a constriction in the inner diameter $L_1$ of shunt lumen 207 for a particular length $L_2$ is calculated based on the Hagen-Poiseuille equation to enable shunt 200 to provide for a target flow rate of CSF (in a range of about 5 ml per hour to about 15 ml per hour) through the shunt 200 at a normal differential pressure, defined as being in a range between about 5 cm H2O to about 12 cm H2O between the subarachnoid space 116 and venous system, as:

$$\Delta P = \frac{128\ \mu L Q}{\pi d^4}$$

$\mu$: viscosity $Q$: flow rate $\Delta P$: differential pressure $L$: length $d$: diameter For example, constricting the inner diameter $L_1$ of shunt lumen 207 to 0.19 mm over a length $L_2$ of 8 mm will maintain a CSF flow rate of 10 mL/hour at a differential pressure of 6.6 cm H2O. In the shunt embodiments without a constriction in the inner lumen, the same equation and approach can be used to configure the inner diameter of the shunt lumen along the entire length of the shunt body 203 to achieve a target flow rate (or range) for a given differential pressure (or range).

In some embodiments, the shunt 200 may include one or more valves to regulate the rate of CSF flow within the shunt 200, while allowing flow of CSF only in one direction, i.e., from the distal portion 202 to the proximal portion 204 of the shunt 200. FIG. 6 depicts a valve 209 disposed within the shunt body 203, in fluid communication with the lumen 207 of the shunt 200. The valve 209 may be disposed at any suitable location within the body 203, for example, proximate to or at the proximal portion 204, to the distal portion 202, and/or in between said portions 202, 204. In certain embodiments, multiple valves can be disposed at different locations within the shunt 200.

Valve 209 can include a specific cracking pressure that, when met or exceeded by the positive pressure gradient between the subarachnoid space and venous system, opens the valve thereby facilitating CSF flow from the CP angle cistern into the jugular vein. For example, the cracking pressure of valve 209 can be configured from about 3 mm Hg to about 5 mm Hg and/or when the differential pressure between the subarachnoid space and venous system reaches from about 3 mm Hg to about 5 mm Hg; however, other cracking pressures can be configured in valve 209 depending on the particular clinical needs of the patient.

Figure 6E:
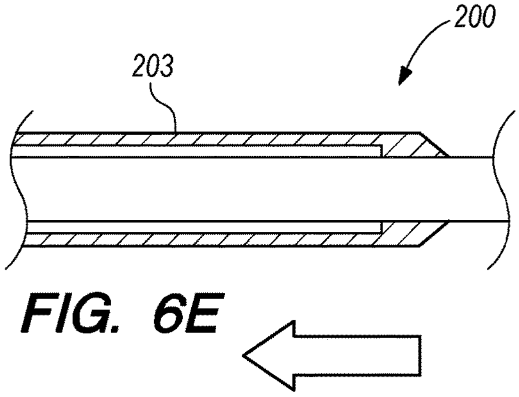
Figure 6B:
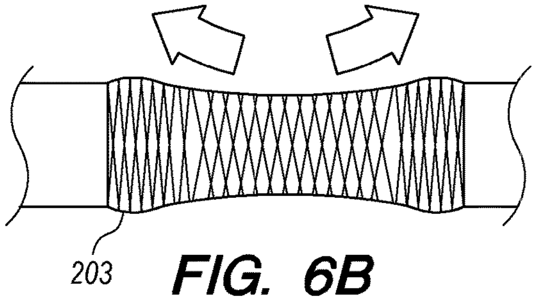
Figure 6F:
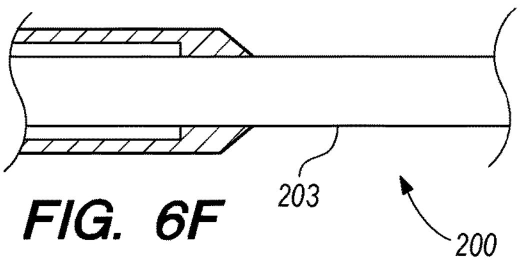
Figure 6C:
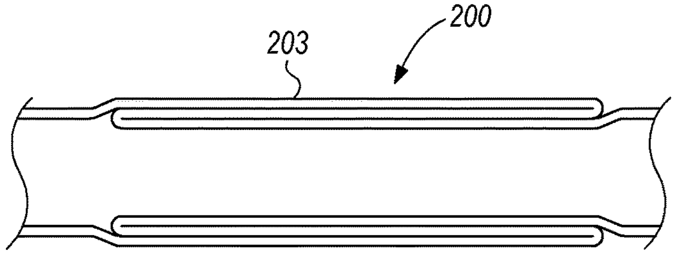
Figure 6G:
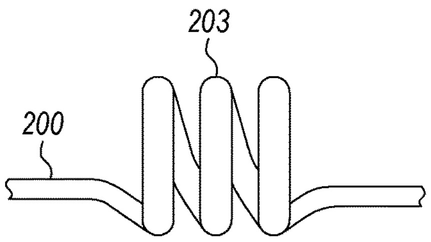
Figure 6D:
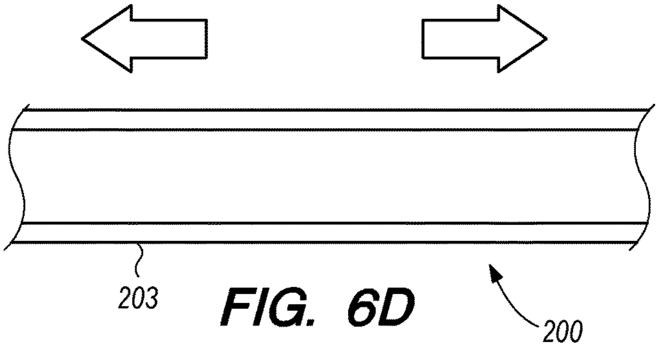
Figure 6H:
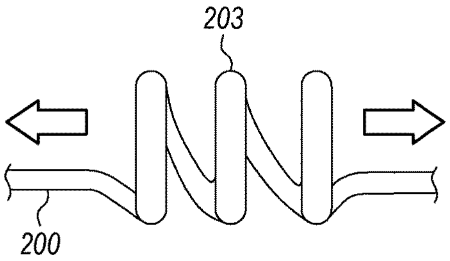
Figure 6I:
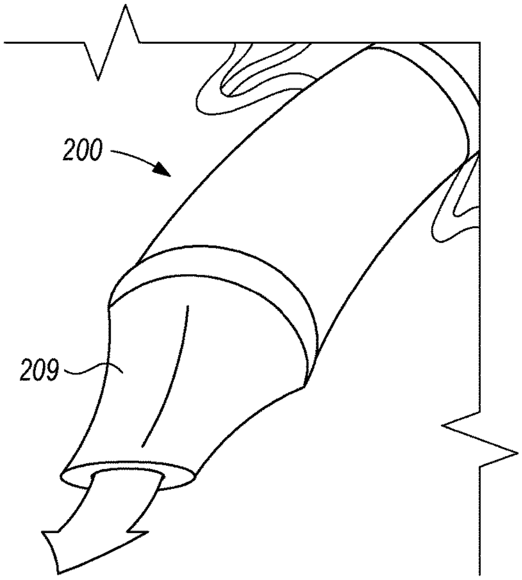
Figure 6J:
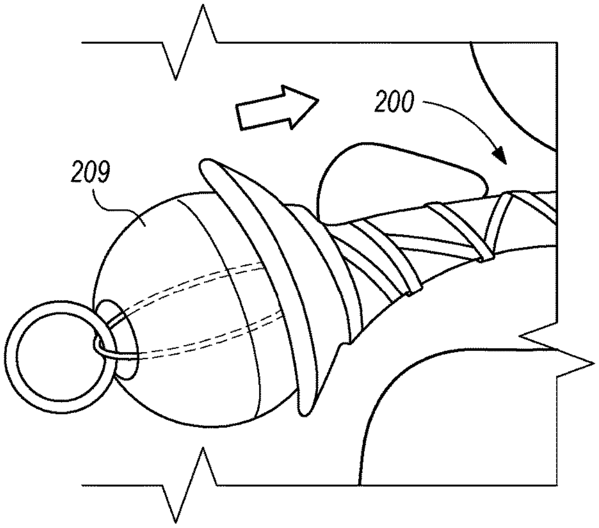
Figure 6K:
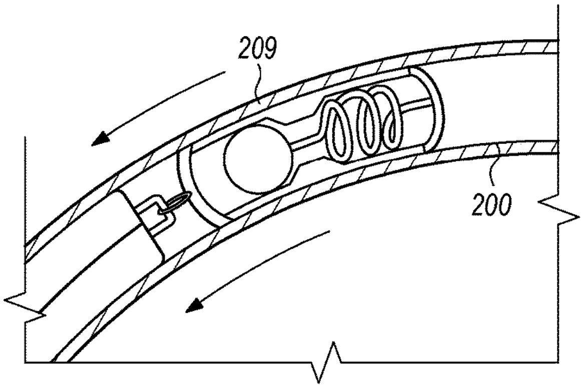
Figure 6L:
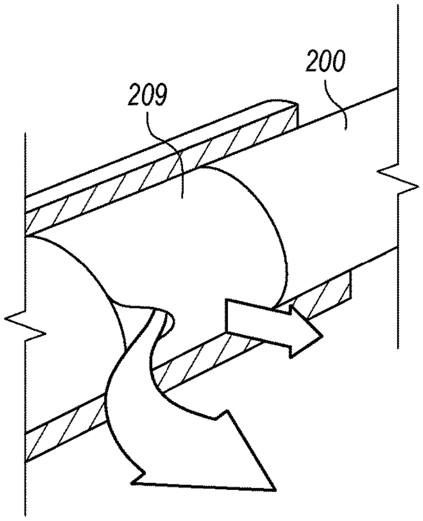

The valve 209 may have a variety of suitable features. For example, the valve 209 is a one-way valve, such as a duck-bill valve, as shown in FIG. 6 and FIG. 6I. Other suitable valves 209 can be used in the shunt 200, such as umbrella valves, pinwheel valves, ball and spring valves (FIGS. 6J-K), concentric tube valves (FIG. 6L), slit valves, check valves, flapper valves (FIG. 6N-O) or the like, or combinations thereof. In addition, a one-way valve can be formed from electrolytically erodible materials that can be selectively eroded to configure the flow rate through the valve by applying current to the valve for a specific period of time. Suitable materials, systems, and methods that can be used to configure such an erodible valve are further described in U.S. Pat. No. 5,976,131, the entire content of which is incorporated herein by reference.

Figure 6M:
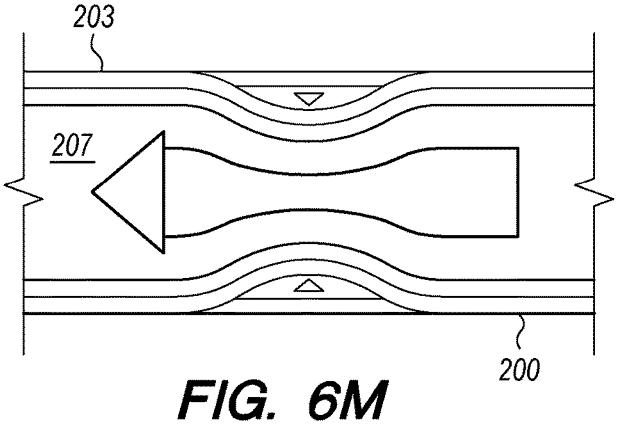
Figure 6N:
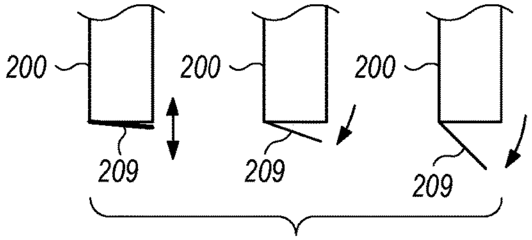
Figure 6O:
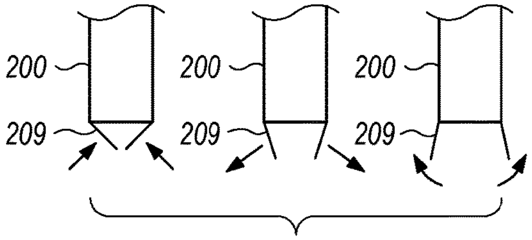
Figure 6P:
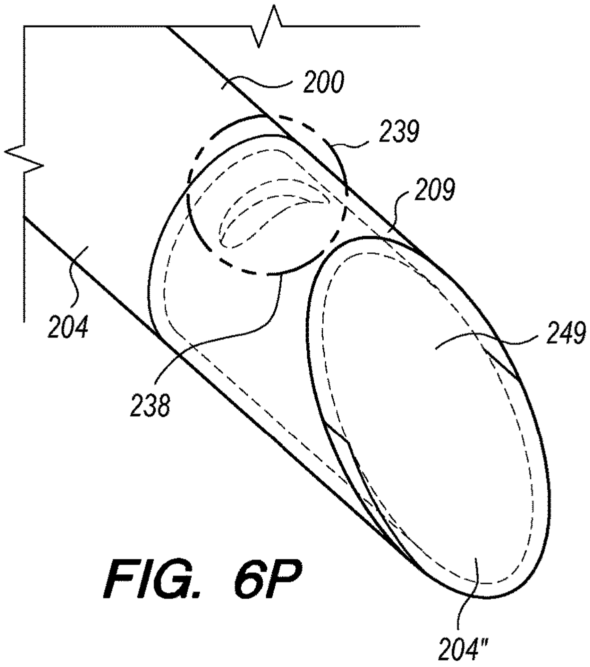
Figure 6Q:
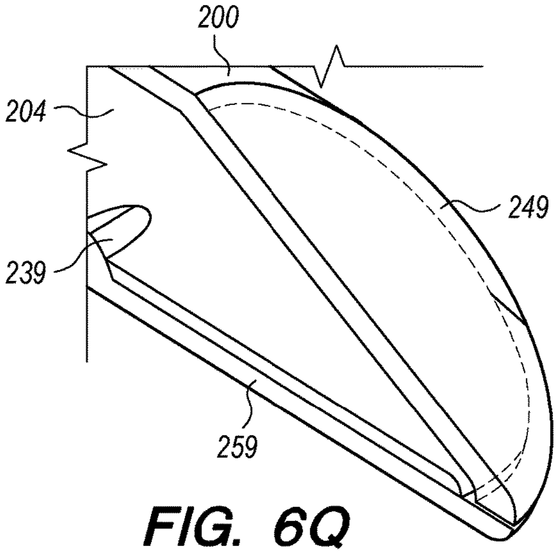
Figure 6R:
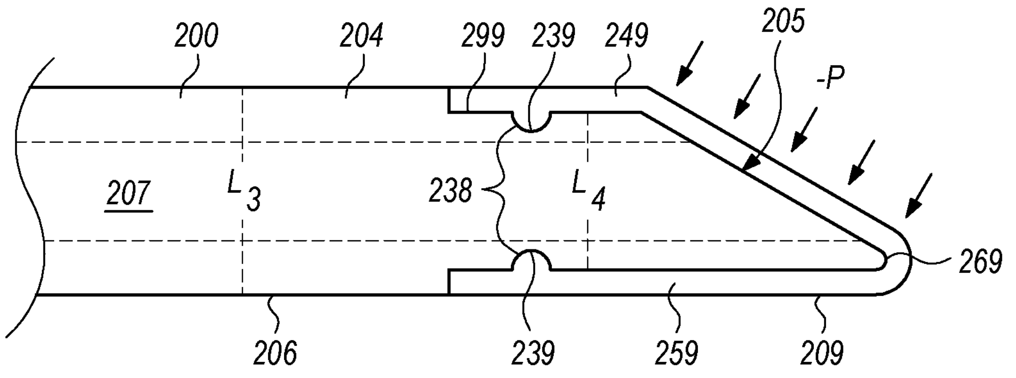
Figure 6S:
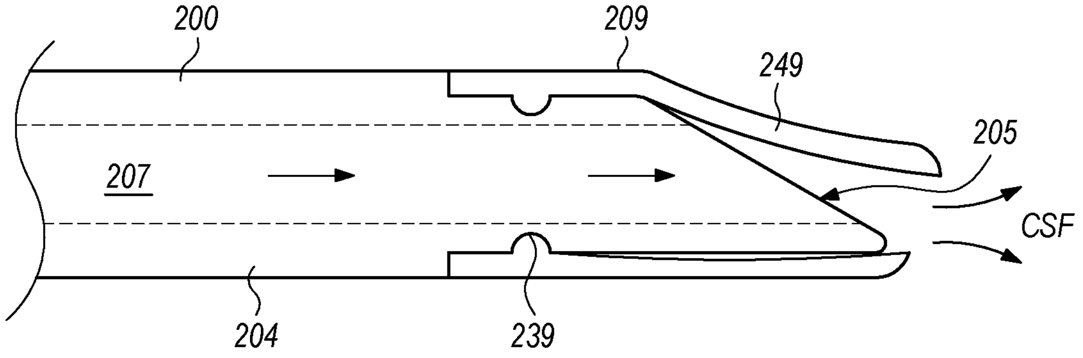
Figure 6T:
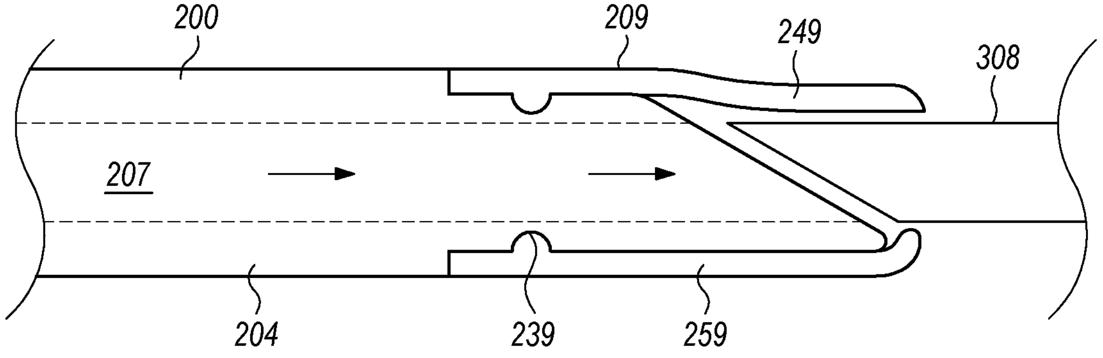

FIGS. 6P-6T illustrate the valve 209 constructed according to one embodiment of the disclosed inventions. As shown in FIG. 6P, the valve 209 comprises a molded silicone element configured to fit over the proximal portion 204 of the shunt 200. The proximal portion 204 of the shunt 200 has a narrowed outer diameter $L_4$ (e.g., dotted line portion of FIG. 6P) relative to the outer diameter $L_3$ of the body 203 of the shunt 200, configured to support the valve 209 over the proximal portion 204 (FIG. 6R). The proximal portion 204 of shunt 200 includes a beveled edge that terminates at a proximal end 204" (e.g., tip) of the shunt 200 (FIGS. 6Q-T). As shown in FIG. 6R, the valve 209 includes a protrusion 239 extending from an inner surface 299 of the valve 209. The protrusion 239 is dimensioned and configured to engage a recess 238 formed in the outer surface 206 of the proximal portion 204 of the shunt 200. When the valve 209 is inserted over the proximal portion 204 of the shunt 200, the protrusion 239 and recess 238 engage, thereby securing the valve 209 over the proximal portion 204 of the shunt 200. The valve 209 can include two or more interlocking protrusions 239, spaced apart (e.g., or on opposing sides of the valve 209 inner surface 299-FIG. 6R), and the shunt 200 includes corresponding recesses 238 in the outer surface 206 configured to engage the respective protrusions 239 of the valve 209. The valve 209 further includes a first portion 249 having a closed configuration, in which the portion 249 seats and/or covers the beveled edge and the proximal opening 205 of the shunt 200 in communication with the lumen 207 stopping fluid flow out of the lumen 207 (FIGS. 6P-R), and having an opened configuration in which the portion 249 separates from the beveled edge and the proximal opening 205 of the shunt 200 in communication with the lumen 207 in a swing motion or hinged-like fashion, allowing fluid flow out of the lumen 207 (FIG. 6S). The valve 209 includes a second portion 259 configured to cover a portion of the outer surface 206 of the shunt 200, as shown in FIGS. 6R-T. The first 249 and second 259 portions of the valve 209 may be formed by creating a cut or slit 269 in the molded silicone element of the valve 209.

When the shunt 200 having the valve 209 of FIGS. 6P-T is implanted at the target site in a patient, as previously described, the first portion 249 can open from the closed configuration (FIGS. 6P-R) to the opened configuration (FIG. 6S) under positive differential pressure conditions between the subarachnoid space 116 (e.g., CP angle cistern 138) and the venous system (e.g., jugular vein 106). A relatively large surface area of first portion 249 provides a substantial swing motion when opening the valve 209 to facilitate clearing of any aggregated materials inside shunt 200 (e.g., CSF proteins, arachnoid layer cells), and can accommodate a wide range of flow rates with relatively low opening or cracking pressure (e.g., about 3 mm Hg to about 5 mm Hg). The first portion 249 can also open to receive the guidewire 308, as shown in FIG. 6T to assist with the navigation and deployment of the shunt 200, as described herein. Under negative differential pressure conditions (e.g., where venous blood pressure exceeds intracranial pressure in subarachnoid space 116, such as during sneezing or coughing events), the first portion 249 closes to seal, shut and/or close the valve 209 (FIG. 6R) preventing venous blood from flowing back through the shunt 200 into the subarachnoid space 116. The large surface area of the first portion 249 provides a substantial area for negative pressure (−P) to compress against and seal the valve 209 closed to prevent backflow of material through shunt 200 (FIG. 6R).

In addition to controlling flow of CSF from the subarachnoid space to the venous system, shunt 200 preferably prevents backflow of blood from the jugular bulb 108 and vein 106 through shunt lumen 207 into the subarachnoid space 116. Having one-way valves in the shunt 200 are particularly advantageous, as they allow CSF to be in fluid communication from the CP angle cistern 138 into the venous circulatory system (e.g., the jugular bulb 108, jugular vein 106), while preventing backflow of venous blood into the subarachnoid space 116 (e.g., CP angle cistern 138).

In some embodiments, the one or more valves in the shunt 200 can be detachable from the shunt 200. For example, referring to FIG. 6, the valve 209 includes an attachment mechanism 211 that connects the valve 209 to the body 203 of the shunt 200. The valve 209 can be detached and removed from the shunt 200, even when the shunt 200 is implanted, by activating the mechanism 211 (e.g., by actuating the mechanism 211 using a guide wire inserted into shunt 200). In some embodiments, the shunt 200 includes a plurality of different valves 209, where each valve allows for a different rate of fluid flow. A clinician can control the rate at which CSF drains from the CP angle cistern 138 into the jugular bulb 108 and/or the jugular vein 106, for example, by selectively connecting one or more suitable valves to the shunt 200.

The valve 209 (or a combination of valves), and/or another type of flow regulating device (e.g., constriction of the inner diameter of shunt 200 for a particular length as previously described, compressed shunt body 203 narrowing lumen 207, FIG. 6M), is configured to achieve a desired rate of flow of CSF from the CP angle cistern 138 into the jugular bulb 108 and/or the jugular vein 106. For example, duckbill, slit, and windsock valve configurations typically cannot regulate flow based on valve cracking pressure alone; once opened, such valves continuously seep fluid and therefore, can be combined with a constriction of the inner diameter of shunt 200 for a particular length as previously described to further regulate CSF flow. A desired rate of flow is in a range between 5 ml per hour to 20 ml per hour and more desirable between 10 ml per hour to 18 ml per hour. In some embodiments, the desired flow rate of CSF is approximately 10 ml per hour. In a 24-hour period, the flow of CSF through shunt 200 can be between 200 ml to 300 ml (e.g., 200, 225, 250, 275, or 300 $cm^3$).

In some embodiments, the shunt 200 can include an anti-thrombotic coating to prevent thrombosis induced by the deployment of the shunt 200. For example, the shunt 200 may include an anti-thrombotic coating 221 disposed along the length of the shunt body 203. Anti-thrombotic coating 221 can generally be applied to any one or more of the inner surfaces and/or outer surface of the shunt 200. In addition, the anti-thrombotic coating 221 can be applied along the entire length of shunt 200, or alternatively, only on selected portions of the inner and/or outer surfaces of shunt 200 (e.g., in the proximate to or in the vicinity of the end(s) of shunt 200). Suitable materials that can be used to form anti-thrombotic coating 221 include, for example, Parylene, polytetrafluoroethylene derivatives, and Heparin.

The shunt 200 is composed of biocompatible materials. Suitable materials include, for example, platinum, Nitinol®, gold, or other biocompatible metal and/or polymeric materials, for example, silicon, or combinations thereof. In some embodiments, the shunt 200 may include materials that are compatible with magnetic resonance imaging and have radiopacity sufficient to allow imaging with the use of the various techniques disclosed above. For example, one or more markings formed of a radio-opaque material may be applied to the surfaces of shunt 200 to assist in vivo imaging of the shunt 200 during delivery and deployment (i.e., implantation in target site). Suitable markers may be included (e.g., embedded) or applied (e.g., coatings) to the outer surface 206 of the shunt 200 in a pattern that is readily recognized by a clinician. An example of radio-opaque materials that can be applied for markings is barium sulfate. Such markers can also be applied to the catheters and/or guidewires used during a shunting procedure to assist in vivo imaging of the various system components during shunt 200 delivery and deployment.

In some embodiments, portions of the shunt 200 may be composed of flexible materials, or the shunt 200 may have portions of various degrees of flexibility. For example, the distal portion 202 is composed of a flexible material so that the distal portion 202 is more flexible than the body 203 of the shunt 200 (FIG. 6). Suitable materials may compose the distal portion 202 of shunt 200, which may include flexible, elastomeric materials such as silicone or Nitinol (e.g., Nitinol hypotube with a reduced wall thickness or an ePTFE-lined Nitinol hypotube with a latticed or relief cut configuration to increase flexibility for navigating tortuous anatomy). The flexible shunt 200, particularly the flexible distal portion 202, facilitates bending of the shunt 200 within delivery catheter 304, so that the shunt 200 creates and/or accesses the anastomosis channel 140 into the CP angle cistern 138 at a suitable angle relative to the IPS 102 (e.g., FIG. 4D). Referring back to FIG. 6, the distal portion 202 composed of flexible materials allows for bending of the portion 202 in an axis 233, so that the distal portion 202 is configured to access the CP angle cistern 138 via the anastomosis channel 140, at an angle "A". The distal portion 202 of the shunt 200 may be pre-curved, biasedly curved, flexible, bendable via control wires or the like or combinations thereof, in an angle with respect to the body 203 axis 231 to form a suitable angle relative to the central axis 103 of the IPS 102 for penetration and/or implantation of the shunt 200 through the anastomosis channel 140. The angle "A" may be in a range of 5 degrees to 80 degrees between axes 231 and 233.

In some embodiments, the distal portion 202 of the shunt 200 can be cut in an angle to form a piercing element (e.g., sharp, tapered, cannula-like end, or bevel, pencil, or Quincke tip) allowing piercing the IPS wall 114 and the arachnoid layer 115. As shown in FIG. 6, the angle "C" of the distal portion 202 with respect to axis 233 can be selected as desired for a particular "sharpness" of the piercing element. In some embodiments, angle "C" is between 5 degrees to 80 degrees with respect to axis 233.

The shunt 200 can include one or more anchoring mechanisms 225 positioned along the body 203 of shunt 200, as shown in FIG. 6. The anchoring mechanisms 225 allow the implanted shunt 200 to be secured in the target site, and allow the shunt 200 to remain in the implanted location (e.g., FIG. 3A). The anchoring mechanisms 225 can include one or more configurations, such as, hooks, barbs, expandable arms, petal-like, coil-like, malecot, elliptecot, T-bar features, or the like, or combinations thereof. The anchoring mechanisms 225 can be disposed in one or more portions of the shunt 200. The anchoring mechanisms 225 include a delivery configuration in which the mechanism 225 is radially constrained, and a deployed configuration in which the mechanism 225 is radially expanded. The anchoring mechanisms 225 may include self-expanding features so that the mechanism radially expands when the shunt 200 is deployed out of the delivery catheter 304 and/or guide catheter 320. Additionally or alternatively, the anchoring mechanisms 225 may be selectively actuated into the deployed configuration, for example, with the use of a guidewire (e.g., guidewire 302, delivery guidewire 308) inserted into the shunt 200.

In some embodiments, the shunt 200 may include one or more anchoring mechanisms 225 disposed at the distal portion 202 of the shunt 200, which secures the implanted shunt 200 in situ at the IPS 102, and particularly securing the distal portion 202 within CP angle cistern 138. In some embodiments, the shunt 200 may further include one or more anchoring mechanisms 225 disposed at the proximal portion 204 of the shunt 200, which secures the implanted shunt 200 in situ at the IPS 102, and particularly securing the proximal portion 204 within the junction 118, jugular bulb 108 and/or jugular vein 106. The anchoring mechanism 225 can be collapsible to allow for shunt retrieval and/or replacement. It will be appreciated that combinations of different anchoring mechanisms may be used in the proximal portion 204 and/or the distal portion 202 of the shunt 200.

Figure 7:
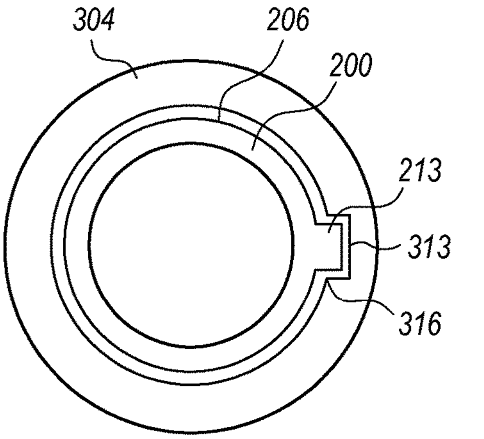
FIG. 7 is a cross-sectional view of an endovascular shunt and a catheter interface according to embodiments of the disclosed inventions.

In some embodiments, the shunt 200 can include one or more features that allow for accurate guidance, navigation and/or control of the shunt 200, particularly when passing the shunt 200 from the jugular bulb 108 or jugular vein 106 through the junction 118 into the IPS 102, and/or into the anastomosis channel 140. FIG. 7 illustrates a cross-sectional view the shunt 200, according to one embodiment of the disclosed inventions. The shunt 200 includes a protruding rib 213 extending along an outer surface 206 of the shunt 200. The rib 213 is dimensioned and configured to engage a cooperating recess 313 in the delivery catheter 304. The recess 313 is formed within an inner surface 316 of the delivery catheter 304. When the shunt 200 is inserted into the delivery catheter 304, the rib 213 and recess 313 slidably engage, allowing the shunt 200 to be guided in a desired orientation within delivery catheter 304.

The embodiment shown in FIG. 7 is an exemplary control feature that can be implemented in connection with the shunt 200. In some embodiments, the shunt 200 and the delivery catheter 304 can include a plurality of such features (e.g., a plurality of ribs that engage with a plurality of recesses). Although the shunt 200 includes a rib 213 in FIG. 7, in an alternative embodiment, the delivery catheter 304 can include a rib, and the shunt 200 may include a recess dimensioned and configured to slidably engage with the delivery catheter 304.

Additionally or alternatively, the guide catheter 320 can include features that engage with the control features of shunt 200 (e.g., one or more rails or recesses) and/or delivery catheter 304. For example, the delivery catheter 304 and the guide catheter 320 can each include one or more features that engage with the control features of shunt 200. Further, the delivery catheter 304 and the guide catheter 320 can include control features (e.g., one or more ribs or recesses) that cooperatively engage, allowing the catheters 304, 320 to move relative to one another in a controlled orientation. Cooperatively engaging features can also be employed between the delivery guidewire 308 and the delivery catheter 304, and between the elongate pusher member 310 and the delivery catheter 304 and/or the guide catheter 320. Examples of such features include any of the features discussed above in connection with shunt 200 and delivery catheter 304.

Figure 8:
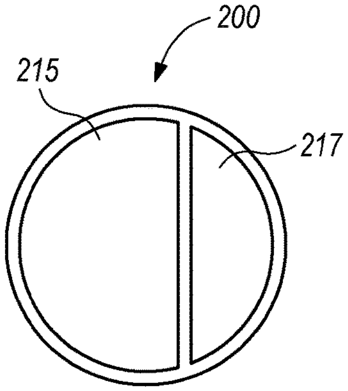
FIG. 8 is a cross-sectional view of an endovascular shunt according to embodiments of the disclosed inventions.

FIG. 8 illustrates a cross-sectional view of the shunt 200 having a first lumen 215 and a second lumen 217 constructed in accordance with embodiments of the disclosed inventions. The first lumen 215 is configured to allow flow of CSF from the CP angle cistern 138 into the jugular bulb 139 and/or the jugular vein 106, as discussed above. The second lumen 217 is configured to allow a guidewire (e.g., guide wire 302, delivery guide wire 308, elongate pusher member 310, tissue penetrating member 250, tissue penetrating member 250, actuating guidewire or the like) to be inserted and slidably disposed into, and through, the shunt 200. The guidewire can be used by a clinician to assist with navigation and deployment of the shunt 200 in a target site. Further, the clinician can use the guidewire within the second lumen 217 to access shunt components (e.g., valves, anchoring mechanisms). In some embodiments, the clinician can use a penetrating element (e.g., tissue penetrating member 306, 250, 350) attached to a guidewire that passes through the second lumen 217 to pierce the IPS wall 114 and access the CP angle cistern 138. Additionally, the clinician can confirm that CSF flow path between the CP angle cistern 138 and the jugular bulb 108 and/or the jugular vein 106 remains open, and/or dislodge any occlusions in either of the lumens 215 and/or 217. In some embodiments, CSF can be withdrawn by the clinician through either lumen 215 or 217 of the shunt 200, confirming that the IPS wall 114 has been penetrated, the CP angle cistern 138 accessed, and the anastomosis 140 has been created. In other embodiments, the shunt 200 may include a plurality of lumens, for example, more than the two lumens 215 and 217.

Figure 9:
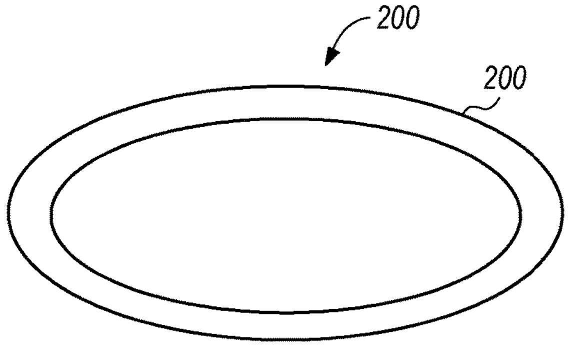
FIG. 9 is cross-sectional view of an endovascular shunt according to another embodiment of the disclosed inventions.

Additionally, the cross-sectional configuration of the shunt 200 may be of any suitable configuration for shunt implantation in the IPS 102. For example, the cross-sectional configuration of the shunt 200 may have a circular (FIG. 8), non-circular (e.g., elliptical), or any other regular or irregular configuration. FIG. 9 illustrates an elliptical cross-sectional configuration of the shunt 200, according to the embodiments of the disclosed inventions. The elliptical cross-sectional configuration of the shunt 200 may be a better support for a sharp, tapered, cannula-like end of the distal portion 202 of the shunt 200 than a circular cross-sectional configuration.

Figure 10:
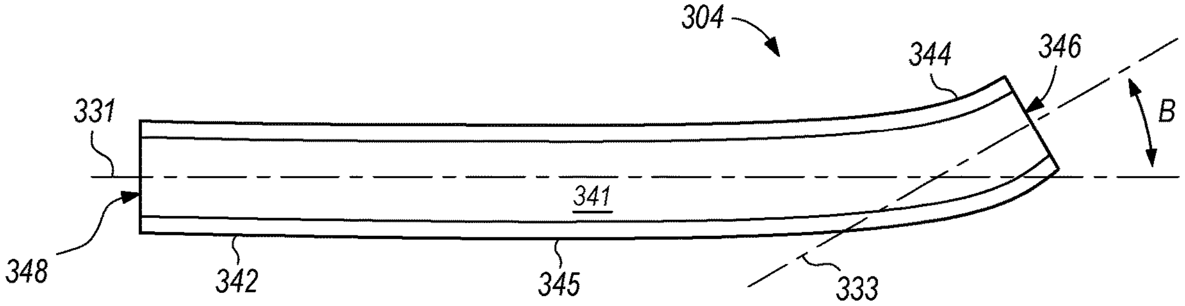
FIG. 10 is a cross-sectional view of a delivery catheter according to embodiments of the disclosed inventions.

FIG. 10 illustrates the delivery catheter 304 constructed according to embodiments of the disclosed inventions. The catheter 304 includes an elongate body 345 that extends along an elongate axis 331. The delivery catheter 304 includes a proximal portion 342, an elongate body 345, a distal portion 344, and a lumen 341 extending therebetween. The delivery catheter 304 includes a proximal opening 348 in the proximal portion 342 in fluid communication with the lumen 341. The delivery catheter 304 further includes a distal opening 346 in the distal portion 344 in fluid communication with the lumen 341. The distal portion 344 of catheter 304 is curved (e.g., pre-curved, biasedly curved, flexible, drivable distal portion via control wires or the like or combinations thereof) relative to the catheter body 345 and/or axis 331. The distal portion 344 allows for bending in an axis 333, so that the distal portion 344 is configured to access the CP angle cistern 138 via the anastomosis channel 140 created during shunt deployment, at an angle "B" for deployment of the shunt 200. The angle "B" may be in a range of 5 degrees to 80 degrees between axes 331 and 333.

In accordance with the disclosed inventions, the distal portions 202, 324, 344 of either of the shunt 200, guide catheter 320 and/or delivery catheter 304 are configured to curve and/or bend. Exemplary variations of some of the largest and smallest straight angles, as well as some the largest and smallest bend angles, for an IPS 102 having a diameter ranging from 2 mm to 4 mm are shown in FIGS. 11A-C. Such angles can also be used to assess whether delivery system assembly 300 and penetrating element 250 or 350 configurations disclosed herein can achieve a desired penetration angle into IPS wall 114 for a given IPS diameter.

It should be appreciated that the angle variations depicted in FIGS. 11A-C are exemplary and not intended to limit the embodiment of FIGS. 11A-C.

FIG. 12 illustrates one embodiment of the shunt 200, constructed in accordance with the disclosed inventions. The shunt 200 includes a plurality of anchoring mechanisms 225. An anchoring mechanism 227 may extend from and/or be disposed on the proximal portion 204 of the shunt 200, and an anchoring mechanism 229 may extend from and/or be disposed on the distal portion 202 of the shunt 200. The anchoring mechanism 227 has a delivery configuration and a deployed configuration, as described above for the anchoring mechanism 225. Alternatively or additionally, the anchoring mechanism 227 and 229 may be disposed on a conduit 400 (e.g., collapsible barbs 425 depicted in FIG. 12).

The anchoring mechanism 227 may include any suitable anchoring configuration, such as, a spring-loaded plug, stent, mesh, malecot, or the like, coupled to the proximal portion 202. The anchoring mechanism 227 may be composed of a shape-memory material such as Nitinol®, expandable material, such as swellable polymeric foams, or the like or combinations thereof. The anchoring mechanism 227 is configured to engage the junction 118 where the IPS 102 enters the jugular bulb 108 and/or jugular vein 106, and/or is configured to engaged the jugular bulb 108 or jugular vein 106, securing and preventing movement of the shunt 200 when implanted, particularly, securing the proximal portion 204 of the shunt 200 in situ. For example, prior to deployment of the shunt 200, the anchoring mechanism 227 is radially constrained allowing passage of the shunt 200 through the junction 118 in the IPS 102. Once the shunt 200 is deployed, the anchoring mechanism 227 radially expands within the junction 118 (e.g., self-expansion, swelling due to absorption of fluid and/or increased temperature) to anchor shunt 200 at the proximal portion 204 as shown in FIG. 12. Additional embodiments of the anchoring mechanism 227 will be described in further detail below.

The anchoring mechanism 229 that extends from the distal portion 202 of the shunt 200 is configured to engage the arachnoid layer 115 and/or the exterior portion of the IPS wall 114 when the shunt 200 is implanted in the target site (e.g., IPS 102, anastomosis channel 140, CP angle cistern 138). The anchoring mechanism 229 has a delivery configuration and a deployed configuration, as described above for the anchoring mechanism 227. The anchoring mechanism 229 may include any suitable anchoring configuration. For example, the anchoring mechanism 229 includes an umbrella-type configuration having a plurality of wires aligned approximately along the axis of shunt 200. Once the shunt 200 accesses the CP angle cistern 138, the anchoring mechanism 229 is actuated, so that the mechanism 229 radially expands securing the distal portion 202 of the shunt 200 in situ. Mechanism 229 advantageously compresses or pins down the arachnoid layer 115, around the penetration site in the subarachnoid space 116, against the dura mater comprising the exterior portion of IPS wall 114, to prevent occlusion of the shunt lumen 207 (e.g., by arachnoid mater). In some embodiments, the anchoring mechanism 229 may be actuated using a guidewire inserted into shunt 200 and coupled to the mechanism 229, so that retracting the guidewire forces the mechanism wires in an outward radial direction from the axis of shunt 200, thereby anchoring the shunt 200. Alternatively, the anchoring mechanism 229 can be a collapsible, self-expanding umbrella-type mechanism that remains radially constrained while in the delivery catheter 304 and/or guide catheter 320, and radially expands upon deployment from such catheters into the CP angle cistern 138. In some embodiments, the anchoring mechanism 229 may include a self-expanding circular basket with multiple collapsible tines and/or a multi-filament globe-like.

The anchoring mechanism 229 forms an anchor by having a diameter, in the deployed configuration (e.g., 3 mm to 5 mm), larger than the diameter of the anastomosis channel 140. Therefore, the deployed anchoring mechanism 229 is sufficiently wide to avoid passage through the anastomosis channel 140, thereby securing the shunt 200 within CP angle cistern 138. Additionally, the anchoring mechanism 229 is configured to form a seal at the anastomosis channel 140 preventing flow of blood into the CP angle cistern 138. The seal formed by the anchoring mechanism 229 further prevents occlusion or clogging of the shunt lumen 207 at the distal portion 202 by avoiding the access of blood into the CP angle cistern 138 from the IPS 102.

In some embodiments, the anchoring mechanism 227 and 229 can be collapsible to facilitate shunt retrieval and/or replacement. Additional aspects and features of suitable anchoring mechanisms for use with shunt 200 are disclosed, for example, in U.S. Patent Application Publication No. 2015/0196741 and published PCT Application WO2015/108917, both filed on Jan. 14, 2015, the entire contents of all of which are incorporated by reference. It will be appreciated that combinations of different anchoring mechanisms may be used in the proximal portion 204 and/or the distal portion 202 of the shunt 200/200'.

In some embodiments, a conduit 400 can be used to house the shunt 200 when deployed within the IPS 102 (FIG. 12). The conduit 400 is composed of a biocompatible material configured to be disposed within the IPS 102 prior to the deployment of the shunt 200 (FIGS. 14A-F). The shunt 200 is configured for deployment within the conduit 400. The conduit 400 includes a tubular configuration having a proximal portion 404, a distal portion 402 and a lumen 407 extending therebetween. The deployed conduit 400 extends proximally from a target penetration site in IPS wall 114 or from within the CP angle cistern 138 adjacent through IPS 102 into the jugular bulb 108 and/or jugular vein 106. The conduit 400 may include one or more anchoring mechanisms 425 that secure the conduit 400 within the IPS 102. The anchoring mechanisms 425 may have any suitable configuration, for example, hooks, barbs or the like that engage the IPS wall 114 when the conduit 400 is deployed. The distal portion 402 of conduit 400 may be curved in a manner similar to the distal portion 202 of shunt 200 and/or delivery catheter 304 to facilitate entry of shunt 200 into CP angle cistern 138 at a desired angle. The conduit 400 is composed of a suitable expanding material, such as, biocompatible polymeric material that expands when heated (i.e., upon deployment into IPS 102).

The conduit 400 may include an expandable stent-graft configuration. FIGS. 13A-C are expandable stent-grafts known in the art that may be used to construct the conduit 400. FIG. 13A illustrates a stent-graft in a collapsed state, FIG. 13B in a partially-expanded state, and FIG. 13C in an expanded state. Further, the conduit 400 may include a self-expandable or collapsible metal stent or metal mesh-like scaffold that supports a biocompatible heat expandable fabric covering the scaffold.

Figure 14A:
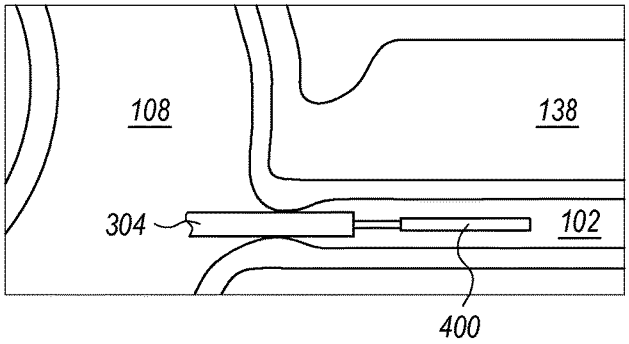
FIGS. 14A-14H are side and cross-sectional views of deployment of a conduit and an endovascular shunt according to yet another embodiment of the disclosed inventions.
Figure 14B:
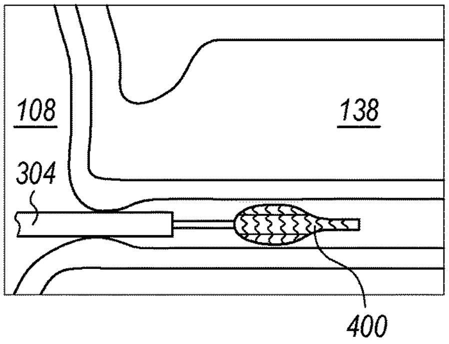
Figure 14C:
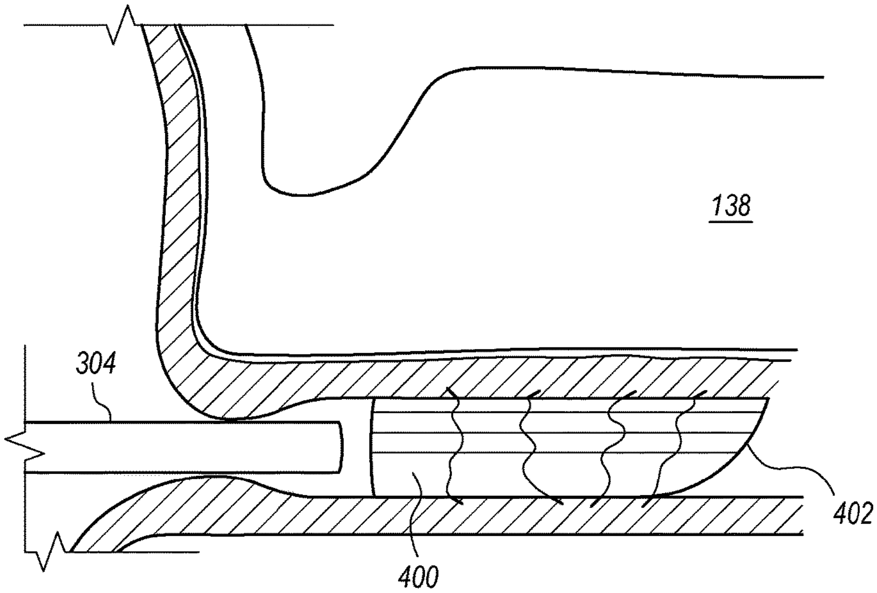
Figure 14D:
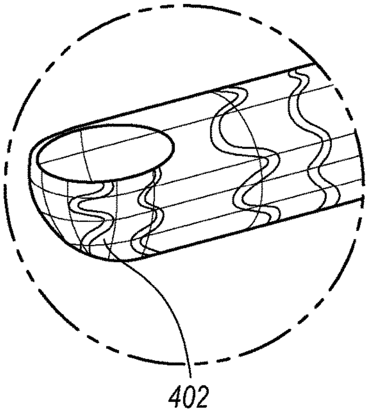
Figure 14E:
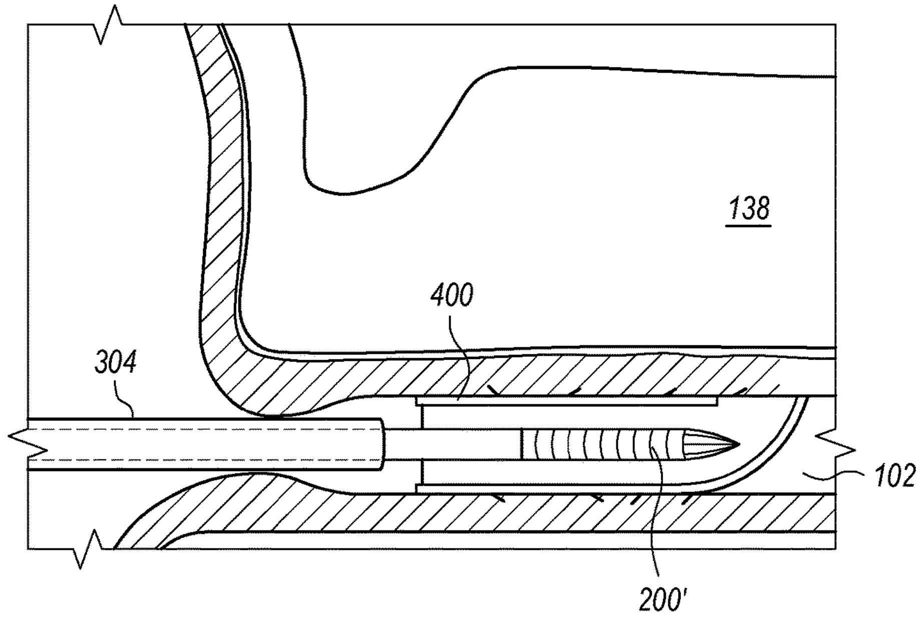
Figure 14F:
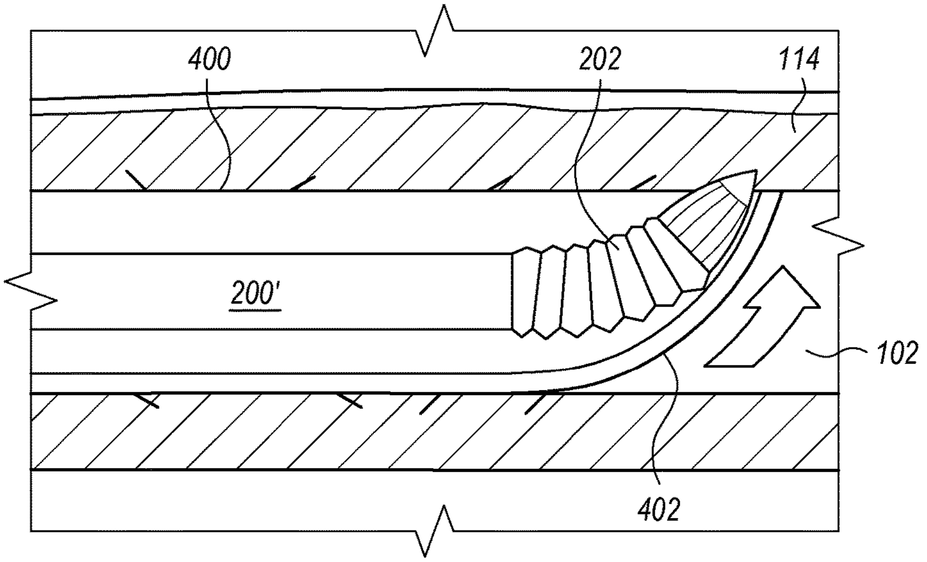
Figure 14G:
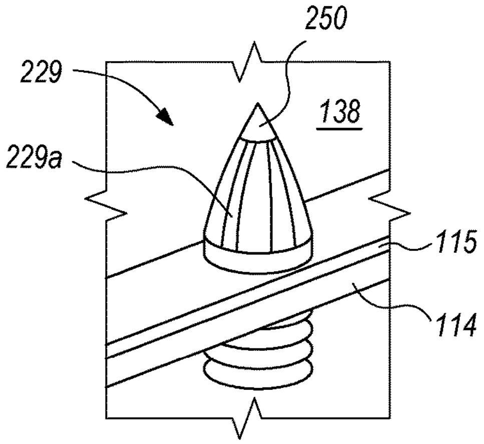
Figure 14H:
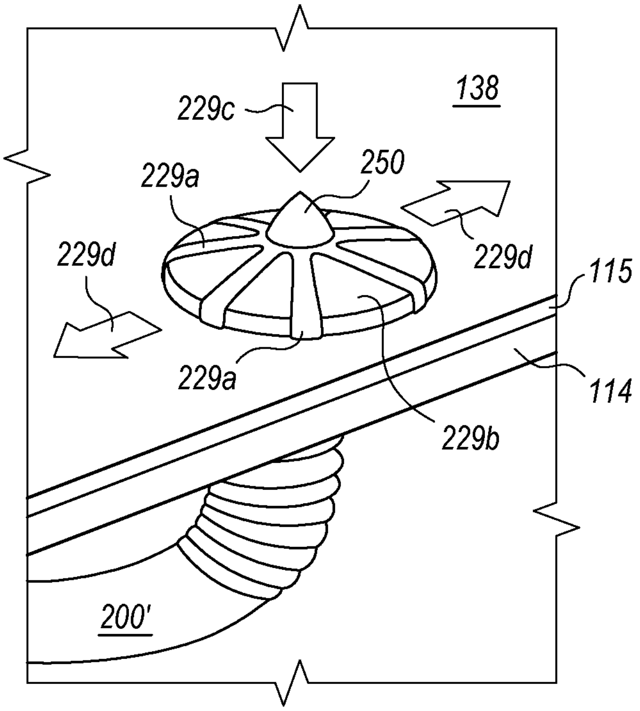

FIGS. 14A-H illustrate an exemplary method of delivering the shunt 200' within the conduit 400 according embodiments of the disclosed inventions. Although, the shunt 200' incorporating a piercing element is used to describe the method of deployment in FIGS. 14A-H, it should be appreciated that any configuration of the shunt 200 may be used in this method of deployment. The conduit 400 is deployed through a catheter (e.g., delivery catheter 304) in a radially constricted configuration (FIG. 14A). The conduit 400 radially expands within the IPS 102, for example, after withdrawal of the delivery catheter 304 if the conduit 400 is self-expanding, or by heating the conduit 400, or the like, or combination thereof (FIG. 14B). The expanded and implanted conduit 400 within the IPS 102 is shown in FIG. 14C. FIG. 14D is an insert of FIG. 14C and illustrates a further detail of the curved distal portion 402 of the conduit 400, which facilitates guidance of shunt 200' into CP angle cistern 138 through the IPS wall 114 and arachnoid layer 115 to create the anastomosis channel 140. In FIG. 14E, the shunt 200' is advanced through the delivery catheter 304 into the conduit 400 implanted in the IPS 102. The navigation and advancement of the shunt 200' may be assisted by the use of a guidewire, as previously disclosed. As shown in FIG. 14F, when the shunt 200' reaches the curved the distal portion 402 of conduit 400, the distal portion 202 of the shunt 200' bends to follow the curved profile of the conduit 400. As the shunt 200' is advanced within the conduit 400, the shunt 200' is directed toward the IPS wall 114. Once the shunt 200' reaches the IPS wall 114, a clinician applies suitable force to the shunt 200' (e.g. via a guidewire coupled to the shunt 200') and the tissue penetrating member 250, incorporated in the shunt 200, penetrates and pierces the IPS wall 114 creating the anastomosis channel 140, so that the distal portion 202 of shunt 200' accesses the CP angle cistern 138 (FIG. 14G). The creation of the anastomosis 140 is also described above in FIGS. 5E-G. The shunt 200' includes the anchoring mechanism 229; in particular, the anchoring mechanism shown in FIGS. 14G-H is the distal portion anchoring mechanism 229, which includes a plurality of deformable elements **229*a* (e.g., arms) and a mesh 229*b*. The deformable elements/arms 229 are expandable members that may include any suitable configuration to allow outward, radial expansion, such as members composed of bendable or deformable materials (e.g. Nitinol®). The mesh 229*b* allows for fluid communication into the lumen 207 of the shunt 200' so that CSF in the CP angle cistern 138 flows through the implanted shunt 200' into the jugular bulb 108 and/or jugular vein 106. The mesh 229*b* functions as the distal opening 219 of the shunt 200', as shown in FIG. 5I, and may comprise any other suitable configurations (e.g. perforations, porous material or the like). The arms 229*a* are coupled to the tissue penetrating member 250, so that when a retrograde force 229*c* is applied (e.g. via a guidewire), the tissue penetrating member 250 retracts causing the arms 229*a* to bend, expand or deform in a radially outward direction 229*d*, as shown in FIG. 14H, anchoring the distal portion 202 of shunt 200' within CP angle cistern 138**.

Alternatively, the arms **229*a* are detachably coupled to the tissue penetrating member 250, so that the tissue penetrating member 250 may be detached and removed from the implanted shunt 200', as shown in FIG. 5**J.

Figure 15A:
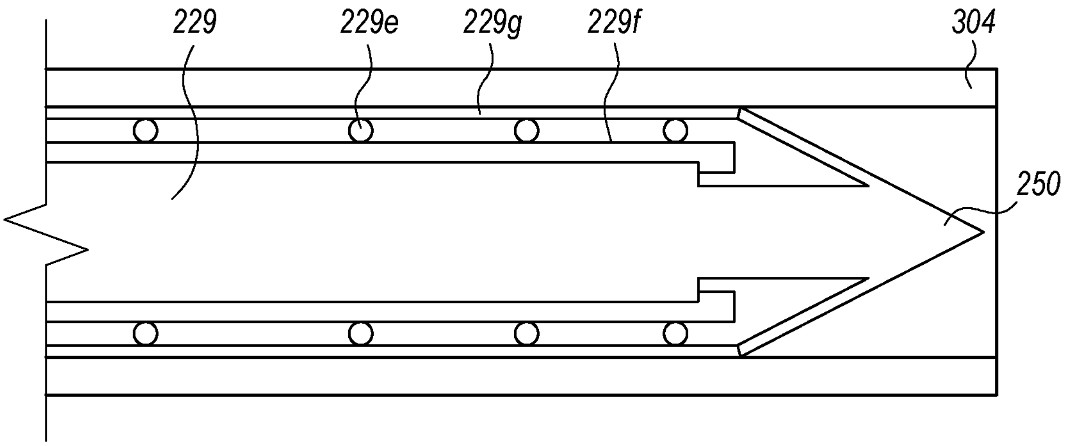
FIGS. 15A-15D are cross-sectional and side views of deployment an endovascular shunt according to one embodiment of the disclosed inventions.
Figure 15B:
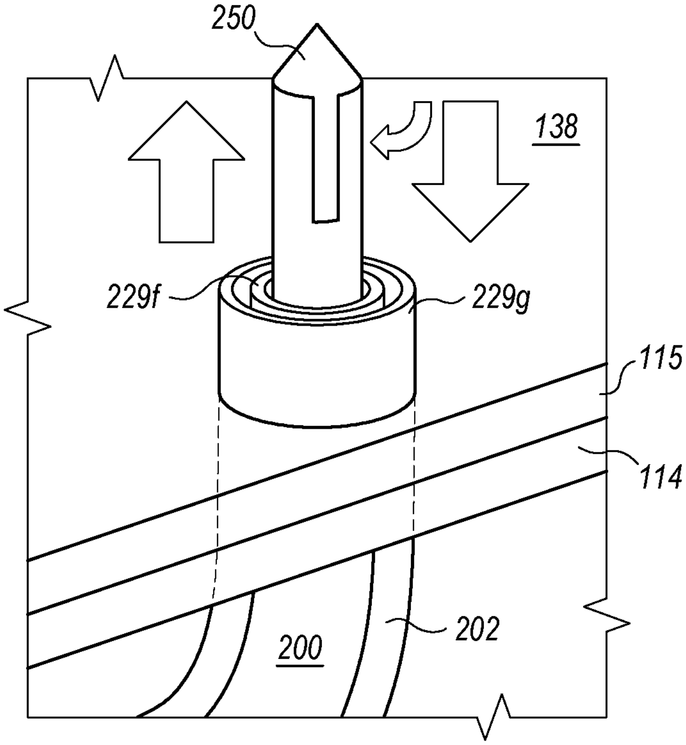
Figure 15C:
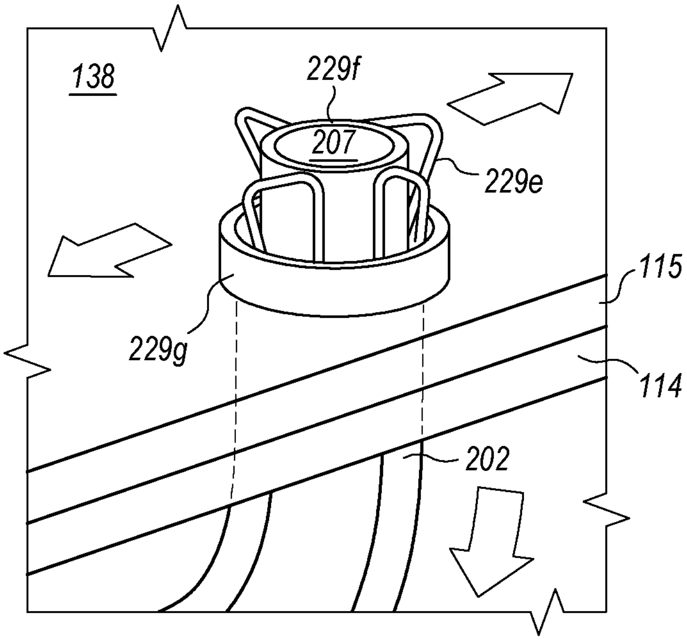
Figure 15D:
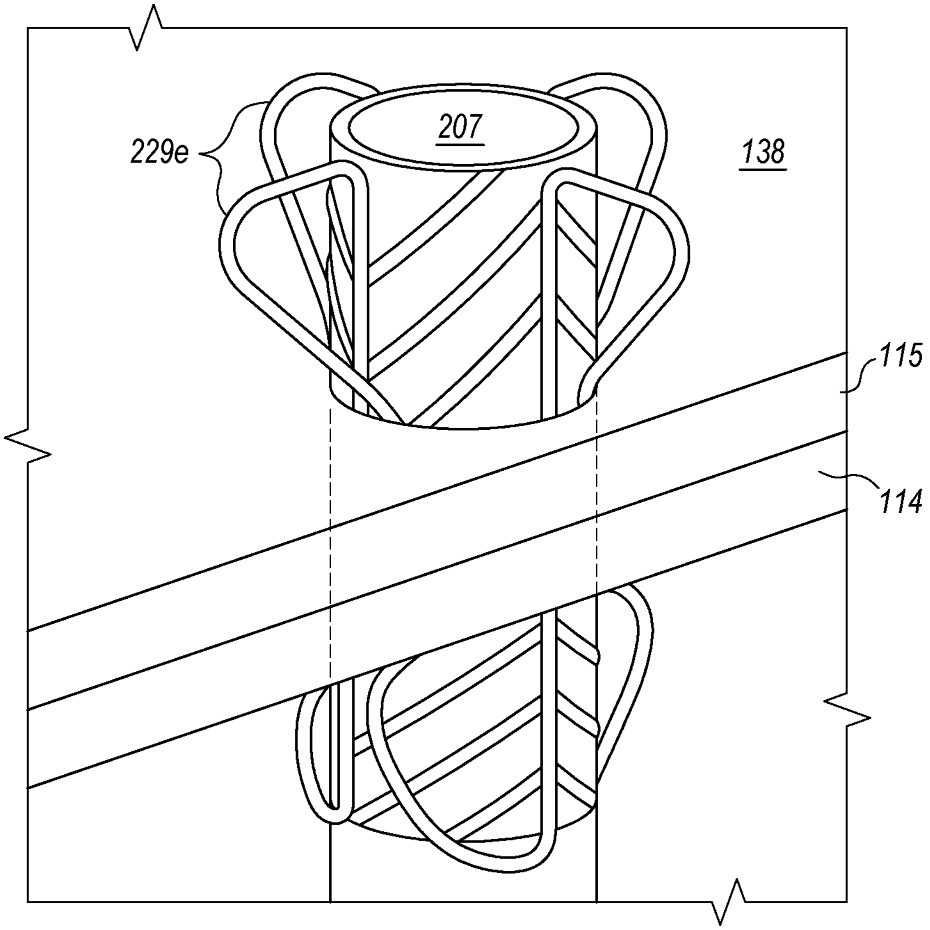

FIGS. 15A-D illustrate detailed cross-sectional views of an alternative embodiment of the anchoring mechanism 229 and, an exemplary method of delivering the shunt 200 at the target site according embodiments of the disclosed inventions. As shown in FIG. 15A, the anchoring mechanism 229 includes an inner sheath **229*f*, a deformable element 229*e*, and an outer sheath 229*g* slidably disposed over the inner sheath 229*f* and element 229*e*. The deformable element 229*e* (e.g., arms, wires, loops, layer, or the like) includes a radially constrained delivery configuration (e.g., outer sheath 229*g* disposed over element 229*e*, as shown in FIGS. 15A-B), and a radially expanded deployed configuration (e.g., withdrawn outer sheath 229*g* as shown in FIG. 15D). The deformable element 229*e* are composed of shape memory material, e.g., Nitinol®, of any suitable biocompatible metal, alloys, polymeric materials or combinations thereof. The elements 229*e* are coupled to the inner sheath 229*f*, for example, by adhesive, thermal bonding, welding or the like, or combinations thereof, or by any other suitable methods. The deployed configuration of the deformable element 229*e* is configured to expand, anchor and secure the distal portion 202 of the shunt 200 at the IPS wall 114 within the CP angle cistern 138. The tissue penetrating member 250, disposed within the anchoring mechanism 229, is detachably coupled to the anchoring mechanism 229 and/or the shunt 200, so that the tissue penetrating member 250 is detached and removed when the shunt 200** is delivered and implanted at the target site.

After the tissue penetrating member 250 has created the anastomosis channel 140 in the IPS wall 114, the distal portion 202 of the shunt 200, including the anchoring mechanism 229, is advanced by applying suitable force in a distal direction (indicated by the arrow in the top left portion FIG. 15B). Portions of the inner sheath **229*f* and the outer sheath 229*g* extend into the CP angle cistern 138 via the anastomosis channel 140. Once inside the CP angle cistern 138, the tissue penetrating member 250 is detached and withdrawn from the shunt 200 by applying suitable force in a proximal direction (indicated by the arrow in the top right portion of FIG. 15B). The outer sheath 229*g* is also withdrawn, therefore exposing the deformable element 229*e* in the deployed configuration, and further exposing the inner sheath 229*f* that defines the lumen 207 of shunt 200, as shown in FIG. 15B. The deformable element 229*e*, shown in FIGS. 15C-D, includes a plurality of Nitinol® wires that radially expand in the deployed configuration, and are configured to anchor and secure the shunt 200 distal portion 202 against arachnoid layer 115 and/or the exterior of IPS wall 114 (i.e., dura mater), and within CP angle cistern 138**.

Figure 16:
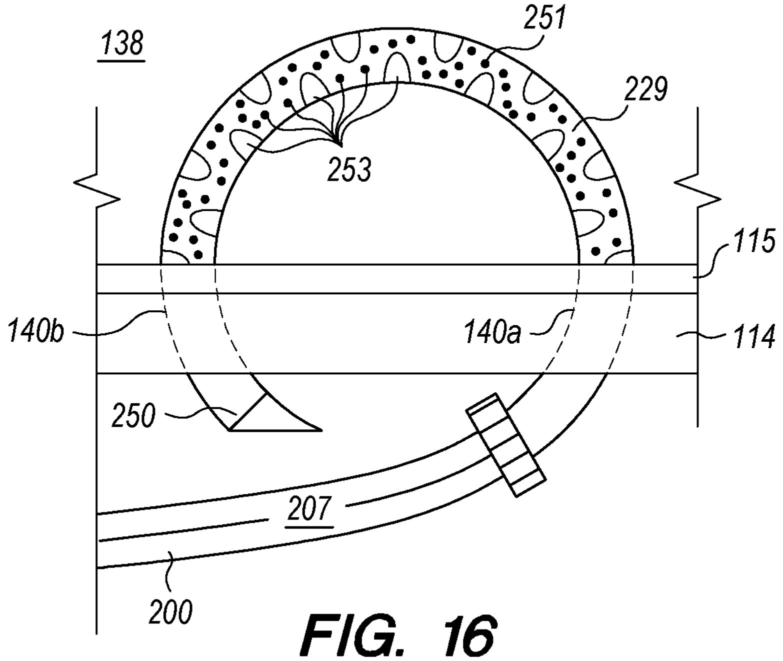
FIG. 16 is a side view of a deployed endovascular shunt according to another embodiment of the disclosed inventions.

FIG. 16 illustrates a side view of an alternative distal anchoring mechanism 229 in accordance to embodiments of the disclosed inventions. The anchoring mechanism 229 includes a body 251 (e.g., pre-curved, biasedly curved, flexible, drivable distal portion via control wires, or the like, or combinations thereof) composed of shape memory materials (e.g., Nitinol®) or other deformable materials, or combinations thereof. The anchoring mechanism 229 comprises a delivery configuration (e.g., elongated for advancement through the delivery assembly 300 and/or conduit 400) and a deployed configuration (e.g., curved or arc between 180 degrees to 340 degrees). The anchoring mechanism 229 further includes an angled tissue penetrating member 250 configured to facilitate the piercing of the IPS wall 114 and arachnoid layer at a first point of entry from within the lumen of IPS 102 into the CP angle cistern 138, creating a first anastomosis channel **140*a*, and at a second point of entry from the CP angle cistern 138 returning into the lumen of IPS 102, creating a second anastomosis channel 140*b*. Particularly, after the first anastomosis channel 140*a* is created and as the body 251 curves and further advances, the tissue penetrating member 250 once again contacts and pierces the IPS wall 114 at the second point of entry creating the second anastomosis 140*b*. Therefore, the distal portion 202 of the shunt 200 is anchored and secured in situ by having portions of the body 251 of the anchoring mechanism 229 disposed through both anastomosis channels 140*a* and 140*b*, preventing dislodging of the implanted shunt 200**.

The body 251 of the anchoring mechanism 229 includes openings 253 (i.e., holes, porous, perforations, or the like, or combinations thereof), allowing fluid communication into the lumen 207 of the shunt 200, so that CSF disposed in the CP angle cistern 138 is drained when the shunt 200 is implanted, according to the embodiments of the disclosed inventions. The openings 253 are formed in the body 251 of the anchoring mechanism 229 configured to be disposed within the CP angle cistern 138 when the shunt 200 is implanted. It should be appreciated that portions of the body 251 of the anchoring mechanism 229 that are configured to be disposed within the IPS wall 114 at the anastomosis channels 140*a* and 140*b* and/or within the IPS 102 (e.g., distal and proximal portions the anchoring mechanism 229), do not include any openings 253, so that blood flow through the shunt 200 is prevented or avoided. The size and position of the openings 253 can be selected to alter the physical properties of the body 251, for example, varying the extent of the curvature, and the stiffness of the body 251 of the anchoring mechanism 229.

FIGS. 17A-B, 18A-B, and 19A-B describe exemplary embodiments of the distal portion 202 of the shunt 200' having the tissue penetrating member 250, configured to achieve a suitable angle for piercing the IPS wall 114 and the arachnoid layer 115 for implantation of the shunt 200' and creating the anastomosis channel 140 into CP angle cistern 138. It should be appreciated that the aspects and features of the embodiments described in FIGS. 17A-B, 18A-B, and 19A-B can be incorporated into the distal portion 202 of the shunt 200, the distal portion 344 of the delivery catheter 304, the distal portion 324 of the guide catheter 320, the distal portions of the guidewires (308, 304, 310) and/or any other element of the delivery assembly 300 configured to be disposed in the proper angle and orientation relative to the IPS wall 114 for penetration and/or implantation, according to the disclosed embodiments.

Figure 17A:
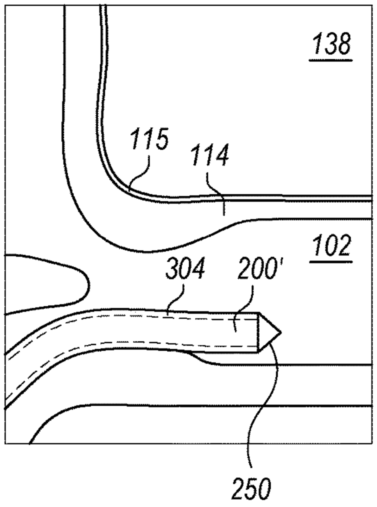
FIGS. 17A-B are cross-sectional views of an endovascular shunt having a pre-curved configuration according to one embodiment of the disclosed inventions.
Figure 17B:
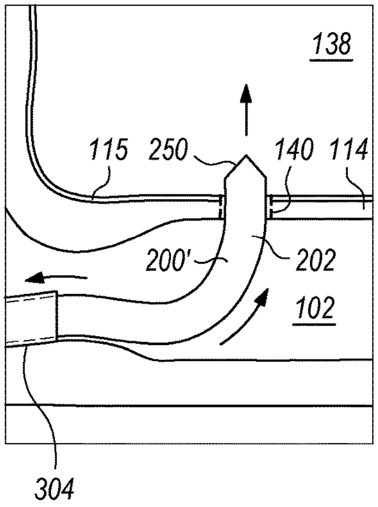

FIGS. 17A-B illustrates an exemplary distal portion 202 of the shunt 200' according to the embodiments of the disclosed inventions. The distal portion 202 of the shunt 200' is composed of shape-memory materials, such as super-elastic nickel titanium alloy, known as Nitinol® or other suitable deformable material, so that the distal portion 202 has a pre-curved or biasedly curved configuration (FIG. 17B). The distal portion 202 of the shunt 200' comprises a delivery configuration, in which the distal portion 202 is elongated for advancement through the delivery catheter 304 (FIG. 17A) or the delivery assembly 300 and/or conduit 400, and a deployed configuration, in which the distal portion 202 assumes its curved configuration when the delivery catheter 304 is withdraw (FIG. 17B), or any other element of the delivery assembly 300 that may radially constrict the distal portion 202 of the shunt 200 is withdrawn. The distal end 202 of the shunt 200 is biasedly curved in a suitable angle towards and/or configured to be oriented towards the IPS wall 114, so that the distal end 202 having the tissue penetrating member 250 is configured for piercing the IPS wall 114 and arachnoid layer 115 creating anastomosis 140 and/or for implantation of the shunt 200' into the CP angle cistern 138.

Figure 18A:
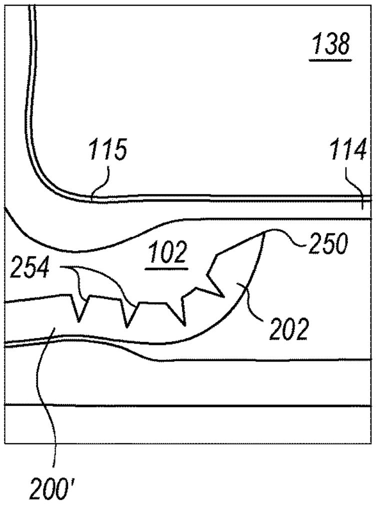
FIGS. 18A-B are cross-sectional views of an endovascular shunt having selective slots according to another embodiment of the disclosed inventions.
Figure 18B:
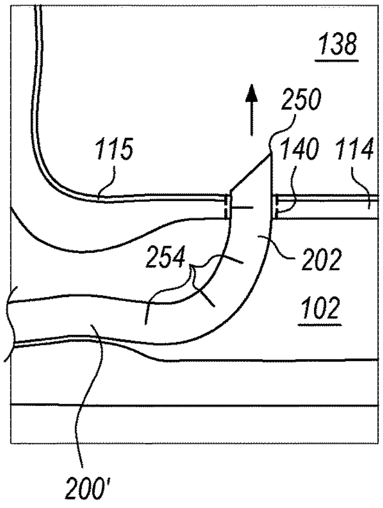

FIGS. 18A-B illustrates another exemplary distal portion 202 of the shunt 200' according to the embodiments of the disclosed inventions. The distal portion 202 of the shunt 200' includes the flexible elongate tubular structure according to the disclosed inventions, and further comprises a plurality of slots 254 (e.g., cuts, openings, perforations, or the like, or combinations thereof) formed within the tubular structure (FIG. 18A). The slots 254 are configured to selectively weaken the axial and flexural strength of the tubular structure causing the distal portion 202 to be more susceptible to bending or folding, when the distal portion 202 is subjected to an external force, for example, when the distal end 202 comes in contact with an object, such as the conduit 400 of FIGS. 12 and 14A-F. As shown in FIG. 18B, the slots 254 are configured to remain closed due to the bend of the distal portion 202 of the implanted shunt 200', so that blood flow through the shunt 200' is prevented or avoided.

Figure 19A:
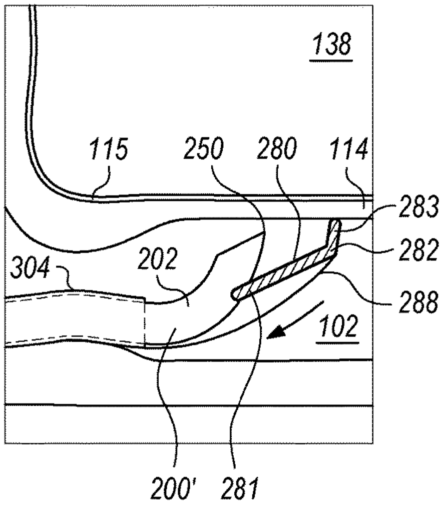
FIGS. 19A-B are cross-sectional views of an endovascular shunt having a elongate member according to yet another embodiment of the disclosed inventions.
Figure 19B:
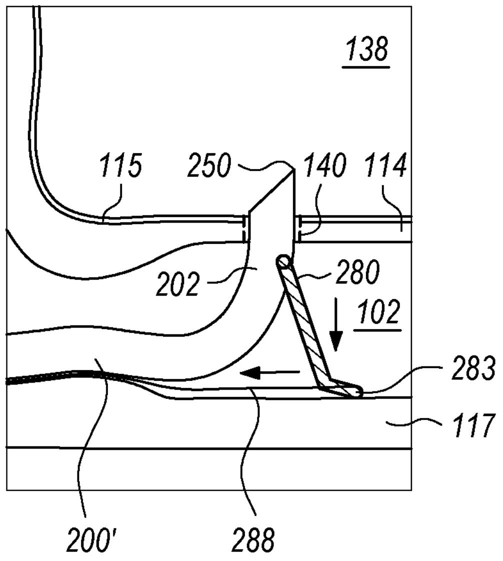

FIGS. 19A-B illustrates yet another exemplary distal portion 202 of the shunt 200' according to the embodiments of the disclosed inventions. The distal portion 202 includes an elongated member 280 (e.g., leg, kickstand, or the like) configured to position the distal portion 202 of the shunt 200' in the proper angle and orientation relative to the IPS wall 114. The elongated member or leg 280 includes a first end 281 coupled to the distal portion 202 of the shunt 200' in a hinge-like configuration, and a second end 282 coupled to a pull wire 288. The leg 280 further includes a stand or foot 283 at the second end 282 configured to assist and stabilize the distal end 202 of the shunt 200' at the desired position within the IPS 102 (FIG. 19B). The leg 280 is composed of any suitable biocompatible material, according to the disclosed inventions. The leg 280 may be attached to the distal portion 202 of the shunt 200' at the first end 281 (e.g. hinge, bonded, welded or other movable attachment) or may be a cut-out of the shunt 200' tubular structure. The leg 280 comprises a delivery configuration for advancement through the delivery catheter 304 or any other elements of the delivery assembly 300 (FIG. 19A), and a deployed configuration, in which the leg 280 assists and stabilizes the distal end 202 of the shunt 200' at the desired position within the IPS 102 (FIG. 19B). By application of suitable retrograde force to the pull wire 288 coupled to the second end 282 of the leg 280, the leg 280 moves in a backward direction so that the foot 280 contacts the lower portion of the IPS 102 (e.g., "stands" on the IPS wall 117 opposite to the IPS wall 114), supporting and stabilizing the distal end 202 of the shunt 200', as shown in FIG. 19B.

Figure 20A:
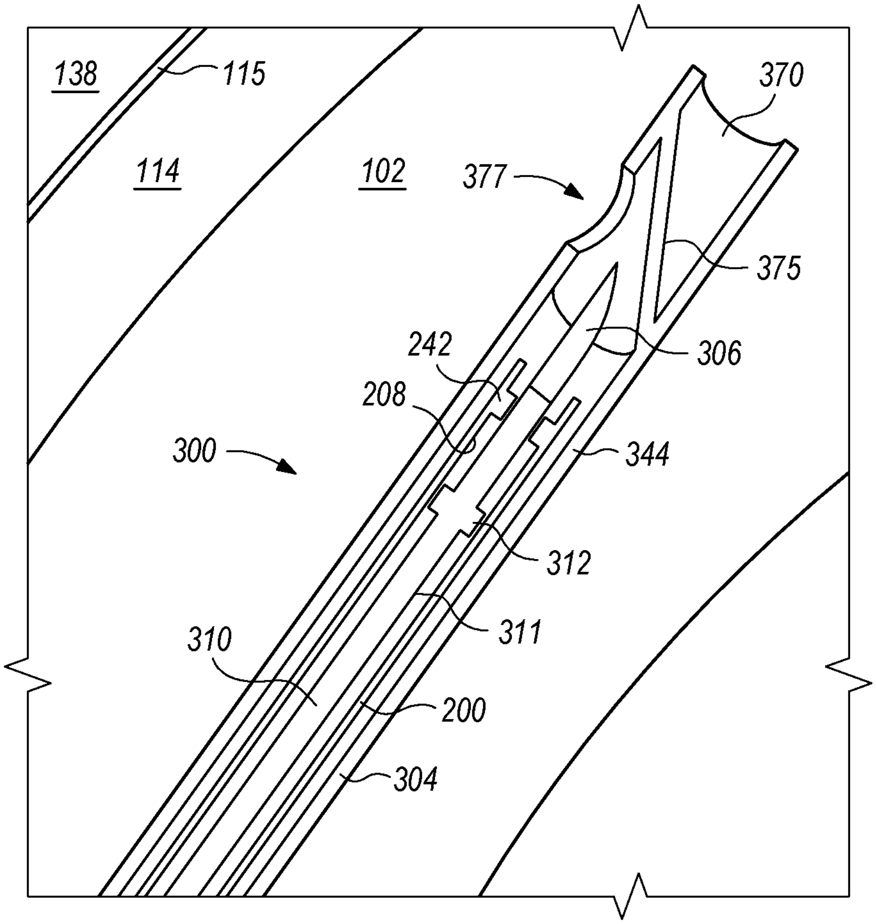
FIGS. 20A-F are cross-sectional views of an endovascular shunt delivery assembly having an end cap and an stabilizing member according embodiments of the disclosed inventions.
Figure 20B:
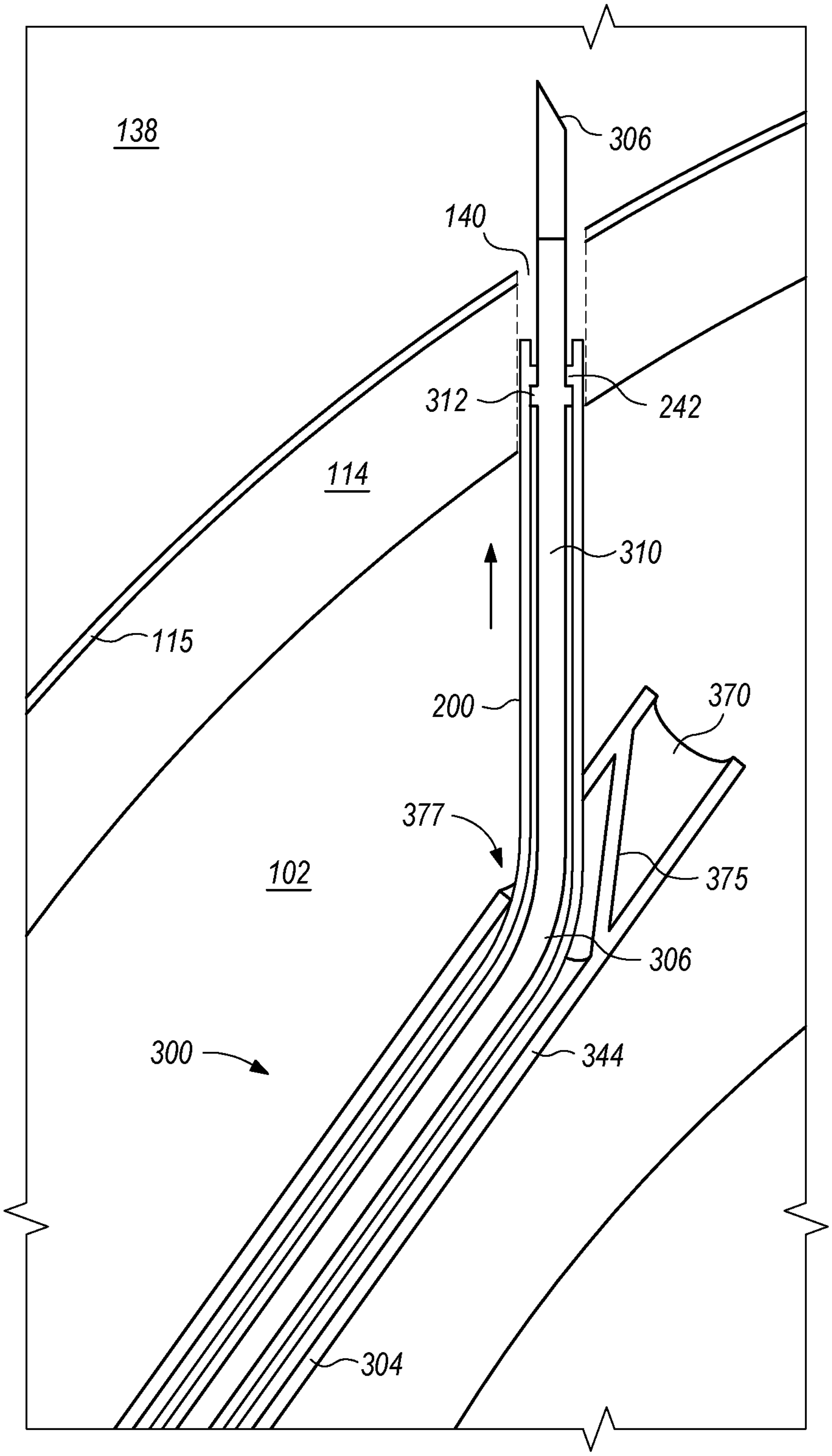
Figure 20C:
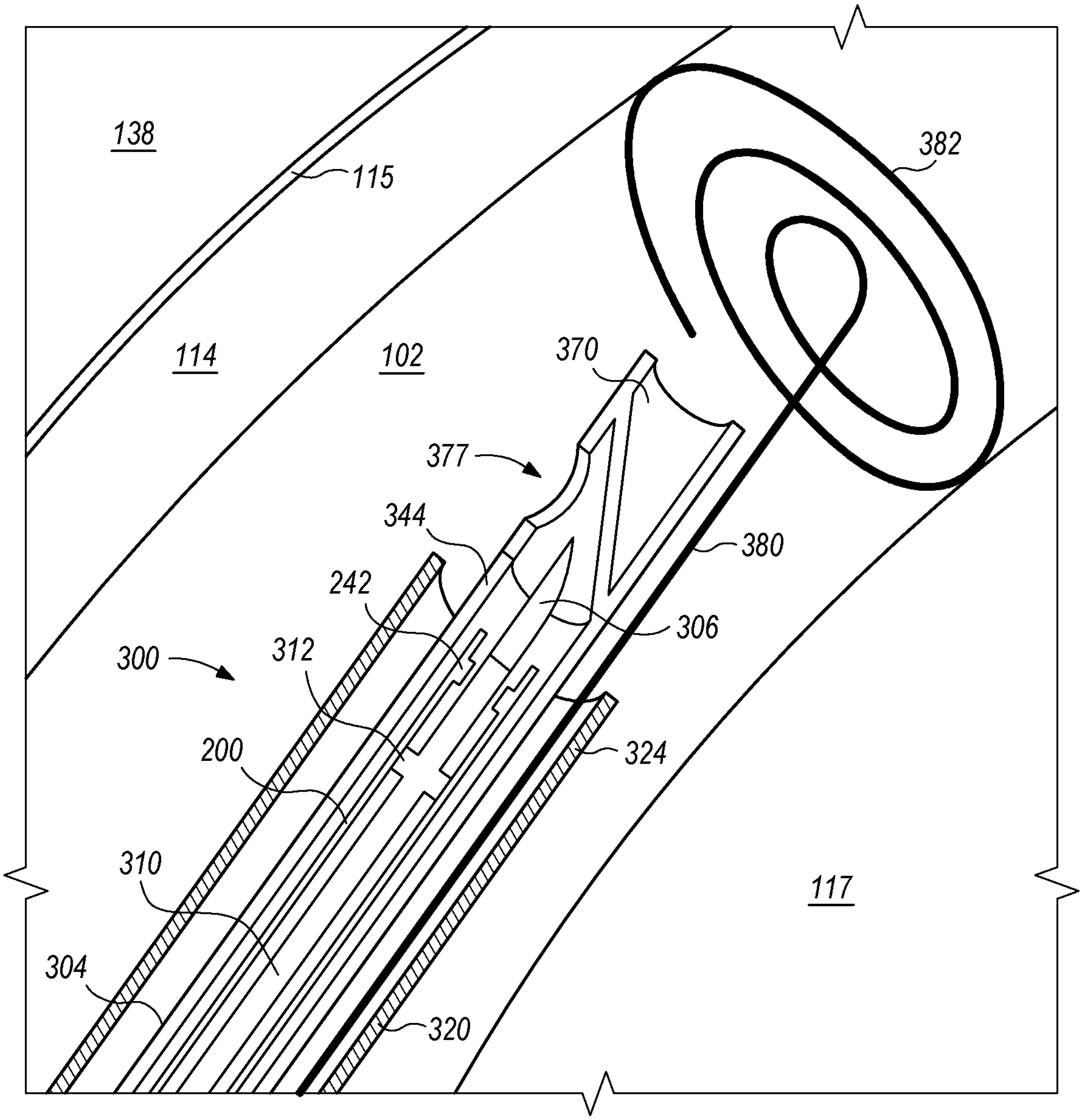
Figure 20D:
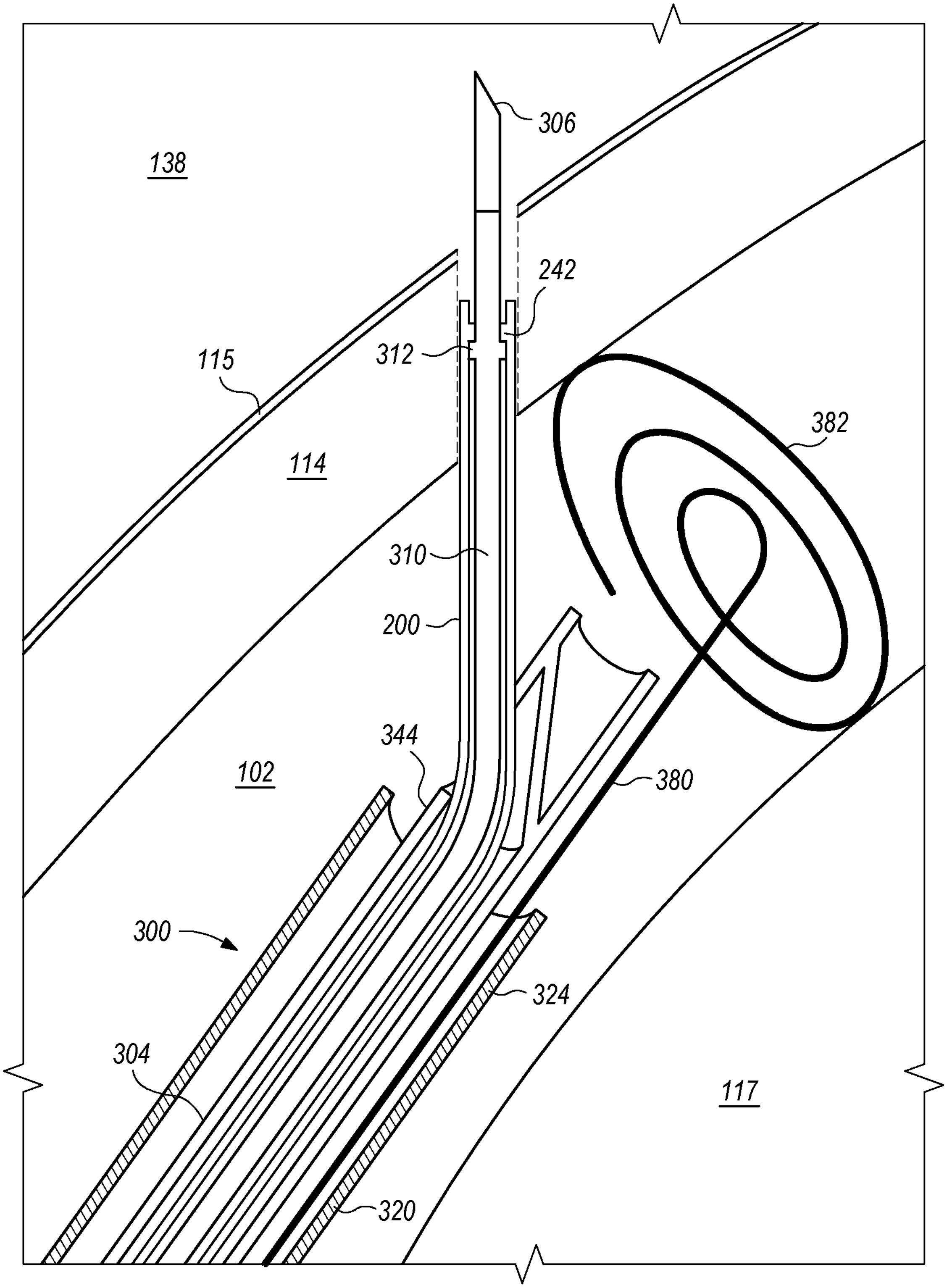
Figure 20E:
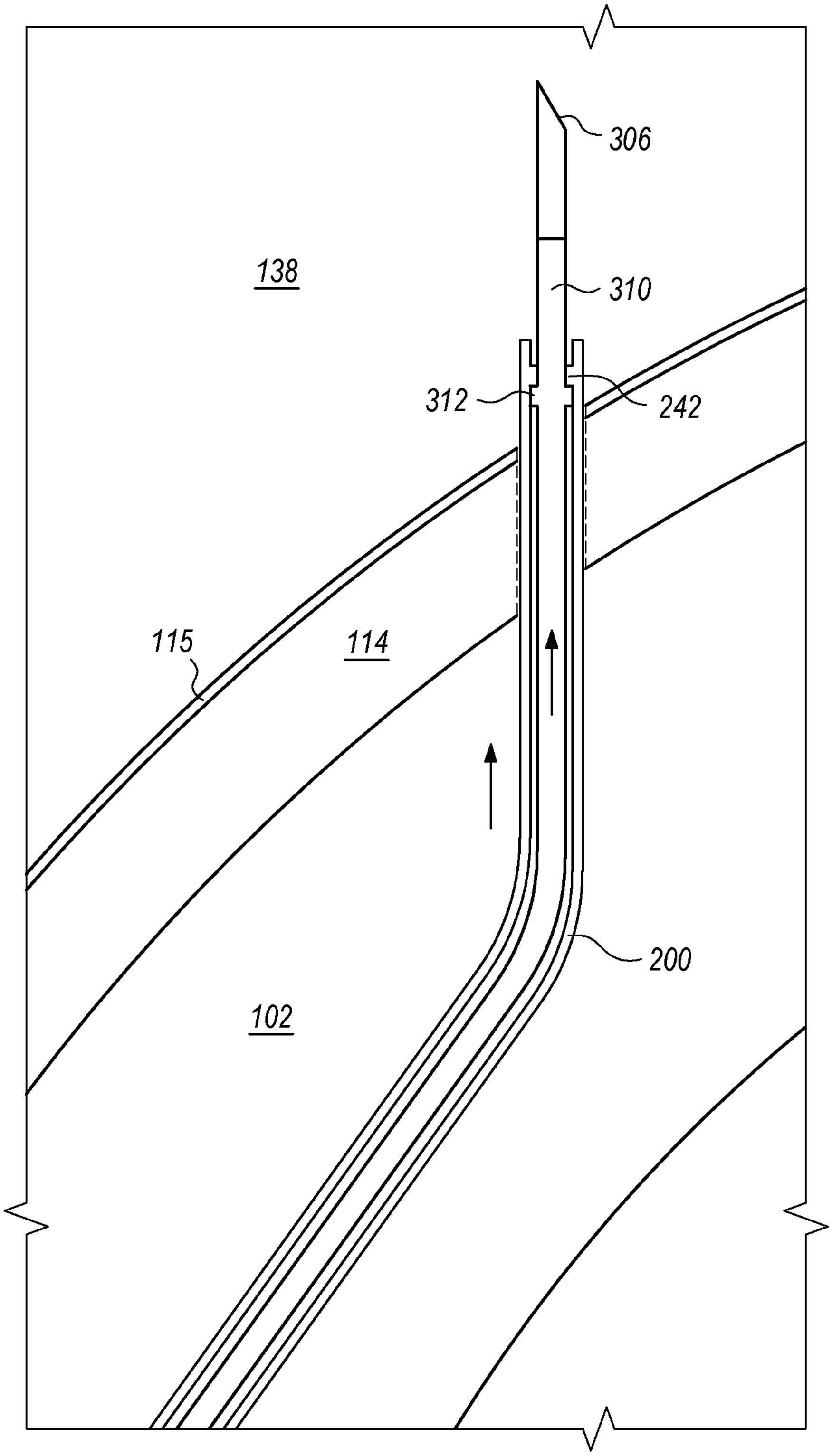
Figure 20F:
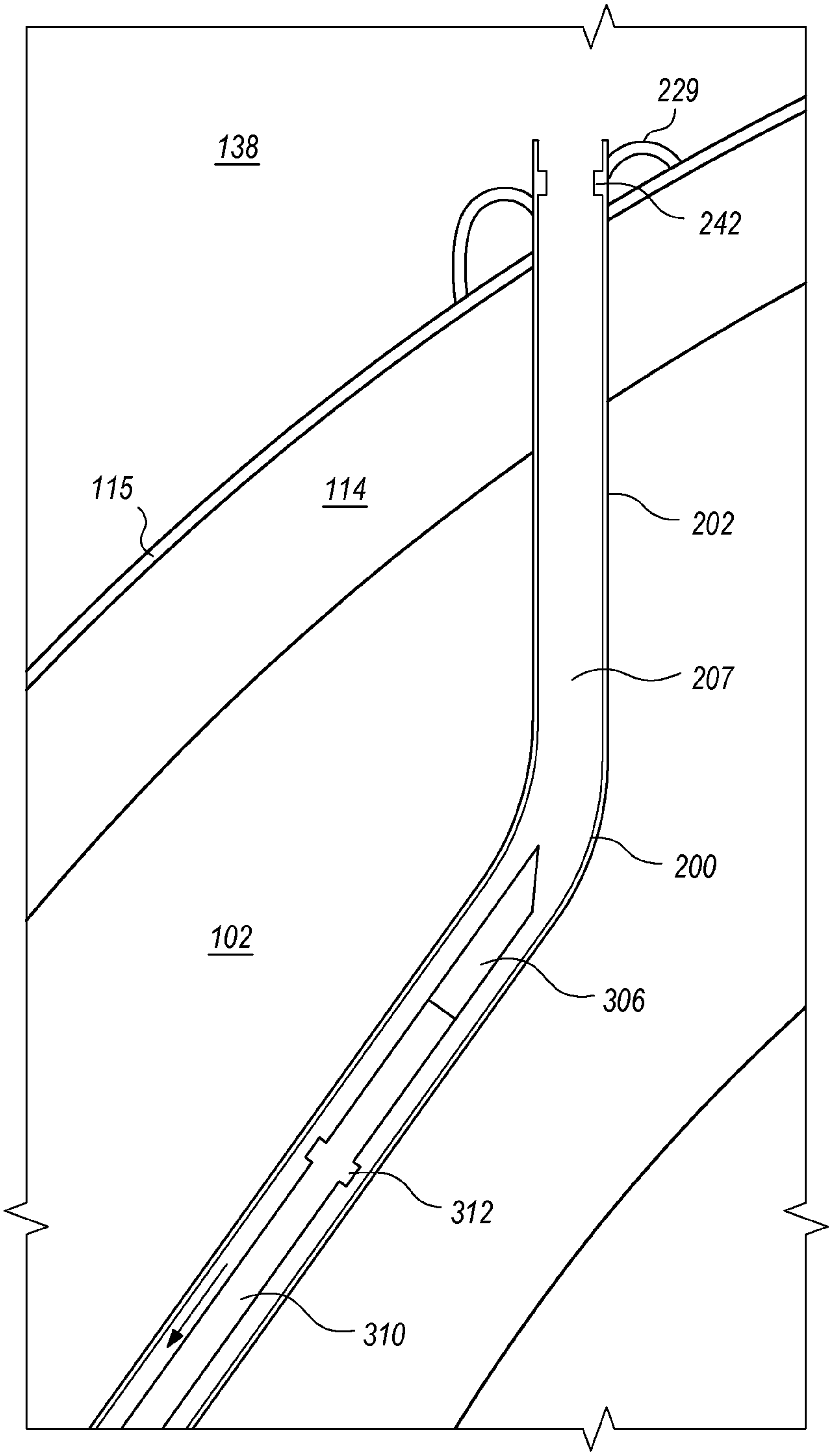

FIGS. 20A-F illustrate the delivery assembly 300 in accordance with one embodiment of the disclosed inventions. The delivery assembly 300 includes the delivery catheter 304, the shunt 200 coaxially disposed within the delivery catheter 304, and the elongate pusher member 310 310 coaxially disposed within the shunt 200. The tissue penetrating member 306 (e.g., surgical tool) is disposed on the distal portion 354 of the elongate pusher member 310 (e.g., piercing micro-wire). The elongate pusher member 310 includes one or more engaging members 312 disposed on an outer surface 311 of the elongate pusher member 310, and the shunt 200 includes one or more engaging members 242 disposed on an inner wall surface 208 of the shunt 200 to form a mechanical interaction with the one or more engaging members 312 of the elongate pusher member 310 (FIG. 20A). The engaging member 242 of the shunt 200 (i.e., first engaging member) protrudes and/or extends radially inward from the inner wall 208 of the shunt 200, the engaging member 312 of the elongate pusher member 310 (i.e., second engaging member) protrudes and/or extends radially outward towards the inner shunt wall 208. The second engaging member engages the first engaging member to thereby advance the distal portion 202 of the shunt 200 from the IPS 102 into the CP angle cistern 138 on the tissue penetrating member 306 (FIG. 20E). The engaging members 312 and 242 may include protrusions, balls, collars, or the like, or combinations thereof, or any other suitable configurations. When the engaging members 312 of the elongate pusher member 310 and the engaging members 241 of the shunt 200 meet and engage with each other (FIGS. 20B and 20E), advancement of the elongate pusher member 310 and penetrating element 306 simultaneously advances the shunt 200 into the target or target penetration site, according to the disclosed inventions. The engaging members 312 and 242 are configured to be engaged in a one-way direction (i.e., forward in the direction of the penetration site of the IPS wall 114, distally toward the subarachnoid space 116-FIGS. 20B, 20D and 20E), so that the engaging members 312 and 242 are disengaged when the elongate pusher member 310 having the penetrating element 306 is withdrawn from the delivery catheter 304 or moved proximally (FIG. 20F).

The tissue penetrating member 306 comprises the elongate pusher member 310 and a tissue penetrating distal tip, the elongate pusher member 310 extends though the valve 209, lumen 207, and distal opening 201 of the shunt 200, respectively, wherein the elongate pusher member 310 is moveable relative to the shunt 200 so that the tissue penetrating 306 distal tip may be advanced out of, and withdrawn into, a distal opening 201 of the shunt 200 in communication with the lumen 207, wherein advancing the distal portion 202 of the shunt 200 from the IPS 102 into the CP angle cistern 138 comprises advancing the elongate pusher member 310 so that the tissue penetrating 306 distal tip penetrates through the dura mater tissue wall of the IPS 114, and through the arachnoid tissue layer 115, respectively, into the CP angle cistern 138, with the distal portion 202 of the shunt 200 being carried on the tissue penetrating member 306 (FIGS. 20A-E). When deploying the shunt 200, the method further comprises, after advancing the distal portion of the shunt into the CP angle cistern, withdrawing the tissue penetrating member 306 through the distal opening 202, lumen 207 and valve of the shunt 200, respectively, wherein CSF flows through the respective distal opening 201, lumen 207 and valve 209 of the shunt 200 after withdrawal of the tissue penetrating member 206 (FIG. 20F). When deploying the shunt 200, the method further comprises advancing the delivery catheter 304 into the IPS 102 with the shunt 200 and tissue penetrating member 306 at least partially disposed in the delivery lumen 305 of the delivery catheter 304, the delivery catheter 304 having a distal opening in communication with the delivery lumen 305 through which the respective tissue penetrating member 306 and shunt 200 may be advanced into the CP angle cistern 138. The method of deploying the shunt further comprises, adjusting a rotational orientation of the delivery catheter 304 about an axis of the delivery catheter 304 so that the tissue penetrating distal tip of the tissue penetrating member 306 is thereafter advanced out of the distal opening of the delivery catheter 304 into contact with the dura IPS wall 114 at an angle in a range of 30 degrees to 90 degrees thereto, prior to advancing the tissue penetrating member 306 into the CP angle cistern 138. The method further comprises imaging the shunt while deploying the shunt in the patient.

It should be appreciated that the aspects, features and functions of the engaging members 312 of the elongate pusher member 310 and the engaging members 241 of the shunt 200, described in FIGS. 20A-B, may be incorporated into the delivery assembly 300', so that the tissue penetrating member 250 coupled to a guidewire assists with the advancement of the shunt 200' into the target site (FIGS. 5E-I), and is configured to be disengaged and removed from the implanted shunt 200' (FIG. 5J).

Referring back to FIGS. 20A-F, the delivery catheter 304 includes a deflecting element 370 coupled to or disposed on the distal portion 344 of the delivery catheter 304. The deflecting element 370 includes a tubular configuration having an angled inner ramp 375 and a side aperture 377. The deflecting element 370 is formed of suitable biocompatible metals, alloys, polymers or their like, or combinations thereof. The deflecting element 370 and particularly, the ramp 375, may be formed of relatively stiff and non-deformable materials, or be covered with a relatively stiff polymeric coating (e.g., polytetrafluoroethylene "PTFE", polyethyleneterephthalate "PET"). The deflecting element 370 may further include radio-opaque materials or include markings for purposes of imaging, according to the disclosed inventions. The deflecting element 370 and ramp 375 are configured to deflect the tissue penetrating element 306, elongate pusher member 310, and shunt 200 engaged to the elongate pusher member 310, towards the aperture 377, so that the tissue penetrating element 306, elongate pusher member 310, and shunt 200 are advanced out of the distal portion 344 of the delivery catheter 304 in a suitable angle for piercing the IPS wall 114 and the arachnoid layer 115 for implantation of the shunt 200 into the target site (FIG. 20B), according to the disclosed inventions.

Prior to the piercing of the IPS wall 114 to create anastomosis and access the CP angle cistern 138, the proper orientation of the distal portion 344 of the delivery catheter 304, particularly, the proper orientation of the deflecting element 370 and/or aperture 377, may be verified according to the imaging methods previously disclosed. When needed, the positioning and orientation of the deflecting element 370 disposed on the distal portion 344 of the delivery catheter 304 may be adjusted, for example, by applying a rotational force directly to the body of the delivery catheter 304, or to the elongate pusher member 310, if the member 310 is engaged to the delivery catheter 304.

Alternatively, a stabilizing element 380 may be used for positioning, orienting, and/or stabilizing the distal end 344 of the delivery catheter 304, and/or the aperture 377 of the deflecting element 370 within the IPS 102, as shown in FIGS. 20C-D. The stabilizing element 380 of the delivery assembly 300 may be coaxially disposed with the guide catheter 320, and includes a distal portion 382 configured to radially expand and engage the IPS 102 walls 114, 117 (i.e., diameter $d_1$, as shown in FIG. 2) when the stabilizing element 380 is advanced out of the distal portion 324 of the guide catheter 320 and/or the guide catheter 320 is withdrawn exposing the distal portion 382 of the stabilizing element 380. The stabilizing element 380 may be composed of any suitable biocompatible shape memory and/or expandable materials according to the disclosed inventions.

In the embodiments of FIGS. 20C-D, the distal portion 382 of the stabilizing element 380 includes a spiral configuration. In other embodiments, the distal portion 382 of the stabilizing element 380 may include any suitable configuration, such as a coil, stent, expandable foams, balloons, or combinations thereof, configured to engage the IPS 102 walls 114, 117 and assist with the position, orientation, and/or stability of the distal end 344 of the delivery catheter 304, and/or the aperture 377 of the deflecting element 370 within the IPS 102. When deployed, the stabilizing element 380 stabilizes the position of the distal end 344 of the delivery catheter 304, and/or the aperture 377 of the deflecting element 370 preventing movement of the catheter distal end 344 and deflecting element 370 within the IPS 102 while the IPS wall 114 is being pierced (FIG. 20D).

FIG. 20E illustrates the further advancement of the shunt 200 into the target site by the advancement of the elongate pusher member 310 (i.e., via engagement of the respective engaging members 312 and 242) of the embodiments of FIGS. 20A-D, along with the withdrawal of the delivery catheter 304 (not shown). Once the shunt 200 is deployed in the target site, the elongate pusher member 310 having the tissue penetrating element 306 is withdrawn (i.e., disengagement of the respective engaging members 312 and 242), as shown in FIG. 20F. Additionally, the anchoring mechanism 229 of the shunt 200 is deployed to secure the distal portion 202 of the shunt 200 in the target site, according to the disclosed inventions.

Figure 21A:
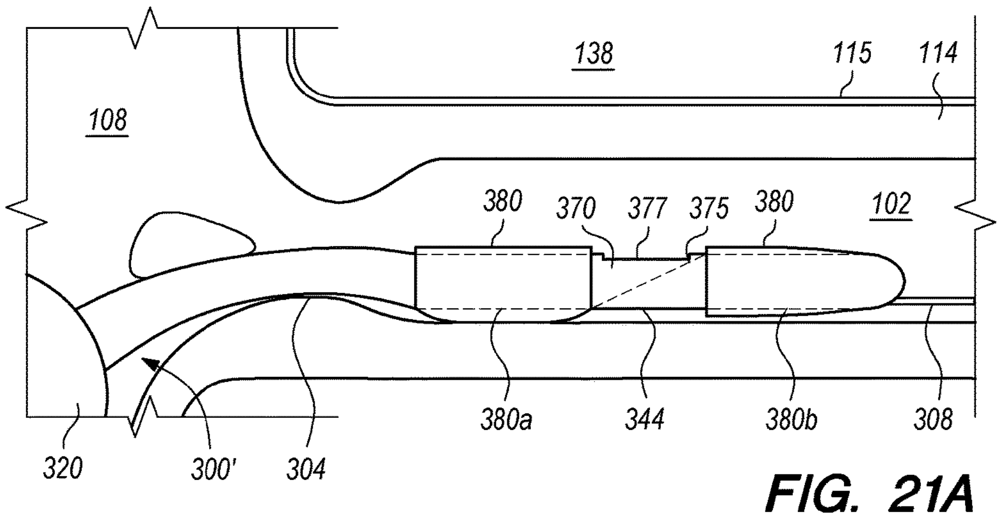
FIGS. 21A-E are cross-sectional views of another endovascular shunt delivery assembly having a deflecting element and a stabilizing member according embodiments of the disclosed inventions.

FIGS. 21A-D illustrate the delivery assembly 300' having one or more stabilizing element 380 in accordance with one embodiment of the disclosed inventions. The delivery assembly 300' includes the guide catheter 320, the delivery catheter 304 and the delivery guidewire 308. The delivery catheter 304 of the delivery assembly 300' includes the stabilizing element 380 that extends from or is disposed on the distal portion 344 of the delivery catheter 304, and the deflecting element 370 disposed in the distal portion 344 of the delivery catheter 304. As shown in FIG. 21A, the stabilizing element 380 comprises a first stabilizing element 380*a*, a second stabilizing element 380*b*, and the deflecting element 370 disposed between the stabilizing elements 380*a* and 380*b*. The stabilizing elements 380*a* and 380*b* include inflatable balloons that may be inflated with contrast dye for imaging proposes, according to the disclosed inventions. In some embodiments, the stabilizing elements 380*a* and 380*b* may include expandable coils, stent, foams, or the like, or combinations thereof. The deflecting element 370 includes the inner angle ramp 375 and the side aperture 377, according to the disclosed inventions (FIGS. 20A-D).

Figure 21B:
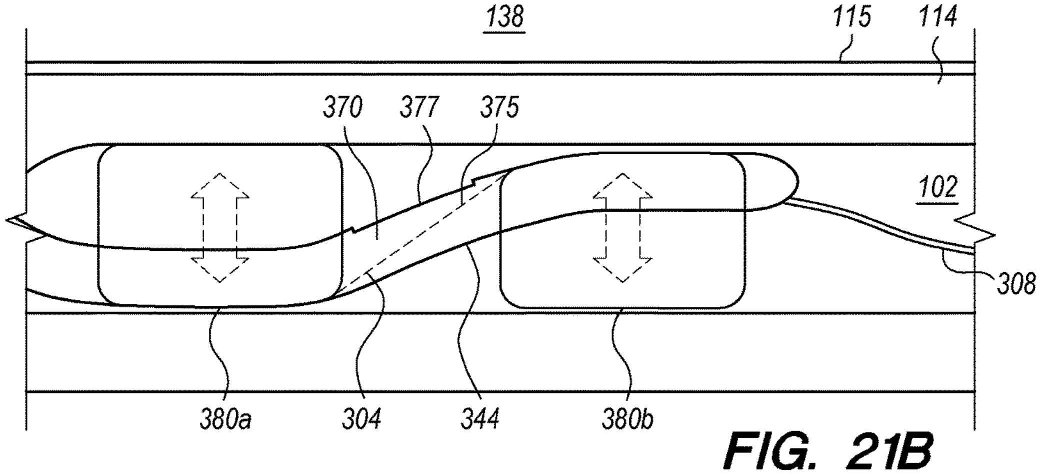
Figure 21C:
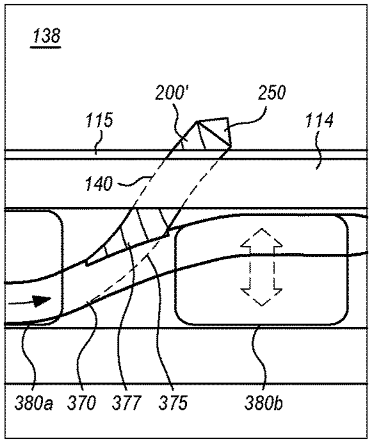
Figure 21D:
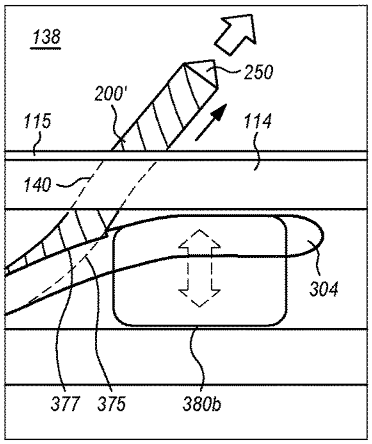
Figure 21E:
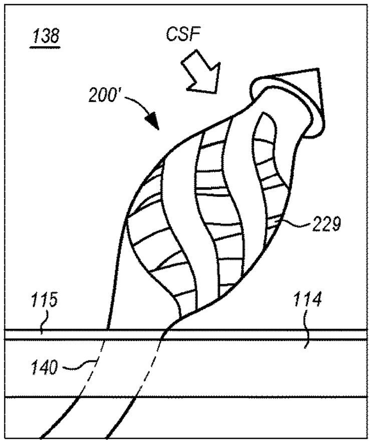

As shown in FIG. 21A, the stabilizing elements 380*a* and 380*b* are deflated and/or radially constricted in the delivery configuration within the IPS 102. Once the proper position and orientation of the distal portion 344 of the delivery catheter 304 and/or of the aperture 377 is achieved according to the methods of the disclosed inventions, the stabilizing elements 380*a* and 380*b* are inflated and/or radially expanded, as shown in FIG. 21B, stabilizing the delivery catheter 304 and/or the aperture 377 within the IPS 102. As shown in FIGS. 21C-D, the shunt 200' incorporating the tissue penetrating member 250 is advanced through the delivery catheter 304, meeting the ramp 375 of the deflecting element 370, so that the shunt 200' is deflected towards the aperture 377 and the tissue penetrating member 250 contacts and pierces the IPS wall 114 and the arachnoid layer 115 in a suitable angle for creation of the anastomosis 140 and implantation of the shunt 200' into the target site (FIG. 21E), according to the disclosed inventions. As shown in FIG. 21E, the distal anchoring mechanism 229 incorporated in shunt 200' expands, anchoring the shunt 200' within the CP angle cistern 138 and further allowing CSF drainage through the shunt 200'. In the embodiments of FIGS. 21C-E, the shunt 200' comprises an elliptecot configuration that will be described in further detail below. It should be appreciated that the embodiments and methods disclosed in FIGS. 21A-E can include any features and steps disclosed herein, including features and steps disclosed in connection with different embodiments (e.g., shunt 200, delivery assembly 300), in any combination as appropriate.

Figure 22A:
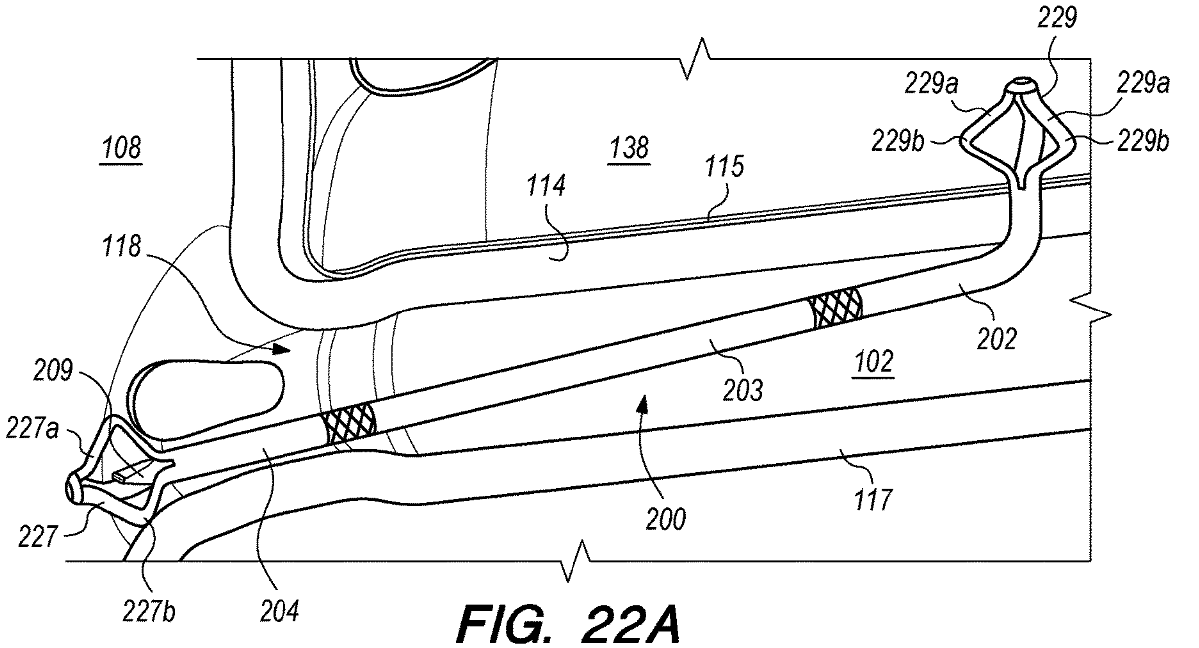
FIGS. 22A-G are side and cross-sectional views of a deployed endovascular shunt according to another embodiment of the disclosed inventions.
Figure 22B:
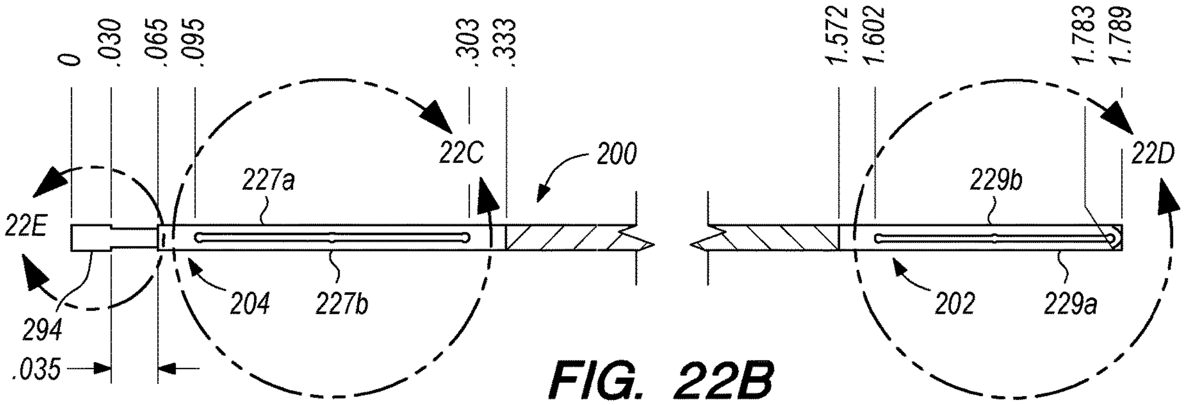
Figure 22C:
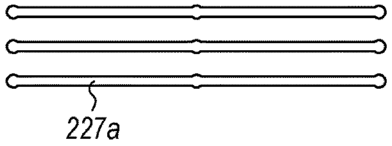
Figure 22D:
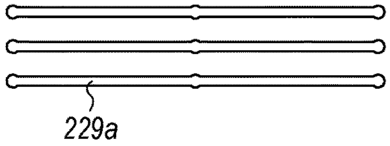
Figure 22E:
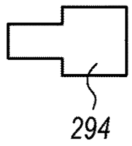
Figure 22G:
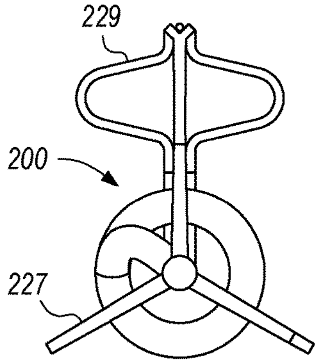
Figure 22F:
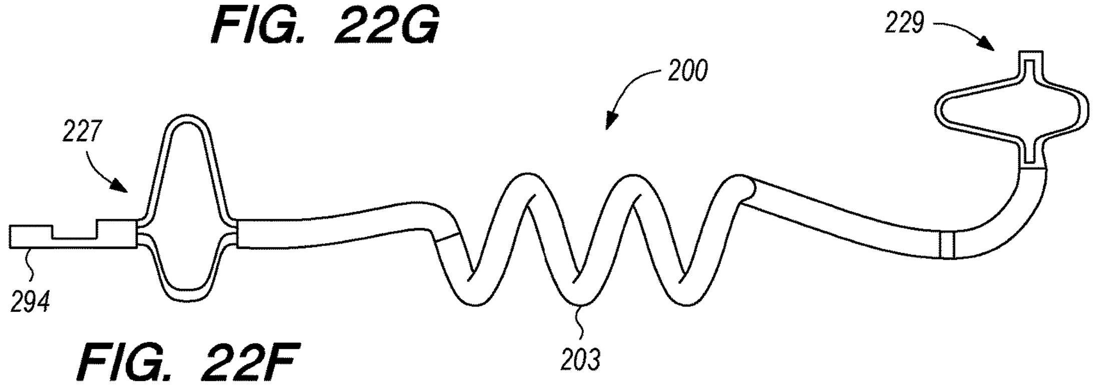

FIGS. 22A-G illustrate an exemplary shunt 200 constructed and implanted according to embodiments of the disclosed inventions. The shunt 200 includes the anchoring mechanism 227 and a duck-bill valve 209 in the proximal portion 204, the anchoring mechanism 229 in the distal portion 202, and the elongate body 203 extending therebetween. The anchoring mechanisms 227 and 229 include a malecot configuration having a plurality of respective deformable elements 227*a* and 229*a* (e.g., arms) that are disposed radially outward in the deployed configuration (FIGS. 22A and 22F-G). The anchoring mechanism 227 and 229 are formed by concentric parallel or radially spaced cuts 222 along the length of the respective proximal 204 and distal 202 portions of the shunt 200, forming the arms 227*a* and 229*a* (FIGS. 22B-D). FIGS. 22C-D illustrate exemplary patterns and dimensions of the cuts 222 in the respective proximal 204 (FIG. 22C) and distal 202 (FIG. 22D) portions. It should be appreciated that the patterns and dimensions of the cuts 222 in the proximal portion 204 may be similar or dissimilar from the patterns and dimensions of the cuts 222 in the distal portion 202. Each deformable element 227*a* and 229*a* has a respective hinge-like point 227*b* and 229*b* (e.g., living hinge, joint, or the like). As shown in FIG. 22A, the hinge-like points 227*b* and 229*b* are configured to move radially outward from the axis of the shunt 200 in a hinge-like fashion, allowing the arms 227*a* and 229*a* to be outwardly disposed so that the shunt 200 is anchored at the target site. Anchoring mechanisms can have a preformed expanded or deployed configuration (e.g., configuration of FIGS. 22A, 22F-G), for example, when constructed from super-elastic materials such as Nitinol. The deployed anchoring mechanism 227 engages the jugular bulb 108, the IPS wall 117, and/or another portion of the IPS 102, anchoring the proximal portion 204 of the shunt 200 within the jugular vein 106, so that the valve 209 is disposed within the jugular vein 106. Alternatively, the anchoring mechanism 227 may engage the IPS walls 114 and 117 at the junction 118 (not-shown). The deployed anchoring mechanism 229 secures the distal portion 202 of the shunt 200 within the CP angle cistern 138 (FIGS. 5H-J), so that CSF flows through the implanted shunt 200 into the jugular vein 106.

Additionally, the shunt 200 may include an interlocking element 294 (e.g., clasp) coupled to the proximal portion 204 of the shunt 200 (FIGS. 22B and 22E). The interlocking element 294 is configured to engage and disengage with an interlocking element coupled to the distal portion of the delivery assembly (not shown) for deployment of the shunt 200 at the target site. FIG. 22E illustrates an exemplary pattern used for laser cutting a tubular portion of super-elastic material to form an embodiment of the interlocking element 294.

Dimensions referenced in FIG. 22B, are provided in inches. It should be appreciated that the dimensions depicted in FIG. 22B are exemplary dimensions of the shunt 200, which are not intended to limit the embodiment of FIGS. 22A-G.

Figure 23A:
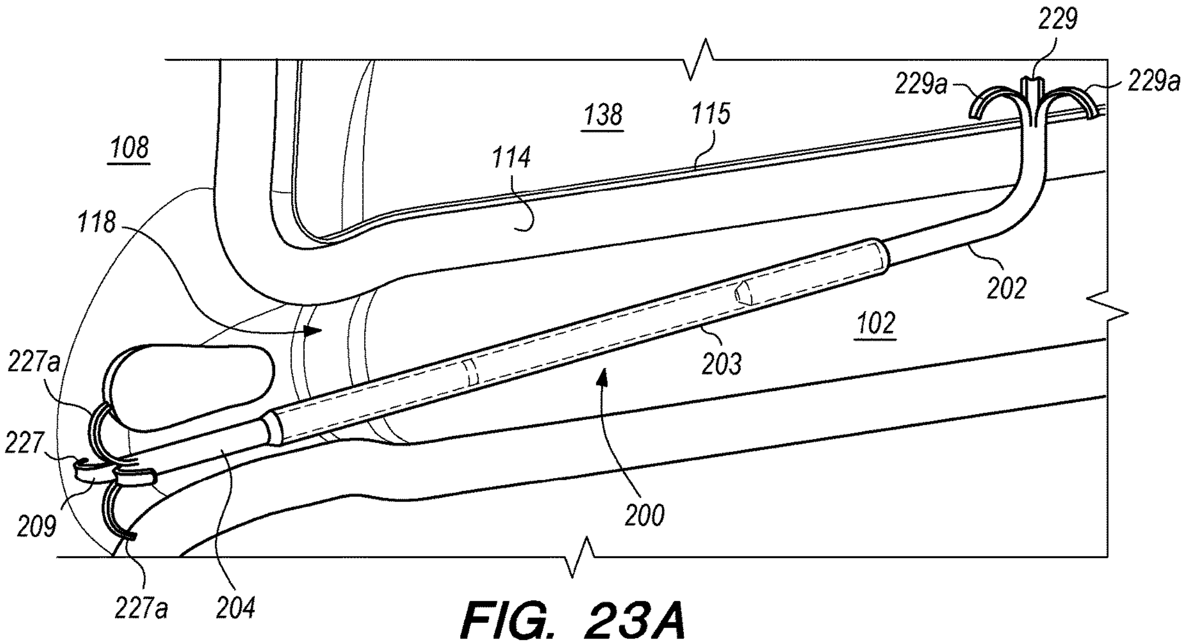
FIGS. 23A-E are side and cross-sectional views of a deployed endovascular shunt according to another embodiment of the disclosed inventions.
Figure 23B:
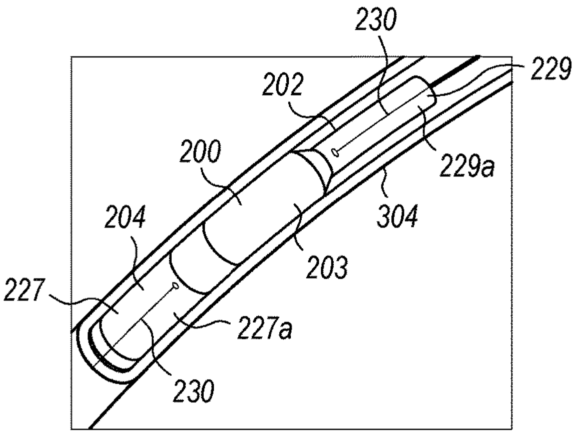
Figure 23C:
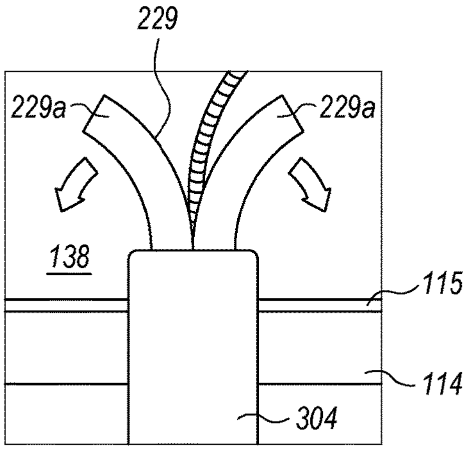
Figure 23D:
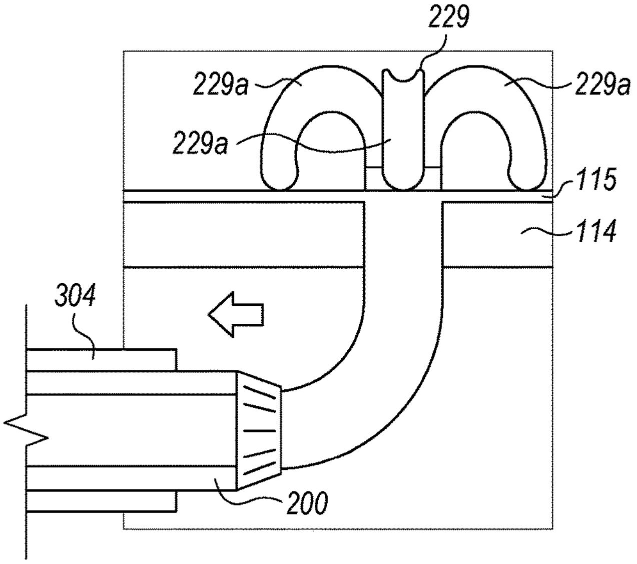
Figure 23E:
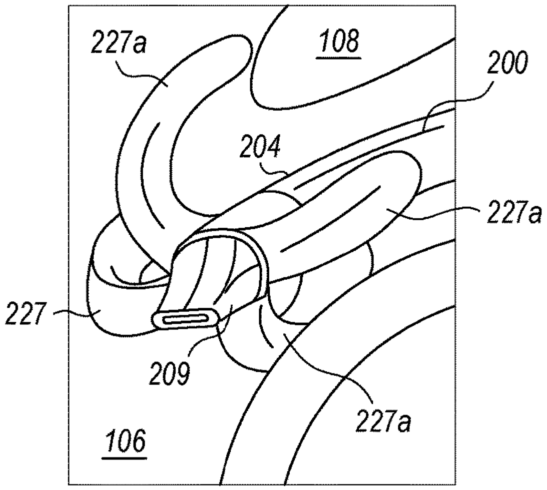

FIGS. 23A-E illustrate another exemplary shunt 200 constructed and implanted according to embodiments of the disclosed inventions. As shown in FIG. 23A, the shunt 200 includes the anchoring mechanism 227 and the duck-bill valve 209 in the proximal portion 204, the anchoring mechanism 229 in the distal portion 202, and the elongate body 203 extending therebetween. The body 203 of the shunt 200 comprises slidably disposed concentric tubular elements, as shown in FIGS. 6E-F, for selective elongation and/or adjustment of the shunt length $L_2$ (FIG. 6) according to the anatomy of the patient (i.e., target site for implantation of the shunt 200. The anchoring mechanisms 227 and 229 include a flower-like configuration having a plurality of respective deformable elements 227*a* and 229*a* (e.g., petals) that are disposed radially outward in the deployed configuration. The deformable petals 227*a* and 229*a* are formed by concentric parallel and/or radially spaced cuts 230 along the length of the respective proximal 204 and distal 202 portions of the shunt 200, as shown in FIG. 23B. The number of petals 227*a* and 229*a* depend on the number of cuts 230 formed into the respective proximal 204 and distal 202 portions. The petals 227*a* and 229*a* are configured to invert, fold and/or expand into their deployed configurations when the shunt 200 is implanted, as shown in FIGS. 23A, and 23C-D. As shown in FIGS. 23C-D, the distal anchoring mechanism 229 is deployed by advancement of the shunt 200 and/or withdrawal of the delivery catheter 304, so that the petals 229*a* invert, fold and/or expand, engaging the arachnoid layer 115 and securing the distal portion 202 of the shunt 200 within the CP angle cistern 138, as shown in FIG. 23D.

Figure 24A:
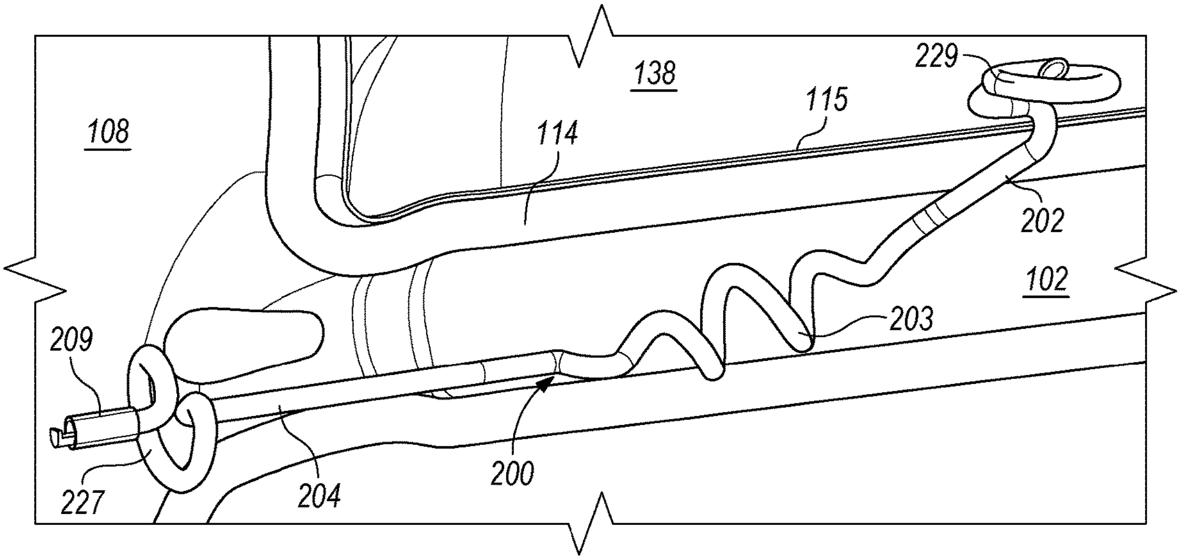
FIGS. 24A-E are side views of deployed endovascular shunts according to others embodiments of the disclosed inventions.
Figure 24B:
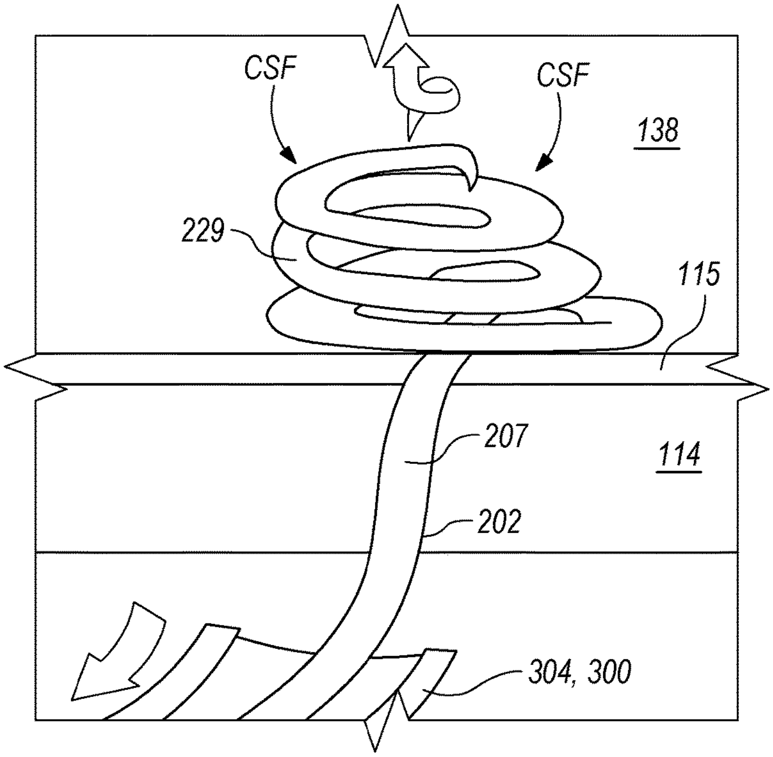
Figure 24C:
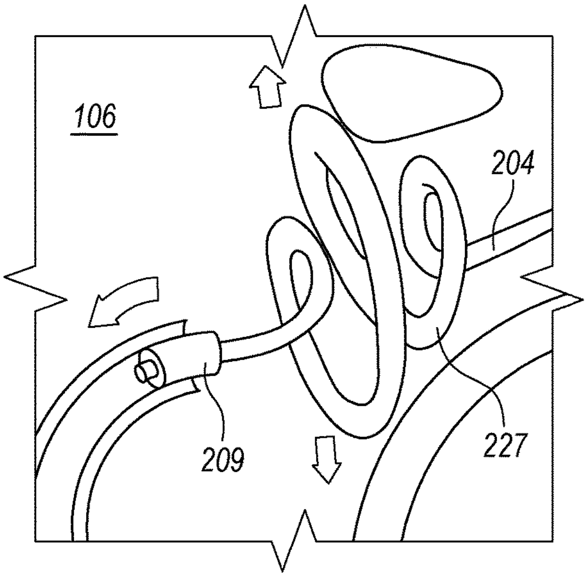
Figure 24D:
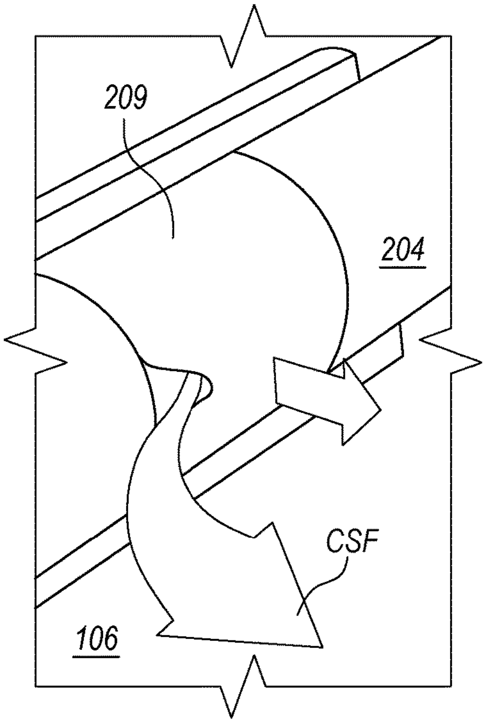
Figure 24E:
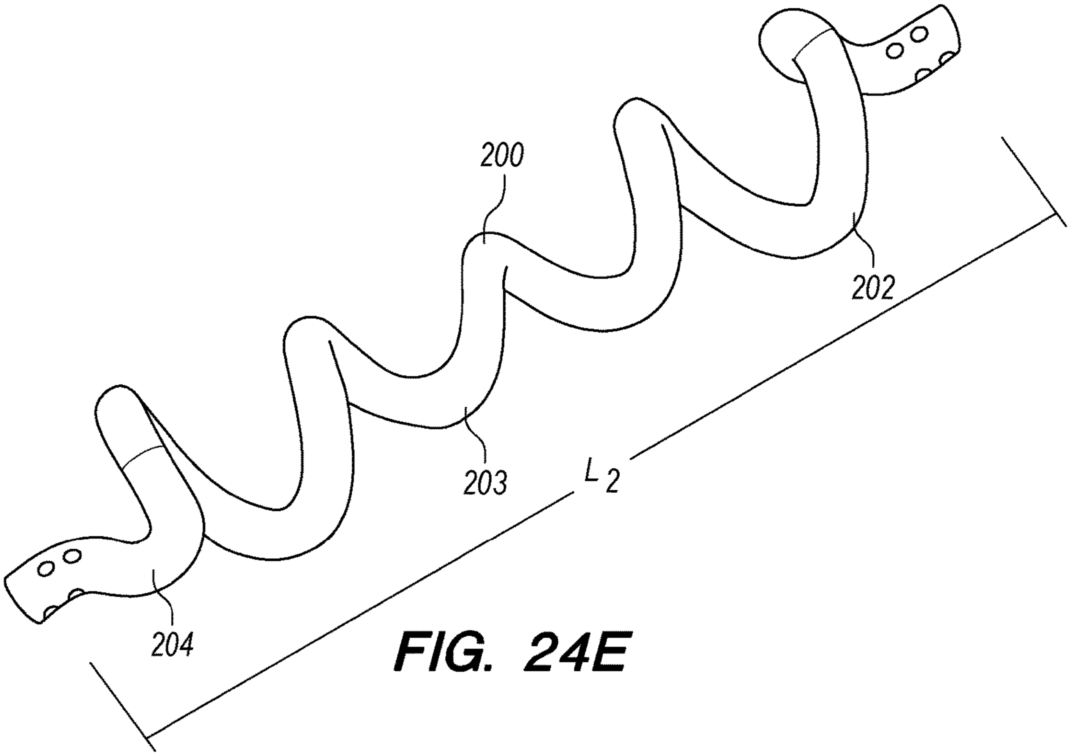

FIGS. 24A-E illustrate yet another exemplary shunt 200 constructed and implanted according to embodiments of the disclosed inventions. The shunt 200 includes the anchoring mechanism 227 and an interlocking valve 209 in the proximal portion 204, the anchoring mechanism 229 in the distal portion 202, and the elongate body 203 extending therebetween. The body 203 of the shunt 200 comprises a spring/coil-like body, as shown in FIGS. 6GH, for selective elongation and/or adjustment of the shunt length $L_2$ (FIG. 6) according to the anatomy of the patient (i.e., target site for implantation of the shunt 200). Further, the spring/coil-like body 203 of the shunt 200 is configured to apply tensional force, at least, between the proximal portion 204 and the distal portion 202 of the shunt 200 maintaining the implanted shunt 200 properly anchored in the target site (e.g., preventing movement of shunt or a loosely anchored shunt). The shunt 200 is composed of shape-memory materials, such as super-elastic nickel titanium alloy, known as Nitinol® or other suitable material, so that the proximal portion 204 forming the anchoring mechanism 227, and the distal portion 202 forming the anchoring mechanism 229, comprise helical-coil or spring-like configurations when deployed, as shown in FIGS. 24A-C. The shunt 200 is elongated for advancement through the delivery assembly 300 in the delivery configuration (FIG. 3B), and assumes the deployed configuration when the delivery assembly 300 that radially constricts the shunt 200 is withdrawn and/or the shunt 200 is advanced out of the delivery assembly 300 (FIGS. 24A-C), so that the anchoring mechanisms 227 (FIGS. 24A and 24C) and 229 (FIGS. 24A-B) are deployed, securing the implanted shunt 200 in the target site. CSF flows through the implanted shunt 200, from the CP angle cistern 138 entering the shunt lumen 207 from distal portion 202 of the shunt (FIG. 24B) and out of valve 209 at the proximal portion 204 of the shunt (FIG. 24D) into the jugular vein 106. As shown in FIG. 24D, the valve 209 comprises a concentric gland seal housed on the proximal portion 204 of the shunt 200 with a slit exposing the opening of the valve, as also shown in FIG. 6L. FIG. 24E illustrates an alternative embodiment of the shunt 200 of FIG. 24A, in which the shunt 200 comprises the spring/coil-like configuration in substantially the entire length $L_2$ of the shunt 200 (i.e., from the proximal portion 204 to the distal portion 202, including the body 203) in the deployed configuration.

Figure 25A:
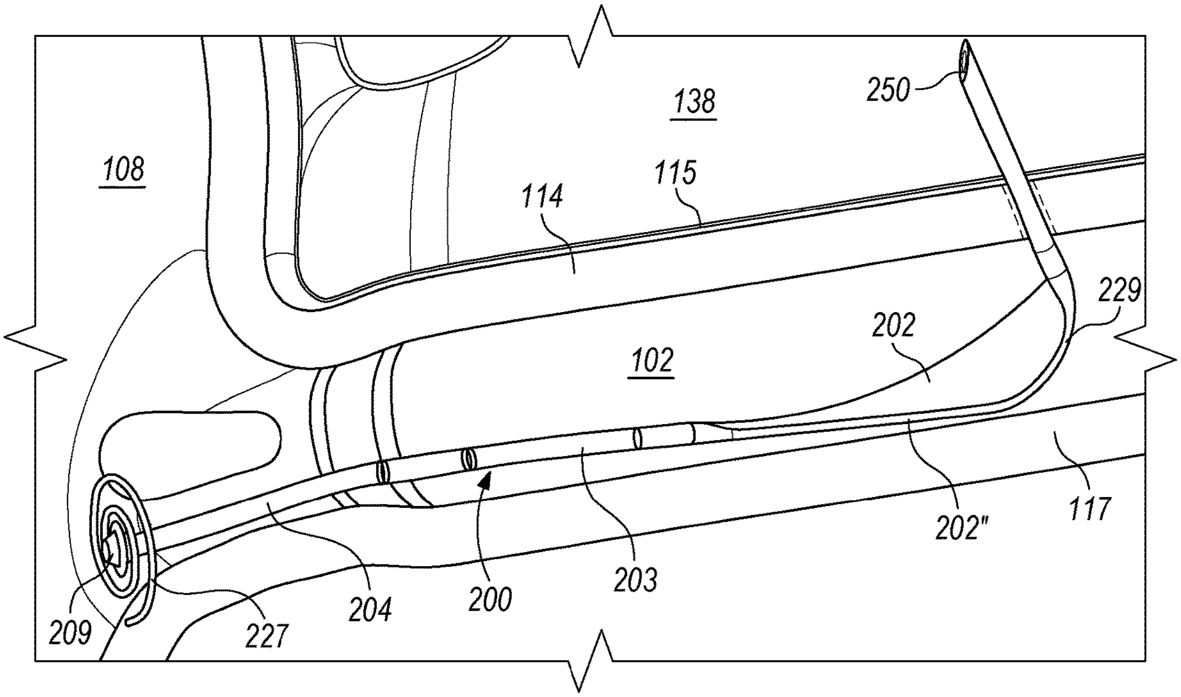
FIGS. 25A-G are side and cross-sectional views of a deployed endovascular shunt according to yet another embodiment of the disclosed inventions.
Figure 25B:
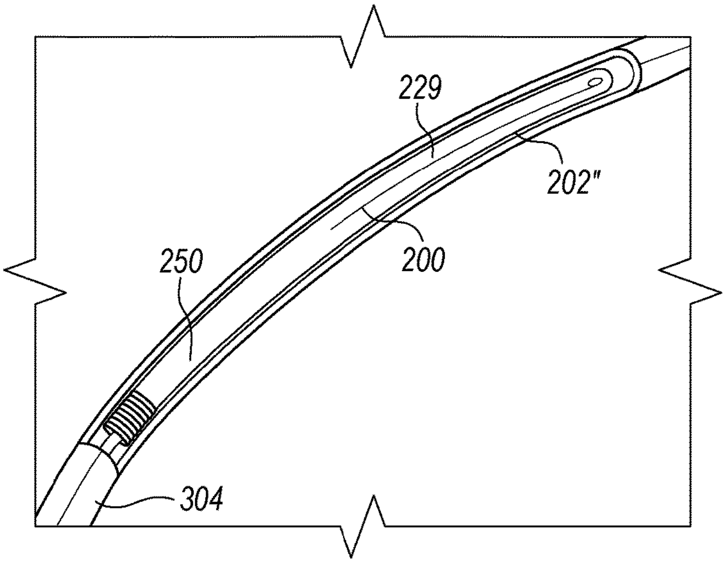
Figure 25C:
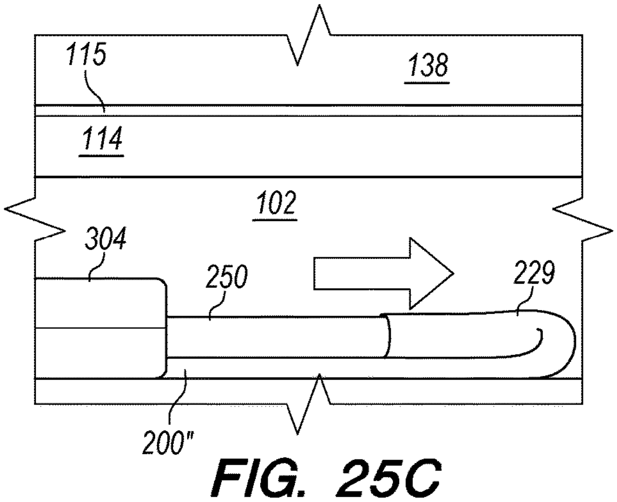
Figure 25D:
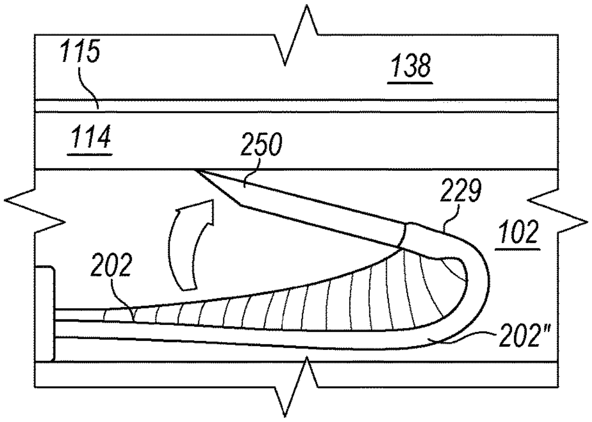
Figure 25E:
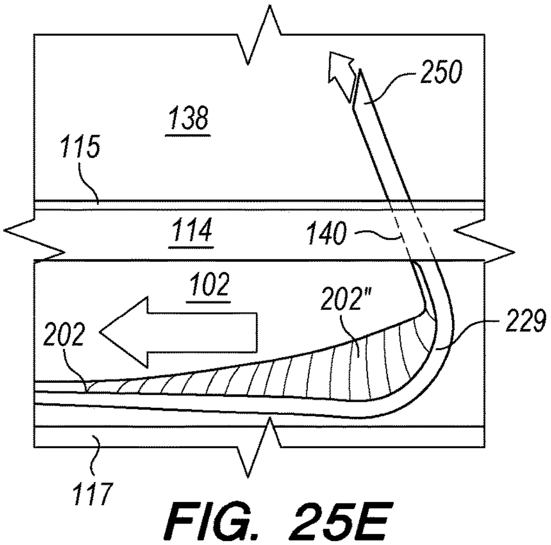
Figure 25F:
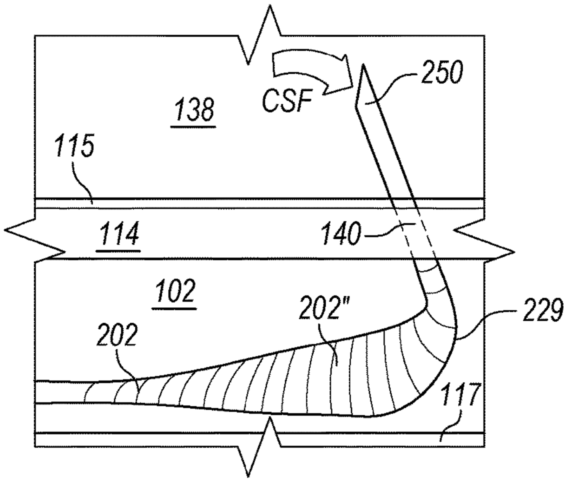
Figure 25G:
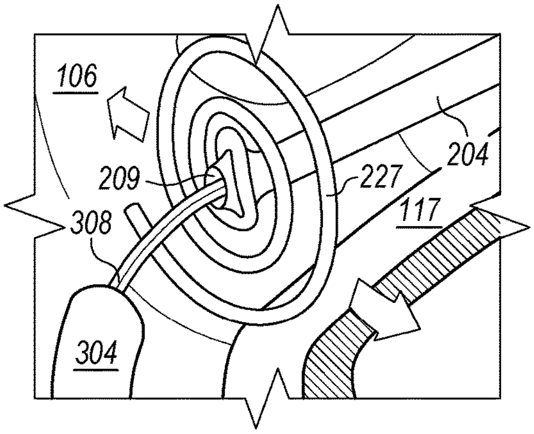

FIGS. 25A-G illustrate yet another exemplary shunt 200 constructed and implanted according to embodiments of the disclosed inventions. As shown in FIG. 25A, the shunt 200 includes the anchoring mechanism 227 and the duck-bill valve 209 in the proximal portion 204, the anchoring mechanism 229 in the distal portion 202, and the elongate body 203 extending therebetween. The body 203 of the shunt 200 comprises slidably disposed concentric tubular elements, as shown in FIGS. 6E-F, for selective elongation and/or adjustment of the shunt length $L_2$ (FIG. 6) according to the anatomy of the patient (i.e., target site for implantation of the shunt 220). The deployed anchoring mechanism 227 disposed on the proximal portion 204 of the shunt 200 comprises a spiral configuration for anchoring the proximal portion 204 of the shunt 200 within the jugular vein 106 by engaging the jugular bulb 108, the IPS wall 117 and another portion of the IPS 102, so that the duck-bill valve 209 is disposed within the jugular vein 106 (FIG. 25G). Alternatively, the anchoring mechanism 227 may engage the IPS wall 114 and 117 at the junction 118 (not shown). The anchoring mechanism 229 of the distal portion 202 of the shunt 200 comprises a retrograde-barb configuration (FIGS. 25A-F), so that when the anchoring mechanism 229 is in the delivery configuration, the tissue penetrating member 250 formed of an elongated cannula is folded over a portion 202" of the distal portion 202 of the shunt 200 (e.g., radially constrained by the delivery catheter 304, FIG. 25B-C), and when the anchoring mechanism 229 is in the deployed configuration, the tissue penetrating member 250 unfolds or expands from the portion 202" in a hinge-like fashion (FIGS. 25A and 25E-F). The portion 202" of the distal portion 202 is configured to radially expand in the deployed configuration, supporting and stabilizing the distal end 202 of the shunt 200 within the IPS 102 (FIGS. 25A and 25E-F). As shown in FIGS. 25B-C, the anchoring mechanism 229 is advanced thorough the delivery catheter 304 into a target site within the IPS 102 (e.g., at a location proximate the jugular bulb 108 or the jugular tubercle (not shown)). The anchoring mechanism 229 is further advanced within the IPS 102 and/or the delivery catheter 304 is withdrawn (FIG. 25C), so that the tissue penetrating member 250 unfolds (FIG. 25D). By application of suitable retrograde force to the shunt 200, the unfolded tissue penetrating member 250, in contact with the IPS wall 114, pierces the dura mater of the IPS wall 114 and the arachnoid layer 115 creating anastomosis 140 into the CP angle cistern 138 (FIGS. 25E-F). The expanded portion 202" of the anchoring mechanism 229 supports and stabilizes the distal end 202 of the deployed shunt 200 (e.g., contacting/"seating on" the IPS wall 117), as shown in FIGS. 25A and 25E-F.

Figure 26A:
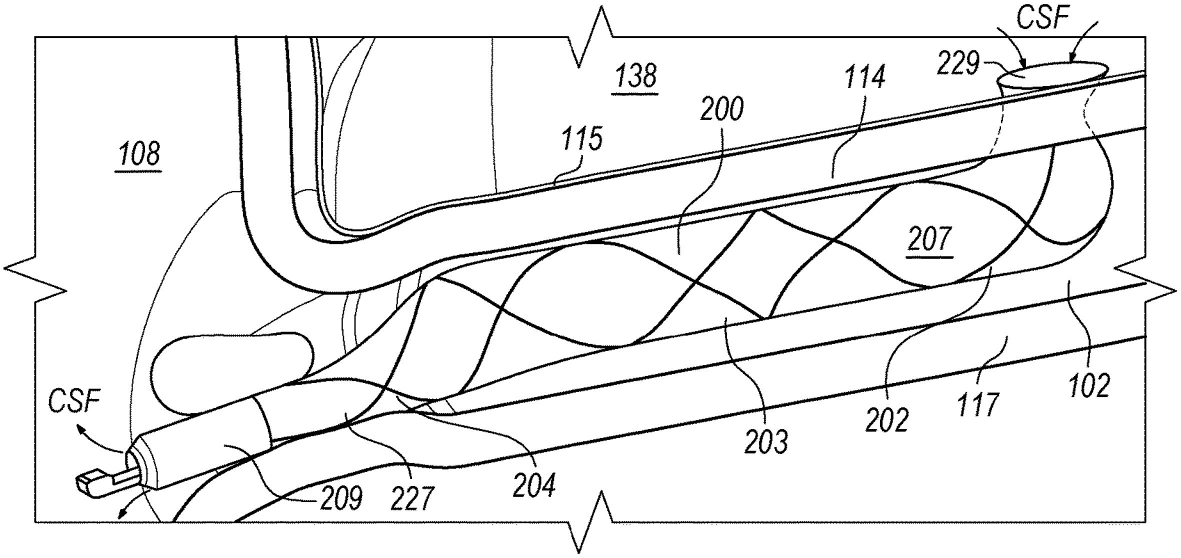
FIGS. 26A-G are side and cross-sectional views of a deployed endovascular shunt according to another embodiment of the disclosed inventions.
Figure 26B:
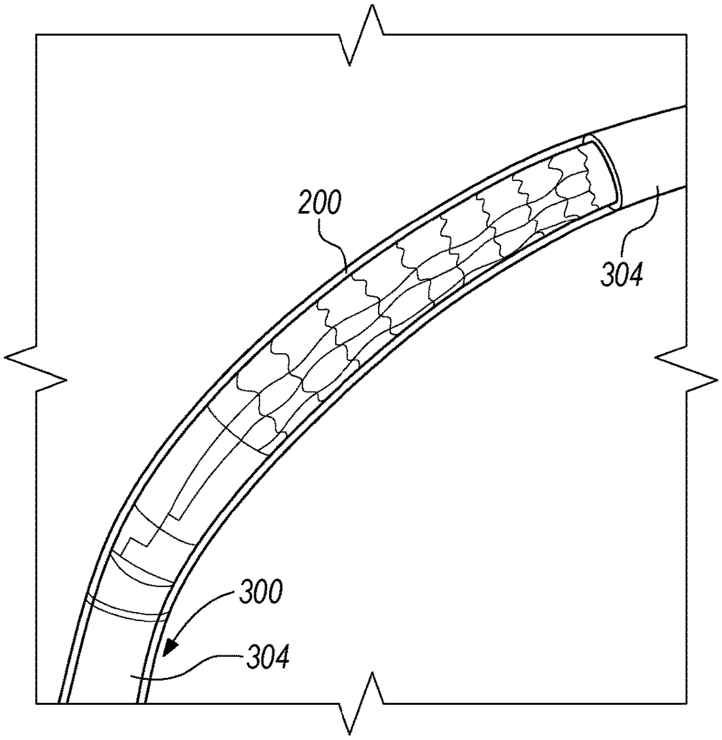
Figure 26C:
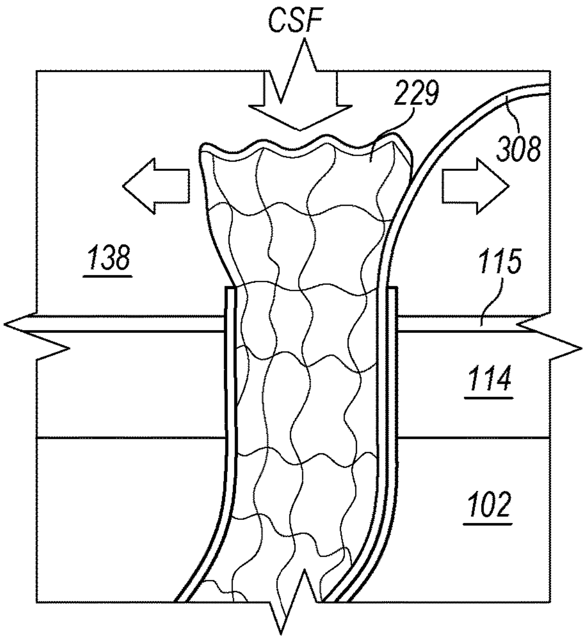
Figure 26D:
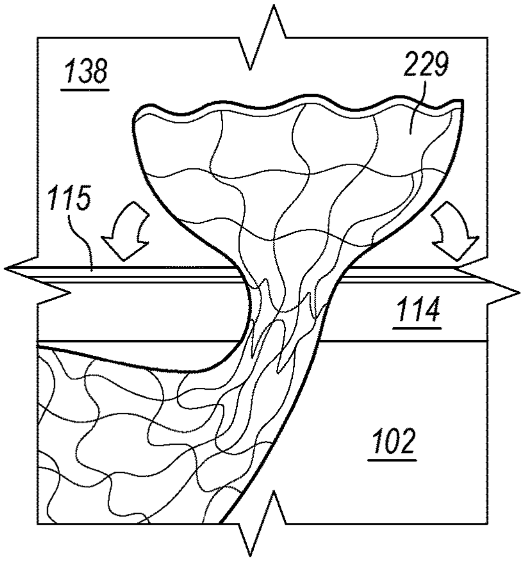
Figure 26E:
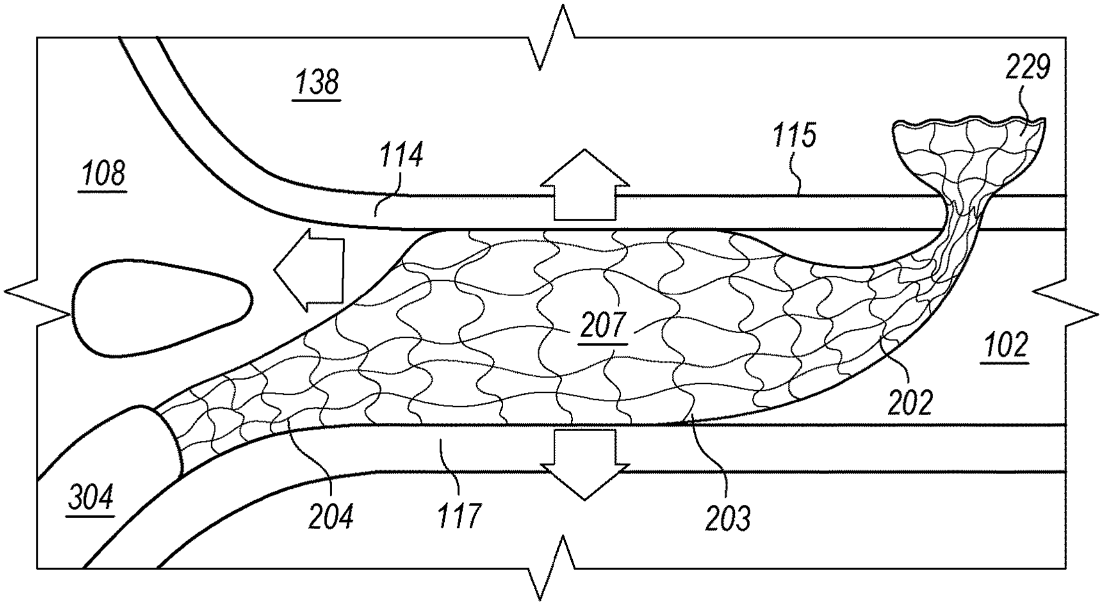
Figure 26F:
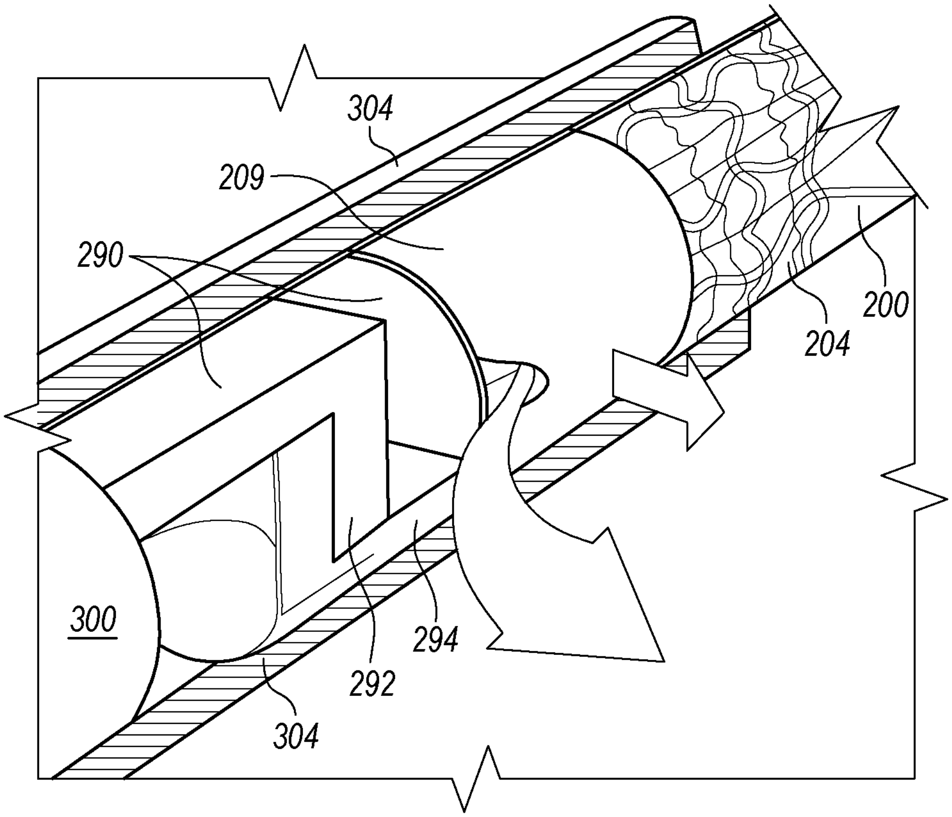
Figure 26G:
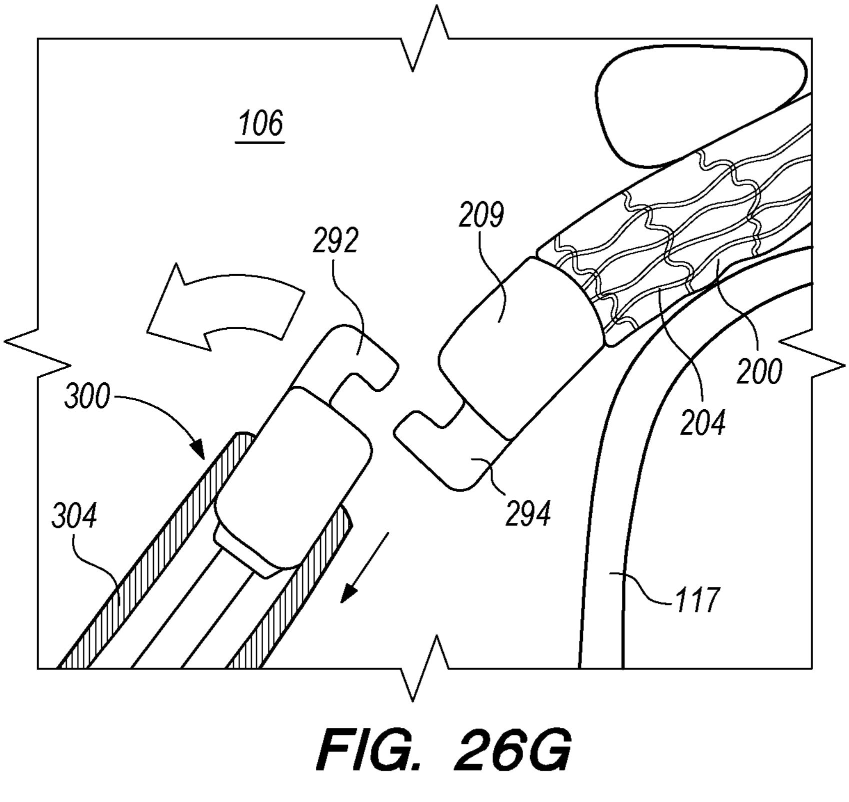

FIGS. 26A-G illustrate another exemplary shunt 200 constructed and implanted according to embodiments of the disclosed inventions. As shown in FIG. 26A, the shunt 200 includes the anchoring mechanism 227 and valve 209 in the proximal portion 204, the anchoring mechanism 229 in the distal portion 202, and the elongate body 203 extending therebetween. As shown in FIG. 26A, the body 203 and distal portion 202 of the shunt 200 comprise a self-expandable stent having an elastomeric/polymeric cover/liner, and/or stent-graft configuration, as shown in FIGS. 12 and 13A-C for the conduit 400. The shunt 200 is elongated for advancement through the delivery catheter 304 in the delivery configuration (FIG. 26B), and assumes the deployed/expanded configuration when the delivery catheter 304 that radially constricts the shunt 200 is withdrawn and/or the shunt 200 is advanced out the distal portion 344 (e.g. distal end opening 346) of delivery catheter 304 (FIGS. 26A, 26C-E), so that the anchoring mechanism 229 (FIGS. 26A and 26C-E) self-expands, securing the implanted shunt 200 in the target site. The anchoring mechanism 227 secures the proximal portion 204 of the shunt 200 within the jugular vein 106 by engaging the jugular bulb 108 and/or the jugular vein 106, the IPS wall 117 and another portion of the IPS 102, so that the valve 209 is disposed within the jugular vein 106 (FIGS. 26A and 26H). CSF flows through the implanted shunt 200, from the CP angle cistern 138 entering the shunt lumen 207 from distal portion 202 of the shunt (FIGS. 26A and 26C) and out of valve 209 at the proximal portion 204 of the shunt (FIG. 26A) into the jugular vein 106. As shown in FIGS. 26A and 26F-G, the valve 209 comprises a concentric gland seal housed on the proximal portion 204 of the shunt 200 with a slit exposing the opening of the valve, as also shown in FIG. 6L. The delivery assembly 300 further comprises an interlocking mechanism 290 configured to detachably couple the shunt 200 to the delivery catheter 304, as shown in FIG. 26F. The interlocking mechanism 290 includes a first interlocking element 292 (e.g., clasp) coupled to the delivery assembly 300 (e.g., via a push wire) and a second interlocking element 294 (e.g., clasp) coupled to the shunt 200 proximal portion 204 (e.g., attached to the valve 209). Once the shunt 200 is properly disposed at the target site, withdrawal of the delivery catheter 304 allows the interlocking mechanism 290 to be uncoupled (FIG. 26G). The interlocking element 294 coupled to the shunt 200 proximal portion 204 also allows for subsequent capture, recovery and/or withdrawal of the implanted shunt 200 (e.g., snare catheter).

Figure 27A:
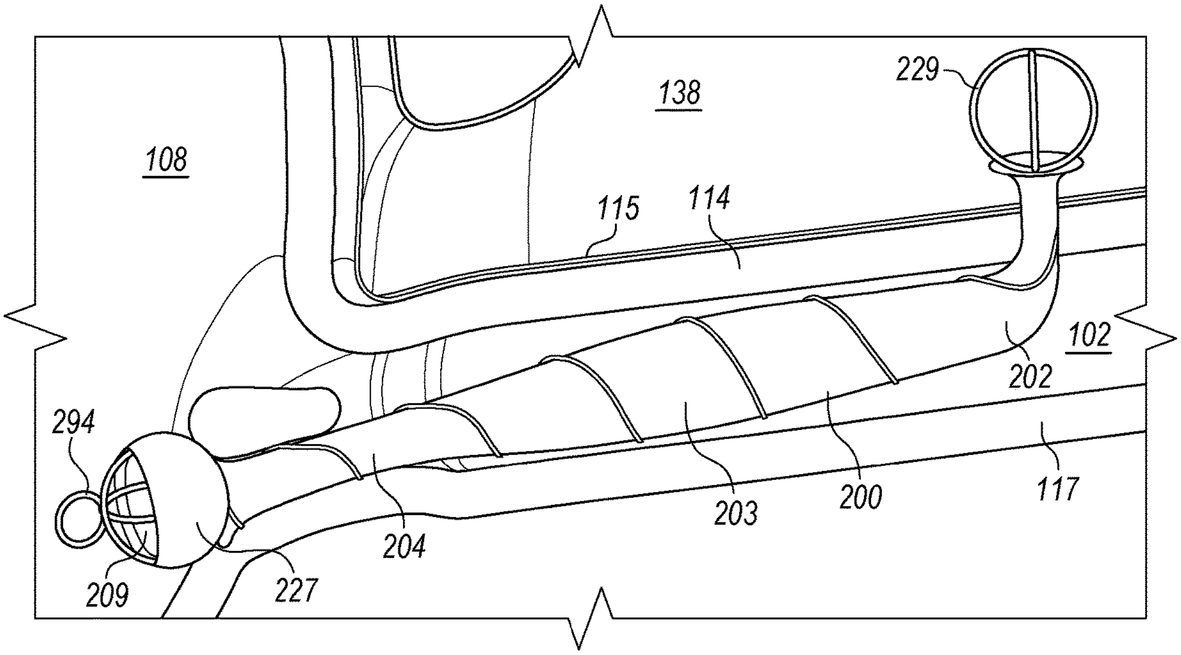
FIGS. 27A-E are side and cross-sectional views of a deployed endovascular shunt according to another embodiment of the disclosed inventions.
Figure 27B:
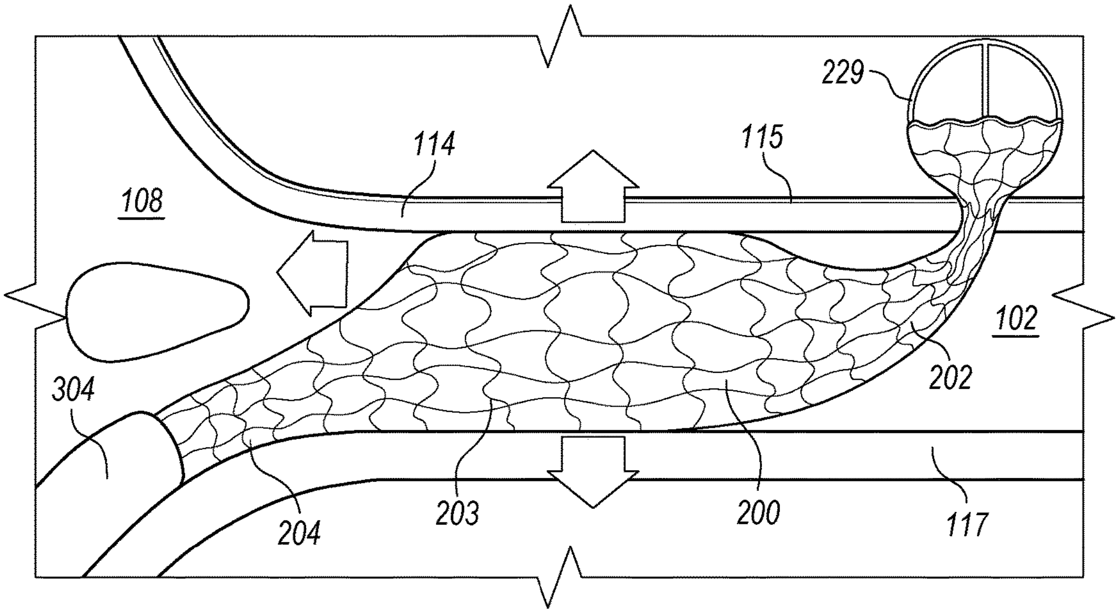
Figure 27C:
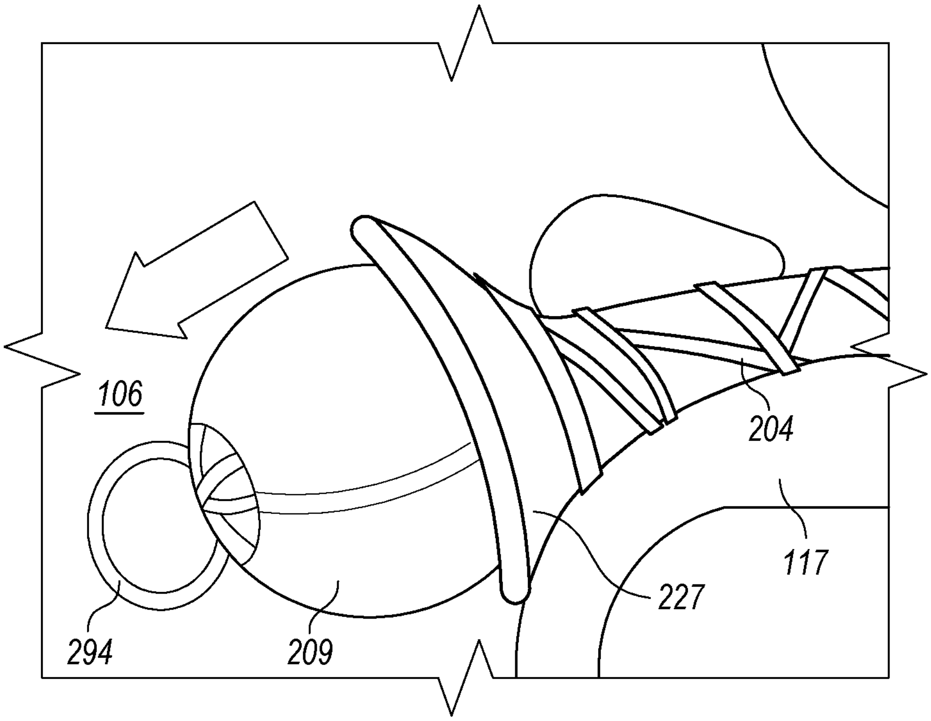
Figure 27D:
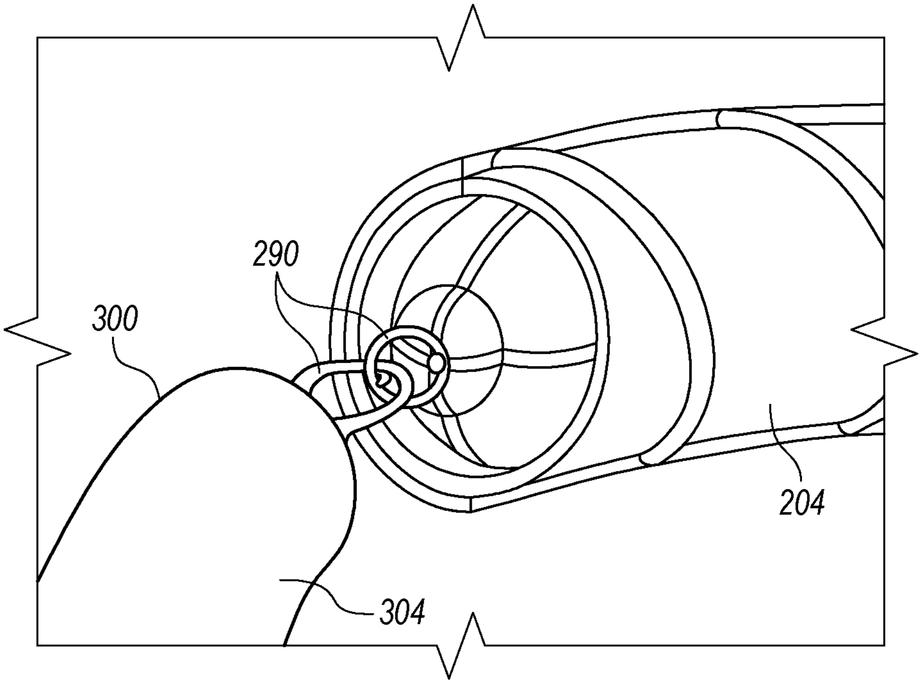
Figure 27E:
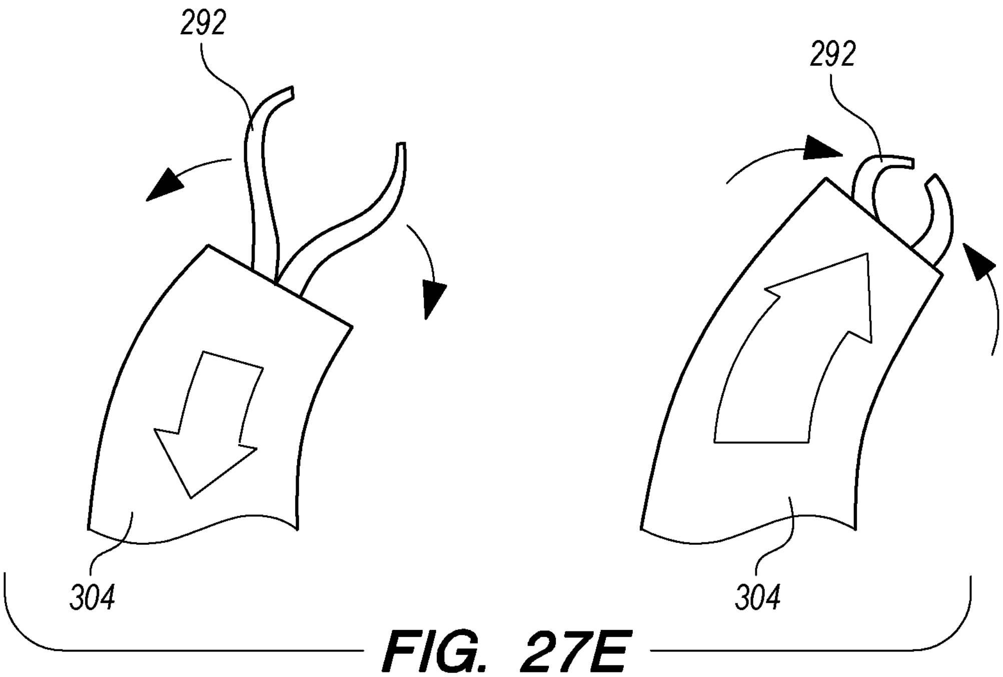

FIGS. 27A-E illustrate another exemplary shunt 200 constructed and implanted according to embodiments of the disclosed inventions. As shown in FIG. 27A, the shunt 200 includes the anchoring mechanism 227 and valve 209 in the proximal portion 204, the anchoring mechanism 229 in the distal portion 202, and the elongate body 203 extending therebetween. As shown in FIGS. 27A-B, the body 203 of the shunt 200 comprises a self-expandable stent having an elastomeric/polymeric cover/liner, and/or stent-graft configuration, as shown in FIGS. 12, 13A-C and 26A-E. The deployed anchoring mechanisms 227 and 229 of the shunt 200 comprises a radially expanded configuration (e.g., mesh or wired sphere, elliptic, wired frame or basket, or the like, or combinations thereof) for anchoring the shunt 200 at the target site (FIG. 27A-B). The anchoring mechanisms 227 and 229 (FIGS. 27A-D) self-expand when the shunt 200 is implanted, thereby securing the implanted shunt 200 in the target site. The anchoring mechanism 227 of the proximal portion 204 of the shunt incorporates the valve 209. The valve 209 comprises a wire frame partially covered with an elastomeric/polymeric liner, so that the CSF flow is regulated by the percentage of liner covering over the wire frame (FIGS. 27A and 27C). For example, the flow rate is lower when the wire frame is substantially covered by the liner, as shown in FIG. 27C, and the flow rate is larger when the wire frame has less liner coverage, as shown in FIG. 27A. As shown in FIGS. 27C-E, the delivery assembly 300 further comprises an interlocking mechanism 290 configured to detachably couple the shunt 200 to the delivery catheter 304. The interlocking mechanism 290 includes a first interlocking element 292 (e.g., claw) coupled to the delivery catheter 304 and a second interlocking element 294 (e.g., ring) coupled to the shunt 200 proximal portion 204 (e.g., attached to the valve 209). Once the shunt 200 is properly disposed at the target site, withdrawal of the delivery catheter 304 and uncoupling of the interlocking mechanism 290 (e.g., disengaging the claw, as shown in FIG. 27E) allows deployment of the shunt 200 (FIG. 27D). The interlocking element 294 (e.g., ring) coupled to the shunt 200 proximal portion 204 also allows for subsequent capture, recovery and/or withdrawal of the implanted shunt 200 (e.g., claw tool/catheter) or revision of valve 209 in proximal portion 204.

Alternatively, the embodiment of shunt 200 depicted in FIGS. 27A-E can be configured for deployment in IPS 102 using a two-step process. First, the body 203 of the shunt 200 comprising a self-expandable elastomeric/polymeric cover/liner, and/or stent-graft configuration, can be deployed in IPS 102. In some embodiments, the cover/liner or stent-graft element resides only within the IPS 102, while in other embodiments, deployment of the cover/liner or stent-graft element includes the step of creating the anastomotic connection between the IPS 102 and the CSF-filled subarachnoid space of the CP angle cistern 138 (e.g., FIGS. 26B-E). In a second step, a self-expanding wire form (e.g., comprising the proximal and distal anchoring mechanisms 227 and 229, respectively, and a stent-like body portion configured to reside within the cover liner or stent-graft) can be delivered through the previously deployed cover/liner and/or stent graft (e.g., FIG. 27B). The anchoring mechanisms 227 and 229 (FIGS. 27B-D) self-expand as the wire form is deployed out the cover/liner and/or stent graft in the CP angle cistern 138 (i.e., mechanism 229) and jugular vein 106 (i.e., mechanism 227), thereby securing the implanted shunt 200 in the target site. A partially covered wire frame comprising the proximal anchoring mechanism 227 forms valve 209 with the cover/liner and/or stent graft as previously disclosed.

Figure 28:
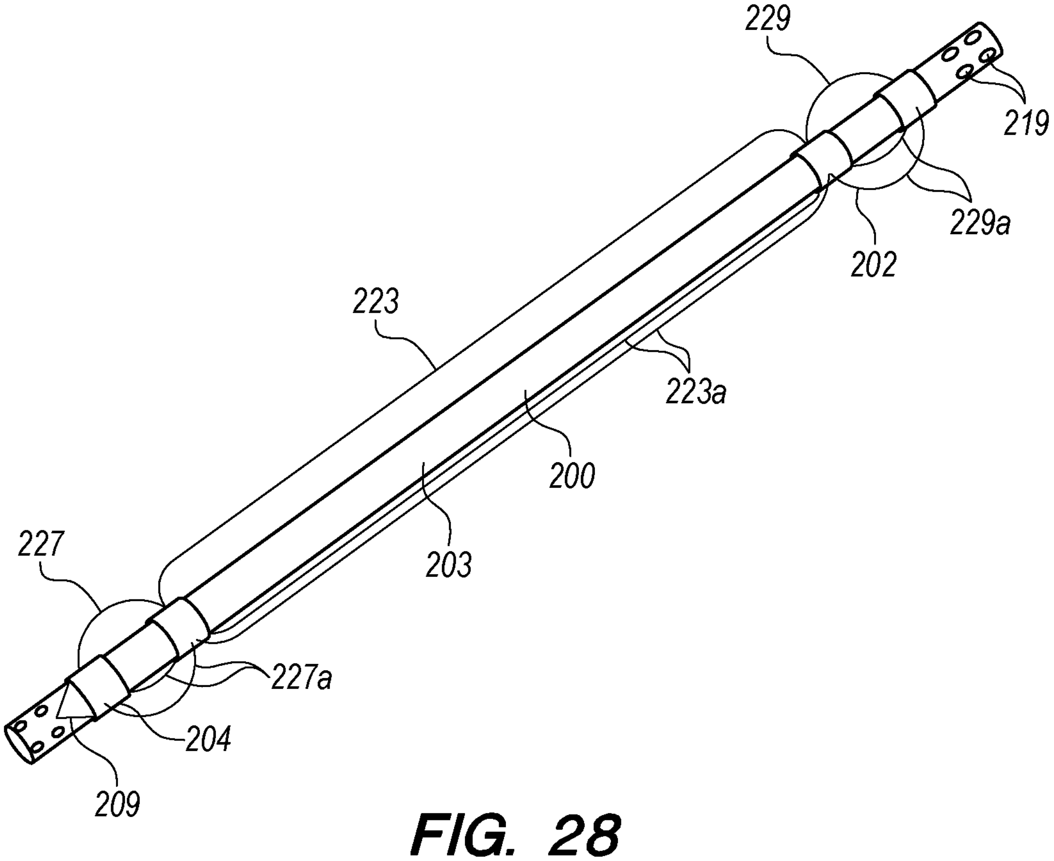
FIG. 28 is a side view of a deployed endovascular shunt according to one embodiment of the disclosed inventions.

FIG. 28 illustrates an exemplary shunt 200 constructed according to embodiments of the disclosed inventions. The shunt 200 includes the anchoring mechanism 227 and a duck-bill valve 209 in the proximal portion 204, the anchoring mechanism 229 in the distal portion 202, and the elongate body 203 extending therebetween, and further including an anchoring mechanism 223. The anchoring mechanisms 223, 227 and 229 include a plurality of respective deformable elements 223*a*, 227*a* and 229*a* (e.g., wires, loops) that are disposed radially outward in the deployed configuration. The deformable elements 223*a*, 227*a* and 229*a* are self-expanding (i.e., expanding from the delivery configuration into the deployed configuration) and configured to move radially outward from the axis of the shunt 200 allowing the shunt 200, including the body 203, to be anchored at the target site. The anchoring mechanism 227 is configured to engage the jugular bulb 108, the jugular vein 106, the IPS wall 117, and/or another portion of the IPS 102, anchoring the proximal portion 204 of the shunt 200 within the jugular vein 106, so that the valve 209 is disposed within the jugular vein 106. The anchoring mechanism 223 is configured to engage the IPS walls 114 and 117, anchoring the body 203 within the IPS 102, and the anchoring mechanism 229 is configured to engage the arachnoid layer 115 anchoring the distal portion 202 of the shunt 200 within the CP angle cistern 138.

Figure 29A:
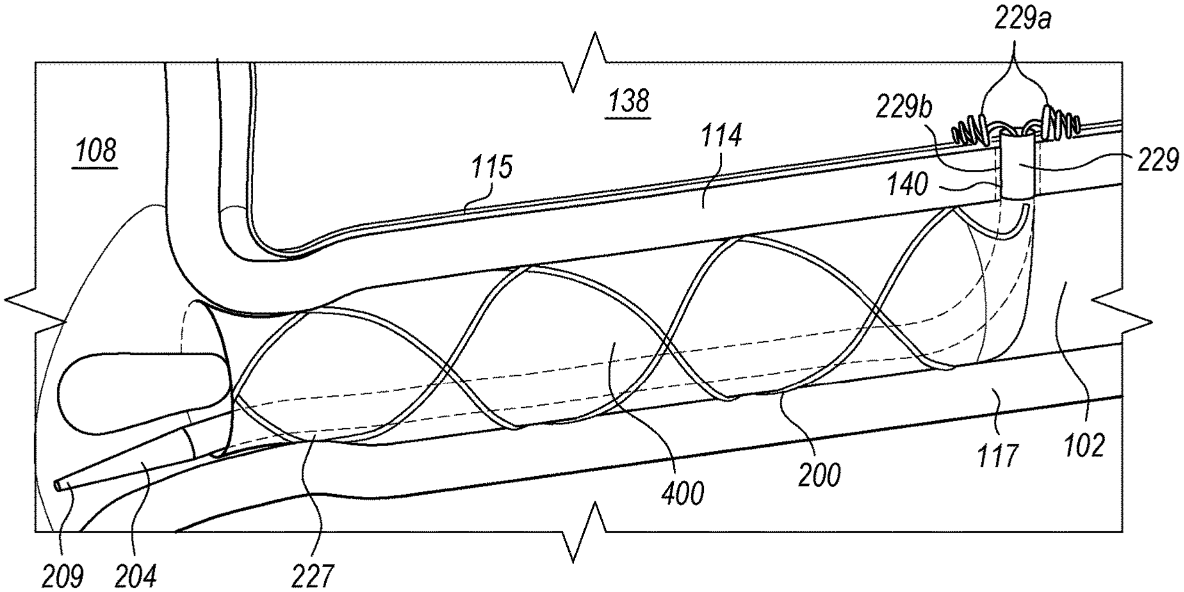
FIGS. 29A-G are side and cross-sectional views of an alternative embodiment of the shunt constructed and implanted according to embodiment of FIGS. 12 and 14A-H of the disclosed inventions.
Figure 29B:
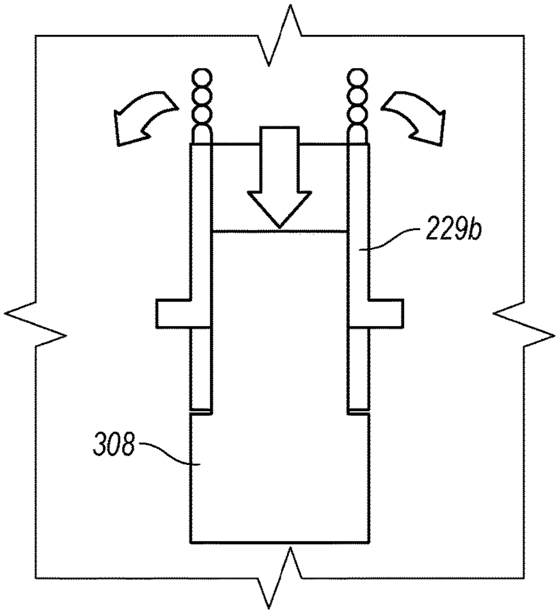
Figure 29C:
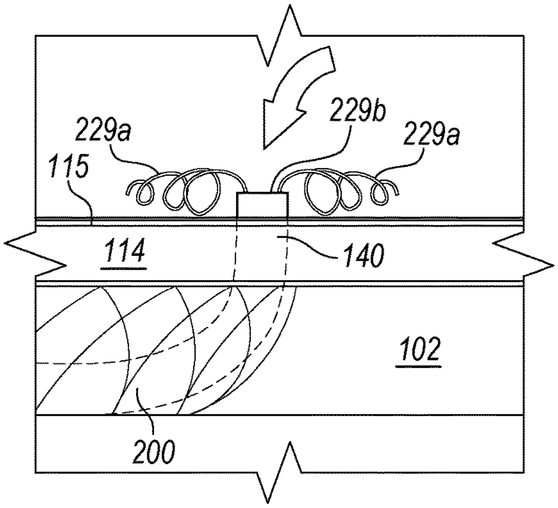
Figure 29D:
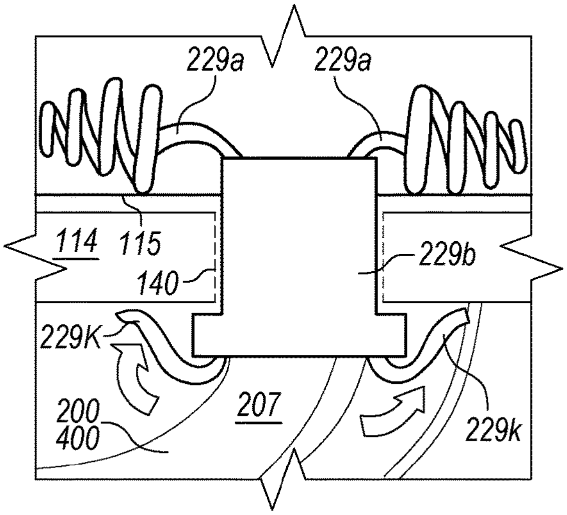
Figure 29E:
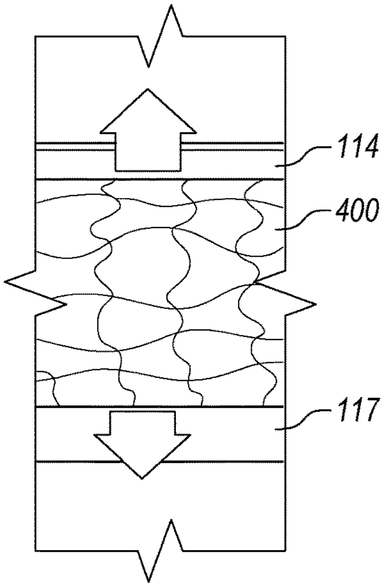

FIGS. 29A-G illustrates an alternative embodiment of the shunt 200 constructed and implanted according to embodiments of FIGS. 12 and 14A-H of the disclosed inventions. In the embodiment of FIGS. 29A-G, the shunt 200 is coupled to the conduit 400; the shunt 200 further includes the valve 209 in the proximal portion 204. Dual conical Nitinol coils 229*a* form a piercing cone (not shown) when constrained by the delivery catheter 304 and conduit 400; coils 229*a* of the piercing cone (e.g., pencil tip configuration) are delivered to IPS 102 in a constrained delivery configuration, thereby providing a sharp penetrating member that passes through dura of IPS wall 114 and arachnoid layer 115. Coils 229*a* can be self-expanding to separate from the penetrating cone form and expand within the subarachnoid space after passing through the dura 114 and arachnoid 115 to compress or pin down the penetrated arachnoid layer 115 within the CP angle cistern 138. Alternatively, the coils 229*a* can be mechanically actuated from a penetrating cone to a deployed configuration, according to previously disclosed embodiments of the anchoring mechanism 229. As shown in FIGS. 29A, 29C-D, and 29F-G, the anchoring mechanisms 227 and 229 are incorporated or disposed on the conduit 400. The conduit 400 comprises a self-expandable stent having an elastomeric/polymeric cover/liner, and/or stent-graft configuration, as shown in FIG. 12. The anchoring mechanism 229 comprises a plurality of deformable elements 229*a* (e.g., coils) and a tubular neck 229*b* (FIGS. 29A, 29C-D). The plurality of deformable elements 229*a* are configured to move radially outward from the axis of the shunt 200 and/or conduit 400, and alternatively, the elements 229*a* are also configured to move downwards (FIGS. 29A, 29C-D). The neck 229*b* is configured to be disposed within the anastomosis channel 140 in the deployed configuration (FIGS. 29A, 29C-D). Additionally, the anchoring mechanism 229 includes engaging members 229*k* (e.g., spring wires, balloons, claws, barbs, or the like, or combinations thereof) coupled to the tubular neck 229*b* and configured to move radially outward and upwards (FIG. 29D). Further, the neck 229*b* and/or engaging members 229*k* comprise a penetration stop preventing the penetrating member (e.g., 306, 250, 350, penetrating cone) and/or the shunt 200/200' from being deployed beyond a suitable distal length into the CP angle cistern 138, allowing suitable clearance between the distal tip of the shunt 200/200' and the brain stem 112, while avoiding abutting or the damaging brain stem 112.

Figure 29F:
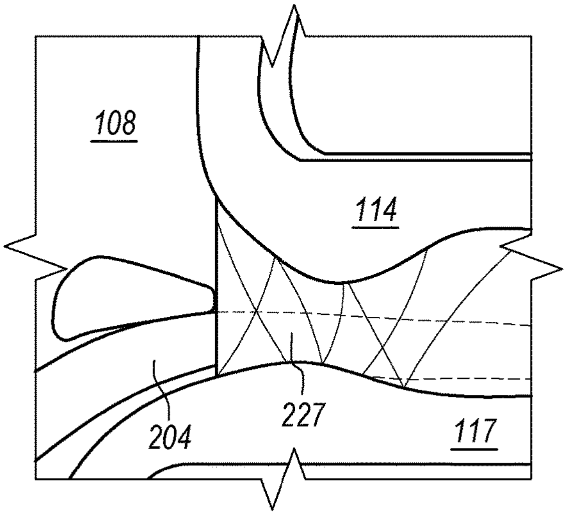
Figure 29G:
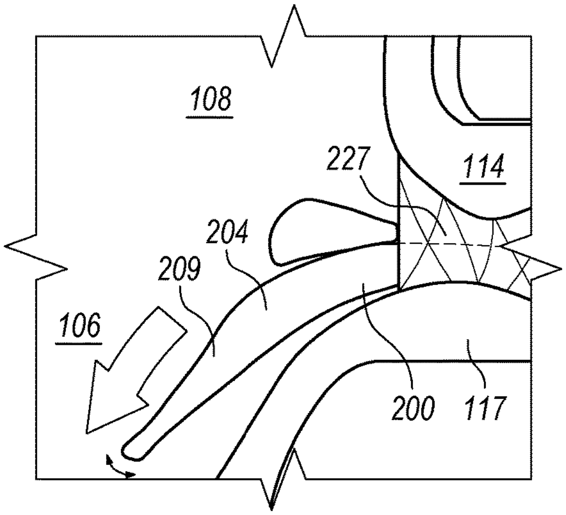

As shown in FIG. 29D, the anchoring mechanism 229 is configured to compress or pin down the arachnoid layer 115 with the deployed elements 229*a* against the dura mater IPS wall 114 with the deployed members 229*k*, to prevent occlusion of the shunt lumen 207 (e.g., by arachnoid mater). The deployed anchoring mechanism 227 engages the jugular bulb 108, the jugular vein 106, the IPS wall 117, and/or another portion of the IPS 102, anchoring the proximal portion 204 of the shunt 200 and/or conduit 400 within the jugular vein 106, so that the valve 209 is disposed within the jugular vein 106 (FIGS. 29A, 29F-G). Valve 209 can have a windsock-like configuration, formed from a collapsible, mesh-like framework of biocompatible polymeric material (e.g., PTFE, ePTFE, i.e., expanded polytetrafluoroethylene, PET). In its open form (e.g., under normal differential pressure between the subarachnoid space and venous system), CSF flows from the CP angle cistern 138 through the shunt lumen 207 and out through the pores of windsock valve 209 into the jugular vein 106. Windsock valve 209 can collapse on itself (e.g., where venous blood pressure exceeds the intracranial pressure in the subarachnoid space such during coughing or sneezing events) to prevent the backflow of blood through shunt 200 into the subarachnoid space 116. As shown in FIG. 29G, the circulation of venous blood flow around the proximal portion 204 of the shunt 200 agitates the valve 209, minimizing, deterring, or avoiding growth of endothelial cells and clogging of the lumen 207 opening at the proximal portion 204 of the shunt 200. As previously disclosed with the embodiments of shunt 200 depicted in the FIG. 27, the embodiments of shunt 200 shown in FIG. 29 can be deployed in a two-step process (e.g., deployment of conduit 400 in at least the IPS 102 in a first step, and deployment of a self-expanding wire form comprising the proximal and distal anchoring mechanisms 227 and 229, a stent-like body portion, and valve 209 in a second deployment step).

Figure 30A:
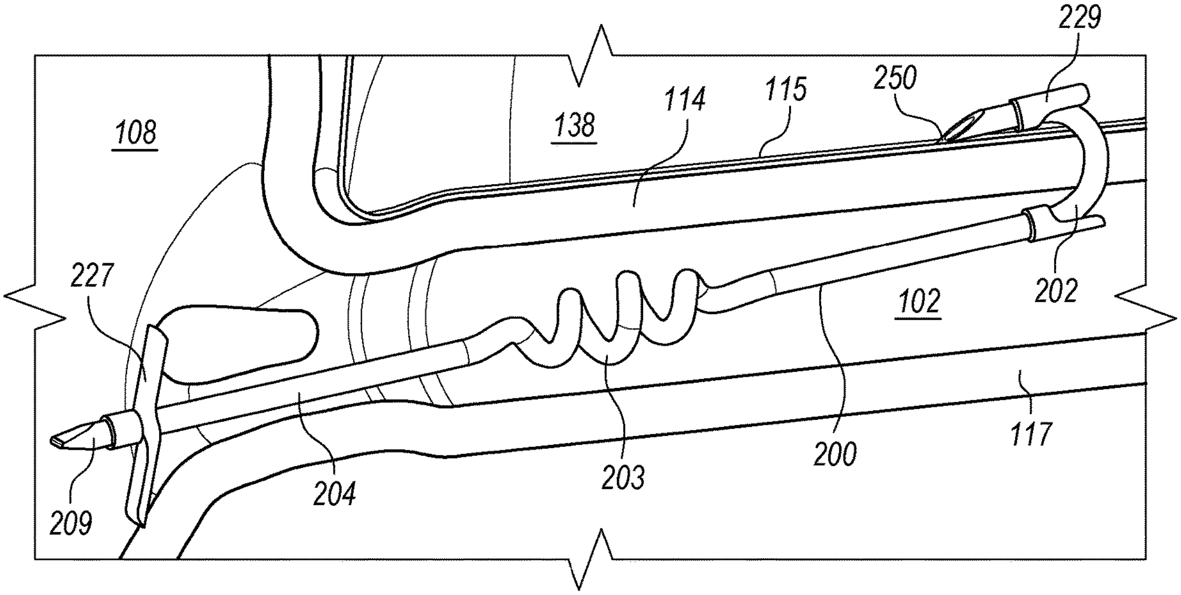
FIGS. 30A-F are side and cross-sectional views of a deployed endovascular shunt according to another embodiment of the disclosed inventions.
Figure 30B:
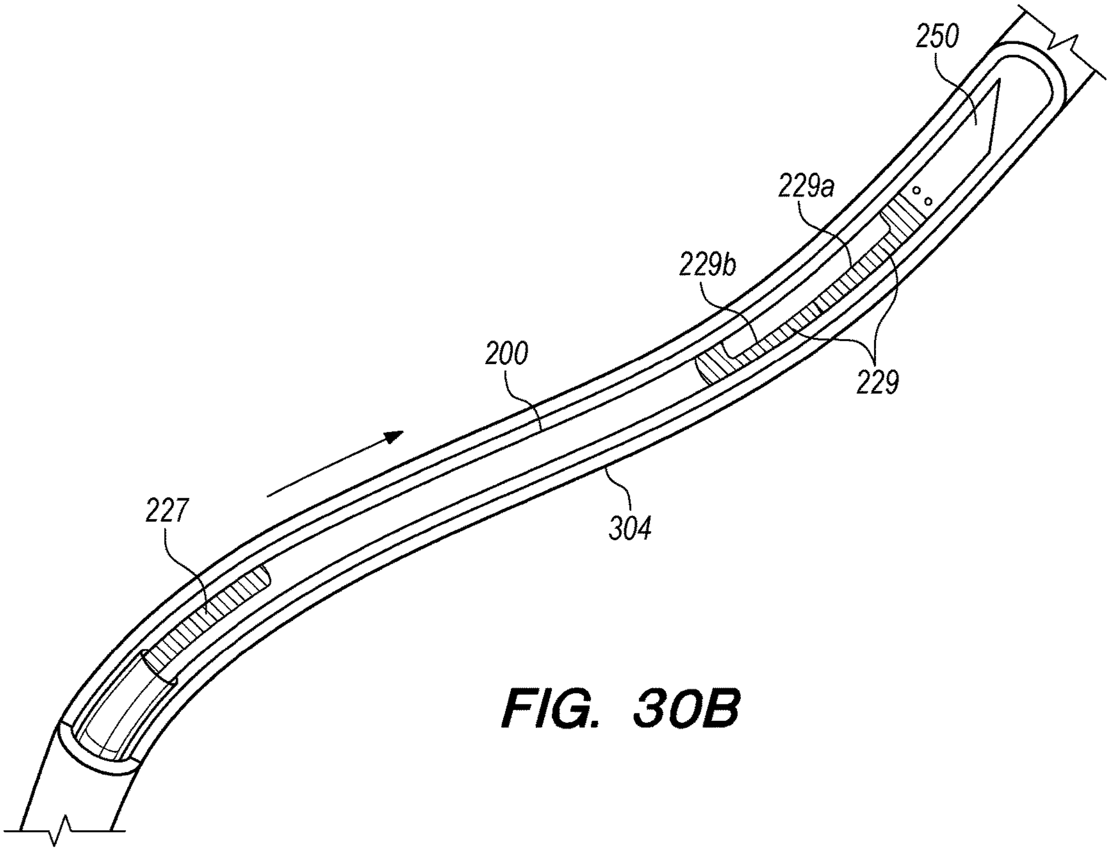
Figure 30C:
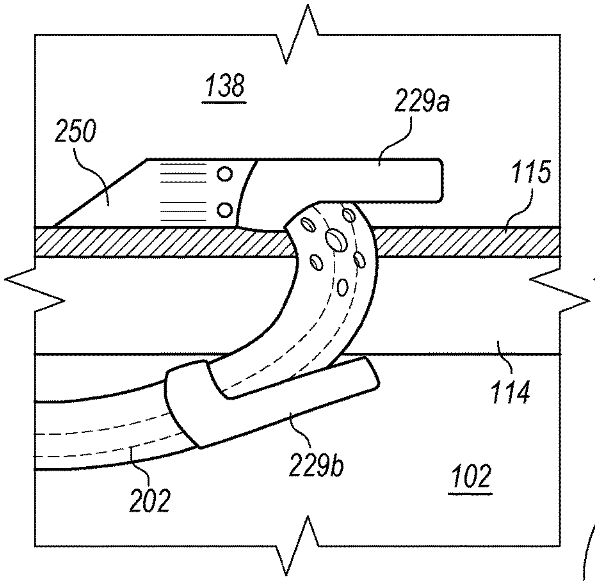
Figure 30D:
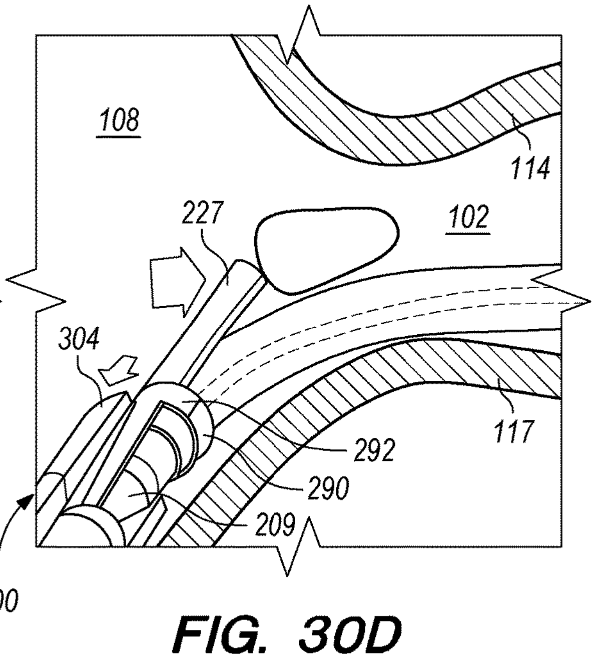
Figure 30E:
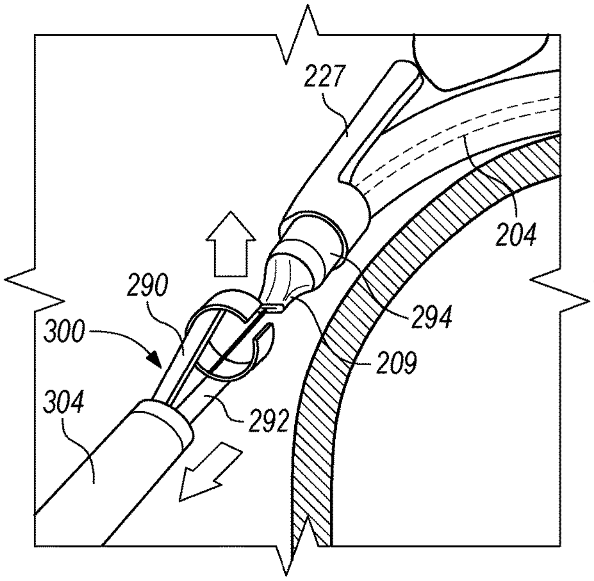
Figure 30F:
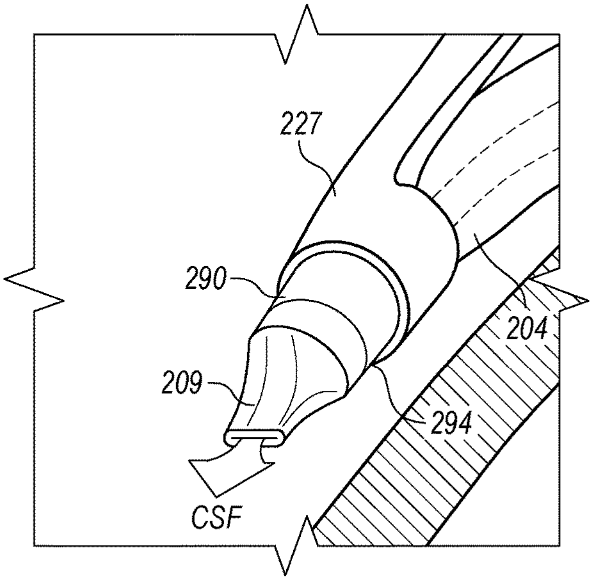

FIGS. 30A-F illustrate another exemplary shunt 200 constructed and implanted according to embodiments of the disclosed inventions. The shunt 200 includes the anchoring mechanism 227 and the duck-bill 209 in the proximal portion 204, the anchoring mechanism 229 and tissue penetrating member 250 in the distal portion 202, and the elongate body 203 extending therebetween. The body 203 of the shunt 200 comprises a spring/coil-like body, as shown in FIGS. 6GH, for selective elongation and/or adjustment of the shunt length $L_2$ (FIG. 6) according to the anatomy of the patient (i.e., target site for implantation of the shunt 220). Further, the spring/coil-like body 203 of the shunt 200 is configured to apply tensional force, at least, between the proximal portion 204 and the distal portion 202 of the shunt 200 maintaining the implanted shunt 200 properly anchored in the target site (e.g., limiting movement of shunt or loosely anchored shunt). The shunt 200 may be composed of thermoplastic elastomer (TPE), and the anchoring mechanisms 227 and 229 may be composed of shape-memory materials, such as super-elastic nickel titanium alloy, known as Nitinol® or other suitable material. The shunt 200 is elongated for advancement through the delivery catheter 304 (FIG. 30B). The anchoring mechanisms 227 and 229 comprise a T-bar tubular configuration, as shown in FIGS. 30A-F. The anchoring mechanism 229 includes a first anchoring element 229*a* configured to be disposed in the CP angle cistern 138, anchoring and/or holding the distal portion 202 of the shunt 200 against the arachnoid layer 115 so that the tissue penetrating member 250 is disposed and held adjacently to the arachnoid layer 115 when the shunt 200 is deployed (FIGS. 30A and 30C). The anchoring mechanism 229 further includes a second anchoring element 229*b* configured to be disposed within the IPS 102 contacting the IPS wall 114, further anchoring and holding the distal end 202 of the shunt 200 when interfacing with the first anchoring element 229*a*, as shown in FIGS. 30A and 30C. The deployed anchoring mechanism 227 engages the jugular bulb 108, the jugular vein 106, the IPS wall 117, and/or another portion of the IPS 102, anchoring the proximal portion 204 of the shunt 200 within the jugular vein 106, so that the valve 209 is disposed within the jugular vein 106, as shown in FIGS. 30A and 30-D-F. The delivery assembly 300 further comprises an interlocking mechanism 290 configured to detachably coupled the shunt 200 to the delivery catheter 304, as shown in FIGS. 30D-F. The interlocking mechanism 290 includes a first interlocking element 292 (e.g., double clasps, claws) coupled to the delivery assembly 300 and a second interlocking element 294 (e.g., annular recess) coupled to the shunt 200 proximal portion 204. Once the shunt 200 is properly disposed at the target site, withdrawal of the delivery catheter 304 and uncoupling of the interlocking mechanism 290 (e.g., disengaging the claw 292 from the recess 294, as shown in FIG. 30E) allows deployment of the shunt 200 (FIGS. 30A and 30F). The interlocking element 294 (e.g., annular recess) disposed in the proximal portion 204 of the shunt 200 also allows for subsequent capture, interrogation, repair, recovery and/or withdrawal of the implanted shunt 200 (e.g., claw tool/catheter).

Figure 31:
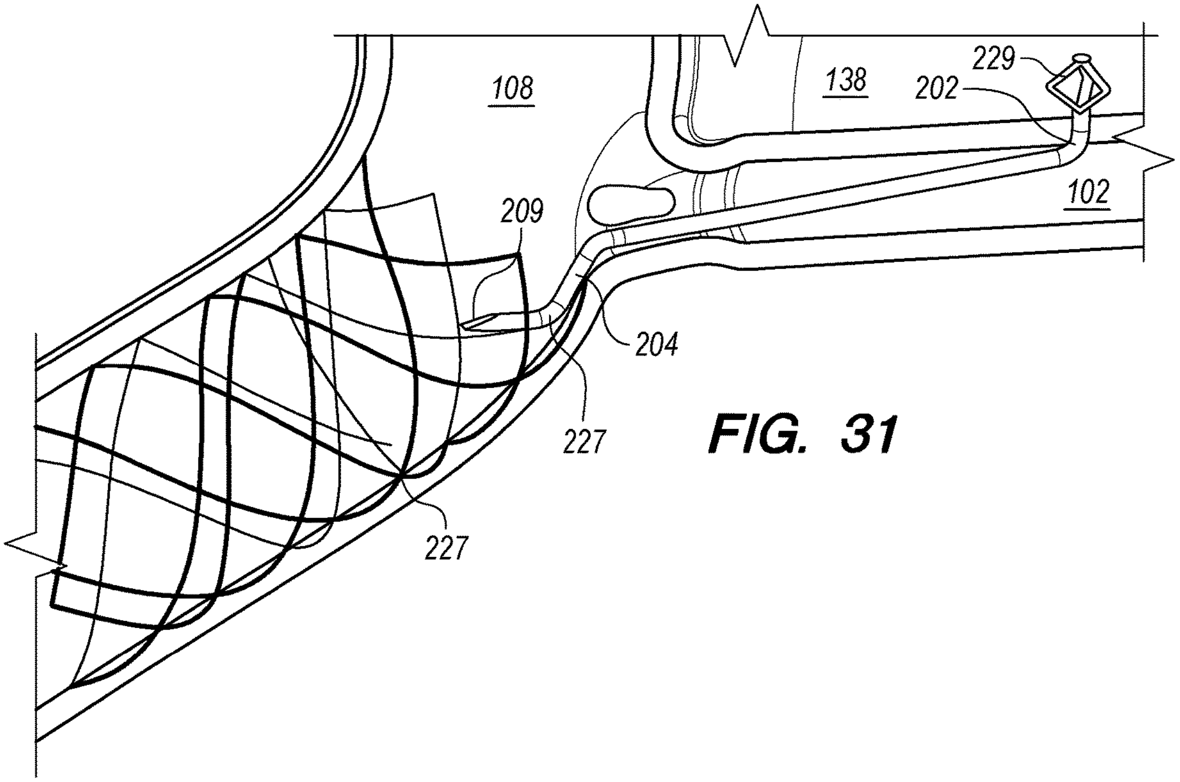
FIG. 31 is a side view an alternative embodiment of the shunt constructed and implanted according to the embodiment of FIGS. 22A-G of the disclosed inventions.

FIG. 31 illustrates an alternative embodiment of the shunt 200 constructed and implanted according to the embodiment of FIGS. 22A-G. The implanted shunt 200 shown in FIG. 31 includes an anchoring mechanism 227 and a duck-bill valve 209 in the proximal portion 204, an anchoring mechanism 229 in the distal portion 202, and an elongate body 203 extending therebetween. The anchoring mechanism 227 includes a pre-curved configuration (e.g., “S” like shape) and may further include a stent disposed within the jugular vein 106, which may be attached to the proximal portion 204 of the shunt 200. The stent portion of the anchoring mechanism 227 maintains the proximal portion of shunt 200 and duck-bill valve 209 in a relatively high blood flow area of the jugular vein to prevent occlusion of valve 209. Such stent portion prevents proximal portion 204 and valve 209 from being incorporated into the wall of the jugular bulb and vein by endothelial cells overgrowing the proximal portion 204 of the shunt 200, which can lead to shunt clogging and failure.

Figure 32:
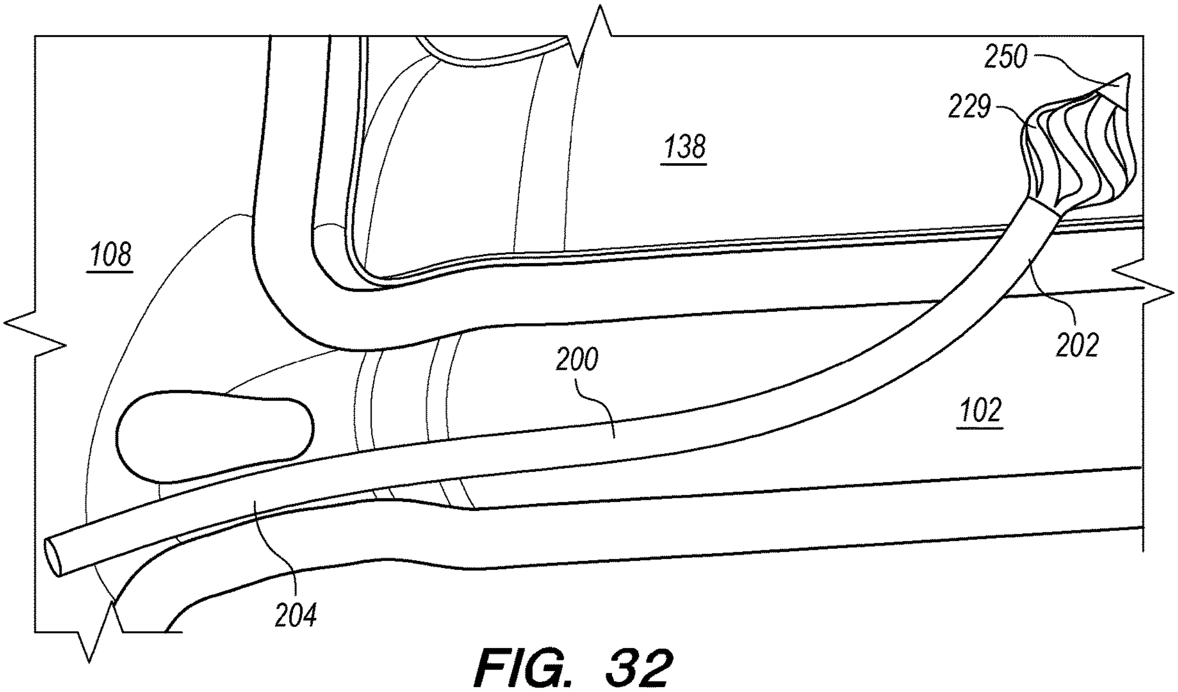
FIG. 32 is a side view an alternative embodiment of the shunt constructed and implanted according to embodiment of FIG. 21E of the disclosed inventions.

FIG. 32 illustrates an alternative embodiment of the shunt 200 constructed and implanted according to embodiment of FIG. 21E. The implanted shunt 200 includes the anchoring mechanism 229 and the tissue penetrating member 250 in the distal portion 202 of the shunt 200. The anchoring mechanism 229 comprises an elliptecot configuration, as previously disclosed.

Figure 33C:
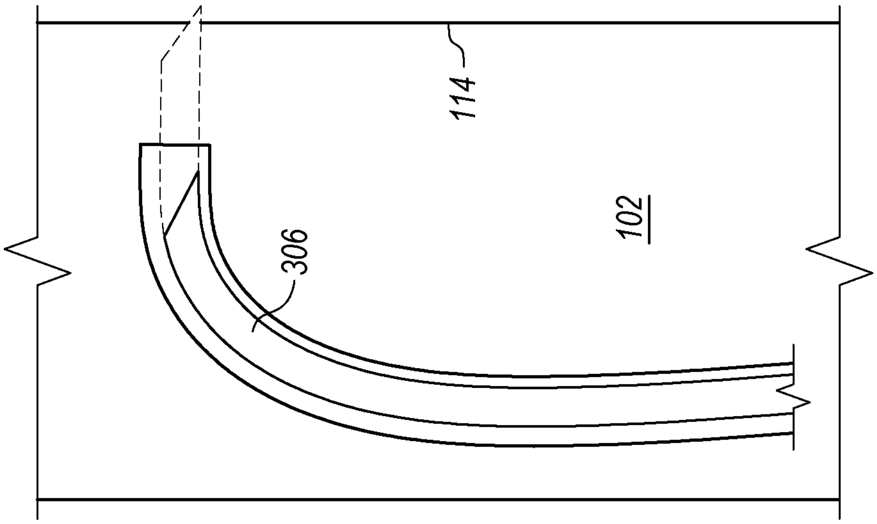
FIGS. 33A-33C are cross-section views of a surgical tool and an endovascular shunt interface according to embodiments of the disclosed inventions.
Figure 33B:
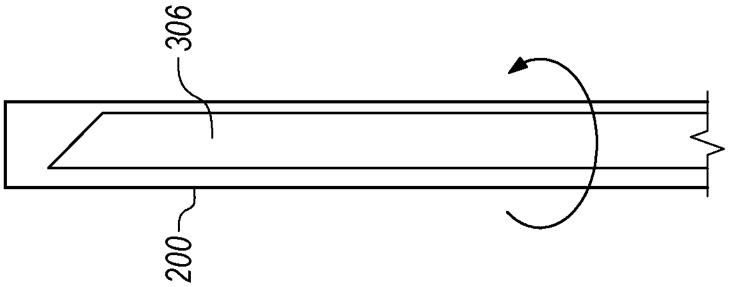
Figure 33A:
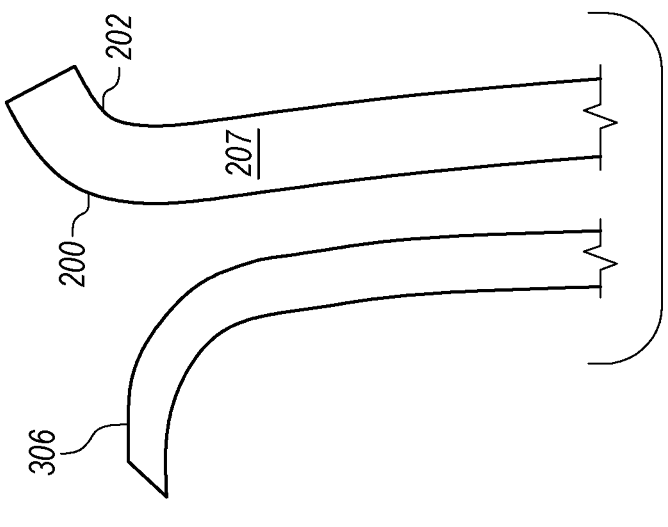

FIGS. 33A-33C depict one embodiment of an interface between the tissue penetrating element 306 and the shunt 200 constructed according to embodiments of the disclosed inventions. The tissue penetrating element 306 includes a hollow tubular trocar configured to be coaxially disposed within the lumen 207 of shunt 200. The tissue penetrating element 306 includes a curved distal portion (e.g., pre-curved, biasedly curved-heat-set Nitinol, flexible, drivable distal portion via control wires, or the like, or combinations thereof) with a sharpened, beveled tip configured to penetrate the IPS wall 114 and the arachnoid layer 115. The shunt 200 also includes a curved distal portion 202 (e.g., pre-curved, biasedly curved-heat-set Nitinol, flexible, or the like, or combinations thereof). As shown in FIG. 33A, the respective curved distal portions of the tissue penetrating element 306 and the shunt 200 are depicted in an opposite directions. The lumen 207 of the shunt 200 is configured to allow passage of the tissue penetrating element 306 thereof, as shown in FIG. 33B. When the tissue penetrating element 306 and the shunt 200 are disposed in a destructive interference (e.g., opposed respective curved distal portions) the tissue penetrating element 306 and shunt 200 create a straightened configuration, as shown in FIG. 33B. In this straight configuration, the tissue penetrating element 306 and the shunt 200 can be navigated through the vasculature via the delivery catheter 304 until reaching the desired deployment location along the IPS wall 114. At such location, the tissue penetrating element 306 can be rotated relative to the shunt 200 such that the respective curved distal portions of the tissue penetrating element 306 and the shunt 200 align along the same arcuate path having a constructive interface cooperatively bending towards the IPS wall 114, as shown in FIG. 33C. The tissue penetrating element 306 can be advanced distally from the shunt 200 to penetrate through IPS wall 114 and arachnoid layer 115 into the subarachnoid space 116, as previously described. The shunt 200 can then be advanced over the tissue penetrating element 306 and be anchored in CP angle cistern 138 (e.g., before, as, or after the tissue penetrating element 306 is withdrawn from the delivery assembly 300). The tissue penetrating element 306 and shunt 200 configuration of FIGS. 33A-33C advantageously allows the tissue penetrating element 306 and shunt 200 to be delivered in a straight configuration while tracking through the vasculature to the IPS 102, and then rotated to a constructive interference of the curved distal portions of the tissue penetrating element 306 and the shunt 200 having a combined strength for penetrating through the IPS wall dura mater 114 and arachnoid layer 115.

Figures 34A, 34B:
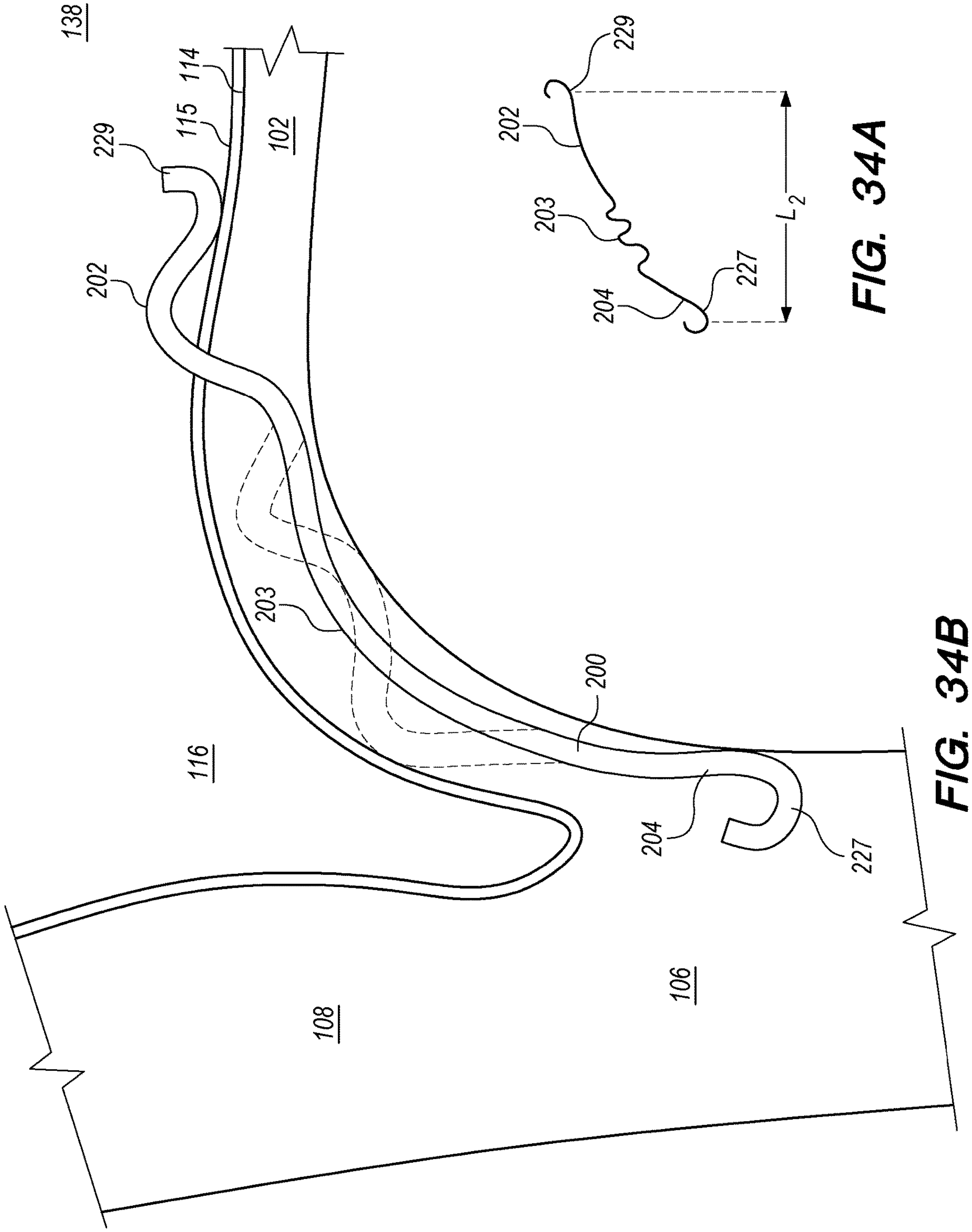
FIGS. 34A-34B are cross-section views of an endovascular shunt according to another embodiment of the disclosed inventions.

FIGS. 34A-34B illustrate another exemplary shunt 200 constructed and implanted according to embodiments of the disclosed inventions. FIGS. 34A-B depict side views of the shunt 200 having the anchoring mechanism 227 extending from the proximal portion 204 of the shunt 200 comprising a shepherd's hook or "J" like shape in the deployed configuration, and the anchoring mechanism 229 extending from the distal portion 202 of the shunt 200 also comprising a shepherd's hook or "J" like shape in the deployed configuration. The anchoring mechanisms 227 and 229 include respective curved (e.g., pre-curved, biasedly curved, flexible, or the like, or combinations thereof) proximal 204 and distal 202 portions of the shunt 200, forming their respective shepherd's hooks or "J" like shape in the deployed configuration. FIG. 34B depicts a cross-section view of the shunt 200 deployed and implanted in the IPS 102, providing a conduit for one-way flow of CSF from the CP angle cistern 138 into the jugular vein 106. The anchoring mechanisms 227 and 229 are configured to secure and anchor the shunt 200 in a desired location by engaging the tissue in the CP angle cistern 138 and jugular vein 106, respectively, as previously described. The shepherd's hooks or "J" like shape of the anchoring mechanisms 227 and 229 in the deployed configuration minimize and/or prevent shunt occlusion and clogging by maintaining the opening into the lumen 207 of the shunt 200 of the distal portion 202 (e.g., CSF inflow portion) separated, apart, or away from the arachnoid layer 115 (FIG. 34B) and the opening out of the lumen 207 of the shunt 200 of the proximal portion 204 (e.g., CSF outflow portion, valve 209) separated, apart, or away from the wall of the jugular vein 106 (FIG. 34B). The shunt 200 comprises a spring/coil-like body 203, as shown in FIGS. 34A and 34B (interrupted line), for selective elongation and/or adjustment of the shunt 200 length $L_2$ according to the anatomy of the patient (i.e., target site for implantation of the shunt 200). Further, the spring/coil-like body 203 of the shunt 200 is configured to apply tensional force, at least, between the proximal portion 204 and the distal portion 202 of the shunt 200 maintaining the implanted shunt 200 properly anchored in the target site.

Several embodiments of the shunt 200 and/or the delivery system 300 have been previously described for penetrating the dura mater of the IPS wall 114 and the arachnoid layer 115 with a penetrating element (e.g., elongate pusher member 310, delivery catheters 304/304'/304", piercing elements 306/250/350, shunt 200', and/or system 300'). It should be appreciated that factors (e.g., design and clinical aspects) can be considered as to determine the embodiments, aspects and configurations of the penetrating element of the system 300, for example: (a) the peak force required to penetrate through tissue (i.e., IPS wall 114 dura mater from within the IPS 102 and the arachnoid layer 115 into the CP angle cistern 138), which force is translated through the delivery system 300 from a peripheral access point such as a delivery catheter inserted at the femoral vein (e.g., proximal portion of a delivery guide wire, catheter, or tool); (b) the tissue damage and severity of the trauma caused from the penetrating/piercing step or force (a) applied to the IPS wall 114 dura mater and arachnoid layer 115; (c) the extent to which the penetration site seals around the deployed shunt or has potential for leaking blood or CSF through the anastomosis 140; (d) the extent of tissue deformation during the penetrating/piercing step or force (a) applied to the IPS wall 114 dura mater and arachnoid layer 115 (e.g., the extent that IPS wall 114 dura mater and/or arachnoid layer 115 expand toward brain stem 116 before the penetrating element passes through the tissue); and (e) the extent that the penetrating element resists bending or buckling while penetrating tissue and/or that such penetrating element requires additional support (e.g., an outer sheath) to translate the forces required to penetrate tissue.

Figure 35:
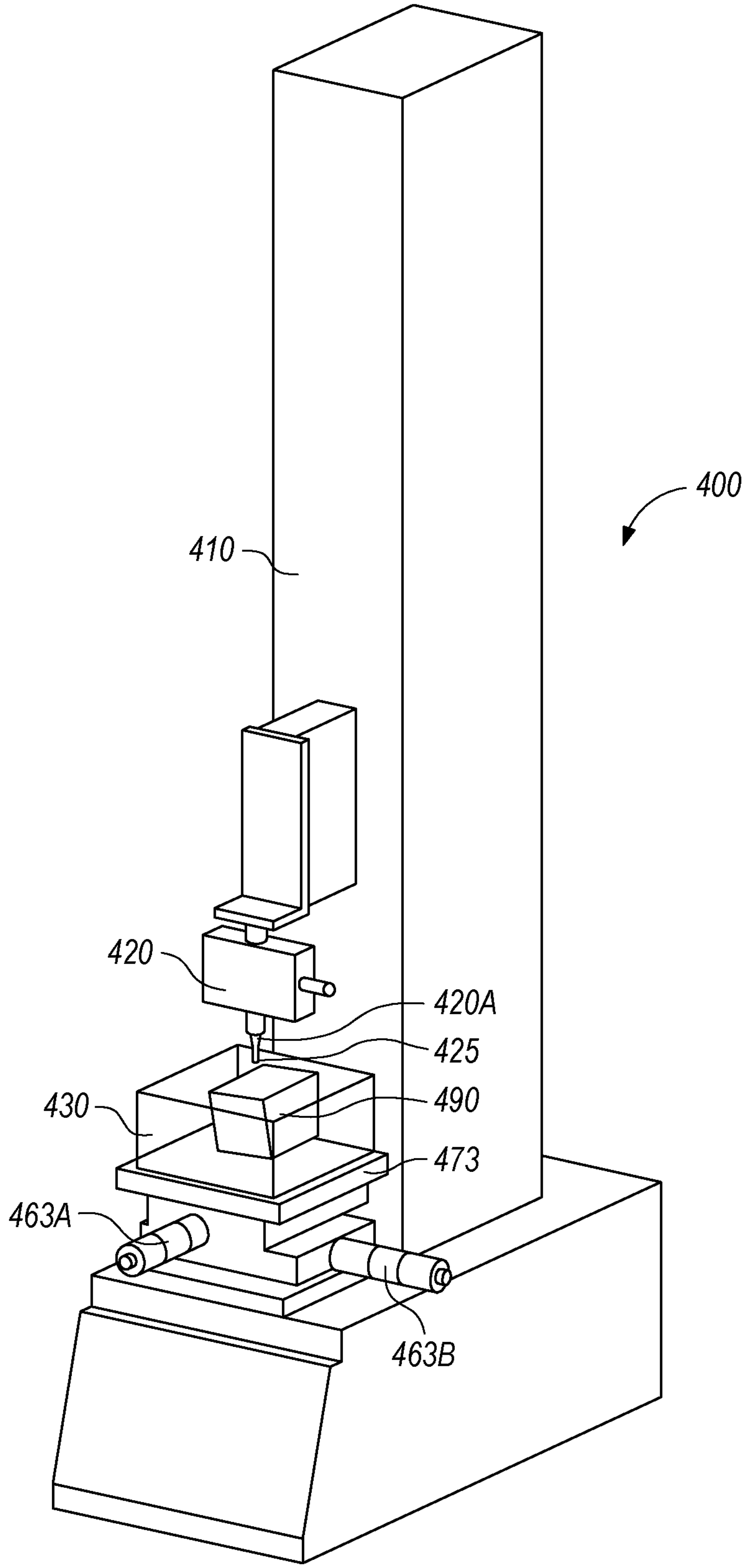
FIG. 35 is a perspective view of a system for testing penetrating components of the endovascular shunt delivery assembly according to embodiments of the disclosed inventions.
Figure 36:
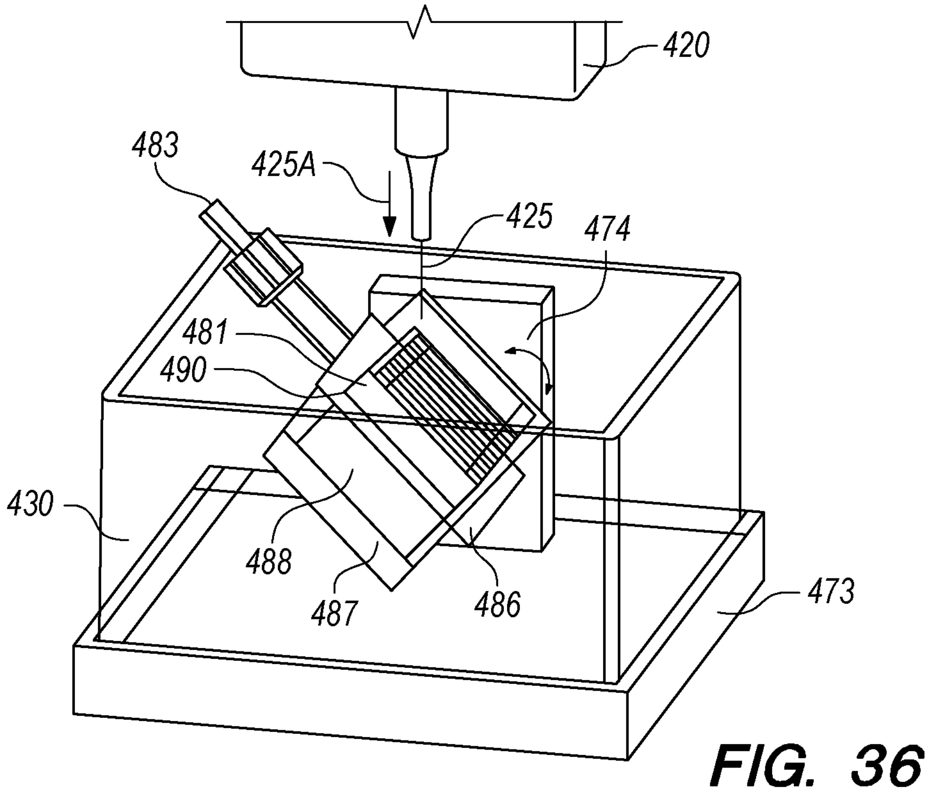
FIG. 36 is a perspective view of a tissue block of the system of FIG. 35.

FIG. 35 depicts a test system 400 for evaluating the aforementioned design and clinical considerations of the penetrating elements of the system 300, according to embodiments of the disclosed inventions. The test system 400 includes a load displacement apparatus 410, and a load cell 420 fitted to a cross-head of the load displacement apparatus 410. The load cell 420 includes a connector 420A for affixing a penetrating element 425 (e.g., elongate pusher member 310, delivery catheter 304, tissue penetrating member 306/250/350, shunt 200') as shown in FIGS. 35, 36, and 38. The connector 420A is sized and configured to fit and hold a variety of penetrating elements 425. A bath fixture 430 is coupled to or mounted on a heating platform 473; the heating platform 473 is coupled to or mounted on stage members 463A and 463B that control the location of the bath fixture 430 relative to the load displacement apparatus 410 in the X (463A) and Y (463B) planes. A tissue block 490 is disposed inside the bath fixture 430, and includes a tissue sample 486 (e.g., human dura, pig dura, a dura surrogate such as Dura-Guard® dural repair patch from Synovis Surgical Innovations, St. Paul, Minnesota) clamped in the tissue block 490 for testing the penetrating element 425, as shown in FIGS. 35-38. Alternatively or additionally, an arachnoid tissue or a suitable surrogate for arachnoid layer 115 (e.g., human arachnoid, pig arachnoid, pig mesentery) can also be clamped in the tissue block 490 for testing the penetrating element 425. The load displacement apparatus 410 can control and vary the speed that penetrating element 425 advances towards the tissue sample 486. The load cell 420 measures the forces generated from the penetrating element 425 piercing tissue samples 486, as well as the forces generated when withdrawing the penetrating element 425 from the pierced tissue sample 486.

As shown in FIG. 36, the tissue block 490 is coupled to a block stand 474 disposed within the bath fixture 430. The tissue block 490 and block stand 474 are rotatably coupled allowing an operator to adjust the orientation of the tissue block 490 relative to the block stand 474 and therefore, relative to the piercing element 425, in the clockwise and counterclockwise directions. The relative rotation of the tissue block 490 and block stand 474 allows the operator to adjust and set a desired angle for the penetrating element 425 to pierce or penetrate the tissue sample 486 clamped in the tissue block 490 when the load displacement apparatus 410 drives penetrating element 425 towards the clamped tissue sample 486 (piercing direction represented by arrow 425A in FIG. 36).

Figure 37:
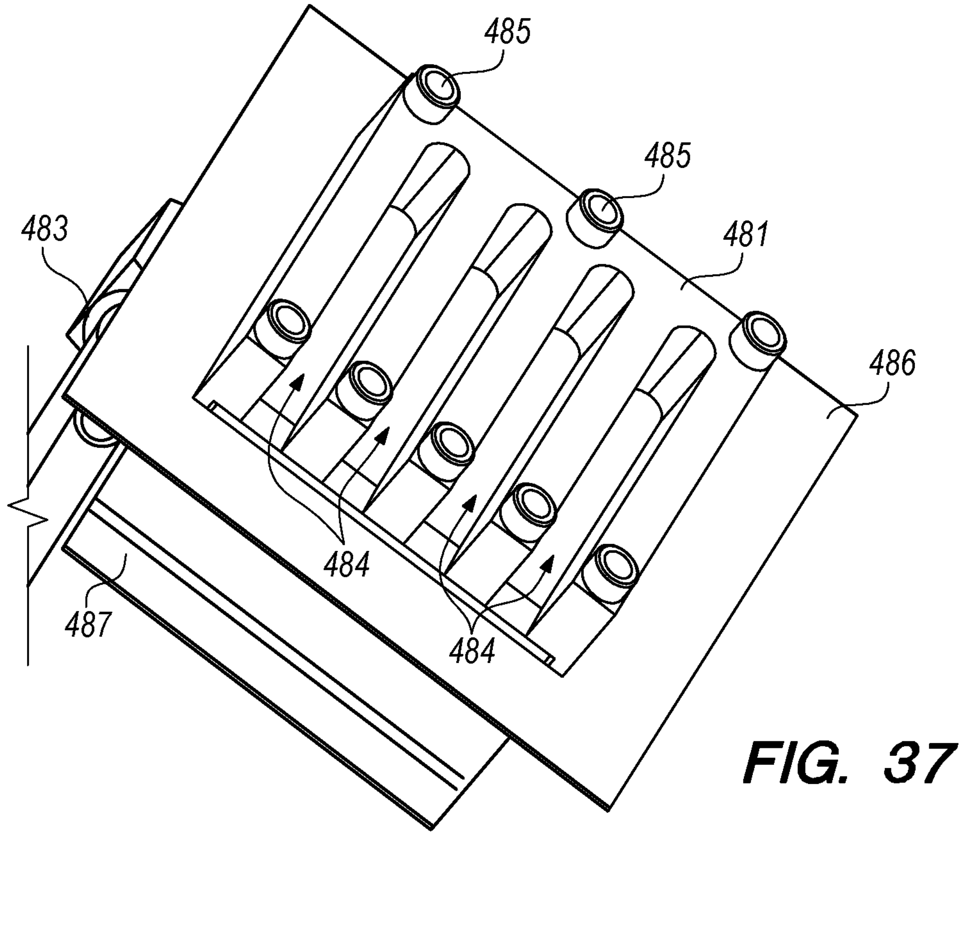
FIG. 37 is a perspective view of the tissue block shown in FIG. 36.
Figures 38, 39:
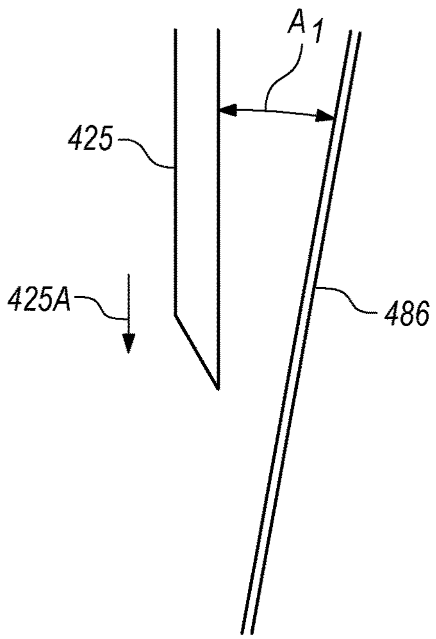
FIG. 38 is a side view of a penetration test of the system of FIG. 35.
FIG. 39 is an experimental data table according to embodiments of the disclosed inventions.

The tissue block 490 includes an upper plate 481 having a plurality of channels 484; the plate 481 is coupled to a lower support block 487, and the lower support block 487 includes a connection port 483 (FIGS. 36 and 37). The tissue sample 486 is clamped under the upper plate 481 and over the lower support block 487 creating a chamber 488 between the sample 486 and the support block 487, as shown in FIGS. 36 and 37. The lower support block 487 can be constructed using a clear material to observe the penetrating element 425 during testing (e.g., observe the extent of tissue deformation or whether arachnoid layer "tents" above the dura surrogate before piercing). The bath fixture 430 can be filled with a temperature controlled solution (e.g., saline) and/or the heating block 473 can be used to control the temperature of the solution within the bath fixture 430. The chamber 488 of the tissue block 490 disposed within the bath fixture 430 can be pressurized with the temperature controlled solution (or other CSF surrogate) via the port 483, such that the chamber 488 represents the subarachnoid space into which penetrating element 425 will pierce during testing. The pressure of the CSF surrogate in the chamber 488 can be controlled to create a differential pressure between the CSF surrogate solution and the temperature controlled solution in the bath fixture 430, which mimics the pressure differential between the subarachnoid space and venous system in patients (e.g. 5-12 cm H2O for non-hydrocephalic patients).

FIG. 37 depicts the tissue sample 486 clamped between the upper plate 481 and the lower support block 487 of the tissue block 490, according to the disclosed inventions. Screws 485 (or other suitable fasteners) secure the upper plate 481 to lower support block 487 clamping the tissue sample 486 between the upper plate 481 and the lower support block 487 to create the chamber 488. The upper plate 481 channels 484 mimicking the IPS 102 (i.e., lumen) such that, the tissue sample 486 represents the IPS wall 114 for testing the penetrating element 425 of the system 300. The channels 484 are configured to expose the clamped tissue sample 486 and allow contact with the penetrating element 425 driven by the load displacement apparatus 410 in the piercing direction 425A (FIG. 36). For example, FIG. 38 shows a tissue sample 486 and the penetrating element 425 (e.g., beveled needle) oriented in the piercing direction 425A to penetrate the tissue sample 486 at a 10-degree penetration angle $A_1$.

Testing the penetrating element 425 having certain configurations, such as shape (e.g., shape of the piercing tip, needle, beveled, or the like), sizes (i.e., gauge number), and material (e.g., stainless steel, Nitinol, or the like) at various penetration speeds ranging from 0.1 mm/s to 5 mm/s and various ranges of penetration angles using the test system 400 as previously described, yielded the exemplary data summarized in FIG. 39. Of the penetrating element 425 tested, the data generally indicates that: (1) blunt needles require a higher force to penetrate dura mater, impose higher deformation on the tissue prior to puncture, and show a risk of coring the tissue during piercing dura mater; (2) pencil tip and beveled needles show consistent retraction forces that translate to the best seal of the anastomotic connection between the IPS 102 and CP angle cistern 138 (e.g., no CSF surrogate leaked between chamber 488 and bath fixture 430 up to a differential pressure of 100 cm H2O); and (3) Quincke and pencil tip needles require the least amount of force to puncture dura mater. While other penetrating elements 425 were evaluated and tested with test system 400, the test data showed that the quincke, pencil, and bevel shape penetrating element 425 may be preferred for embodiments of the disclosed inventions based on the relatively low tissue penetration force require to pierce dura mater, minimal tissue damage caused during tissue penetration, the sealing characteristics of the penetration tract through the tissue, minimal tissue deformation during penetration, and minimal additional support requirements of the penetrating element 425 to prevent buckling or bending during penetration.

Figure 40:
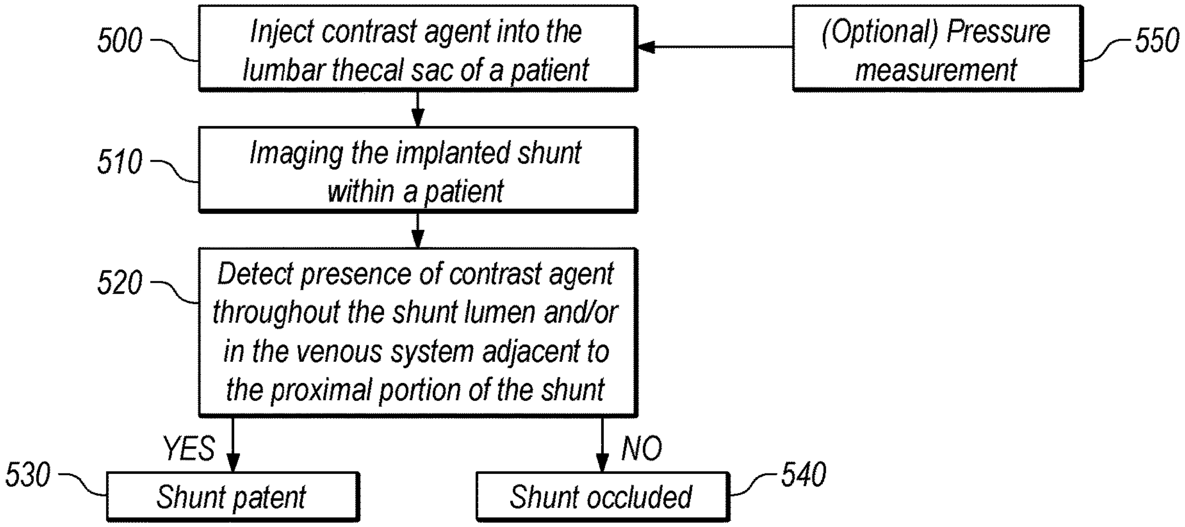
FIG. 40 is a schematic flow diagram of an exemplary method of assessing the patency of an implanted shunt according to the disclosed inventions.

Methods can be used to assess the patency of the shunt 200 or 200' (e.g., of lumen 207 and valve 209) after deployment and implantation of the shunt 200 or 200', according to embodiments of the disclosed inventions. In one exemplary method of accessing the patency of the implanted shunt 200 or 200', with reference to FIG. 40, a clinician can inject an iodinated contrast agent into the lumbar thecal sac of the patient by a lumbar puncture or spinal tap 500. After the injection step 500 (e.g., approximately five to ten minutes after 500), the contrast agent will disperse from the lumbar subarachnoid space into the CSF in the intracranial subarachnoid space around the brain stem from the circulation of CSF within the subarachnoid space. Using one or more of the imaging methods previously described herein, the presence of contrast agent in the CSF will be apparent by the clinician (e.g., highlight in an imaging system) 510. If the imaging step 510, detects the presence of contrast agent 520 throughout shunt lumen 207 and/or in the venous system immediately adjacent the proximal portion 204 of the shunt 200, then shunt 200 is patent (i.e., not occluded) 530, as evidenced by the contrast agent dispersing from the flow of CSF in the CP angle cistern through the shunt 200. If the imaging step 530 does not detect the presence of contrast agent throughout shunt lumen 207 and/or in the venous system immediately adjacent the proximal portion 204 of the shunt 200, then shunt 200 is not patent (i.e., occluded) 540. Additionally, during the lumbar puncture step 500, a CSF pressure measurement can be obtained 550. A pressure measurement within normal ranges further confirms that the deployed shunt 200 is draining CSF from the intracranial subarachnoid space into the venous system, and a pressure measurement higher than the normal ranges further confirms that the deployed shunt 200 is or may be occluded.

Figure 41:
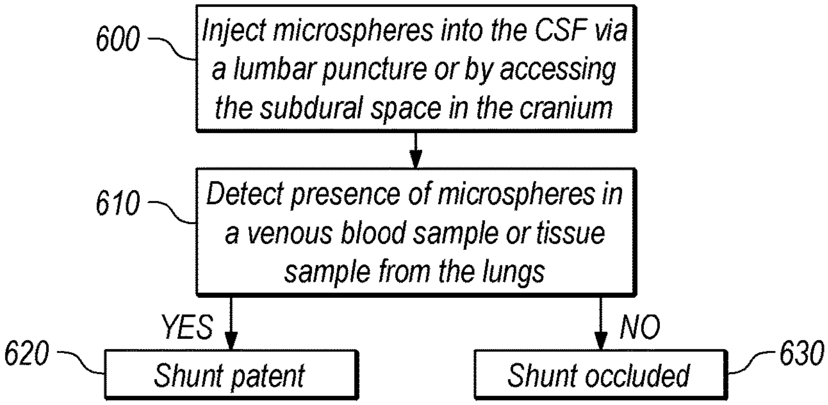
FIG. 41 is a schematic flow diagram of another exemplary method of assessing the patency of an implanted shunt according to the disclosed inventions.

In another exemplary method of assessing the patency of the implanted shunt 200 or 200', with reference to FIG. 41, a clinician can evaluate CSF flow through the deployed shunt 200 or 200' by injecting 600 radioactive or neutron-activated microspheres (e.g., microspheres from BioPAL, Worcester, Massachusetts) into the CSF via a lumbar puncture or by accessing the subdural space in the cranium. Microspheres with a diameter of 15 microns or larger would not pass through the arachnoid granulations, which absorb CSF from the subarachnoid space into the venous system, yet should be selected such that the microspheres can pass through lumen 207 of a deployed shunt (e.g., having a diameter ranging from 0.1 mm to 2 mm). Assuming a properly functioning deployed shunt 200 according to the disclosed inventions, the presence of microspheres in the CSF would only enter the blood stream via a patent shunt 200; a venous blood sample or tissue sample from the lungs can be collected and assessed for the presence of microspheres 610. The number of microspheres obtained via a venous sampling at various points in time reflects the flow rate through the shunt 200 and the number of microspheres injected into the CSF 620. Samples obtained via a biopsy of lung tissue are also proportional to the total flow of microspheres through the shunt and the number of microsphere injected into the CSF. Collected samples without any microspheres suggest that CSF is not flowing through the deployed shunt 200, and the shunt 200 is occluded 630. For example, the venous blood sample can be obtained from the guide or delivery catheter in the vasculature for shunt deployment and within 15 to 20 minutes of injecting microspheres into the CSF. This sampling technique can provide a sensitive measurement of the CSF flow through the shunt 200 if assessed by radioactive or neutron-activated microspheres because it maximizes the collection of microspheres flowing through the shunt 200. The neutron activated microsphere assay is extremely sensitive with the limits of detection almost down to 1 microsphere. Venous blood or lung tissue samples can be sent to a commercial testing service, such as BioPAL, that uses neutron activation technology to measure the microsphere content of the sample.

FIGS. 43A-D illustrate an alternative delivery catheter 304' for delivering the shunt 200 into a target site of a patient, constructed in accordance with embodiments of the disclosed inventions. For ease in illustration, the features, functions, and configurations of the delivery catheter 304' that are the same as in the assembly 300 of FIGS. 3B and 4A-D and/or are the same as in the assembly 300' of FIGS. 5A-J are given the same reference numerals. The delivery catheter 304' is dimensioned to reach remote locations of the vasculature and is configured to deliver the shunt 200 percutaneously to the target location (e.g., inferior petrosal sinus). The delivery catheter 304' may comprise variable stiffness sections (e.g., varying ratio of material, including selective reinforcement, such as braids, coils, or the like) suitable to provide sufficient "pushability" and "torqueability" to allow the catheter 304' to be inserted, advanced and/or rotated in the vasculature to position the distal portion 344 of the catheter at the target site within the IPS 102. Further, the distal portion 344 should have sufficient flexibility so that it can track and maneuver into the target site. Variable stiffness in the catheter 304' is achieved, for example, by locally varying the properties or distribution of the materials used and/or varying the durometer or thickness of the materials during the process of manufacturing. By way of non-limiting examples, the materials used in manufacturing the catheter 304' may include polyether block amide (Pebax®) and Nylon. Other suitable materials that may be contemplated for making the catheter 304' include homopolymers, copolymers or polymer blends containing polyamides, polyurethanes, silicones, polyolefins (e.g., polypropylenes, polyethylenes), fluoropolymers (e.g., FEP, TFE, PTFE, ETFE), polycarbonates, polyethers, PEEK, PVC, and other polymer resins known for use in the manufacture of catheters. It should be appreciated that when appropriate, the delivery catheter 304' may be used in combination with the delivery assembly 300/300' previously described.

The delivery catheter 304' comprises a tissue penetrating member 350 coupled to the distal portion 344 of the catheter 304'. The tissue penetrating member 350 comprises a tubular configuration having a lumen 355 fluidly coupled to the lumen 305 of the delivery catheter 304' (FIG. 43C), which allows the shunt 200 (i.e., slidably disposed in the lumen 305 of the catheter 304') to be deployed into the target site when the anastomosis channel 140 is created (not shown). The tissue penetrating member 350 comprises a piercing edge 351 and a piercing tip 352 (FIGS. 43A, 43C-D), which will be described in further detail below. It should be appreciated that when using the delivery catheter 304' to deliver and deploy the shunt 200 into the target site, the tissue penetrating element 306 of the delivery assembly 300 and/or the tissue penetrating member 250 incorporated in the shunt 200' may not be required.

The delivery catheter 304' further comprises an expandable element 390 coupled to, or disposed on the distal portion 344 of the delivery catheter 304'. The expandable element 390 is proximately disposed to the piercing tip 352 of the tissue penetrating member 350, as to drive and/or advance the tissue penetrating member 350 into the IPS wall 114 to create anastomosis between the IPS 102 and the CP angled cistern 138 (FIG. 44C). The expandable element 390 may comprise an expandable balloon, foam, stent, or combinations thereof. In the embodiments of FIGS. 43A-44C, the expandable element 390 is an expandable balloon. The expandable element 390 comprises a collapsed configuration (i.e., deflated, as shown in FIGS. 43A-D and 44A), a first expanded configuration (e.g., partially inflated or first expanded state, as shown in FIG. 44B), and a second expanded configuration (i.e., inflated or second expanded state, as shown in FIG. 44C). It will be appreciated that the expandable element 390 provides an off-axis expanded configuration (FIGS. 44B-C). In other embodiments, the expandable element 390 may include any suitable expandable configuration, such as, a conical, tapered, accordion-like, angled configurations, or combinations thereof.

The expandable element 390, when expanded/inflated to the first expanded state, the expandable element 390 causes the tip of the tissue penetrating element 350 to engage the dura matter of the IPS wall 114, and thereafter inflated to the second expanded state causes the tissue penetrating element 350 and tip to penetrate through the IPS wall 114 and arachnoid layer 115, respectively, into the CP angle cistern 138, as shown in FIGS. 44B-E. Further, when the expandable element 390 is expanded/inflated to the first expanded state, the element 390 orients the tissue penetrating member 350 towards the IPS wall 114 and initiates tissue engagement as shown in FIG. 44B thereby locking delivery catheter 304' in the IPS 102 relative to the target penetration site in the IPS wall 114. By way of example, the height of the bulb portion of expandable element 390 expandable element 390 (e.g., inflation/volume of an interior cavity 391 of the expandable element 390 expandable element 390) in its first expanded state shown in FIG. 44B, as measured from IPS wall 117, can be between 0.5 mm to 2.5 mm (e.g., 1.5 mm). Additional expansion/inflation of expandable element 390 expandable element 390 from its first expanded configuration to its second expanded configuration advances the tissue penetrating member 350 through the IPS wall 114 as shown in FIG. 44C. Again, by way of example, the height of the bulb portion of expandable element 390 expandable element 390 (e.g., inflation/volume of the balloon's interior 391) in its second expanded state shown in FIG. 44C, as measured from IPS wall 117, can be between 2.5 mm to 4.0 mm (e.g., 3.0 mm). It should be appreciated that the height of the bulb portion of expandable element 390 may also be smaller than 2.5 mm in patients with smaller diameter IPS 102, or larger than 4.0 mm in patients with larger diameter IPS 102.

Additionally, while the expandable element 390 is being expanded/inflated to transition from the deflated configuration (FIG. 44A) to the partially inflated configuration (FIG. 44B), and into the fully inflated configuration (FIG. 44C), the tissue penetrating member 350 transitions from being disposed substantially parallel relative to the IPS wall 114 (FIG. 44A) into being disposed in angles of interaction relative to the IPS wall 114 (FIGS. 44B-C). The angles of interaction of the tissue penetrating member 350 from the delivery configuration may vary from approximately 0° to approximately 150° relative to the IPS wall 114, preferably from approximately 5° to approximately 90°.

The delivery catheter 304' further comprises an inflation lumen 309 fluidly coupled to the interior 391 of the expandable element 390 (FIGS. 43B-C), and to a source of inflation media (not shown) for supplying fluid and/or gas to selectively inflate and deflate the expandable element 390. For example, the inflation media source may have a predetermined volume of fluid/gas to adequately inflate the expandable element 390 causing the advancement of the tissue penetrating member 350 into the IPS wall 114. Additionally, the source of inflation media may include aspiration means to deflate the expandable element 390 by withdrawing the fluid/gas from the expandable element 390. The inflation media source may optionally include a pressure sensor to measure the inflation pressure to ensure adequate inflation without over inflation of the expandable element 390. The expandable element 390 may be inflated with one or more fluids (e.g., saline, contrast agent, or the like) or with gas (e.g., air), and/or a combination thereof. For example, the expandable element 390 may be inflated with a mixture of saline and contrast agent (i.e., fluid containing radio-opaque materials) for purposes of imaging, according to the disclosed inventions (e.g., mixture comprising 50% saline and 50% contrast agent).

The expandable element 390 coupled to the delivery catheter 304' may be made of or otherwise include compliant, semi-compliant, or non-compliant polymeric materials, such as silicone, urethane polymer, thermoplastic elastomer rubber, santoprene, nylon, polytetrafluoroethylene "PTFE", polyethylene terephthalate "PET", and other suitable materials or combinations thereof. In embodiments comprising compliant materials, the expandable element 390 is preferably composed of urethanes (e.g., Pellethane or Chronoprene).

In another embodiment, the expandable element 390 is composed of a non-compliant material, such as polyurethane terephthalate "PET", which allows and facilitates inflation of the expandable element 390 by a source of inflation media filled with a predetermined volume of fluid/gas. The predetermined volume of fluid/gas may correspond to, for example, a preformed volume of the expandable element 390, which will be described in further detail below. Having a source of inflation media filled with a predetermined volume of fluid to inflate the noncompliant material of expandable element 390 reduces the risk of overinflating and overextending of the expandable element 390 in its deployed configuration. Additionally, the expandable element 390 composed of non-compliant material is configured to withstand higher inflation pressure without deforming or overextending, as compared to balloons composed of compliant materials.

Figure 44A:
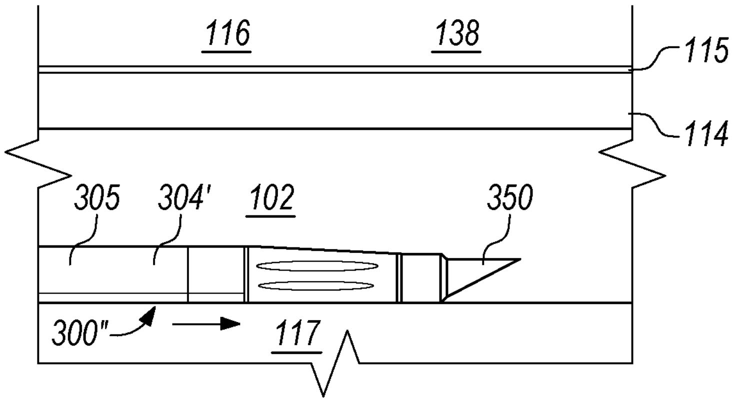
FIGS. 44A-E are side and cross-sectional views of the creation of anastomosis using the delivery catheter of FIGS. 43A-D.
Figure 44B:
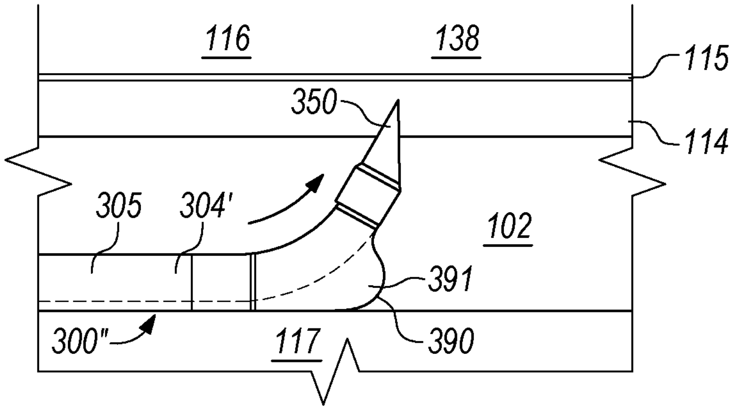
Figure 44C:
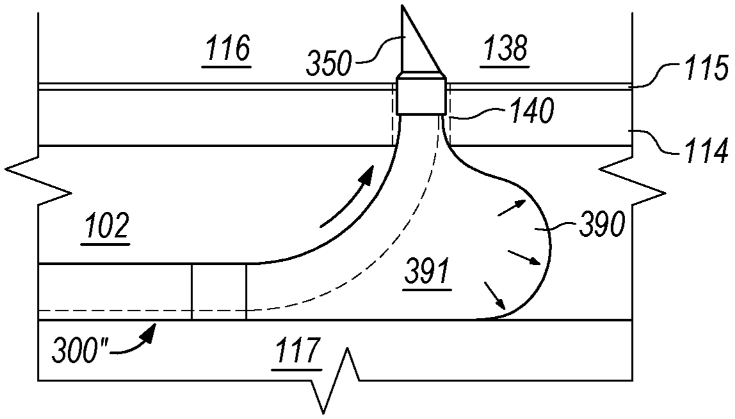

FIGS. 44A-C illustrate a method for creating anastomosis via an endovascular approach to deliver and implant the shunt 200 into the target site using the delivery catheter 304', in accordance with embodiments of the disclosed inventions. The distal portion 344 of the delivery catheter 304' having the tissue penetrating member 350 in a delivery orientation, and the expandable element 390 in the collapsed configuration, is advanced into the target site within the IPS 102, as shown in FIG. 44A. Prior to the piercing of the IPS wall 114 and the arachnoid layer 115 to create anastomosis and access the CP angle cistern 138, proper orientation of the distal portion 344 of the delivery catheter 304', particularly, proper orientation of the tissue penetrating member 350 and the expandable element 390, may be verified prior to actuation according to the imaging methods previously disclosed. For example, markers may be used for positioning and orienting the distal portion 344 of the delivery catheter 304'. When needed, the positioning and orientation of the tissue penetrating member 350 and the expandable element 390 disposed on the distal portion 344 of the delivery catheter 304' may be adjusted, for example, by applying a rotational force directly to the body of the delivery catheter 304'.

Once proper positioning and orientation of the distal portion 344 of the delivery catheter 304' is achieved, the expandable element 390 is inflated transitioning into its partially expanded configuration and bending the distal portion 344 of delivery catheter 304' away from IPS wall 117 so as to orient the tissue penetrating member 350 into the IPS wall 114 at a suitable angle, as shown in FIG. 44B. Continuing inflation until the expandable element 390 reaches its fully expanded configuration advances the tissue penetrating member 350 causing piercing and penetration of IPS wall 114, and penetration through the arachnoid layer 115 until reaching the CSF-filled subarachnoid space 116 and/or the CP angle cistern 138 creating the anastomosis channel 140, as shown in FIG. 44C. Simultaneously or consecutively with the creation of the anastomosis channel 140, the shunt 200 is advanced, deployed and implanted at the target site, as previously described. Once the shunt 200 is implanted, the balloon 290 is deflated—preferably after the deployment of the distal anchoring mechanism 229 of shunt 200—and the delivery catheter 304' is withdrawn out of the patient (not shown). As illustrated in FIGS. 44A-C, expansion of expandable element 390 inside the lumen of IPS 102 limits the penetration depth of tissue penetrating member 350 into CP angle cistern 138; that is, the configuration of expandable element 390 and the anatomical confines from the lumen of IPS 102 and IPS wall 114 prevent expandable element 390 in its expanded configuration, from further expansion that could advance the coupled tissue penetrating member 350 too far distally into the subarachnoid space 116 and/or the CP angle cistern 138. The penetration depth limit illustrated in FIGS. 44C and 44E, in turn, maintains adequate space in CP angle cistern 138 between arachnoid layer 115 and brain stem 112 (not shown) or expansion envelope for a distal portion of the shunt and/or distal anchoring mechanism to deploy in the subarachnoid space without damage critical anatomical structures.

Figure 44D:
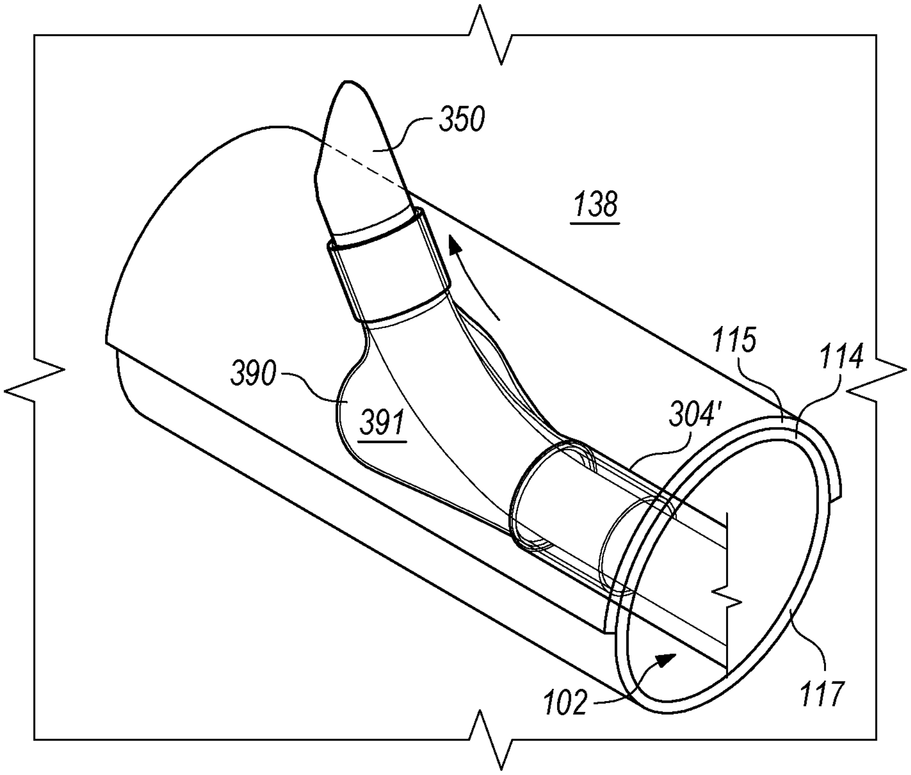
Figure 44E:
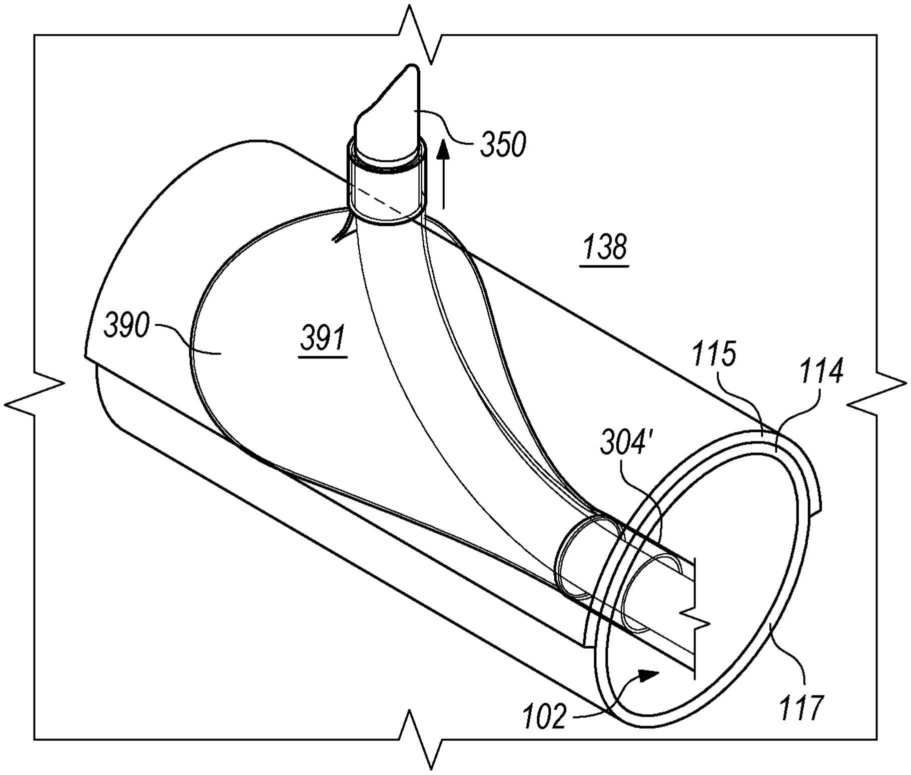

FIGS. 44A-C depict tissue penetrating member 350 as it transitions through a 90-degree turn (e.g., in a range of 30 degrees to 90 degrees) from its delivery orientation (i.e., coaxial with the longitudinal axis of delivery catheter 304' and IPS lumen 102) to a fully penetrated orientation (i.e., orthogonal to IPS wall 114) as expandable element 390 transitions to a fully expanded configuration. For illustration purposes, FIGS. 44D-E are perspective views of FIGS. 44B-C respectively, depicting a top-side view of the tissue penetrating member 350 transitioning into an expanded configuration which facilitates full penetration of the IPS wall 114 and arachnoid layer 115 into the CP angle cistern 138. The narrow diameter and/or tortuous pathway of the IPS lumen may not allow tissue penetrating member 350 to penetrate orthogonal to IPS wall 114 in all patients; thus, the tissue penetrating member 350 may only transition through about a 30-degree turn to 70-degree turn while expandable element 390 expands before completely penetrating IPS wall 114. For example, the clinician may expand expandable element 390 to a first expanded state where penetrating element 350 engages the dura of IPS wall 114 at an angle of about 45 degrees or less, without fully penetrating into the CP angle cistern 138, as shown in FIG. 44B. At this step, the clinician can confirm the trajectory of the penetrating element 350 (e.g., using one or more of the imaging methods described herein) before completing the penetration step of the procedure. If unsatisfied with the trajectory presented, the clinician can deflate expandable element 390 to its collapsed or delivery configuration, adjust the position or orientation of delivery catheter 304', and re-expand expandable element 390 to a first expanded configuration where penetrating element 350 engages IPS wall 114 on a suitable trajectory for further penetration through the IPS wall into CP angle cistern 138. Thereafter, the clinician can further expand expandable element 390 until the penetrating element 305 has completely penetrated through the IPS wall 114 and arachnoid layer 115 underlying the CP angle cistern 138. (e.g., at an angle of about 70 degrees).

Additionally to the method for creating anastomosis 140 via an endovascular approach of FIGS. 44A-C, a clinician may apply a suitable mechanical force to the delivery catheter 304' further assisting with the advancement of tissue penetrating member 350 driven by the expandable element 390 into the IPS wall 114.

Additionally to the expandable element 390 disclosed above, delivery catheter 304' may include a second expandable balloon, foam, stent, or combination thereof, located proximally from the distal end of the catheter (e.g., about 1 cm to about 3 cm from the distal end of the catheter). The second expandable member (not shown), when expanded from a collapsed to expanded configuration, further secures delivery catheter 304' about the target penetration site in IPS wall 114. In embodiments where the second expandable member is a balloon, the balloon can be composed of non-compliant or compliant materials and communicate fluidly with inflation lumen 309 or a similar yet fluidly distinct lumen. Further, the second balloon can be configured within the dimensional ranges previously disclosed with respect to expandable element 390. The second expandable member can extend circumferentially around the exterior of the delivery catheter or may comprise a smaller portion of the delivery catheter circumference (e.g., approximately 25%, approximately 50%, approximately 75%). In embodiments where the second expandable member comprises a smaller portion of the delivery catheter circumference, such expandable member can be located on the opposite side of delivery catheter 304' when compared to the expandable element 390 or, alternatively, on the same side of delivery catheter 304' as the expandable element 390, or in some relative clocking between fully aligned and fully opposed orientations.

In some embodiments, deploying the shunt 200 comprises advancing the distal portion 202 of the shunt 200 from the IPS 102 into the CP angle cistern 138 using the tissue penetrating member 350. The tissue penetrating member 350 may be coupled to a distal portion 202 of the shunt 200, so that advancing the distal portion 202 of the shunt 200 from the IPS 102 into the CP angle cistern 138 comprises advancing the tissue penetrating member 350 and distal portion 202 of the shunt 200' through the dura mater tissue wall of the IPS 114, and through the arachnoid tissue layer 115, respectively, into the CP angle cistern 138. During advancement of the distal portion 202 of the shunt 200, the distal portion 202 of the shunt 200 is at least partially disposed in the delivery lumen 305 of the delivery catheter 304', the tissue penetrating member 350 comprising a tissue penetrating tip of the delivery catheter 304', and where advancing the distal portion 202 of the shunt 200 from the IPS 102 into the CP angle cistern 138 comprises advancing the delivery catheter 304 so that the tissue penetrating tip penetrates through the dura mater tissue wall of the IPS 114, and through the arachnoid tissue layer 115, respectively, into the CP angle cistern 138. The delivery catheter 304' distal portion 344 assumes a curved configuration that guides the tissue penetrating tip into contact with the dura mater of the IPS 114 at an angle in a range of 30 degrees to 90 degrees, as shown in FIGS. 44B-C. As shown in FIGS. 44A-E, the distal portion 344 of the delivery catheter 304' comprises the expandable element 390 (or wall portion that is expanded) to cause the distal portion of the delivery catheter 304' to assume the curved configuration. The delivery catheter 304' comprising one or more radiopaque markers located and dimensioned to indicate a position and orientation of the distal portion 344 of the delivery catheter when in the curved configuration. Deploying the shunt 200 further comprises withdrawing the distal portion of the delivery catheter 304' from the CP angle cistern 138, while maintaining the distal portion 202 of the shunt 200 at least partially disposed in the CP angle cistern 138.

FIGS. 45A-D illustrate an exemplary tissue penetrating member 350 constructed according to embodiments of the disclosed inventions. The tissue penetrating member 350 comprises a tubular configuration having a proximal end portion 353 and a distal end portion 357, and lumen 355 extending therebetween (FIG. 45B). The distal end portion 357 of the tissue penetrating member 350 comprises a tapered/beveled piercing edge 351 that terminates in the piercing tip 352 (FIGS. 45A-5 B). FIGS. 45D and 46G illustrate exemplary dimensions (in inches), angles and properties of the tissue penetrating member 350, which are not intended to limit the embodiment of FIGS. 45A-C.

Figure 46A:
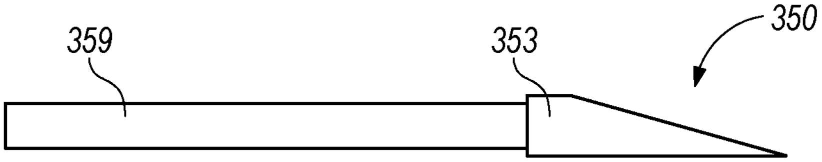
Figure 46B:
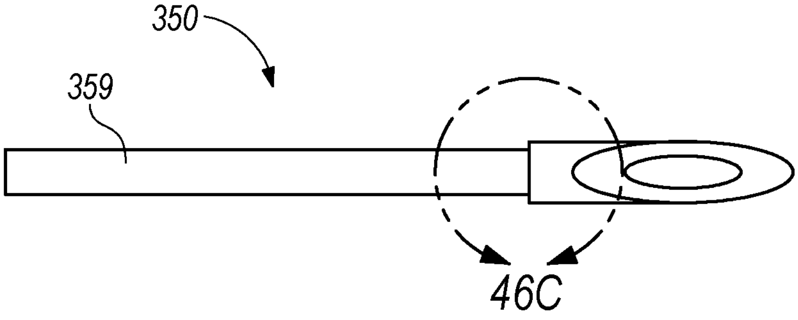
Figure 46C:
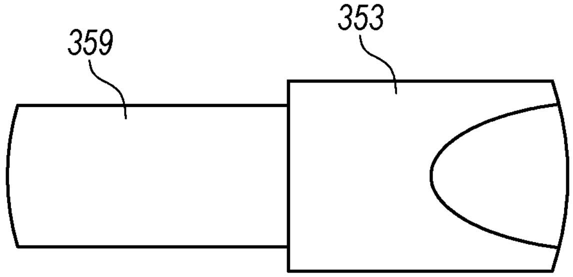
Figure 46D:
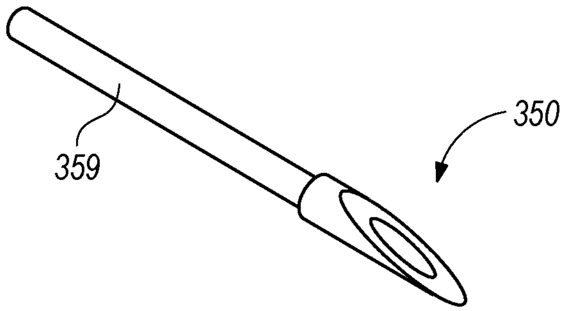

FIGS. 46A-G illustrate other exemplary piercing elements 350 constructed according to embodiments of the disclosed inventions. The proximal end portion 353 of tissue penetrating member 350 further extends (FIGS. 46E-F) or it is coupled to an elongated tubular member 359 (FIGS. 46A-D). The elongated tubular member 359 comprises a smaller outer diameter and profile than the outer diameter and profile of the proximal end portion 353 of the tissue penetrating member 350 (FIGS. 46A-D). The elongated tubular member 359 of FIGS. 46A-D and the extending proximal portion 353 of FIGS. 46E-F are shaped and dimensioned to be disposed within the lumen 305 of the distal portion 344 of the delivery catheter 304'. The tissue penetrating member 350 embodiment shown in FIGS. 46E-F includes cut portions along the length of the tubular member 359 shown as a spiral cut pattern in FIGS. 46E-F. The cut portions advantageously provide sufficient flexibility for the penetrating element, for example, to bend from a delivery to expanded configuration if incorporated into the expandable element 390 embodiment shown in FIGS. 43, 44, and 47, while maintaining sufficient column strength of the tissue penetrating member 350 to penetrate through dura and arachnoid tissues. In the embodiments of FIGS. 46A-D, the outer diameter and profile of tissue penetrating member 350 may match the outer diameter and profile of the distal portion 344 of the delivery catheter 304'.

It should be appreciated that the dimensions, angles and properties of the tissue penetrating member 350 of FIGS. 45A-46D may be incorporated into the tissue penetrating element 306 of the delivery assembly 300 and/or the tissue penetrating member 250 of the shunt 200'.

FIGS. 47A-49C illustrate expandable expandable element 390 constructed according to various embodiments of the disclosed inventions. The expandable expandable element 390 is shown in a preformed molded configuration (FIGS. 47A, 48A and 49A) before it is mounted on or coupled to the distal portion 344 of the delivery catheter 304'. The expandable element 390 includes a first-end portion 392 (e.g., proximal), a middle-body portion 393 (e.g., expandable) and a second-end portion 394 (e.g., distal), collectively defining an interior 391 of the expandable element 390 through which the delivery catheter 304' or other type of elongate structure extends. The first-end portion 392 and second-end portion 394 of the expandable element 390 may include respective tubular or other suitable configurations to be coupled to the distal portion 344 of the delivery catheter 304' by adhesive, thermal bonding or the like, interlocking geometries, mechanical fastening, sutures or combinations thereof.

Figure 48A:
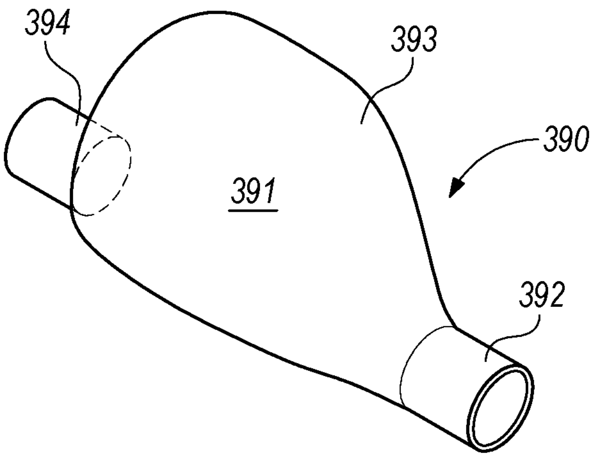
Figure 48B:
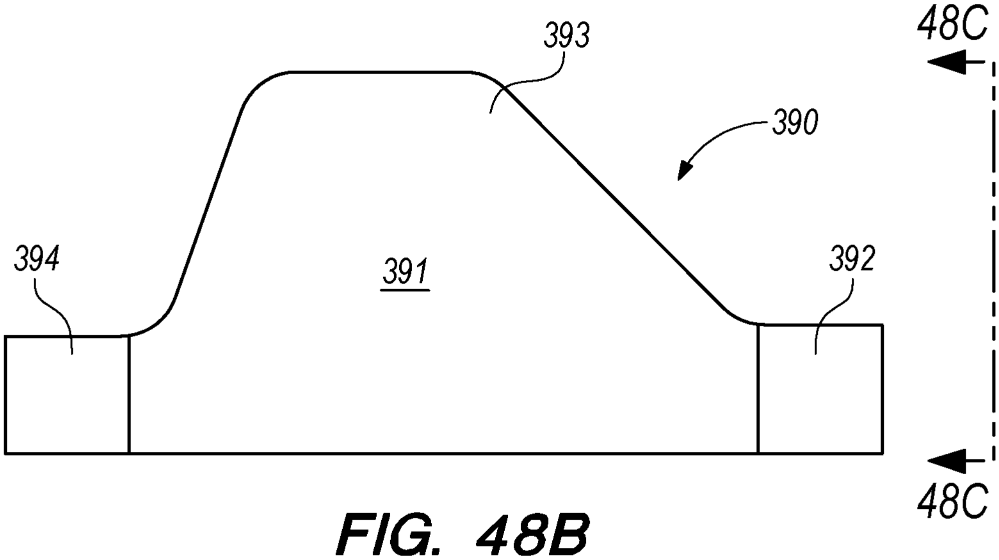
Figure 48C:
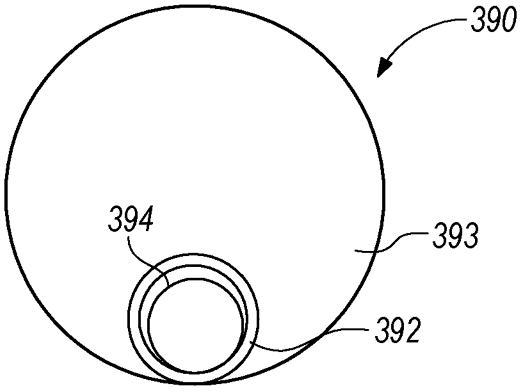
Figure 48D:
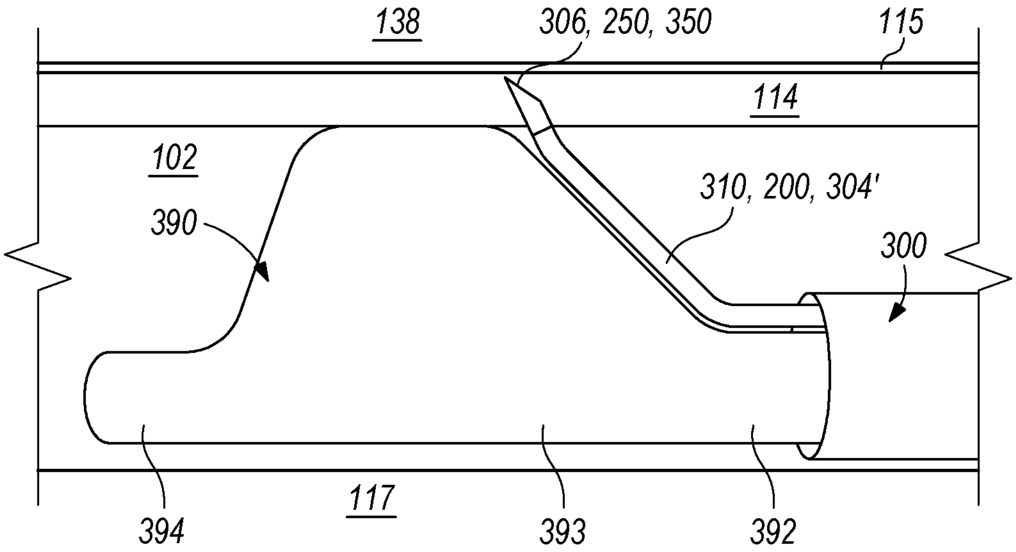
Figure 49A:
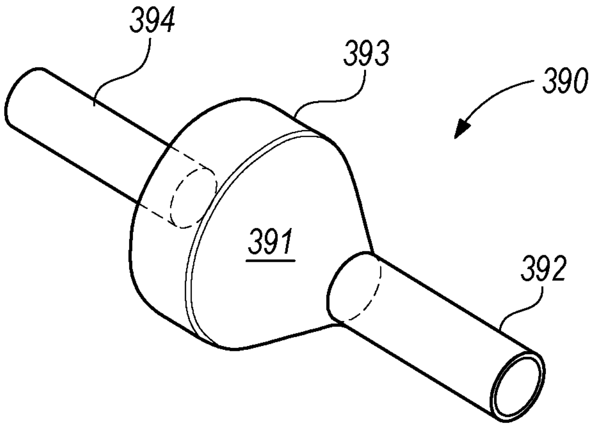
Figure 49B:
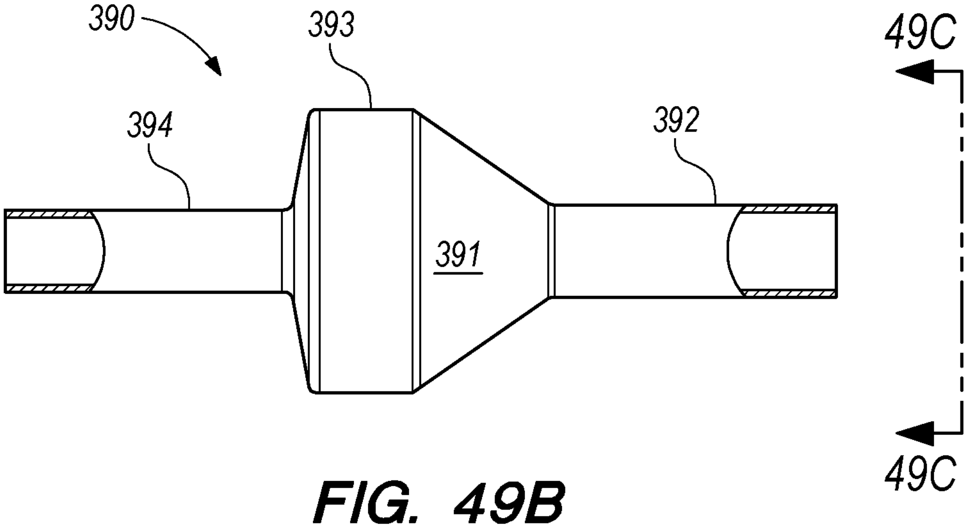
Figure 49C:
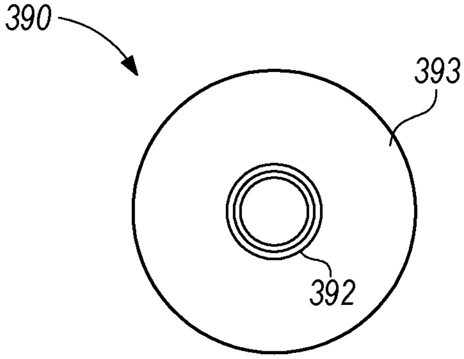
Figure 49D:
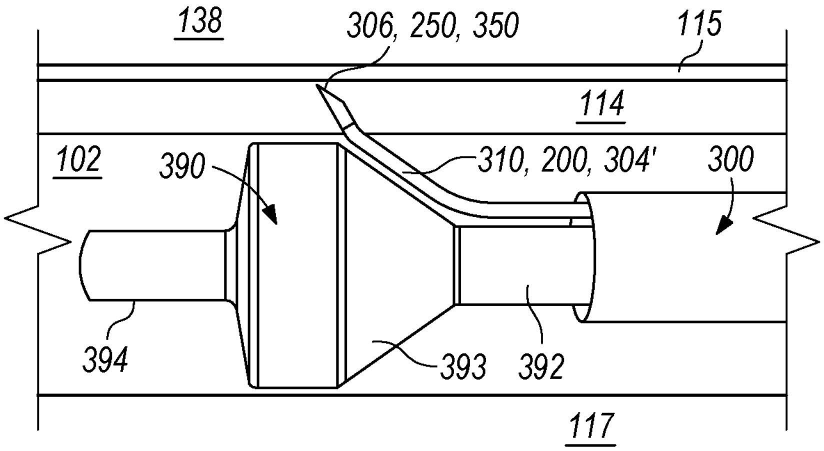

In comparison to the expandable expandable element 390 embodiment of FIG. 47A-C where a shunt is delivered through a lumen of the expandable element 390, the balloon embodiments of FIGS. 48A-D, 49A-D, when in an expanded configuration, provide a ramp to deflect a penetrating element 306 of the elongate pusher member 310, penetrating element 250 of the shunt 200' or penetrating element 350 of the delivery catheter 304' toward IPS wall 114, similar to the deflecting element 370 coupled to or disposed on the distal portion 344 of the delivery catheter 304 described in connection with FIGS. 20A-F. In an expanded configuration, the transition from first-end portion 392 to middle-body portion 393 of the expandable element 390 of FIGS. 48A-D, 49A-D deflects the piercing element away from the central axis of the delivery catheter to penetrate IPS wall 114. That is, the piercing element or a sheath housing the piercing element can emerge from delivery catheter 304 at a location proximal to first-end portion 392 of the balloon; as the piercing element advances distally; the transitioned portion of the inflated balloon directs the piercing element into the tissue of IPS wall 114 (FIGS. 48D and 49D). As described herein, the piercing element used with the balloon embodiments of FIGS. 48A-D, 49A-D can be configured such that the shunt is delivered through a lumen of the piercing element or such that the piercing element extends through the shunt lumen to deploy the shunt distal end (e.g., anchor 229) within the CP angle cistern.

The expandable element 390 may be composed of material previously described that may have a shore durometer range between 40 A to 90 A, and/or a shore durometer range between 25 A to 100 A. For example, the expandable element 390 may be manufactured with standard processing equipment to obtain a molded balloon having a wall thickness of approximately between 0.00025 inches (0.00635 mm) to 0.003 inches (0.0762 mm) in the middle expandable portion 393. Further, the wall thickness of the expandable element 390 may vary from thicker, in and around the first-end portion 392 and in and around the second-end portion 394 to thinner in and around the a middle-body portion 393 at least. For example, the first-end portion 392 may have a wall thickness greater than a wall thickness of the middle-body portion 393.

Portions 392, 393, and/or 394 of expandable element 390 can have a non-uniform thickness. For the expandable element 390 embodiment shown in FIG. 43, 44, 47 and with reference to FIG. 47, a central region of middle portion 393 comprises a thicker wall thickness than the first and second end regions of middle portion 393; the localized thinning of expandable element 390 at the end regions of middle portion 393 provides the eccentric expansion of expandable element 390 depicted in FIGS. 43-44. In some embodiments of expandable element 390, the central region of middle portion 393 comprises the thickest portion of expandable element 390.

In embodiments of the invention and with the use of standard blow and/or dip molding principles, an angled (FIGS. 47A-C), an off-axis (FIGS. 44A-E, 48A-C), or a conical molded configuration (FIGS. 49A-C) of the expandable element 390 may be manufactured. By way of example, the expandable element 390 can have a variety of shapes in the molded, mounted or inflated configurations, including but not limited to: diamond, circular, oval, multi-sided, or irregular shapes, and/or angles that are adapted to orient and advance the tissue penetrating member 350 into the IPS wall 114 and arachnoid layer 115 to create the anastomosis channel 140, as previously described.

Figure 50A:
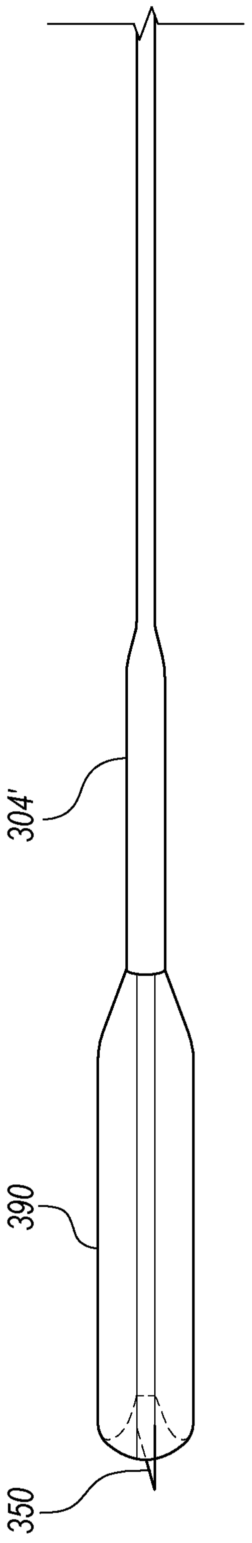
Figure 50B:
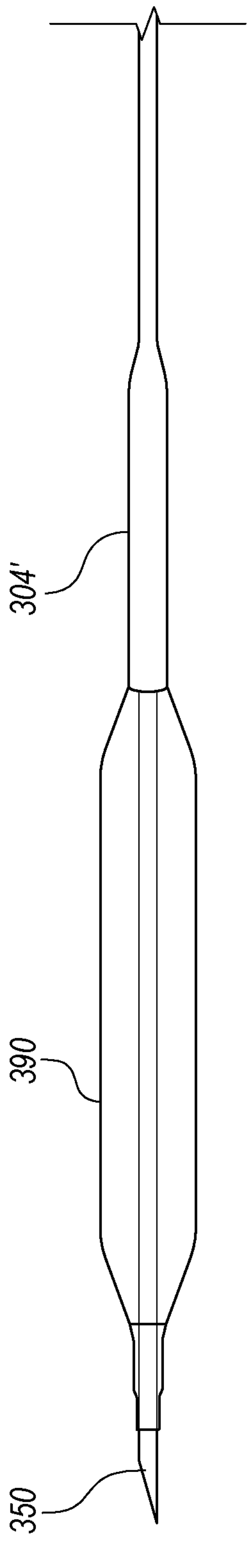

For example, FIGS. 50A-B depict a straight mounted configuration of the expandable element 390, in which FIG. 50A shows the collapsed configuration and FIG. 50B shows the expanded configuration of the expandable element 390. In addition, penetrating element 350 can be folded further inward than as depicted in FIG. 50A, proximally along the length of expandable element 390 such that the tip of penetrating element 350 does not extend past or emerge from the distal end of expandable element 390 in a collapsed or delivery configuration. As the balloon is inflated, the length of expandable element 390 unfurls causing penetrating element 350 to emerge from the infolded balloon to its expanded configuration shown in FIG. 50B.

FIGS. 47A-50B illustrate exemplary dimensions, angles and properties of the expandable element 390, which are not intended to limit the embodiments of expandable element 390. FIG. 47D illustrates exemplary tabulated material properties of the expandable element 390 depicted in 47A-C, which are not intended to limit the embodiment of FIGS. 47A-C.

FIGS. 51A-54C illustrate further exemplary piercing elements for creating anastomosis via the endovascular approach, constructed in accordance with embodiments of the disclosed inventions. The tissue penetrating member 250 comprises a stylet (i.e., solid elongated element with a piercing distal tip), as shown in FIGS. 51A-54C. Alternatively, the tissue penetrating member 250 may comprise a needle (i.e., hollow tubular element with a piercing distal tip), as shown in FIGS. 45A-46D, which may be incorporated and/or detachably coupled to the shunt 200', previously described. The tissue penetrating member 250 further comprises a proximal portion 258, an elongated body portion 252, and a distal portion 255 that terminates in a distal tip 255'. The distal end tip 255 is configured for piercing the IPS wall 114 and arachnoid layer 114 and creating the anastomosis channel 140, as shown, for example in FIGS. 5C-J. Embodiments of the tissue penetrating member 250 of FIGS. 51A-54C can be incorporated into the distal end of the various delivery assembly 300 or delivery catheter 304 embodiments disclosed herein.

Figure 51A:
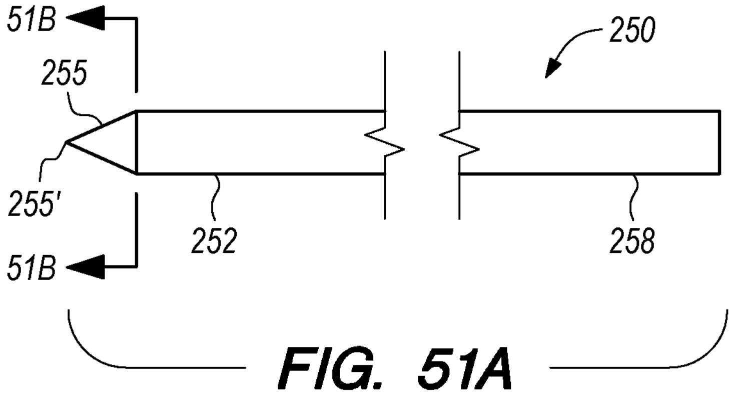
FIGS. 51A-54C are perspective, side and cross-sectional views of piercing elements constructed according to various embodiments of the disclosed inventions.
Figure 51B:
Figure 51C:
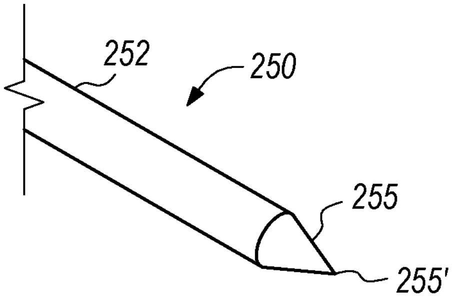
Figure 52A:
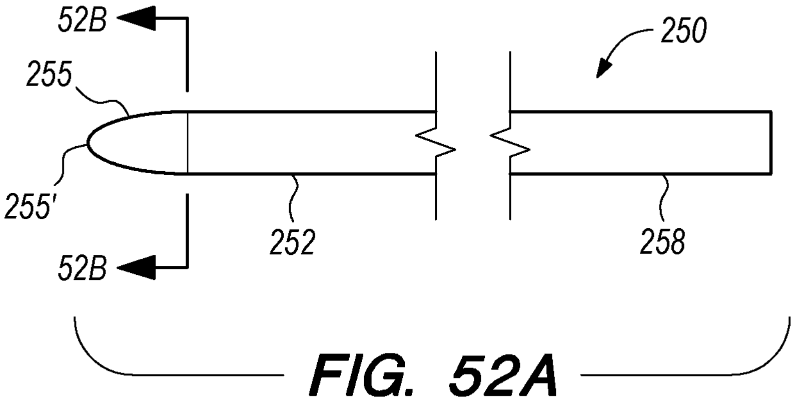
Figure 52B:
Figure 52C:
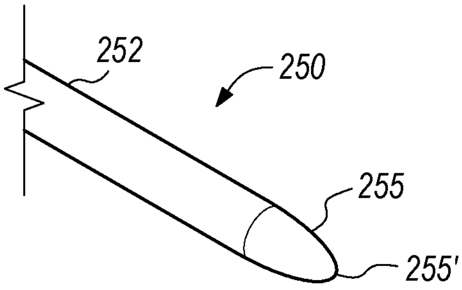
Figure 53A:
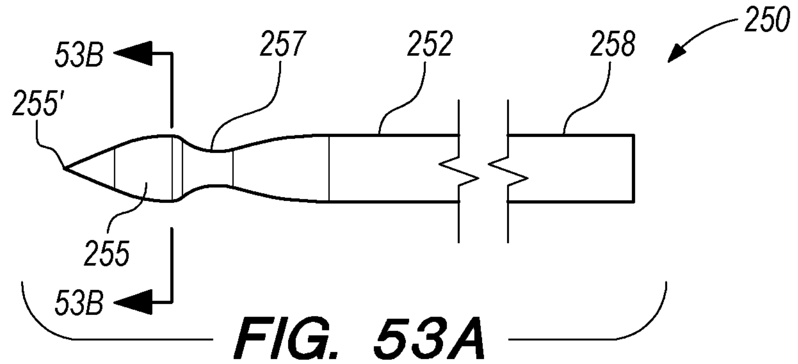
Figure 53B:
Figure 53C:
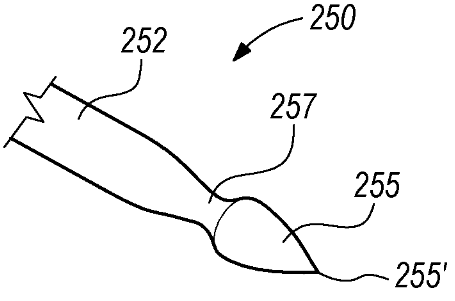

The distal portions 255 of the tissue penetrating member 250 of FIG. 51A and FIG. 53A terminate in a straight point distal tips 255'. FIGS. 51B, 52B, 53B and 54B are cross-section views of a portion of tissue penetrating member 250 along the respective axis B-B shown in FIGS. 51A, 52A, 53A and 54A. The diameter of the tissue penetrating member 250, along the distal portion 255 and/or elongated body 252 can range from approximately 0.006 inches (0.1524 mm) to 0.030 inches (0.762 mm). It should be appreciated that other suitable diameters of the tissue penetrating member 250 may be provided, as long as the shunt 200 and the delivery assembly 300 accommodate the dimensions of the tissue penetrating member 250. FIG. 51C and FIG. 53C depict a perspective view of the distal portion 255 of tissue penetrating member 250 having the straight point distal tips 255'. Alternatively, the distal portions 255 of the tissue penetrating member 250 of FIG. 52A and FIG. 54A terminates in a rounded distal tip 255' (e.g., bullet-nose, elliptical cross-section, blunt configuration). The cross-sectional views of the tissue penetrating member 250 in FIG. 52C and FIG. 54C depict exemplary elliptical curvatures of the rounded distal tips 255'.

Further, the tissue penetrating member 250 may comprise a neck portion 257 proximately disposed to the distal portion 255, as shown in FIGS. 53A, 53C and FIGS. 54A, 54C. The neck portion 257 comprises a smaller outer diameter relative to the elongated body 252 and distal portion 255 of the tissue penetrating member 250. The outer diameter of the neck portion 257 can be, for example, approximately 25% to 75% smaller than the outer diameter of the elongated body 252 and distal portion 255 of the tissue penetrating member 250. The neck portion 257 provides a recess in the tissue penetrating member 250 for the distal portion 202 and/or the distal anchoring mechanism 229 of the shunt 200/200' to reside in a delivery configuration as the tissue penetrating member 250 passes through the IPS wall 114. The distal portion shunt 200 is detachably coupled to neck portion 257 of the tissue penetrating member 250 200', and once the anastomosis channel 140 is created, the shunt 200' implanted in the target site (e.g., as shown in FIGS. 5H-J).

Figure 54A:
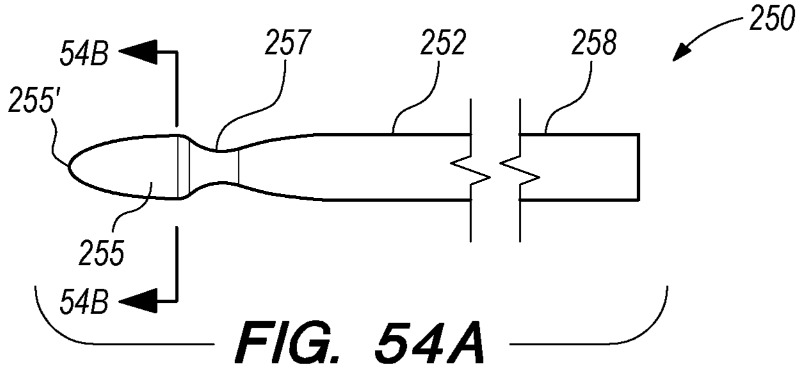
Figure 54B:
Figure 54C:
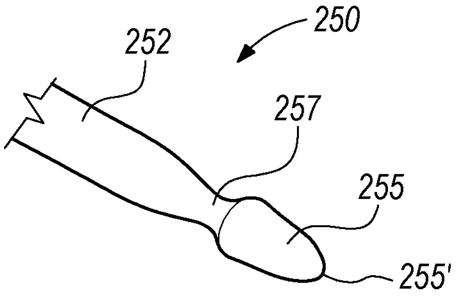

In some embodiments, the tissue penetrating member 250 may have a more abrupt transition between the distal portion 255 of the tissue penetrating member 250 and the neck portion 257, compared to the transition of the elongated body portion 252 of the tissue penetrating member 250 and the neck portion 257, as shown in FIGS. 53A and 54A. These transitions or curved profile of neck portion 257 (e.g., as shown in FIGS. 53A, 53C, 54A, and 54C) facilitate the delivery of shunt 200 through IPS wall 114 in a collapsed or delivery configuration. Optionally, an outer sheath (not shown) can be used to hold shunt 200 over the tissue penetrating member 250 in a delivery configuration as the tissue penetrating member 250 and shunt 200 are advanced through the patient's vasculature. For example, the distal end of the sheath covering the shunt disposed over the piercing element can be advanced to the target penetration site in IPS wall 114 such that the distal end of the sheath abuts, but does not pass through, the IPS wall 114 as tissue penetrating member 250 and the shunt 200 penetrate the IPS wall 114 and the arachnoid layer 115 into CP angle cistern 138.

In other embodiments, the proximal portion 258 and/or the elongated body portion 252 of the tissue penetrating member 250 can have a greater outer diameter than distal portion 255 of tissue penetrating member 250 (e.g., an outer diameter of approximately 25% to 75% greater than the outer diameter of body or distal portions of the piercing element). The increased outer diameter of the proximal portion 258 and/or the elongated body portion 252 of the tissue penetrating member 250 prevents the shunt 200 from sliding proximally over the tissue penetrating member 250 during navigation through the patient's vasculature and the penetration step, and serves as a penetration stop by preventing the tissue penetrating member 250 (and accompanying delivery system) from passing beyond IPS wall 114 and arachnoid layer 115 into the subarachnoid space 116. Once a distal portion of shunt 200 and/or distal anchoring mechanism 229 has been deployed in CP angle cistern 138, the tissue penetrating member 250 can be withdrawn from the shunt lumen 207, delivery assembly 300.

In some embodiments, the tissue penetrating member 250 may be coupled to an energy source (not shown) to facilitate the piercing and/or advancement through the IPS wall 114 and arachnoid layer 115 that separates the lumen of IPS 102 from the subarachnoid space 116/CP angle cistern 138. The energy source can provide one or more energy types, including, but not limited to, radio frequency energy (RF), thermal energy, acoustic energy or the like. For example, the piercing elements 250 of FIGS. 51A-54C, particularly, the piercing elements 250 having the bullet-nose tip 255' of FIGS. 52A, 52C and FIG. 54A, 54C may be coupled to a source of high frequency RF energy to assist with the advancement through the IPS wall 114 and arachnoid layer 115 to create anastomosis 140 between IPS 102 and CP angle cistern 138. The use of RF energy in the piercing elements 250 coagulates tissue while creating the anastomosis channel 140 thereby eliminating or reducing bleeding into the subarachnoid space, and can eliminate the need for a sharpened penetrating element facing brainstem 112 after passing through the IPS wall 114 and arachnoid layer 115 into the CP angle cistern 138.

By way of non-limiting example, the tissue penetrating member 250 of FIGS. 51A, 51C that includes the straight point distal tip 255' for delivering RF energy to penetrate the IPS wall 114 and arachnoid layer 115. The straight point distal tip 255' can focus the RF energy at the distal most point of tissue penetrating member 250 to facilitate penetrating through the IPS wall 114 and arachnoid layer 115, without dispersing electrical current to nearby tissue or structures. The gradual transition from straight point distal tip 255' to distal portion 255 of the tissue penetrating member 250 gently dilates the tissue of IPS wall 114 during the penetration step to minimize tissue damage during the delivery and deployment of shunt at the target site. In some embodiments, the tissue penetrating member 250 of FIGS. 51A-54C is configured to pass through shunt lumen 207 of the various embodiments of shunt 200 disclosed herein such that the shunt can be delivered through the IPS wall 114 as the tissue penetrating member 250 penetrates through the IPS wall 114 and arachnoid layer 115 into CP angle cistern 138.

The tissue penetrating member 250 of FIGS. 51A-54C can be made from Nitinol or other conductive materials. The tissue penetrating member 250 can be a straight, rigid piece of material incorporated into the distal end of a delivery catheter 304 or other element of delivery assembly 300. Alternatively, the tissue penetrating member 250 can be primarily flexible, similar to flexible micro guide wires known in the art. Shunt 200 disposed over a flexible tissue penetrating member 250 can provide sufficient column strength to the combination of the shunt/piercing element, which allows navigation through the patient's vasculature, to the target penetration site in IPS wall 114, and into CP angle cistern 138. The flexible configuration of tissue penetrating member 250 provides additional safety if the tissue penetrating member 250 advances too far distally into the cistern 138; the floppy, guide wire-like configuration further reduces the risk that the tissue penetrating member 250 will damage local critical structures such as the brain stem or cranial nerves.

The tissue penetrating member 250 of FIGS. 51A-54C and delivery assembly 300 can be configured for use with an electrosurgical unit that generates and supplies RF energy to the distal tip of tissue penetrating member 250. Several manufacturers and distributors provide electrosurgical units suitable for use with embodiments of the disclosed inventions (e.g., Aaron® Product Line, Bovie Medical Corporation, Clearwater, Florida). As will be appreciated by those of skill in the art, all but the distal most portion of the tissue penetrating member 250 (e.g., distal most 1 mm to 15 mm) may be insulated such that only the distal tip 255' or distal portion 255 of the tissue penetrating member 250 delivers RF energy to IPS wall 114 (and not the delivery assembly 300 and/or delivery catheter 304). Standard electrosurgical units provide multiple settings that can optimize the use of such systems for use with the disclosed embodiments. For example, monopolar versus bipolar operation focuses the RF energy around a pinpoint penetration site from the distal tip 255' and/or distal portion 255 of tissue penetrating member 250 in IPS wall 114, without damaging nearby tissue or structures. Coagulation and/or blended settings, as opposed to pure cut, can further pinpoint the RF energy to the contact point between the distal tip 255' and/or distal portion 255 of the tissue penetrating member 250 and IPS wall 114 without generating excess heat and vaporizing cells. Such coagulation or blended settings advantageously provide a controlled delivery of RF energy to pass the tissue penetrating member 250 through the target penetration site, without dispersing RF energy to the surrounding tissues, while also coagulating the tissue to prevent localized bleeding from IPS wall 114. Adjustable power settings allow for further optimization of electrosurgical units with the disclosed embodiments. For example, with a coagulation setting, a power setting from about 5 watts to about 20 watts, and preferably from about 8 watts to about 12 watts, can be used with tissue penetrating member 250 to penetrate from IPS 102 into CP angle cistern 138. In addition, an electrosurgical unit can be configured to stop the delivery of RF energy to the tissue penetrating member 250 upon detecting a change in impedance; a detector on the tissue penetrating member 250 can provide impedance feedback to the electrosurgical unit to differentiate between dura mater and CSF as the distal tip 255' of the tissue penetrating member 250 emerges from the IPS wall 114 and arachnoid layer 114 into the CSF-filled subarachnoid space 116 and/or CP angle cistern 138.

Figure 55A:
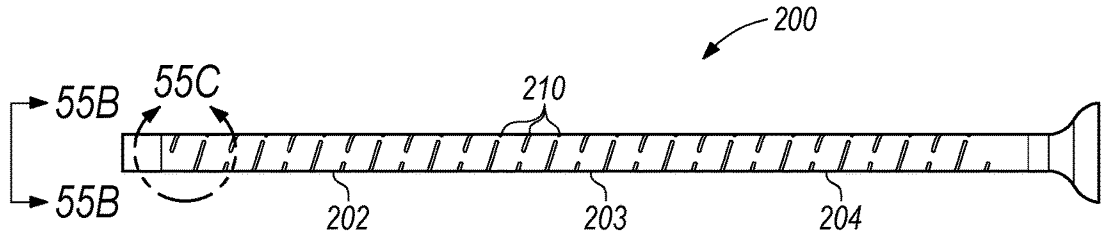
FIGS. 55A-55E are perspective, side and cross-sectional views of cuts in the elongated body of the shunt, constructed according to one embodiment of the disclosed inventions.
Figure 55C:
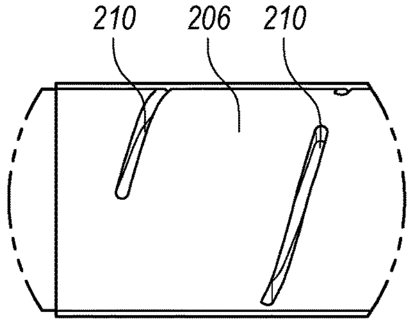
Figure 55B:
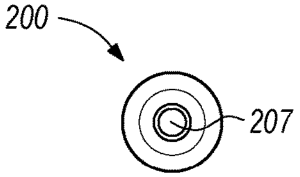
Figure 55D:
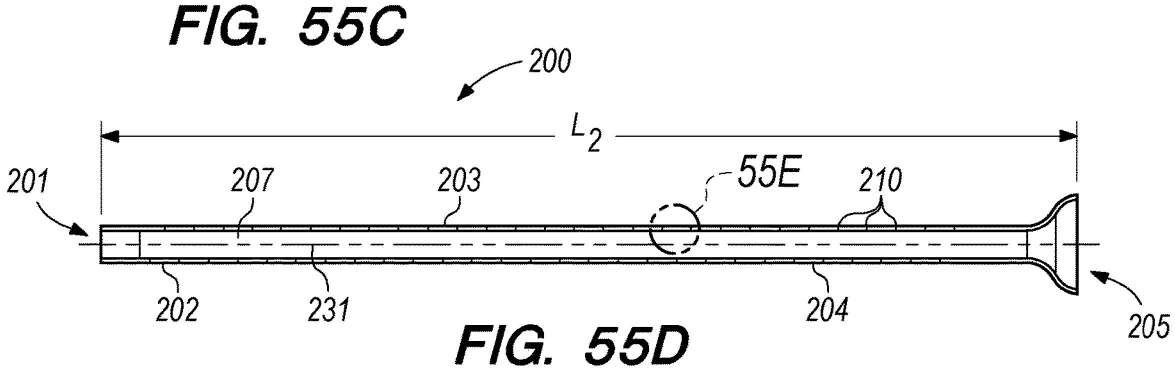

FIGS. 55A-E illustrate an exemplary elongated portion 203 of the shunt 200, according to embodiments of the disclosed inventions. As described above, the shunt 200 includes the proximal portion 204, the distal portion 202, and the elongate body 203 extending therebetween. The shunt 200 further includes lumen 207 extending from the proximal opening 205 to the distal opening 201 of the shunt 200. In the embodiment of FIGS. 55A, 55D, length $L_2$, measured along the elongate central axis 231 of the shunt 200, is approximately 0.5 inches (1.27 cm) in the delivery configuration. In other embodiments, $L_2$ may range between 10 mm to 30 mm in the delivery configuration. Further, in the embodiment of FIG. 55D, the inner diameter (ID) of the shunt 200 (e.g., lumen 207) measured in a direction orthogonal to axis 231, is approximately 0.0144 inches (0.3657 mm). In other embodiments, the ID of the shunt 200 may range between 0.002 inches (0.0508 mm) to 0.020 inches (0.508 mm). It should be appreciated that the ID, $L_2$ and any other length, width, or thickness may have any suitable dimension for implantation of the shunt 200 in the target site (e.g., IPS, CP angle cistern, or the like).

As previously described, the shunt 200 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. The shunt 200, particularly the elongated body 203 of FIGS. 55A-E, is composed of Nitinol. The shunt 200 further comprises one or more cuts 210 (e.g., kerfs, slots, key-ways, recesses, or the like) along the elongated body 203. The cuts 210 of the elongated body 203 may have a variety of suitable patterns, as shown in FIGS. 55A-60C. The cuts 210 and their patterns are preferably manufactured by laser cutting the elongated body 203 of the shunt 200. Alternatively, the cuts 210 and their patterns may be manufactured by etching or other suitable techniques. In the embodiment of FIG. 55C, each cut 210 may have a width of 0.001 inches (0.0254 mm). The width, length and depth of each cut 210 and patterns in the elongated body 203 of the shunt 200, may comprise any suitable dimensions. The cuts 210 of the elongated body 203 are configured to increase the flexibility of the shunt 200 for navigating tortuous anatomy during delivery and/or to assume a pre-determined configuration (e.g., secondary shape, for example helical/coil shape of FIGS. 6G-H, 24A, 24E, 34A-B) when deployed and implanted at the target site.

Figure 55E:
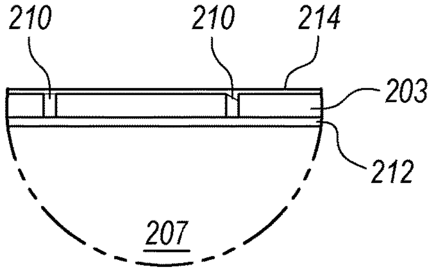
Figure 56A:
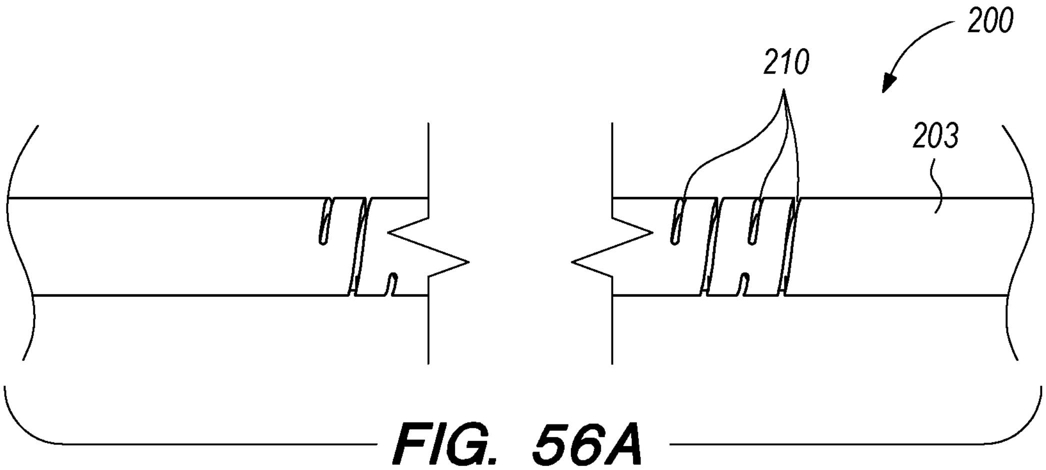
FIGS. 56A-60C are perspective and side views of patterns of the cuts in the elongated body of the shunt, constructed according to various embodiments of the disclosed inventions.
Figure 56B:
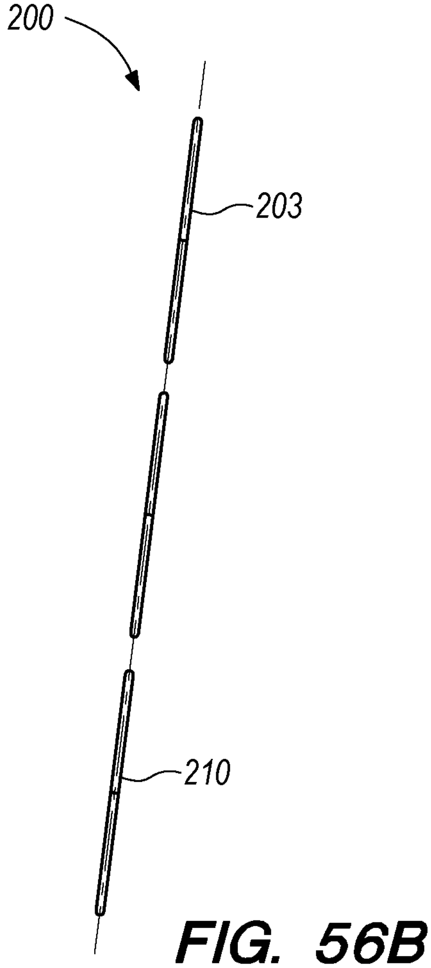
Figure 57A:
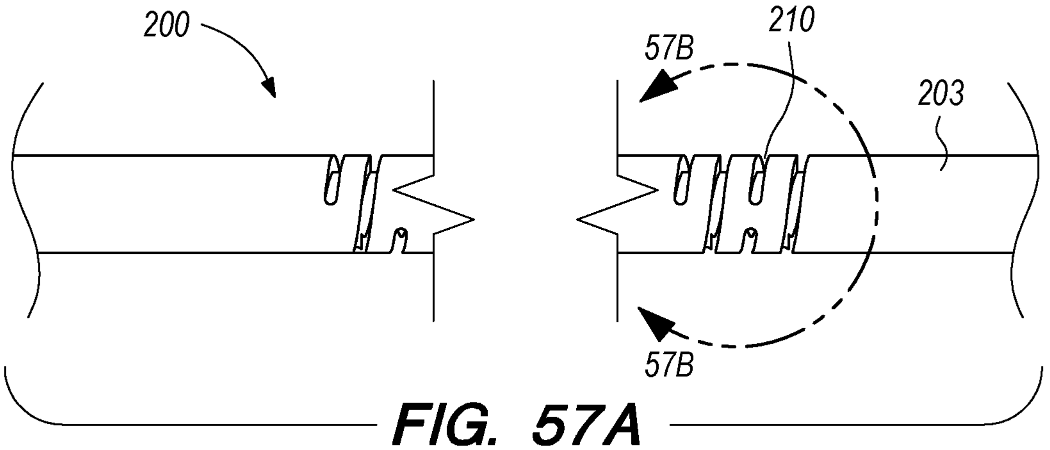
Figure 57C:
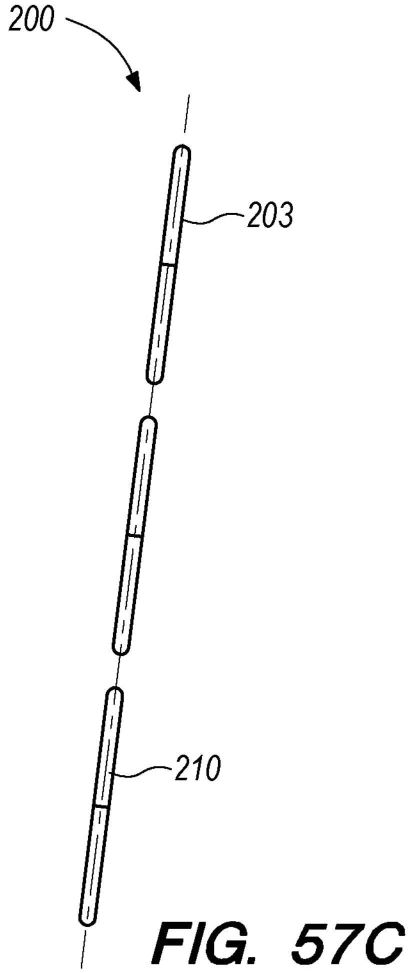
Figure 57B:
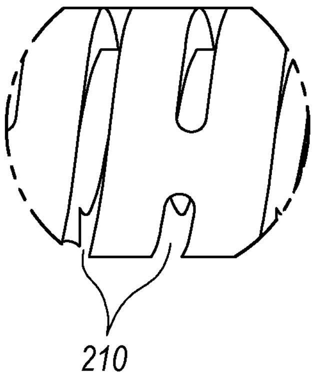
Figure 58A:
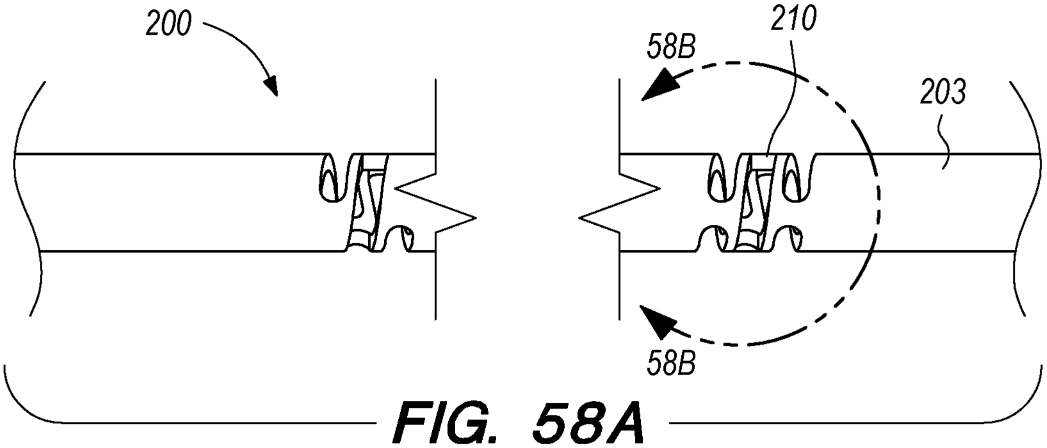
Figure 58C:
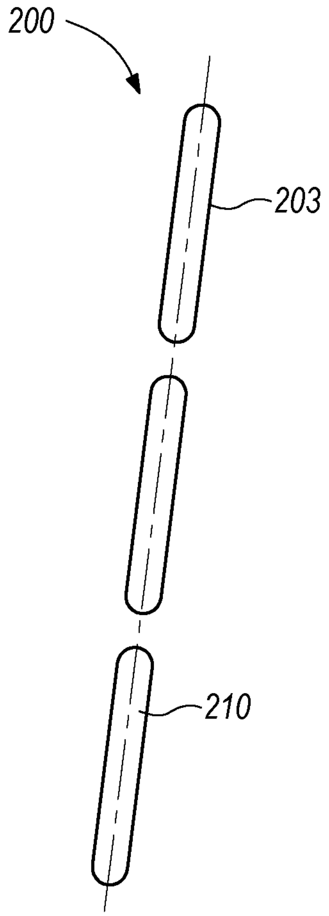
Figure 58B:
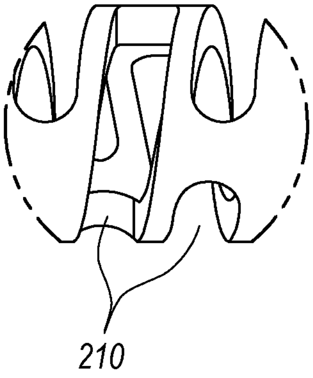
Figure 59A:
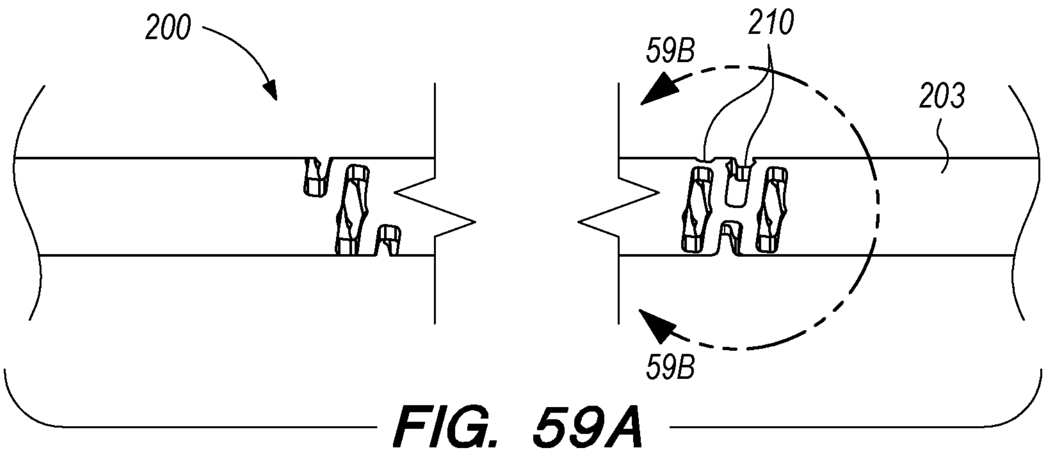
Figure 59C:
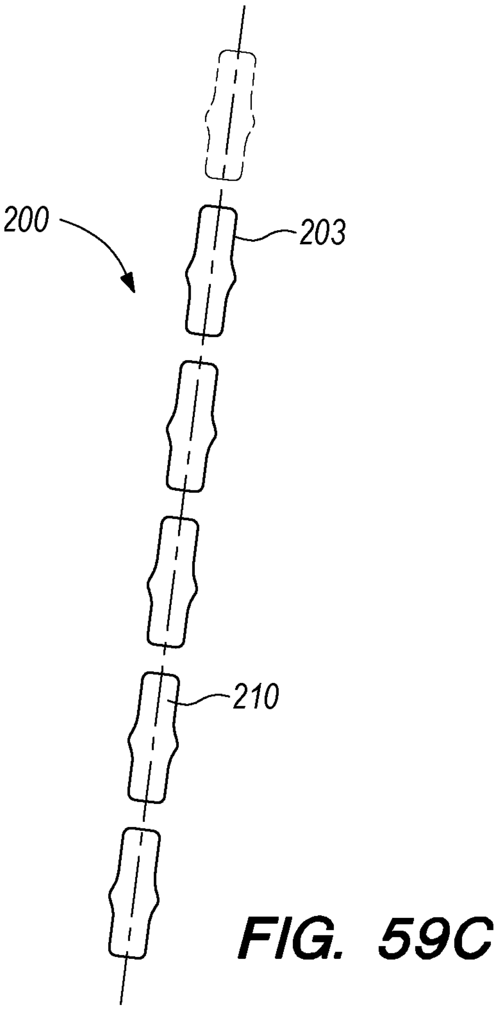
Figure 59B:
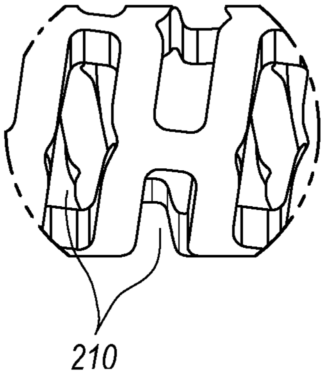

Additionally, the shunt 200 comprises an inner liner 212 and an outer jacket 214, as better seen in FIG. 55E. The inner liner 212 and outer jacket 214 are composed of suitable implantable polymeric materials, such as polytetrafluoroethylene "PTFE", polyethyleneterephthalate "PET", High Density Polyethylene "HDPE", expanded polytetrafluoroethylene "ePTFE", urethane, silicone, or the like. Preferably, inner liner 212 is composed of materials that resist aggregation of CSF proteins and cells flowing through shunt lumen 207 to maintain long-term shunt lumen patency such as HDPE, PET, PTFE, or silicone. The inner liner 212 and outer jacket 214 are configured to cover—completely or partially—the cuts 210 of the elongated body 203, from within shunt lumen 207 and over shunt body 203, respectively; in such configuration, the elongated body 203 becomes a frame that supports the inner liner 212 and outer jacket 214. Shunt 200 with its inner liner 212, shunt body frame 203, and outer jacket 214 is impermeable to venous and sinus blood flow, and the integrated liner-frame-jacket configuration maintains the flexibility and pre-determined configuration that the cuts 210 provide to the shunt 200.

Inner liner 212 provides a smooth surface within shunt lumen 207 and maintains a laminar flow profile for CSF flowing through the shunt under normal differential pressure (5-12 cm H2O) between the subarachnoid space 116 and cistern 138. In addition to material selection criteria for liner 212 previously described, maintaining laminar flow within shunt lumen 207 further eliminates or reduces the risk of occlusion from protein accumulation and cell aggregation. Liner 212 can be configured to line the interior of shunt body 203 using an extrusion process. Alternatively, the liner material can de deposited (e.g., using a dispersion technique) on a mandrel (e.g., nickel coated copper); thereafter, the liner-coated mandrel can be placed within shunt body 203 for application of outer jacket 214 and adhering inner liner 212 to shunt body 203, after which the mandrel can be withdrawn from shunt 200 leaving inner liner 212 in place within shunt lumen 207. Without an inner liner 212, cuts 210 inside the lumen 207 can provide surfaces for proteins and cells to accumulate, which could occlude lumen 207 and prevent CSF from flowing from the subarachnoid space into the venous system.

Outer jacket 214 provides a smooth exterior surface to shunt 200, which reduces the risk of thrombus formation in the IPS 102 compared to shunt 200 with cuts 210 on the exterior surface of shunt body 203. As noted above, the outer jacket 214 can comprise one or more implant-grade polymers including, but not limited to, polyurethane or silicone-polyurethane blends. In some embodiments, a gas or liquid dispersion of polymer is applied to shunt body 203 and inner liner 212, which forms the outer jacket 214 and bonds the inner liner 212, the shunt body 203, and outer jacket 214 together in an integrated configuration of shunt 200, for example, as shown in FIG. 55E.

Outer jacket 214 can completely cover the exterior surface of shunt body 203; however, in other embodiments, the outer jacket can be placed selectively along portions of shunt body 203 to adhere inner liner 212 to shunt body 203. By way of non-limiting example, a liquid dispersion of polymer or an epoxy-based adhesive can be placed at discrete locations along the length of shunt body 203 (e.g., proximal portion, middle portion, and/or distal portion of shunt body 203). Alternatively, the exterior surface of inner liner 212 can be coated with polymer or adhesive, and then placed within shunt body 203; the polymer or adhesive can seep into cuts 210, completely or partially filling some or all of the cuts 210 along shunt body 203. In these embodiments, exterior portions of the shunt body 203 material are exposed to the implant site within the patient.

In the embodiment of FIG. 55E, the inner liner 212 may have a thinness of 0.0007 inches (0.01778 mm), the elongated body 203 wall may have a thinness of 0.0018 inches (0.04572 mm) and, the outer jacket 214 may have a thickness of 0.0005 inches (0.0127 mm). It should be appreciated that the inner liner 212, elongated body 203 and outer jacket 214 may comprise any suitable dimensions.

Figure 60A:
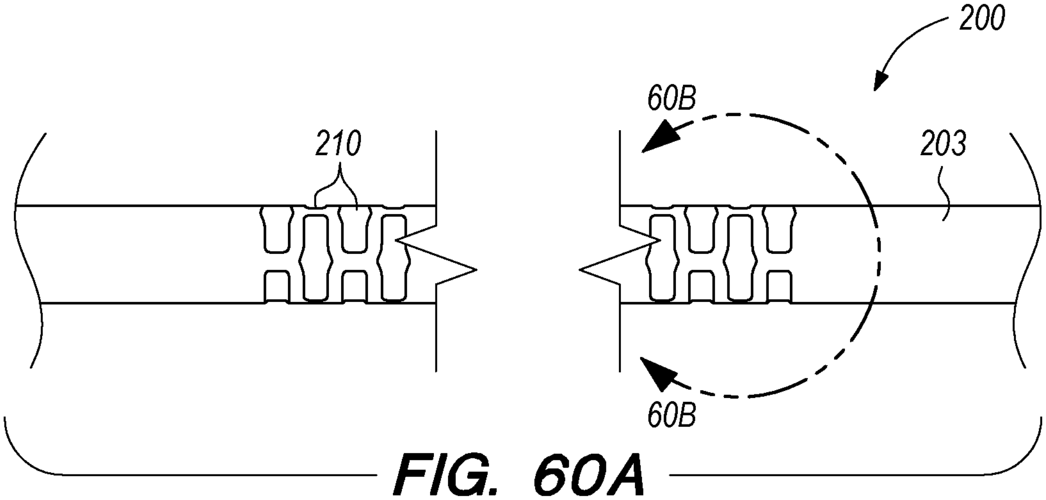
Figure 60C:
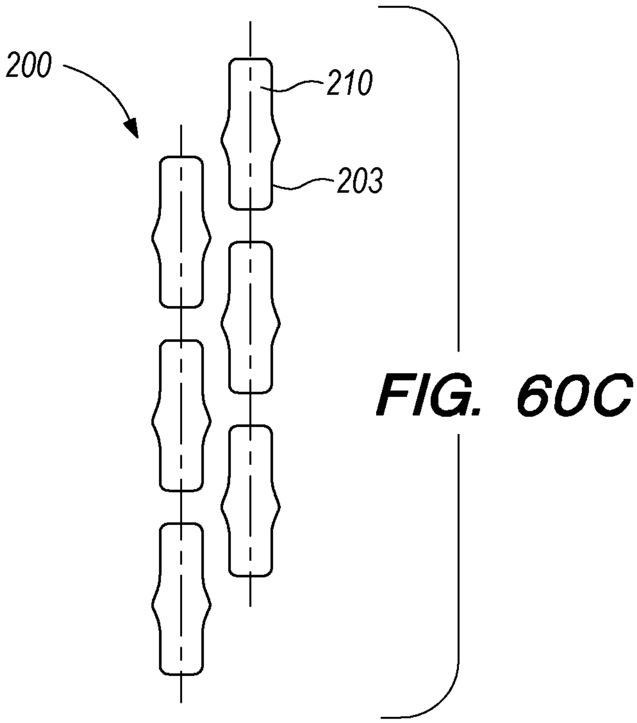
Figure 60B:
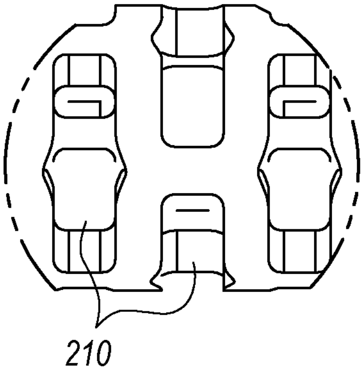

FIGS. 56A-60C illustrate exemplary patterns of the cuts 210 of the elongated body 203 of the shunt 200, according to embodiments of the disclosed inventions. As shown in FIGS. 56A-60C, the elongated bodies 203 of shunts 200 comprise a variety of exemplary patterns of the cuts 210. In these embodiments, the patterns of the cuts 210 are achieved by laser cutting the elongated body 203 while rotating the body at a selected angle as the laser and body move with respect to one another. For example, with a laser oriented orthogonal to the longitudinal axis of the body 203 and with a laser capable of holding body 203 while rotating and advancing the body relative to the fixture, the laser can be activated and deactivated to form specific cut patterns in shunt body 203. FIGS. 56B, 57C, 58C, 59C and 60C depict exemplary cut patterns in a two dimensional view of their respective tubular elongated bodies 203 of FIGS. 56A, 57A, 58A, 59A and 60A. In the embodiments of FIGS. 56A-58C, the laser cutting of the elongated body 203 creates 1.5 cuts 210 per rotation of the body, having a cut balance of about 210° of rotation with laser on, and then 30° of rotation with laser off. In the embodiments of FIGS. 59A-C, the laser cutting of the elongated body 203 creates 2.5 cuts 210 per rotation, having a cut balance of about 116° of rotation with laser on, followed by 28° of rotation with laser off. In the embodiments of FIGS. 60A-C, the laser cutting of the elongated body 203 creates 2.5 cuts 210 per rotation, having a cut balance of about 116° on, 28° off. Further, while the pitch of the cut pattern is approximately 0.0070 inches (0.1778 mm) in the embodiments of FIGS. 56A-59C, each cut 210 may have a variety of widths; for example 0.0010 inches (0.0254 mm) (FIGS. 56A-B), 0.0022 inches (0.05588 mm) (FIGS. 57A-C), 0.0049 inches (0.12446 mm) (FIGS. 58A-C) or 0.0039 (0.09906 mm) (FIGS. 60A-C). In the embodiment of FIGS. 60A-C, each cut 210 has a width of 0.00399 inches (0.10134 mm) and is oriented orthogonal to the tube's longitudinal axis, illustrating a zero-pitch pattern. It should be appreciated that the above disclosed units are exemplary dimensions, angles and properties of the cuts 210 and their patterns, which are not intended to limit the embodiment of FIGS. 56A-60C.

Figure 61A:
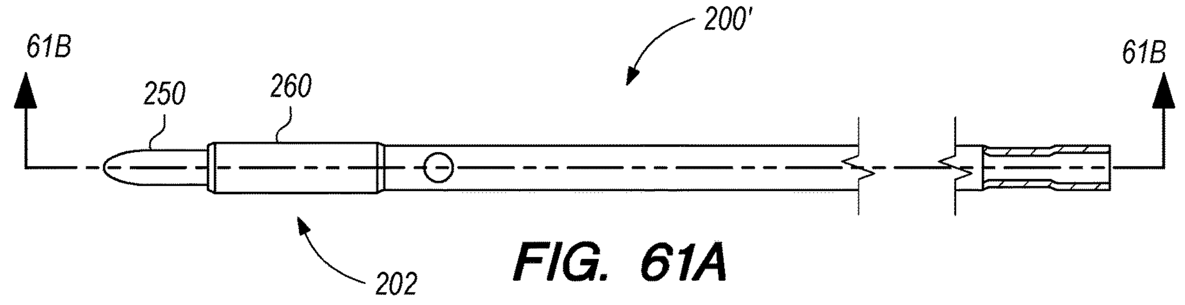
FIGS. 61A-D are side and cross-sectional views of an alternative embodiment of the shunt having a piercing element cover, constructed according to one embodiment of the disclosed inventions.
Figure 61B:
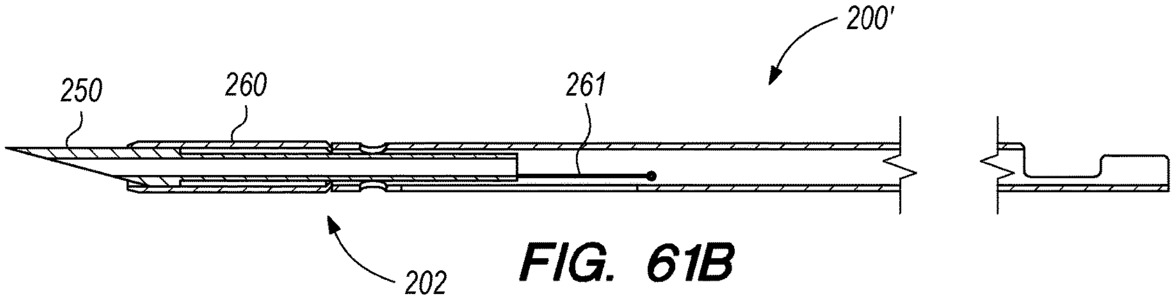
Figure 61C:
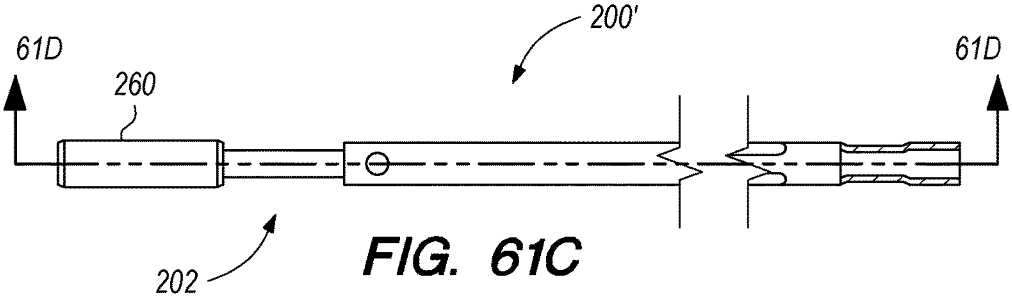
Figure 61D:
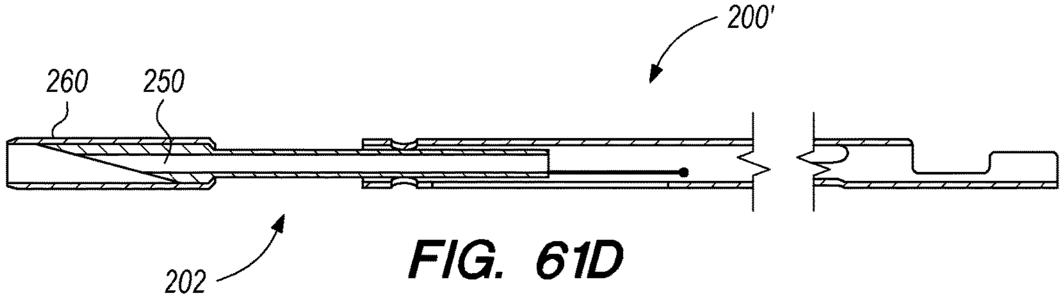

FIGS. 61A-D illustrate an exemplary shunt 200', constructed in accordance with embodiments of the disclosed inventions. In these embodiments, the tissue penetrating member 250 is fixedly coupled to the distal portion 202 of the shunt 200'. The shunt 200' further comprises a cover 260 disposed over and slidably coupled to the tissue penetrating member 250 and to the distal portion 202 of the shunt 200'. The cover 260 comprises a first configuration, in which the cover 260 is withdrawn, exposing the tissue penetrating member 250 of the shunt 200' (FIGS. 61A-B). The cover 260 further comprises a second configuration, in which the cover 260 is advanced, covering or hiding the tissue penetrating member 250 (FIGS. 61C-D). The cover 260 may be actuated from the first to the second configuration by the deployment of the shunt 200' into the target site. For example, the cover 260 is disposed in the first configuration (FIGS. 61A-B) while the tissue penetrating member 250 is piercing the IPS wall 114 and arachnoid layer 115 creating the anastomosis channel 140, as previously described (e.g., FIGS. 5E-I). The distal portion 202 of the shunt 200' including the tissue penetrating member 250 and the cover 260 are further advanced into the CP angle cistern until the cover 260 is also disposed within the cistern (not shown). Then, suitable withdrawal forces are applied to the shunt 200' creating an interface between the arachnoid layer 115 and the cover 260, actuating the cover 260 into the second configuration (FIGS. 61C-D), so that the tissue penetrating member 250 is covered and hidden by the cover 260 when the shunt 200' is deployed and implanted in the target site (not shown). Alternatively, the cover 260 may be actuated from the first to the second configuration using an actuation member (e.g., tether 261, or the like) coupled to the cover 260, or any other suitable methods. As a further alternative, penetrating element 250 can be made from bioresorbable/bio-absorbable materials (e.g., comprising magnesium or zinc) that degrade over time and mitigate the risk of leaving a sharp element implanted within the patient.

Figure 62A:
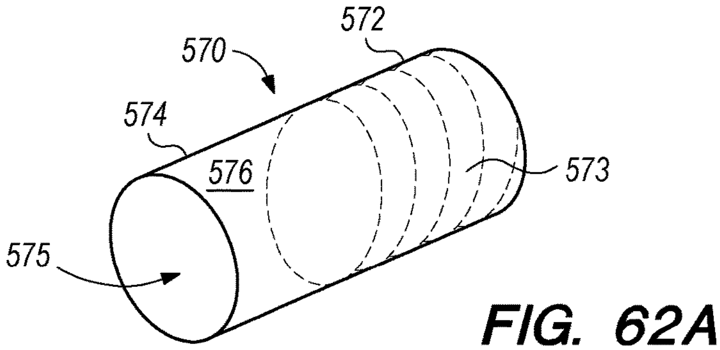
FIGS. 62A-D are cross-sectional views of a shuttle element for covering piercing elements during delivery of the shunt, according to an embodiment of the disclosed inventions.

FIGS. 62A-D illustrate a shuttle element 570 for guarding piercing elements during delivery of the shunt into a target site, in accordance with embodiments of the disclosed inventions. As shown in FIG. 62A, the shuttle element 570 comprises a proximal portion 574 having a proximal end opening 575 and a lumen 576, and a distal portion 572 having a bumper 573. The proximal portion 574 forms a cover or sleeve-like configuration suitable for a nesting interface with the puncture element 250. The shuttle 570 is composed of any suitable biocompatible materials, previously described. Further, the bumper 573 is composed of any suitable material configured to withstand meeting and engaging the piercing element without being pierced, torn, and/or broken prematurely. Further, the bumper 573 may be covered or coated with a suitable polymeric material that may assist the bumper 373 to withstand the engagement with the piercing element (e.g., polyurethane, silicone, ePTFE) and/or assist with the advancement of the bumper 373 through the vasculature (e.g., hydrophilic coatings or their like).

The shuttle 570 is configured to cover and guard piercing elements during delivery of the shunt 200 to the target site, protecting the patient's vasculature from unintended tear or puncturing during delivery from the venous access point in the patient to the target penetration site in the IPS wall 114. The shuttle 570 may be used in combination with any piercing element, for example, the tissue penetrating member 250 of the shunt 200', the tissue penetrating element 306 of the delivery system 300, and/or the tissue penetrating member 350 of the delivery catheter 304'. Additionally, the shuttle 570 may be used, for example, with the embodiments of FIGS. 43A-44E and 47A-50B, such that the shuttle 570 may cover the deflated expandable element 390 (not shown) during the delivery of the shunt into the target site. It can be appreciated from FIGS. 44A and 62B-C that incorporation of the shuttle into embodiments involving expandable balloons may further aid in balloon folding and reduce effective crossing profile while tracking through the vasculature.

Figure 62B:
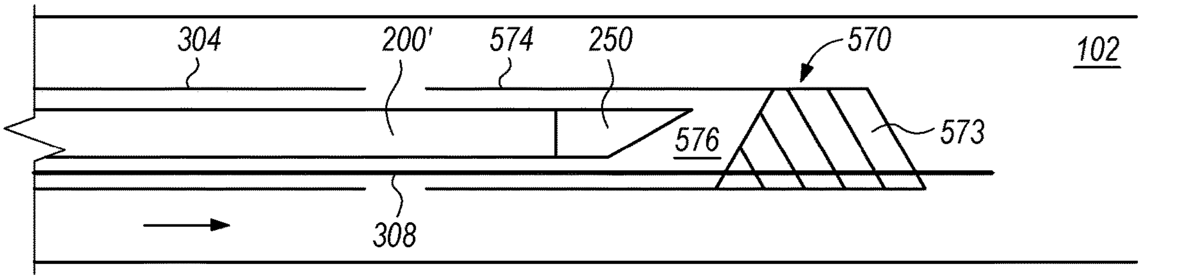
Figure 62C:
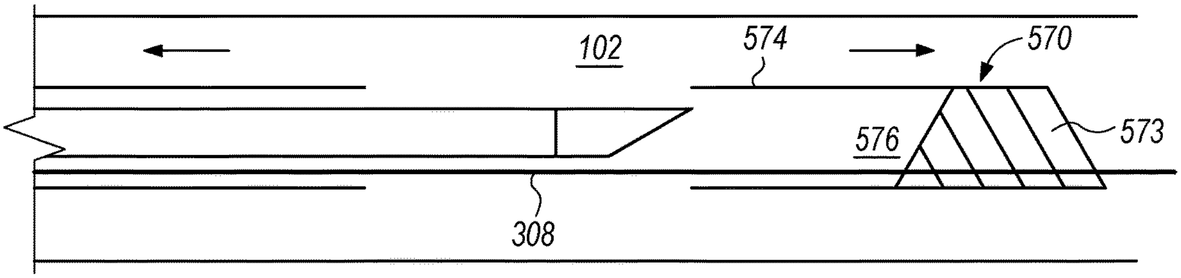
Figure 62D:
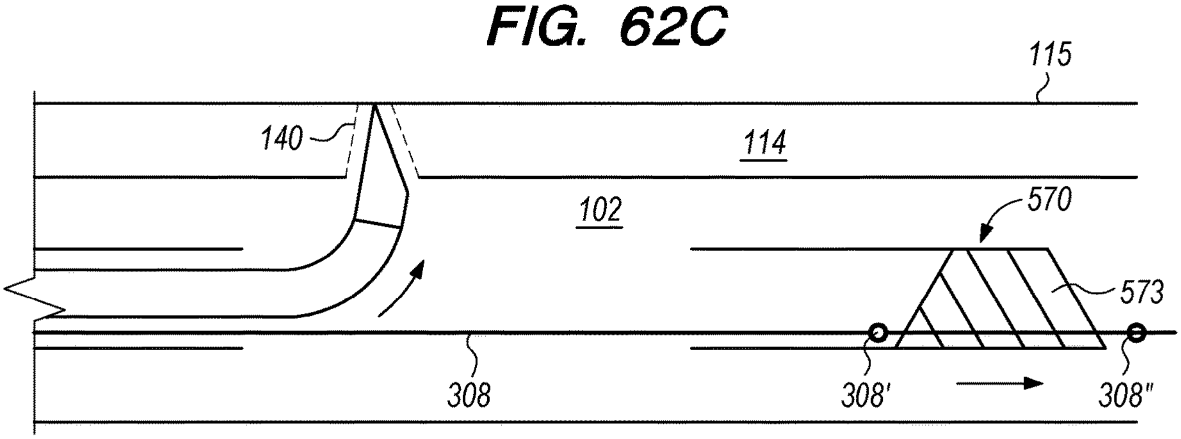

FIGS. 62B-D depict an exemplary interface of the shuttle 570 with the shunt 200' and tissue penetrating member 250. As shown in FIG. 62B, the tissue penetrating member 250 is disposed within the lumen 576 of the shuttle 570 during advancement of the shunt 200' through the delivery catheter 304. The proximal portion of the shuttle 570 covers and protects the tissue penetrating member 250 during advancement into the target site. The tissue penetrating member 250 may meet and engage the bumper 573 of the shuttle 570 during delivery of the shunt 200'. The shuttle 570 is advanced by the engagement and advancement of the tissue penetrating member 250 (e.g., pushing the shuttle), by being coupled to the delivery guidewire 308 (e.g., axial translation of the guidewire), by being advanced with a plunger or push element (not shown), or any other suitable actuation mechanisms and methods. For example, the shuttle 570 may be slidably coupled to the guidewire 308 comprising a first stop 308' and a second stop 308", as shown in FIG. 62D. In the embodiments where the shuttle 570 is slidably disposed over the exemplary guidewire 308 of FIG. 62D, the bumper 573 is disposed between the first 308' and second 308" stops, so that advancement of the guidewire 308 causes the first stop 308' to engage the bumper 573 thus advancing the shuttle 570 (FIG. 62D), and withdrawal of the guidewire 308 causes the second stop 308" to engage the bumper 573 therefore withdrawing the shuttle 570 (not shown). The first stop 308' and second stop 308" may be constructed for varying degrees of interference with the bumper 573 such that a predetermined amount of tensile or compressive force would allow the bumper 573 to bypass the first stop 308' or second stop 308" selectively throughout the course of a given procedure. Once the shunt 200' is disposed within the IPS 102, shown in FIG. 62B, the delivery catheter 340 and/or shunt 200' are withdrawn exposing the tissue penetrating member 250, or the shuttle 570 is advanced exposing the tissue penetrating member 250. Alternatively, the withdrawal of the delivery catheter 340 and/or shunt 200', and the advancement of the shuttle 570 occurs simultaneously or consecutively to expose the tissue penetrating member 250. Additionally, the shuttle 570 may be configured with a slit along its longitudinal axis that facilitates side-exit of the tissue penetrating member 250 through the application of sufficient axial and/or bending loads. The tissue penetrating member 250 is then oriented and advanced towards the IPS wall 114, with any of the methods described herein, to pierce the IPS wall 114 and the arachnoid layer 115 creating the anastomosis channel 140 (FIG. 62D).

Figure 63A:
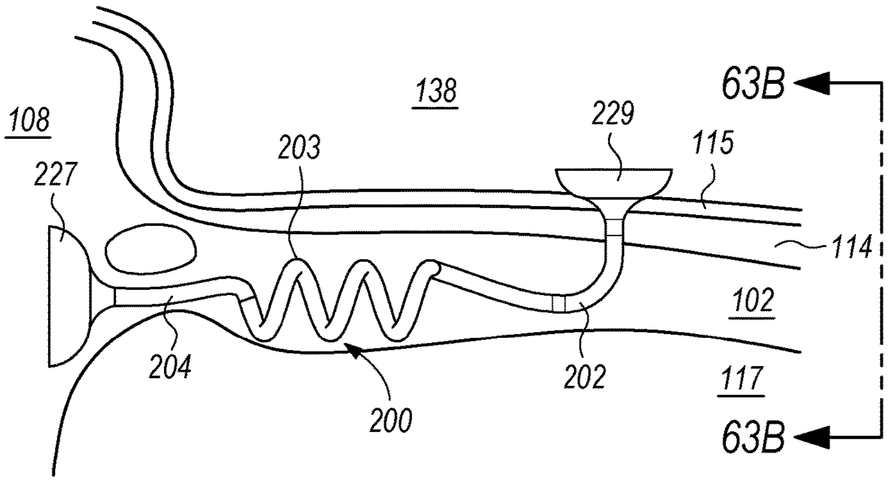
FIGS. 63A-G are perspective and cross-sectional views of an endovascular shunt according to yet another embodiment of the disclosed inventions.
Figure 63B:
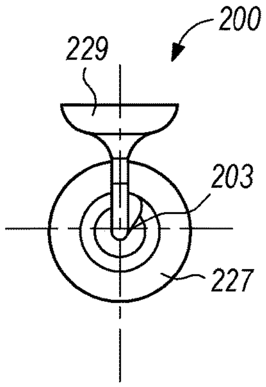
Figure 63C:
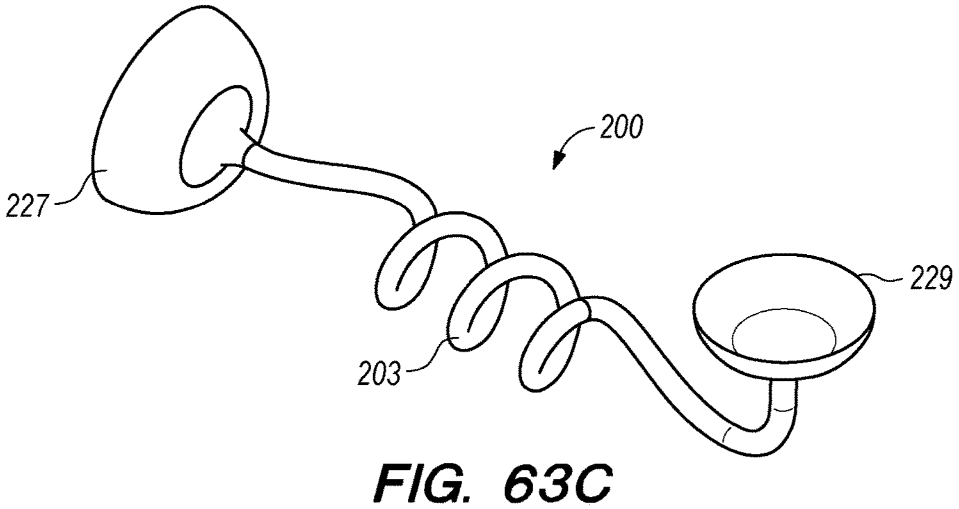
Figures 63D, 63E, 63F, 63G:
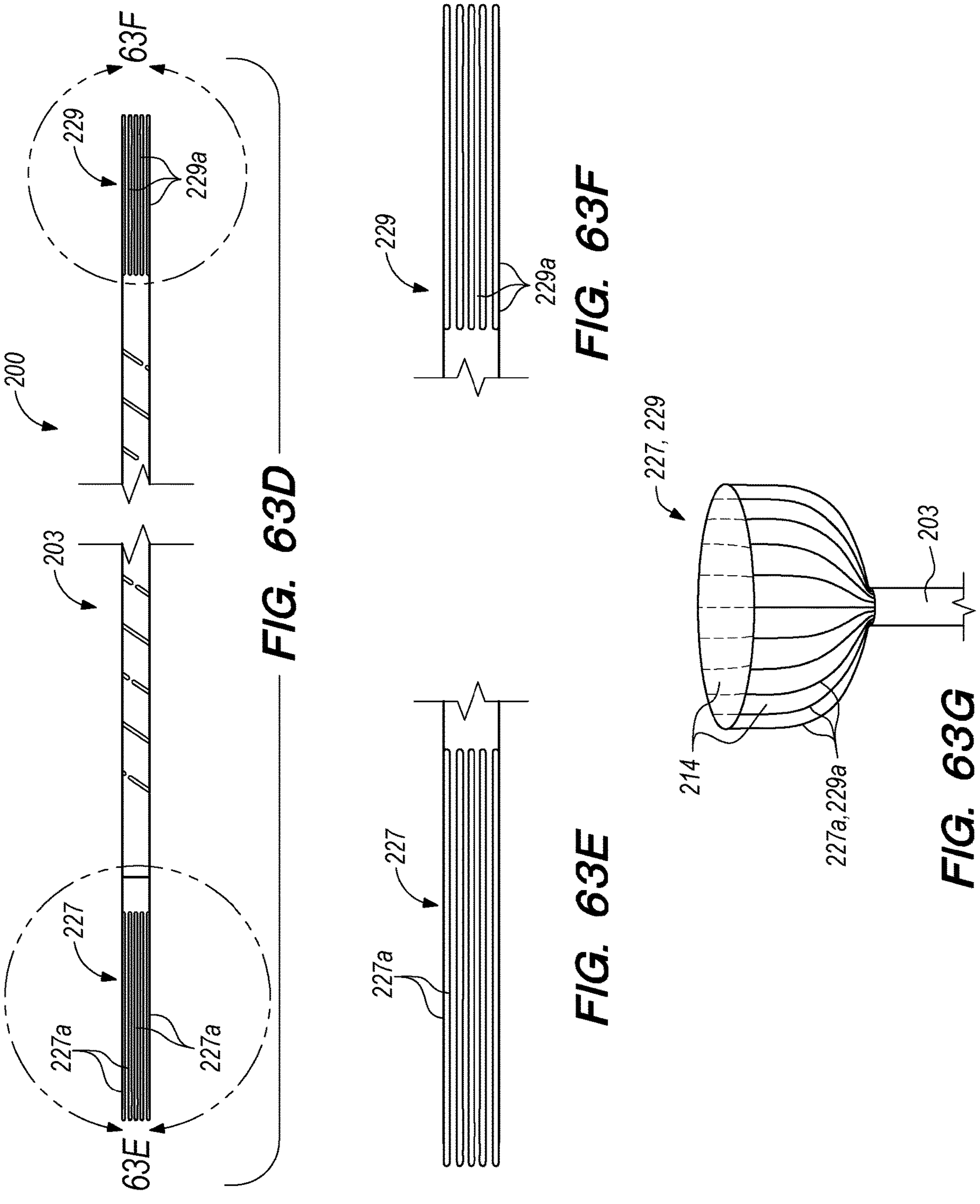

FIGS. 63A-G illustrate another exemplary shunt 200 constructed and implanted according to embodiments of the disclosed inventions. The shunt 200 includes the anchoring mechanism 227 in the proximal portion 204, the anchoring mechanism 229 in the distal portion 202, and the elongate body 203 extending therebetween. The anchoring mechanisms 227 and 229 include a flared-basked configuration (FIGS. 63A-C). The flared-basked anchoring mechanisms 227 and 229 include a plurality of respective elements 227*a* and 229*a* manufactured by selective cutting the respective proximal 204 and distal 202 portions of the shunt 200 (FIGS. 63D-F), using any suitable cutting method (e.g., laser cutting). FIGS. 63E-F depicts detailed exemplary patterns of the cuts of the respective proximal 204 and distal 202 portions of the shunt 200. The plurality of respective elements 227*a* and 229*a* can be biased into a radially outward configuration for deployment (e.g., as shown in FIG. 63G), and compressed in a delivery configuration until deployment of the shunt 200. While the plurality of respective elements 227*a* and 229*a* do not incorporate an liner or outer jacket as shown in FIG. 63G, in alternate embodiments the plurality of respective elements 227*a* and 229*a* and the elongated body 203 of the shunt 200 are covered by a coating and/or liner, as for example, the liner 214 described in FIG. 55E. The liner is configured to allow the respective elements 227*a* and 229*a* to expand radially outward in the deployed configuration of the shunt 200, assuming the flared-basked configuration of the anchoring mechanisms 227 and 229, as for example, shown in FIGS. 63A-C, 63G. Alternatively, or in addition to the lined anchoring mechanisms 227 and 229, the inner liner 212 extends out the longitudinal axis of shunt body 203 at the proximal and/or distal end of shunt body 203 by a predetermined distance ranging from one to several millimeters. For example, on the distal end portion 203 of the shunt, the liner can extend approximately 3 mm above the portion of anchoring mechanism 229 that rests atop arachnoid layer 115, thereby maintaining the shunt lumen 207 separated or away from arachnoid cells. By way of further example, in the proximal end portion 204 of the shunt, the liner can extend from shunt body 203 into or onto valve 209, without lining proximal anchoring mechanism 227.

As shown in FIG. 63A, the deployed anchoring mechanism 227 engages the jugular bulb 108, the IPS wall 117, and/or another portion of the IPS 102, anchoring the proximal portion 204 of the shunt 200 within the jugular vein 106, so that the valve of the proximal portion 204 (not shown) is disposed within the jugular vein 106. Alternatively, the anchoring mechanism 227 may engage the IPS walls 114 and 117 at the junction 118 (not-shown). The deployed anchoring mechanism 229 secures the distal portion 202 of the shunt 200 within the CP angle cistern 138, so that CSF flows through the implanted shunt 200 into the jugular vein 106. FIG. 63B-C depict further perspective views of the shunt 200.

Figure 64C:
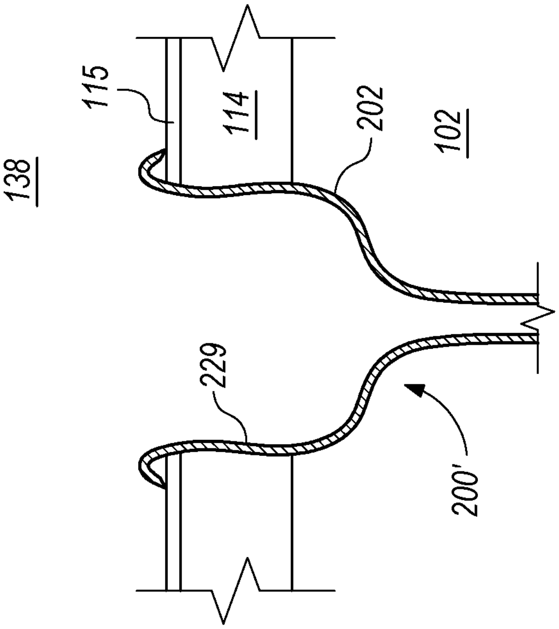
FIGS. 64A-C are cross-sectional views of a distal anchoring mechanism of an endovascular shunt according embodiments of the disclosed inventions.
Figure 64B:
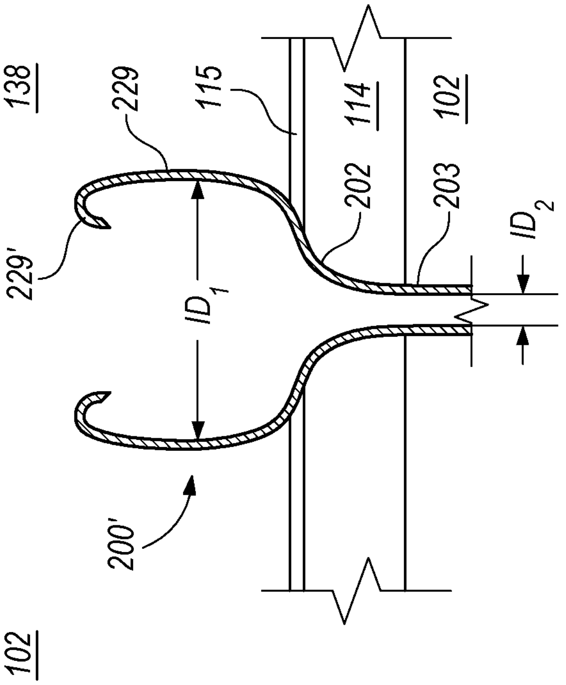
Figure 64A:
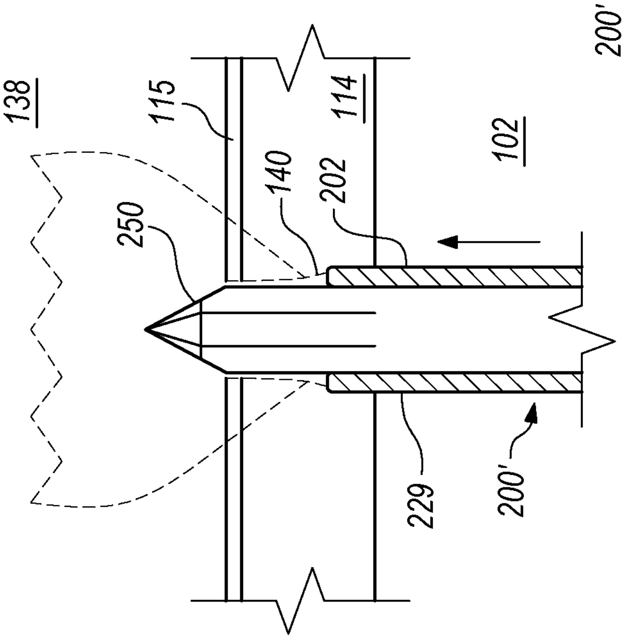
Figure 65A:
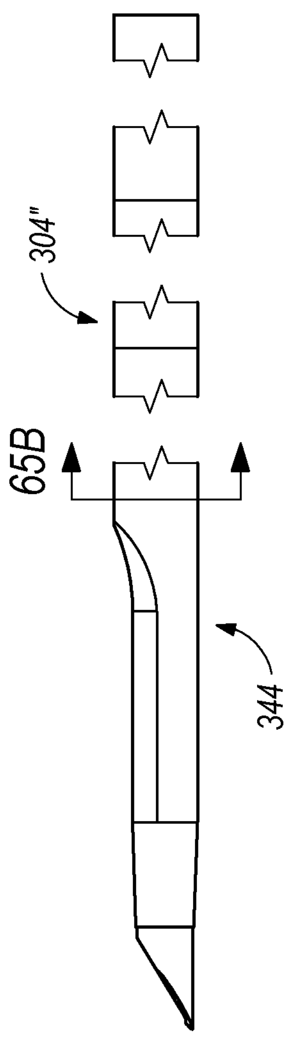
FIGS. 65A-E are perspective, side and cross-sectional views of a delivery catheter, according to another embodiment of the disclosed inventions.
Figure 65B:
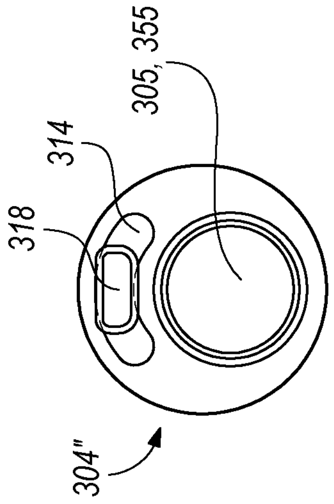

FIGS. 64A-C illustrate another exemplary distal anchor of the shunt, constructed and implanted according to embodiments of the disclosed inventions. As shown in FIG. 65A, the tissue penetrating member 250 is advanced from the IPS 102, piercing the IPS wall 114 and arachnoid layer 115, creating the anastomosis channel 140 into the CP angle cistern 138. The distal portion 202 of the shunt 200' is advanced into the CP angle cistern, so that the distal anchoring mechanism 229 is deployed, securing the distal portion 202 of the shunt 200' at the target site. The deployed anchoring mechanism 229 expands the distal portion 202 of the shunt 200', and is configured to assume a larger inner diameter $ID_1$ than the inner diameter $ID_2$ of the elongated body 203 of the shunt 200', as shown in FIG. 64B. The anchoring mechanism 229 comprises a distal edge 229' configured to invert and/or be disposed radially inward in the deployed configuration (FIG. 64B). Alternatively, the anchoring mechanism distal edge 229' may be configured to evert and/or be disposed radially outward in the deployed configuration (FIG. 64C). It should be appreciated that the anchoring mechanism 229 of FIGS. 64B-C may be used with any of the embodiments of the shunts described herein, as appropriate.

FIGS. 65A-D illustrate an exemplary delivery catheter 304" for delivering the shunt 200 into a target site of a patient, constructed in accordance with embodiments of the disclosed inventions. For ease in illustration, the features, functions, and configurations of the delivery catheter 304" that are the same as in the assembly 300 of FIGS. 3B and 4A-D, in the assembly 300' of FIGS. 5A-J, and/or in the catheter 304' of FIGS. 43A-D, are given the same reference numerals. The delivery catheter 304" is dimensioned to reach remote locations of the vasculature and is configured to deliver the shunt 200 percutaneously to the target location (e.g., inferior petrosal sinus). The delivery catheter 304" may comprise variable stiffness sections (e.g., varying ratio of material, including selective reinforcement, such as braids, coils, or the like) suitable to provide sufficient "pushability" and "torqueability" to allow the catheter 304" to be inserted, advanced and/or rotated in the vasculature to position the distal portion 344 of the catheter at the target site within the IPS 102. Further, the distal portion 344 should have sufficient flexibility so that it can track and maneuver into the target site. Variable stiffness in the catheter 304" is achieved, for example, by locally varying the properties and/or distribution of the materials used and/or varying the durometer or thickness of the materials during the process of manufacturing. By way of non-limiting examples, the materials used in manufacturing the catheter 304" may include polyether block amide (Pebax®) and Nylon, and any other suitable materials, such as the materials previously described for manufacturing the catheter 304'. It should be appreciated that when appropriate, the delivery catheter 304" may be used in combination with the delivery assembly 300/300' also previously described.

Figure 65C:
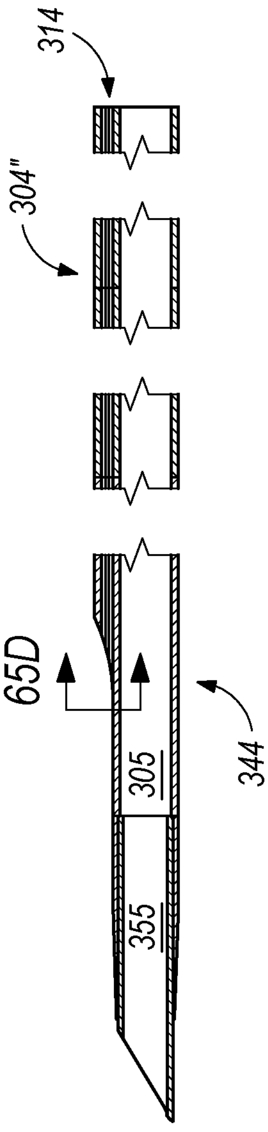
Figure 65D:
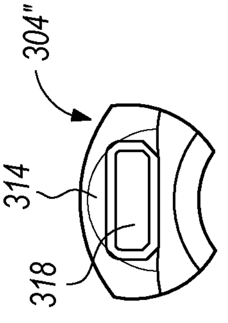
Figure 65E:
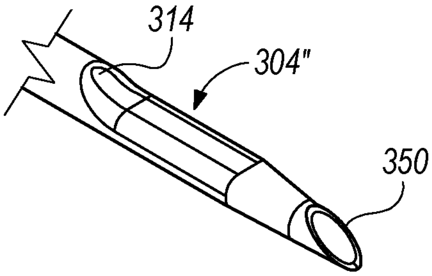

The distal portion 344 of the delivery catheter 304" comprises the tissue penetrating member 350 having lumen 355 fluidly coupled to the lumen 305 of the delivery catheter 304" (FIG. 65C). The shunt 200 is configured to be deployed into the target site via lumens 305, 355, when the anastomosis channel 140 is created (not shown). It should be appreciated that when using the delivery catheter 304" to deliver and deploy the shunt 200 into the target site, the tissue penetrating element 306 of the delivery assembly 300 and/or the tissue penetrating member 250 incorporated in the shunt 200' may not be required.

Figure 66:
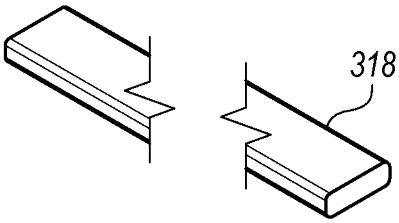
FIG. 66 is a perspective views of a guidewire, according to one embodiment of the disclosed inventions.

The delivery catheter 304" further comprises a lumen 314 configured for advancement of a guidewire 318, supplying and/or withdrawing fluid to the vasculature and/or any other suitable function (FIGS. 65B-E). The elongated guidewire 318 includes a flattened profile, as seen in the cross-sectional views of the wire 318 in FIG. 65B and FIG. 66, and the wire 318 is formed of Nitinol. In other embodiments, the wire 318 may comprise any suitable profile and materials. The delivery catheter 304" may be advanced over the wire 318 extending through the lumen 314, until the distal end portion 344 of the delivery catheter 304 is positioned in the IPS 102 (not shown).

Figure 67A:
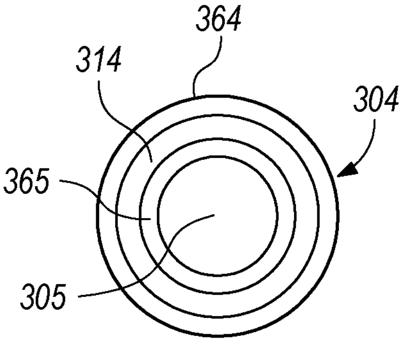
FIGS. 67A-D are cross-sectional views of delivery catheters, according embodiments of the disclosed inventions.
Figure 67B:
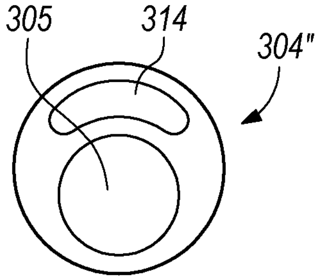
Figure 67C:
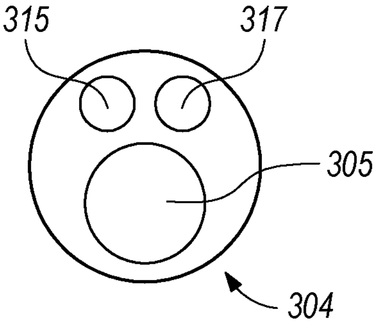
Figure 67D:
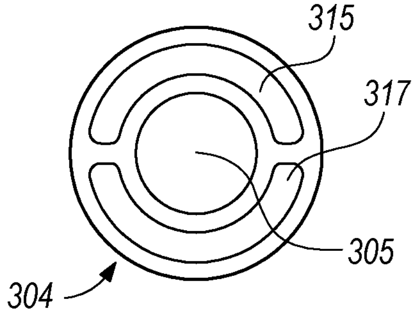

FIGS. 67A-D illustrate exemplary cross-sectional views of the delivery catheters for delivering the shunt 200 into a target site of a patient, constructed in accordance with embodiments of the disclosed inventions. FIG. 67A depicts a cross-sectional view of the delivery catheter 304 comprising a tubular interface having an outer tubular member 364 and an inner tubular member 365 coaxially disposed within the outer tubular member 364. The coaxial tubular interface of the catheter 304 comprises the lumen 305 configured to deliver the shunt 200 into the target site, and the lumen 314 configured for advancement of guidewires, supplying and/or withdrawing fluid to expandable members (e.g., balloons, or their like) or to the vasculature and/or any other suitable function. FIG. 67B depicts a cross-sectional view of the previously described delivery catheter 304" of FIGS. 65A-E. FIGS. 67C-D depict cross-sectional views of the delivery catheter 304' comprising the lumen 305 configured to deliver the shunt 200 into the target site, and two additional lumens, a guidewire lumen 315 and an inflation lumen 317. It should be appreciated that any other configuration of the delivery catheter and lumens suitable for delivering the shunt 200 into the target site may be used.

Lumens of the catheter embodiments depicted in FIGS. 65A-67D can be configured to conform to the various delivery assembly 300 elements used such catheters. Lumen 314 of delivery catheter 304" depicted in FIG. 65B comprises a crescent shaped profile, distinct from the flattened profile of wire 318. In other embodiments, the profile of all or a portion of lumen 314 can be configured to more closely match the exterior profile of wire 318. For example, the bottom left and right portions of lumen 314 shown in FIG. 65D can be formed to match the straight and angled edges on the bottom portion of the wire 318. As another example, lumen 314 can match the profile of the wire 318 depicted in FIG. 66. Conformed catheter lumens can eliminate the risk that the element passing through inadvertently changes orientation or trajectory within the catheter during the shunt implant procedure. In addition, any combination of conformed lumens can be used with or in place of the circular and crescent lumen 314 embodiments shown in FIG. 67A-D. It will be appreciated by those of skill in the art, however, that certain lumen 314 configurations (e.g., crescent lumen versus rectangular lumen of equal size) can conserve more cross-sectional area of the catheter to accommodate other lumens and componentry.

The lumens of the catheter embodiments depicted in FIGS. 65A-67D and disclosed elsewhere in this application (e.g., delivery catheter 304, guide catheter 320) can include a liner to increase the lubricity of the delivery assembly 300 and reduce friction between the specific catheter lumen and delivery system components delivered through such lumen. The catheter liner may comprise homopolymers, copolymers or polymer blends containing polyamides, polyurethanes, silicones, polyolefins (e.g., polypropylenes, polyethylenes), fluoropolymers (e.g., FEP, TFE, PTFE, ETFE), polycarbonates, polyethers, PEEK, PVC, and other polymer resins. The liner thickness can range from approximately 0.0005 inches to 0.003 inches. In addition, the catheter embodiments can include hydrophilic coatings commonly known in the art to further increase the lubricity and navigability of the delivery assembly 300 components within the patient.

In the embodiments of the disclosed inventions, a method for relieving a patient's elevated intracranial pressure by implanting the shunt 200/200' in the patient is provided. The shunt 200/200' comprising one or more cerebrospinal fluid (CSF) intake openings 201 in a distal portion 202 of the shunt 200/200', the valve 209 disposed in a proximal portion 204 of the shunt 200/200', and the lumen 207 extending between the one or more CSF intake openings 201 and the valve 209 (e.g., as shown in FIG. 6). The method comprises: introducing the deployment system 300/300' including the tissue penetrating element 306/250/350 and the shunt 200 from a venous access location in the patient; navigating the deployment system 300/300', including the penetrating element 306/250/350 and shunt 200/200', from the venous access location to a target penetration site within the IPS 102 of the patient, via the jugular vein (JV) 106 of the patient; assessing a trajectory of the tissue penetrating element 306/250/350 at the target penetration site from the IPS 102 into the angle cistern 138 of the patient; advancing the tissue penetrating element 306/250/350 through dura IPS wall 114 and arachnoid tissue layer 115 at the target penetration site, and into the CP angle cistern 138; advancing the distal portion 202 of the shunt 200/200' into the CP angle cistern 138 through an opening (e.g., anastomosis channel 140) in the respective dura IPS wall 114 and arachnoid tissue layer 115 created by the tissue penetrating element 306/250/350; deploying the distal anchoring mechanism 229 of the shunt 200/200' in the CP angle cistern 138; withdrawing the delivery system 300/300' from the target penetration site towards the JV 106, wherein the shunt 200/200' is expelled from the delivery system 300/300' and thereby deployed in the IPS 102 as the delivery system 300/300' is withdrawn toward the JV 106; deploying the proximal anchoring mechanism 227 of the shunt 200/200' about a junction 118 of the JV 106 and IPS 102, such that the proximal portion 204 of the shunt 200/200' is oriented away from a medial wall of the JV 106; and removing the delivery system 300/300' from the patient, wherein the deployed shunt 200/200' provides a one-way flow path for CSF to flow from the CP angle cistern to the JV 106 via the shunt lumen 207 in order to maintain a normal differential pressure between the patient's subarachnoid space and venous system. The method may further comprise confirming that the tissue penetrating element 306/250/350 has accessed the CP angle cistern 138 by withdrawing CSF from the CP angle cistern 138 through the delivery system 300/300' prior to withdrawing the delivery system 300/300' from the patient.

In the embodiments of the disclosed inventions, a method for treating normal pressure hydrocephalus (NPH) using the shunt 200/200' is provided. The shunt 200/200' comprising one or more cerebrospinal fluid (CSF) intake openings 201 in the distal portion 202 of the shunt 200, the valve 209 disposed in the proximal portion 204 of the shunt 200/200', and the lumen 207 extending between the one or more CSF intake openings 201 and the valve 209, the lumen 207 having an inner diameter in a range of 0.008" to 0.014". The method comprises: deploying the shunt 200/200' in a body of an NPH patient so that the distal portion 202 of the shunt 200/200' is at least partially disposed within the CP angle cistern 138 of the patient, the body 203 of the shunt 200/200' is at least partially disposed within the IPS 102 of the patient, and the proximal portion 204 of the shunt is at least partially disposed within, or proximate to, the jugular vein (JV) 106 of the patient, wherein the shunt valve 209 opens at a pressure differential between the CP angle cistern 138 and JV 106 in a range of 3 mm Hg to 5 mm Hg, so that, after deployment of the shunt 200/200', CSF flows from the CP angle cistern 138 to the JV 106 via the shunt lumen 207.

When the shunt 200/200' is deployed, the proximal portion 204 of the shunt 200/200' may be disposed adjacent to a jugular bulb 108.

The methods and devices disclosed herein provide a number of significant advantages relative to other methods and systems intended to treat hydrocephalus or relieve elevated ICP.

Conventional VP shunt placement surgery is an invasive procedure performed under general anesthesia and typically requires about three to five days hospitalization. During the procedure, the physician makes a bore hole in the patient's skull and then passes a catheter through such hole and further, through brain tissue (e.g., cerebral cortex grey matter, brain white matter, ventricles) to access CSF within the cerebral ventricles. Ventricular catheter placement typically requires coagulating the cortex of the brain and passing the catheter through cerebral cortex and subcortical white matter one or several times. Thereafter, the ventricular catheter is attached to an inflow portion of a valve mechanism that the physician implants underneath the patient's scalp, often behind the ear. The outflow portion of the valve mechanism is attached to a silicone catheter that is tunneled under the patient's skin down through the neck and into the abdomen. The implanted shunt provides a one-way flow path for CSF to travel from the patient's ventricle and into the peritoneal cavity.

VP shunts are prone to clogging, particularly in the ventricular catheter and peritoneal tubing. As excess CSF is removed from the ventricles through the catheter, the ventricles become smaller. Often, as the ventricles shrink, the choroid and other cells of the surrounding ventricle shrink down around the CSF inlets of the catheter and obstruct the flow of CSF into the VP shunt. The peritoneal tubing often clogs from cell ingrowth (e.g., endothelial cells) and/or clogs from incorporation into the abdominal wall. VP shunt placement surgery has a relatively high rate of infection especially when compared to minimally invasive, endovascular procedures. VP shunts are subject to a siphoning effect due to the long, hydrostatic column created between the CSF inflow (i.e., ventricle) and outflow (i.e., peritoneum) locations of the implanted shunt. Draining CSF too rapidly or draining too much CSF from the ventricles presents significant risk to the patient from, e.g., collapsed ventricles or subdural hematoma. Complicated anti-siphoning valves have been developed in attempt to mitigate the siphoning effect in VP shunts.

In contrast, by using an endovascular deployment method and deploying shunt 200 from within IPS 102 into CP angle cistern 138 such that CSF drains into the jugular bulb or vein, the risks and clogging complications due to invasive surgery, surrounding brain tissues, infection, and siphoning effect can be eliminated or significantly mitigated. In many patients, particularly those less than 70 years old, there is little or no space between the arachnoid layer and brain parenchyma within the subarachnoid space to accommodate an endovascular shunt in a venous sinus other than IPS 102. In such cases, shunt deployment techniques and shunt features move brain parenchyma and/or create or augment a cistern in the subarachnoid space for CSF to pool for inflow to the shunt. Such techniques increase the risk of injury to brain tissue and increase the risk of subsequent shunt clogging at the proximal end from surrounding brain tissue. The methods, systems, and devices disclosed herein significantly reduce or eliminate these risks.

Some advantages of the endovascular access system and method for navigating a catheter into a target site (e.g., inferior petrosal sinus) and placing an endovascular shunt to drain CSF from a cerebral cistern (e.g., cerebellopontine (CP) angle cistern) to treat communicating hydrocephalus including NPH, and pseudotumor cerebri, are disclosed herein, thereby minimizing undesired effects of traditional VPS placement, avoiding boring into a patient's skull, coagulating the cortex of the brain, passing a shunt catheter through cerebral cortex and subcortical white matter one or several times, and other invasive surgical techniques used in current hydrocephalus treatments.

The anatomy of CP angle cistern 138 and its proximity to IPS 102 make it a preferred location for deploying an endovascular CSF shunt, compared to the sigmoid sinus or other intracranial venous sinuses (e.g., the transverse sinus, the cavernous sinus, the sagittal sinus, and/or the straight sinus). CP angle cistern 138 typically features a large CSF-containing space and a greater separation between the arachnoid layer and the closest surrounding brain parenchyma than any other CSF cisterns accessible from venous conduits. Accordingly, positioning shunt 200 within CP angle cistern 138 is easier and more fault tolerant than positioning the shunt within other cisterns, and the rate at which CSF can be communicated to venous circulation is greater on account of the larger pool of CSF within CP angle cistern 138.

Venous blood flow rates in jugular vein 106 can be significantly higher than the blood flow rates in larger diameter dural venous sinuses (i.e., sagittal, sigmoid, straight, transverse), which favor long-term shunt patency of the disclosed embodiments compared to other implant locations.

In addition, the anatomy of IPS 102 facilitates long-term stability of shunt 200. The relatively long length and narrow diameter of IPS 102 provides a natural housing to accommodate shunt 200 along its length. The foundation provided by the grooved portion of the clivus bone that surrounds about two-thirds of the IPS circumference further supports long-term stability of the shunt 200, and presents a stable platform that delivery systems disclosed herein can leverage during shunt implant procedures. The situation differs in the other venous sinuses, which are not as well adapted naturally to house a shunt. Further, if IPS 102 occludes due to occupation by shunt 200, thereby restricting or preventing blood flow through IPS 102, there is little to no risk to the patient given the relatively minor role of IPS 102 in the overall intracranial venous blood circulation system. Occlusion of larger diameter venous sinuses (e.g., sagittal, sigmoid, straight, transverse), on the other hand, poses a serious risk for the patient.

Further, despite the advantages of the endovascular approach to deliver and implant the shunt according to the disclosed inventions, it should be appreciated that other delivery methods may be used to deliver and implant the shunts described herein, such as, using open and/or invasive surgical procedures.

It should be appreciated that prior to use in humans, the embodiments of the disclosed inventions can be deployed and tested in suitable animal surrogates having venous vascular and intracranial subarachnoid features that resemble or closely approximate the IPS and CP angle cistern in humans. Pigs (e.g., Yorkshire pigs or Yucatan mini-pigs) have a suitable deployment site for testing embodiments of the disclosed inventions. In the pig model, the system can navigate a shunt to the basilar sinus (e.g., via the internal jugular vein or venous vertebral plexus), and deploy the shunt through dura and arachnoid tissues to access CSF-filled subarachnoid space (e.g., basilar cisterns, pontine cisterns) for testing. Suitable surrogates for the IPS and CP angle cistern in humans are feasible in other animal models (e.g., dogs and primates).

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A shunt configured for endovascular deployment in a patient, the shunt comprising:

a distal portion configured for being introduced from a venous system of the patient into, and disposed within, a subarachnoid space of the patient, the subarachnoid space containing cerebrospinal fluid (CSF);

a proximal portion configured for being disposed within the venous system when the distal portion is disposed with the subarachnoid space; and a shunt body comprising a lumen, the lumen extending from the distal portion to the proximal portion, wherein the lumen is in fluid communication with one or more CSF intake openings in the distal portion, and with one or more CSF outflow openings in the proximal portion, wherein the distal portion comprises an expandable distal anchoring mechanism configured to retain the distal portion within the subarachnoid space and to maintain the one or more CSF intake openings separated, apart, and/or directed away from an arachnoid layer of the subarachnoid space, such that, when the distal portion of the shunt is disposed within the subarachnoid space, and the proximal portion of the shunt disposed within the venous system, CSF flows from the subarachnoid space, through the one or more CSF intake openings, shunt lumen, and the one or more CSF outflow openings, respectively, into the venous system.

2. The shunt of claim 1, wherein the distal anchoring mechanism is configured to prevent passage of the distal portion shunt from the subarachnoid space through an anastomosis in a dura layer proximate the subarachnoid space through which the distal portion of the shunt was introduced into the subarachnoid space.

3. The shunt of claim 1, wherein the distal anchoring mechanism is configured to compress or pin down the arachnoid layer within the subarachnoid space in order to prevent blockage of the one or more CSF intake openings and/or occlusion of the shunt lumen by the arachnoid layer.

4. The shunt of claim 1, wherein the distal anchoring mechanism is configured to self-expand from a collapsed delivery configuration to an expanded deployed configuration as the distal portion of the shunt is introduced into the subarachnoid space.

5. The shunt of claim 1, the distal anchoring mechanism comprising expandable members for securing the shunt distal portion against a side of a dura layer adjacent the subarachnoid space.

6. The shunt of claim 1, wherein the distal anchoring mechanism comprises one or more expandable arms, petals, coils, malecots, ellipticots, or t-bar features for securing the shunt distal portion within the subarachnoid space.

7. The shunt of claim 1, wherein the subarachnoid space comprises an intracranial subarachnoid space.

8. The shunt of claim 1, wherein the one or more CSF outflow openings comprise one or more slit valves in the shunt body.

9. The shunt of claim 8, wherein the one or more slit valves and shunt lumen are configured and dimensioned to achieve a target flow rate of 5 ml of CSF per hour to 20 ml of CSF per hour through the shunt lumen under normal differential pressure conditions between the subarachnoid space and venous system of the patient.

10. The shunt of claim 8, wherein the one or more slit valves are configured to open at a pressure differential between the subarachnoid space and the venous system.

11. The shunt of claim 8, wherein the valve is configured to prevent or resist backflow of venous blood through the shunt lumen and into the subarachnoid space.

12. The shunt of claim 1, wherein the proximal portion of the shunt comprises a proximal anchoring mechanism configured to anchor the proximal portion of the shunt within the venous system.

13. The shunt of claim 2, wherein the distal anchoring mechanism is configured to form a seal at the anastomosis.

14. The shunt of claim 13, wherein the seal is configured to prevent venous blood from entering the subarachnoid space through the anastomosis.

15. The shunt of claim 1, further comprising a second lumen configured to receive or slide over a delivery guidewire.

16. The shunt of claim 1, wherein the proximal portion of the shunt comprises a first interlocking element configured to engage and disengage with a second interlocking element coupled to a distal portion of a shunt delivery assembly.

17. The shunt of claim 4, wherein the distal anchoring mechanism comprises a plurality of members, tines or wires aligned along an axis of the shunt when distal the anchoring mechanism is in the collapsed delivery configuration.

18. A method for treating a patient with communicating hydrocephalus, the method comprising:
- percutaneously introducing the shunt of claim 1 into a venous system of the patient;
- navigating the shunt through the venous system to a target location proximate the subarachnoid space;
- advancing a penetrating element through a dura layer and arachnoid layer at the target location and into the subarachnoid space, to thereby create an anastomosis in the dura layer and arachnoid layer; and
- introducing the distal portion of the shunt through the anastomosis and into the subarachnoid space.

19. The method of claim 18, wherein the distal portion of the shunt accompanies the penetrating element into the subarachnoid space.

20. The method of claim 18, wherein the penetrating element is attached to the shunt when the penetrating element is advanced into the subarachnoid space.

21. The method of claim 20, further comprising detaching the penetrating element from the shunt and withdrawing the penetrating element from the patient after the penetrating element has been advanced into the subarachnoid space.

22. The method of claim 18, wherein the penetrating element is configured to limit a distance that the penetrating element advances into the subarachnoid space.

23. The method of claim 18, further comprising compressing or pinning down the arachnoid layer within the subarachnoid space to prevent occlusion of the shunt lumen.

24. The method of claim 18, further comprising anchoring the shunt proximal portion in the venous system.

25. The method of claim 18, wherein the dura layer comprises a wall of a dural venous sinus.

26. The method of claim 18, wherein the subarachnoid space comprises an intracranial subarachnoid space.

27. The method of claim 26, wherein the intracranial subarachnoid space comprises a cerebellopontine angle cistern.

28. The method of claim 18, wherein advancing the tissue penetrating element through the dura layer dilates the dura layer.

* * * * *